(12) United States Patent
Verkman et al.

(10) Patent No.: US 9,062,073 B2
(45) Date of Patent: Jun. 23, 2015

(54) PYRIMIDO-PYRROLO-OXAZINE-DIONE COMPOUND INHIBITORS OF THE CYSTIC FIBROSIS TRANSMEMBRANE CONDUCTANCE REGULATOR PROTEIN AND USES THEREFOR

(75) Inventors: Alan S. Verkman, San Francisco, CA (US); David S. Snyder, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/119,405

(22) PCT Filed: May 25, 2012

(86) PCT No.: PCT/US2012/039715
§ 371 (c)(1),
(2), (4) Date: Nov. 21, 2013

(87) PCT Pub. No.: WO2012/166658
PCT Pub. Date: Dec. 6, 2012

(65) Prior Publication Data
US 2014/0080821 A1    Mar. 20, 2014

Related U.S. Application Data

(60) Provisional application No. 61/491,151, filed on May 27, 2011.

(51) Int. Cl.
*C07D 498/14* (2006.01)
*C07D 487/14* (2006.01)
*A61K 31/5383* (2006.01)

(52) U.S. Cl.
CPC ............ *C07D 498/14* (2013.01); *C07D 487/14* (2013.01)

(58) Field of Classification Search
CPC ........................... C07D 498/14; C07D 487/14
USPC .......................... 544/99, 247; 514/229.5, 250
See application file for complete search history.

(56) References Cited

U.S. PATENT DOCUMENTS

| | | | |
|---|---|---|---|
| 7,235,573 B2 | 6/2007 | Verkman et al. | |
| 7,414,037 B2 | 8/2008 | Verkman et al. | |
| 7,638,543 B2 | 12/2009 | Verkman et al. | |
| 7,888,332 B2 | 2/2011 | Verkman et al. | |
| 8,609,661 B2 * | 12/2013 | Verkman et al. | 514/250 |
| 2006/0160815 A1 | 7/2006 | Sabatucci et al. | |
| 2008/0064666 A1 | 3/2008 | Verkman et al. | |
| 2008/0171793 A1 | 7/2008 | Verkman et al. | |
| 2008/0269206 A1 | 10/2008 | Russell et al. | |
| 2009/0005386 A1 | 1/2009 | Abbott et al. | |
| 2009/0253799 A1 | 10/2009 | Verkman et al. | |

FOREIGN PATENT DOCUMENTS

| | | |
|---|---|---|
| WO | 98/05642 A1 | 2/1998 |
| WO | 98/28301 A1 | 7/1998 |
| WO | 2004/111014 A1 | 12/2004 |
| WO | 2005/039589 A2 | 5/2005 |
| WO | 2008/079897 A2 | 7/2008 |
| WO | 2009/076593 A1 | 6/2009 |
| WO | 2009/120803 A2 | 10/2009 |
| WO | 2011/019737 A1 | 2/2011 |
| WO | WO 2011019737 A1 * | 2/2011 |
| WO | 2012/166658 A1 | 12/2012 |

OTHER PUBLICATIONS

Azas et al., "Antiparasitic activity of highly conjugated pyrimidine-2,4-dione derivatives," *Il Farmaco* 58:1263-1270, 2003.
Brill et al., "Immunolocalization of ion transport proteins in human autosomal dominant polycystic kidney epithelial cells," *Proc. Natl. Acad. Sci. USA* 93:10206-10211, Sep. 1996.
Caci et al., "Evidence for direct CFTR inhibition by $CFTR_{inh}$-172 based on $Arg^{347}$ mutagenesis," *Biochem. J.* 413:135-142, 2008.
Clarke et al., "Defective Epithelial Chloride Transport in a Gene-Targeted Mouse Model of Cystic Fibrosis," *Science* 257:1125-1128, Aug. 21, 1992.
Cotton et al., "PKD and CF: An Interesting Family Provides Insight Into the Molecular Pathophysiology of Polycystic Kidney Disease," *Am. J. Kidney Dis.* 32(6):1081-1083, 1998.
Davidow et al., "The cystic fibrosis transmembrane conductance regulator mediates transepithelial fluid secretion by human autosomal dominant polycystic kidney disease epithelium in vivo," *Kidney International* 50:208-218, 1996.
Dawson et al., "CFTR: Mechanism of Anion Conduction," *Physiological Reviews* 79(Suppl., No. 1):S47-S75, Jan. 1999.
Edwards et al., "Induction of a glibenclamide-sensitive K-current by modification of a delayed rectifier channel in rat portal vein and insulinoma cells," *Br. J. Pharmacol.* 110:1280-1281, 1993.
Field, "Intestinal ion transport and the pathophysiology of diarrhea," *J. Clin. Invest.* 111(7):931-943, 2003.
Gabriel et al., "Cystic Fibrosis Heterozygote Resistance to Cholera Toxin in the Cystic Fibrosis Mouse Model," *Science* 266:107-109, Oct. 7, 1994.
Gadsby et al., "The ABC protein turned chloride channel whose failure causes cystic fibrosis," *Nature* 440(7083):477-483, Mar. 23, 2006.
Hanaoka et al., "cAMP Regulates Cell Proliferation and Cyst Formation in Autosomal Polycystic Kidney Disease Cells," *J. Am. Soc. Nephrol* 11:1179-1187, 2000.

(Continued)

*Primary Examiner* — Kahsay Habte
(74) *Attorney, Agent, or Firm* — Seed IP Law Group PLLC

(57) ABSTRACT

Provided herein are benzopyrimido-pyrrolo-oxazine-dione (BPO) compounds and pyrimido-pyrrolo-quinoxalinedione (PPQ) compounds, and compositions comprising these compounds, that inhibit cystic fibrosis transmembrane conductance regulator (CFTR) mediated ion transport and that are useful for treating diseases and disorders associated with aberrantly increased CFTR chloride channel activity, such as polycystic kidney disease and secretory diarrheas. The compounds and compositions comprising the compounds described herein may be used for inhibiting expansion or preventing formation of cysts in persons who have polycystic kidney disease.

34 Claims, 10 Drawing Sheets

(56) References Cited

OTHER PUBLICATIONS

Kunzelmann et al., "Electrolyte Transport in the Mammalian Colon: Mechanisms and Implications for Disease," *Physiol. Rev.* 82:245-289, 2002.

Li et al., "The relationship between cell proliferation, Cl⁻ secretion, and renal cyst growth: A study using CFTR inhibitors," *Kidney International* 66:1926-1938, 2004.

Lohi et al., "Upregulation of CFTR expression but not SLC26A3 and SLC9A3 in ulcerative colitis," *Am. J. Physiol. Gastrointest. Liver Physiol.* 283:G567-G575, 2002.

Ma et al., "Thiazolidinone CFTR inhibitor identified by high-throughput screening blocks cholera toxin-induced intestinal fluid secretion," *J. Clin. Invest.* 110(11):1651-1658, 2002.

Magenheimer et al., "Early Embryonic Renal Tubules of Wild-Type and Polycystic Kidney Disease Kidneys Respond to cAMP Stimulation with Cystic Fibrosis Transmembrane Conductance Regulator/Na⁺,K⁺,2Cl⁻ Co-Transporter-Dependent Cystic Dilation," *J Am Soc Nephrol* 17:3424-3437, 2006.

McCarty, "Permeation through the CFTR chloride channel," *The Journal of Experimental Biology* 203:1947-1962, 2000.

Muanprasat et al., "Discovery of Glycine Hydrazide Pore-occluding CFTR Inhibitors: Mechanism, Structure-Activity Analysis, and In Vivo Efficacy," *J. Gen. Physiol.* 124:125-137, Aug. 2004.

Nagata et al., "Tricyclic Quinoxalinediones: 5,6-Dihydro-1*H*-pyrrolo[1,2,3-*de*]quinoxaline-2,3-diones and 6,7-Dihydro-1*H*,5*H*-pyrido[1,2,3-*de*]quinoxaline-2,3-diones as Potent Antagonists for the Glycine Binding Site of the NMDA Receptor," *J. Med. Chem.* 37:3956-3968, 1994.

Namkung et al., "In Situ Measurement of Airway Surface Liquid [K⁺] Using a Ratioable K⁺-sensitive Fluorescent Dye," *The Journal of Biological Chemistry* 284(23):15916-15926, Jun. 5, 2009.

O'Sullivan et al., "Cystic Fibrosis and the Phenotypic Expression of Autosomal Dominant Polycystic Kidney Disease," *American Journal of Kidney Diseases* 32(6):976-983, 1998.

Oels et al., "Reinvestigation of the Synthesis of 3-Dimethylallyl-4-hydroxy-2-quinol-ones. A Novel Route to Tetracyclic Heteroaromatic Compounds," *J. Chem. Soc. Perkin Trans.* 23:2546-2551, 1977.

Routaboul et al., "Discovery of α-Aminoazaheterocycle-Methylglyoxal Adducts as a New Class of High-Affinity Inhibitors of Cystic Fibrosis Transmembrane Conductance Regulator Chloride Channels," *The Journal of Pharmacology and Experimental Therapeutics* 322(3):1023-1035, 2007.

Schultz et al., "Pharmacology of CFTR Chloride Channel Activity," *Physiological Reviews* 79(Suppl., No. 1):S109-S144, Jan. 1999.

Sheppard et al., "Mechanism of glibenclamide inhibition of cystic fibrosis transmembrane conductance regulator Cl⁻ channels expressed in a murine cell line," *Journal of Physiology* 503.2:333-346, 1997.

Sheppard et al., "Structure and Function of the CFTR Chloride Channel," *Physiological Reviews* 79(Suppl. No. 1):S23-S45, Jan. 1999.

Snyder et al., "Absolute Configuration and Biological Properties of Enantiomers of CFTR Inhibitor BPO-27," *ACS Med. Chem. Lett.* 4:456-459, 2013.

Snyder et al., "Potent, Metabolically Stable Benzopyrimido-Pyrrolo-Oxazinedione (BPO) CFTR Inhibitors for Polycystic Kidney Disease," *J Med Chem.* 54(15):5468-5477, 2011.

Sonawane et al., "α-Aminoazaheterocyclic-Methylglyoxal Adducts Do Not Inhibit Cystic Fibrosis Transmembrane Conductance Regulator Chloride Channel Activity," *The Journal of Pharmacology and Experimental Therapeutics* 325(2):529-535, 2008.

Sonawane et al., "In Vivo Pharmacology and Antidiarrheal Efficacy of a Thiazolidinone CFTR Inhibitor in Rodents," *Journal of Pharmaceutical Sciences* 94(1):134-143, 2005.

Sonawane et al., "Lectin Conjugates as Potent, Nonabsorbable CFTR Inhibitors for Reducing Intestinal Fluid Secretion in Cholera," *Gastroenterology* 132:1234-1244, 2007.

Sonawane et al., "Luminally active, nonabsorbable CFTR inhibitors as potential therapy to reduce intestinal fluid loss in cholera," *The FASEB Journal* 20:130-132, Jan. 2006.

Sonawane et al., "Thiazolidinone CFTR inhibitors with improved water solubility identified by structure-activity analysis," *Bioorganic & Medicinal Chemistry* 16:8187-8195, 2008.

Taddei et al., "Altered channel gating mechanism for CFTR inhibition by a high-affinity thiazolidinone blocker," *FEBS Letters* 558:52-56, 2004.

Thiagarajah et al., "Prevention of Toxin-Induced Intestinal Ion and Fluid Secretion by a Small-Molecule CFTR Inhibitor," *Gastroenterology* 126:511-519, 2004.

Torres et al., "Mechanisms of Disease: autosomal dominant and recessive polycystic kidney diseases," *Nature Clinical Practice—Nephrology* 2(1):40-55, Jan. 2006.

Tradtrantip et al., "Nanomolar Potency Pyrimido-pyrrolo-quinoxalinedione CFTR Inhibitor Reduces Cyst Size in a Polycystic Kidney Disease Model," *J Med Chem.* 52(20):6447-6455, 2009.

Tradtrantip et al., "Thiophenecarboxylate Suppressor of Cyclic Nucleotides Discovered in a Small-Molecule Screen Blocks Toxin-Induced Intestinal Fluid Secretion," *Molecular Pharmacology* 75(1):134-142, 2009.

Tsupak et al., "Pyrrolopyrimidines. 5. Interaction of 6-amino-1,3-dimethylpyrrolo[3,4-*d*]-pyrimidin-2,4(1*H*,3*H*)-diones with 1,3-diketones," *Khim. Geterotsikl. Soedin.*7:1096-1102, 2003.

Tsupak et al., "Pyrrolopyrimidines. 5. Reaction of 6-Amino-1,3-Dimethyl-Pyrrolo[3,4-*d*]Pyrimidine-2,4(1H,3H)-Diones with 1,3-Diketones," *Chemistry of Heterocyclic Compounds* 39(7):953-959, 2003.

Tsupak et al., "[3,4]-Annulated pyrroles 1. Polynuclear heterocyclic systems based on pyrrolo[3,4-*d*]pyrimidine-2,4-dione," *Russ. Chem. Bull.* 55(12):2265-2270, 2006.

Verkman et al., "CFTR Inhibitors," *Curr Pharm Des.* 19(19):3529-3541, 2013.

Verkman et al., "Chloride channels as drug targets," *Nat. Rev. Drug Discov.* 8(2):153-171, Feb. 2009.

Xu et al., "Autosomal dominant polycystic kidney disease coexisting with cystic fibrosis," *J. Nephrol.* 19:529-534, 2006.

Yang et al., "Small-Molecular CFTR Inhibitors Slow Cyst Growth in Polycystic Kidney Disease," *J Am Soc Nephrol* 19:1300-1310, 2008.

Zhou et al., "Probing an Open CFTR Pore with Organic Anion Blockers," *J. Gen. Physiol.* 120:647-662, Nov. 2002.

Zhou et al., "The Two ATP Binding Sites of Cystic Fibrosis Transmembrane Conductance Regulator (CFTR) Play Distinct Roles in Gating Kinetics and Energetics," *J. Gen. Physiol.* 128(4):413-422, 2006.

\* cited by examiner

PYRIMIDO-PYRROLO-OXAZINE-DIONE COMPOUND INHIBITORS OF THE CYSTIC FIBROSIS TRANSMEMBRANE CONDUCTANCE REGULATOR PROTEIN AND USES THEREFOR

CROSS-REFERENCE TO RELATED APPLICATION

This application is a U.S. national stage application filed under 35 U.S.C. §371 of International Patent Application PCT/US2012/039715, accorded an international filing date of May 25, 2012, which claims benefit under 35 U.S.C. §119 (e) of U.S. Provisional Patent Application Ser. No. 61/491, 151, filed May 27, 2011, which is incorporated herein by reference in its entirety.

STATEMENT OF GOVERNMENT INTEREST

This invention was made with government support under Grant Numbers DK86125, DK72517, HL73856, EP00415, DK35124, and EY13574 awarded by the National Institutes of Health. The government has certain rights in this invention.

BACKGROUND

1. Technical Field

Therapeutics are needed for treating diseases and disorders related to aberrant cystic fibrosis transmembrane conductance regulator protein (CFTR)-mediated ion transport, such as polycystic kidney disease, increased intestinal fluid secretion, and secretory diarrhea. Small molecule compounds are described herein that are potent inhibitors of CFTR activity and may be used for treating such diseases and disorders.

2. Description of the Related Art

The cystic fibrosis transmembrane conductance regulator protein (CFTR) is a cAMP-activated chloride ($Cl^-$) channel expressed in epithelial cells in mammalian airways, intestine, pancreas, and testis (see, e.g., Sheppard et al., *Physiol. Rev.* 79:S23-45 (1999); Gadsby et al., *Nature* 40:477-83 (2006)). Hormones, such as a β-adrenergic agonist, or a toxin, such as cholera toxin, lead to an increase in cAMP, activation of cAMP-dependent protein kinase, and phosphorylation of the CFTR $Cl^-$ channel, which causes the channel to open. An increase in cell $Ca^{2+}$ can also activate different apical membrane channels. Phosphorylation by protein kinase C can either open or shut $Cl^-$ channels in the apical membrane. CFTR is predominantly located in epithelia where it provides a pathway for the movement of $Cl^-$ ions across the apical membrane and a key point at which to regulate the rate of transepithelial salt and water transport.

CFTR chloride channel function is associated with a wide spectrum of disease, including cystic fibrosis (CF) and with polycystic kidney disease, secretory diarrhea, and some forms of male infertility. Cystic fibrosis is a hereditary lethal disease caused by mutations in CFTR (see, e.g., Quinton, *Physiol. Rev.* 79:S3-S22 (1999); Boucher, *Eur. Respir. J.* 23:146-58 (2004)). Observations in human patients with CF and mouse models of CF indicate the functional importance of CFTR in intestinal and pancreatic fluid transport, as well as in male fertility (see, e.g., Grubb et al., *Physiol. Rev.* 79:S193-S214 (1999); Wong, *Mol. Hum. Reprod.* 4:107-110 (1997)). CFTR is also expressed in enterocytes in the intestine and in cyst epithelium in polycystic kidney disease (see, e.g., O'Sullivan et al., *Am. J. Kidney Dis.* 32:976-983 (1998); Sullivan et al., *Physiol. Rev.* 78:1165-91 (1998); Strong et al., *J. Clin. Invest.* 93:347-54 (1994); Mall et al., *Gastroenterology* 126:32-41 (2004); Hanaoka et al., *Am. J. Physiol.* 270: C389-C399 (1996); Kunzelmann et al., *Physiol. Rev.* 82:245-289 (2002); Davidow et al., *Kidney Int.* 50:208-18 (1996); Li et al., *Kidney Int.* 66:1926-38 (2004); Al-Awqati, *J. Clin. Invest.* 110:1599-1601 (2002); Thiagarajah et al., *Curr. Opin. Pharmacol.* 3:594-99 (2003)).

Polycystic kidney disease (PKD) is one of the most common human genetic diseases and a major cause of chronic renal insufficiency requiring dialysis and kidney transplantation (see, e.g., Torres et al., *Lancet.* 369, 1287-301 (2007)). Cyst growth in PKD involves fluid secretion into the cyst lumen coupled with epithelial cell hyperplasia. PKD is characterized by massive enlargement of fluid-filled cysts of renal tubular origin that compromise normal renal parenchyma and cause renal failure (see, e.g., Arnaout, *Annu. Rev. Med.* 52: 93-123, 2001; Gabow *N. Engl. J. Med.* 329: 332-342, 1993; Harris et al., *Mol. Genet. Metab.* 81: 75-85, 2004; Wilson *N. Engl. J. Med.* 350: 151-164, 2004; Sweeney et al., *Cell Tissue Res.* 326: 671-685, 2006; Chapman *J. Am. Soc. Nephrol.* 18: 1399-1407, 2007). Human autosomal dominant PKD (AD-PKD) is caused by mutations in one of two genes, PKD1 and PKD2, encoding the interacting proteins polycystin-1 and polycystin-2, respectively (see, e.g., Wilson, supra; Qian et al., *Cell* 87: 979-987, 1996; Wu et al., *Cell* 93:177-88, 1998; Watnick et al., Torres et al., *Nat Med* 10: 363-364, 2004 *Nat. Genet.* 25: 143-44 (2000)).

Cyst growth in autosomal dominant polycystic kidney disease (ADPKD) involves progressive fluid accumulation (see, e.g., Grantham et al., *Clin. J. Am. Soc. Nephrol.* 1:148-57 (2006); Ye et al., *N. Engl. J. Med* 329:310-13 (1993)). Fluid secretion into the cyst lumen requires chloride secretion by the cystic fibrosis transmembrane conductance regulator (CFTR) protein, (see, e.g., Hanaoka et al., *J. Am. Soc. Nephrol.* 11:1179-87 (2000); Magenheimer et al., *J. Am. Soc. Nephrol.* 17:3424-37 (2006)), a cAMP-regulated chloride channel, which, when mutated, causes the genetic disease cystic fibrosis (see, e.g., Riordan, *Annu. Rev. Biochem.* 77:701-26 (2008)). CFTR is expressed strongly in epithelial cells lining cysts in ADPKD (see, e.g., Brill et al., *Proc. Natl. Acad. Sci. USA* 93:10206-11 (1996)). Cystic fibrosis (i.e., CFTR-deficient) mice are resistant to cyst formation and CFTR inhibitors block cyst formation in cell/organ culture and in vivo models (see, e.g., Davidow et al., *Kidney Int.* 50:208-18 (1996); Li et al., *Kidney Int.* 66:1926-38 (2004)). In rare families affected with ADPKD and cystic fibrosis, individuals with both ADPKD and CF have less severe renal disease than those with ADPKD only (see, e.g., Cotton et al., *Am. J. Kidney Dis.* 32:1081-83 (1998); O'Sullivan et al., *Am. J. Kidney Dis.* 32:976-83 (1998); Xu et al., *J. Nephrol.* 19:529-34 (2006)).

Several CFTR inhibitors have been discovered, although many exhibit weak potency and lack CFTR specificity. The oral hypoglycemic agent glibenclamide inhibits CFTR $Cl^-$ conductance from the intracellular side by an open channel blocking mechanism (see, e.g., Sheppard et al., *J. Physiol.*, 503:333-346 (1997); Zhou et al., *J. Gen. Physiol.* 120:647-62 (2002)) at high micromolar concentrations where it affects other $Cl^-$ and cation channels (see, e.g., Edwards & Weston, 1993; Rabe et al., *Br. J. Pharmacol.* 110:1280-81 (1995); Schultz et al., *Physiol. Rev.* 79:S109-S144 (1999)). Other non-selective anion transport inhibitors, including diphenylamine-2-carboxylate (DPC), 5-nitro-2(3-phenylpropylamino)benzoate (NPPB), and flufenamic acid, also inhibit CFTR by occluding the pore at an intracellular site (see, e.g., Dawson et al., *Physiol. Rev.*, 79:S47-S75 (1999); McCarty, *J. Exp. Biol.*, 203:1947-62 (2000)).

High-affinity CFTR inhibitors also have clinical application in the therapy of secretory diarrheas. Secretory diarrheas caused by enterotoxins, such as cholera and Travelers' diarrhea (enteropathogenic *E. coli*), require functional CFTR for primary chloride secretion into the intestinal lumen, which secondarily drives sodium and water secretion (see, e.g., Kunzelmann et al., *Physiol. Rev.* 82:245-89 (2002); Thiagarajah et al., *Curr. Opin. Pharmacol.* 3:594-9 (2003)). Cell culture and animal models indicated that intestinal chloride secretion in enterotoxin-mediated secretory diarrheas occurs mainly through CFTR (see, e.g., Clarke et al., *Science* 257: 1125-28 (1992); Gabriel et al., *Science* 266:107-109 (1994); Kunzelmann and Mall, *Physiol. Rev.* 82:245-89 (2002); Field, *J. Clin. Invest.* 111:931-43 (2003); and Thiagarajah et al., *Gastroenterology* 126:511-519 (2003)). Several classes of small molecule CFTR inhibitors have been described previously (see, e.g., review by Verkman et al., *Nat. Rev. Drug Discov.* 8:153-71 (2009)).

Diarrheal disease in children is a global health concern: Approximately four billion cases among children occur annually, resulting in at least two million deaths. Travelers' diarrhea affects approximately 6 million people per year. Antibiotics are routinely used to treat diarrhea; however, the antibiotics are ineffective for treating many pathogens, and the use of these drugs contributes to development of antibiotic resistance in other pathogens. Oral replacement of fluid loss is also routinely used to treat diarrhea, but is primarily palliative. Therapy directed at reducing intestinal fluid secretion ('anti-secretory therapy') has the potential to overcome limitations of existing therapies.

A need exists for CFTR inhibitors, particularly those that are safe, non-absorbable, highly potent, inexpensive, and chemically stable.

BRIEF SUMMARY

Briefly, provided herein are pyrimido-pyrrolo-oxazine-dione (BPO) compounds and certain pyrimido-pyrrolo-quinoxalinedione (PPQ) compounds, and compositions comprising such compounds, that inhibit cystic fibrosis transmembrane conductance regulator (CFTR) mediated ion transport. The BPO and PPQ compounds described herein, are highly potent CFTR inhibitors, metabolically stable, and have desirable polarity and thus have excellent aqueous solubility. The compounds described herein are useful for treating diseases and disorders associated with aberrantly increased CFTR chloride channel activity and thereby are useful for treating diseases and disorders treatable by inhibiting CFTR-mediated ion transport. Methods are provided for inhibiting enlargement of kidney cysts or preventing or inhibiting the formation of cysts and thereby treating polycystic kidney disease by administering the compounds described herein. Methods are also provided for treating diseases and disorders associated with aberrantly increased intestinal fluid secretion, such as secretory diarrhea and Traveler's diarrhea, by administering the compounds and compositions described herein.

Provided herein are compounds, compositions, methods and uses as set forth in the following embodiments.

Embodiment 1. A compound having the following structure (I):

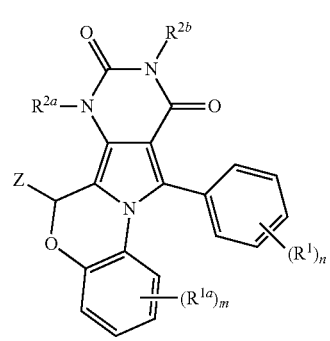

as an isolated enantiomer or a racemic mixture of enantiomers, or as a pharmaceutically acceptable salt, hydrate, solvate, N-oxide, or prodrug thereof, wherein:

m is 1, 2, 3, or 4;

n is 1, 2, 3, 4 or 5;

p is an integer from 0 to 4;

q is an integer from 1 to 4;

$R^1$ at each occurrence is the same or different and independently H, halo, haloalkyl, $C_{1-6}$ alkyl, —$(CH_2)_p$—C(O)—$R^{4a}$, —$S(O)_2R^{4a}$, —$NO_2$, or tetrazolyl;

$R^{1a}$ at each occurrence is the same or different and independently H, halo, haloalkyl, $C_{1-6}$ alkyl, —$(CH_2)_p$—C(O)—$R^{4a}$, —$S(O)_2R^{4a}$, —$NO_2$, or tetrazolyl;

$R^{2a}$ and $R^{2b}$ are each the same or different and independently H or $C_1$-$C_6$ alkyl;

$R^{4a}$ is —$OR^7$, —$NR^7R^8$, —$O(CH_2)_q$—$OC(O)R^7$, an amino acid residue, or a peptide;

$R^7$ and $R^8$ are each the same or different and independently H, $C_{1-20}$ alkyl, a saccharide, an amino acid residue, or a peptide; and Z is aryl or heteroaryl.

Embodiment 2. The compound of Embodiment 1, wherein $R^{2a}$ and $R^{2b}$ are each methyl, and Z is optionally substituted furanyl or optionally substituted thienyl, and the compound has the following structure (IA) or (IB), respectively:

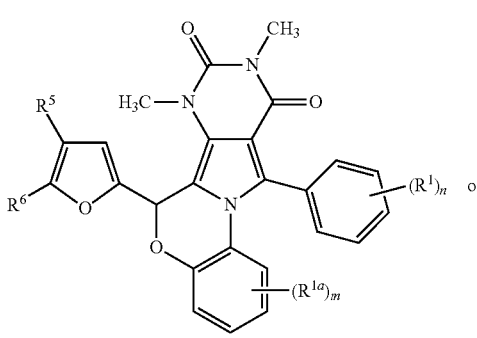

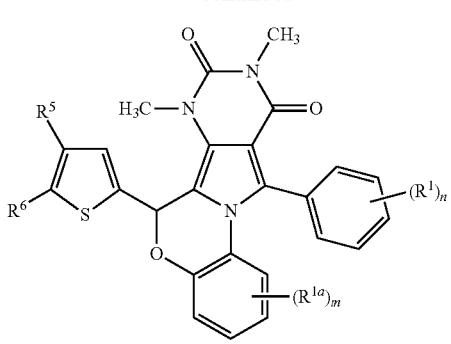

(IB)

as an isolated enantiomer or a racemic mixture of enantiomers, or as a pharmaceutically acceptable salt, hydrate, solvate, N-oxide, or prodrug thereof,
wherein:
m is 1, 2, 3, or 4;
n is 1, 2, 3, 4 or 5;
p is an integer from 0 to 4;
q is an integer from 1 to 4;
$R^1$ at each occurrence is the same or different and independently H, halo, haloalkyl, $C_{1-6}$ alkyl, —$(CH_2)_p$—C(O)—$R^{4a}$, —S(O)$_2R^{4a}$, —NO$_2$, or tetrazolyl;
$R^{1a}$ at each occurrence is the same or different and independently H, halo, haloalkyl, $C_{1-6}$ alkyl, —$(CH_2)_p$—C(O)—$R^{4a}$, —S(O)$_2R^{4a}$, —NO$_2$, or tetrazolyl;
$R^{4a}$ is —OR$^7$, —NR$^7R^8$, —O(CH$_2$)$_q$—OC(O)R$^7$, an amino acid residue, or a peptide;
$R^5$ is H, halo, or $C_{1-6}$ alkyl;
$R^6$ is H, halo, $C_{1-6}$ alkyl, or $C_{1-6}$ haloalkyl; and
$R^7$ and $R^8$ are each the same or different and independently H, $C_{1-20}$ alkyl, a saccharide, an amino acid residue, or a peptide.

Embodiment 3. The compound of Embodiment 1 or Embodiment 2, wherein $R^{2a}$ and $R^{2b}$ are each methyl, p is 0, $R^{4a}$ is —OR$^7$, Z is optionally substituted furanyl, n is 1 and $R^1$ is meta to the linking carbon and the compound has the following structure (IA1):

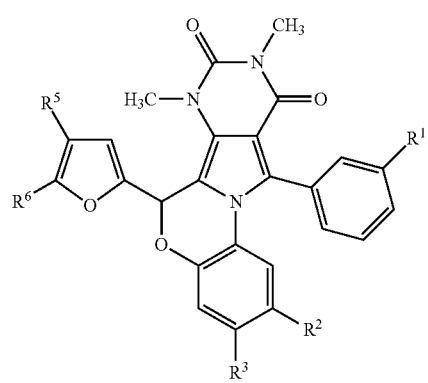

(IA1)

wherein:
$R^1$ is H, halo, or $C_{1-6}$ alkyl;
$R^2$ and $R^3$ are each the same or different and independently H, halo, —NO$_2$, $C_{1-6}$ alkyl, tetrazolyl, —S(O)$_2$OR$^7$, or —C(=O)OR$^7$;
$R^5$ is H, halo, or $C_{1-6}$ alkyl;
$R^6$ is halo, $C_{1-6}$ alkyl, or $C_{1-6}$ haloalkyl; and $R^7$ is H, $C_{1-6}$ alkyl, a saccharide, an amino acid residue, or a peptide.

Embodiment 4. The compound of Embodiment 1 or Embodiment 2, wherein $R^{2a}$ and $R^{2b}$ are each methyl, p is 0, $R^{4a}$ is —OR$^7$, Z is optionally substituted thienyl, n is 1 and $R^1$ is meta to the linking carbon, and the compound has the following structure (IB1):

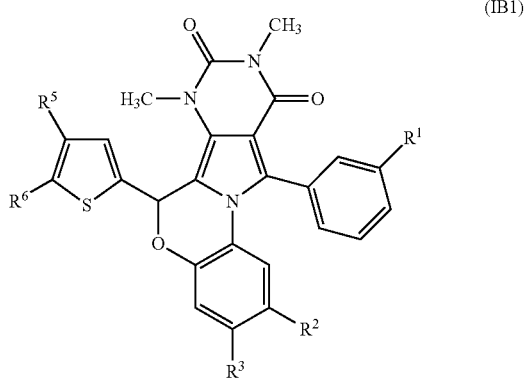

(IB1)

wherein:
$R^1$ is H, halo, or $C_{1-6}$ alkyl;
$R^2$ and $R^3$ are each the same or different and independently H, halo, —NO$_2$, $C_{1-6}$ alkyl, tetrazolyl, —S(O)$_2$OR$^7$, or —C(=O)OR$^7$;
$R^5$ is H, halo, or $C_{1-6}$ alkyl;
$R^6$ is halo, $C_{1-6}$ alkyl, or $C_{1-6}$ haloalkyl; and
$R^7$ is H, $C_{1-6}$ alkyl, a saccharide, an amino acid residue, or a peptide.

Embodiment 5. The compound of Embodiment 1, wherein $R^{2a}$ and $R^{2b}$ are each methyl, and Z is optionally substituted phenyl, and the compound has the following structure (IC):

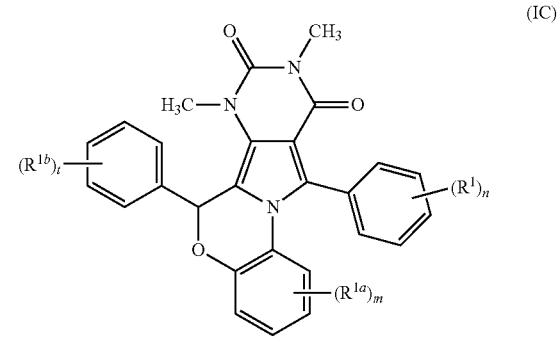

(IC)

as an isolated enantiomer or a racemic mixture of enantiomers, or as a pharmaceutically acceptable salt, hydrate, solvate, N-oxide, or prodrug thereof,
wherein:
m is 1, 2, 3, or 4;
n is 1, 2, 3, 4 or 5;
p is an integer from 0 to 4;
q is an integer from 1 to 4;
t is 1, 2, 3, 4 or 5;
$R^1$ at each occurrence is the same or different and independently H, halo, haloalkyl, $C_{1-6}$ alkyl, —$(CH_2)_p$—C(O)—$R^{4a}$, —S(O)$_2R^{4a}$, —NO$_2$, or tetrazolyl;
$R^{1a}$ at each occurrence is the same or different and independently H, halo, haloalkyl, $C_{1-6}$ alkyl, —$(CH_2)_p$—C(O)—$R^{4a}$, —S(O)$_2R^{4a}$, —NO$_2$, or tetrazolyl;

$R^{1b}$ at each occurrence is the same or different and independently H, halo, —OH, —NO$_2$, C$_{1-6}$ alkyl, C$_{2-6}$ alkenyl, or C$_{1-6}$ alkoxy;

$R^{4a}$ is —OR$^7$, —NR$^7$R$^8$, —O(CH$_2$)$_q$—OC(O)R$^7$, an amino acid residue, or a peptide;

$R^7$ and $R^8$ are each the same or different and independently H, C$_{1-20}$ alkyl, a saccharide, an amino acid residue, or a peptide.

Embodiment 6. The compound of Embodiment 1 or Embodiment 5, wherein $R^{2a}$ and $R^{2b}$ are each methyl, p is 0, $R^{4a}$ is —OR$^7$, n is 1 and $R^1$ is meta to the linking carbon and the compound has the following structure:

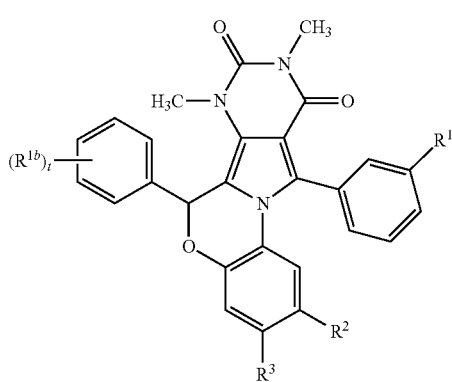

(IC1)

wherein:
$R^1$ is H, halo, or C$_{1-6}$ alkyl;
$R^2$ and $R^3$ are each the same or different and independently H, halo, —NO$_2$, C$_{1-6}$ alkyl, tetrazolyl, —S(O)$_2$OR$^7$, or —C(=O)OR$^7$;
t is 1, 2, 3, 4 or 5;
$R^{1b}$ at each occurrence is the same or different and independently H, halo, —OH, —NO$_2$, C$_{1-6}$ alkoxy, or C$_{1-6}$ alkyl; and
$R^7$ is H, C$_{1-6}$ alkyl, a saccharide, an amino acid residue, or a peptide.

Embodiment 7. A compound having the following structure (II):

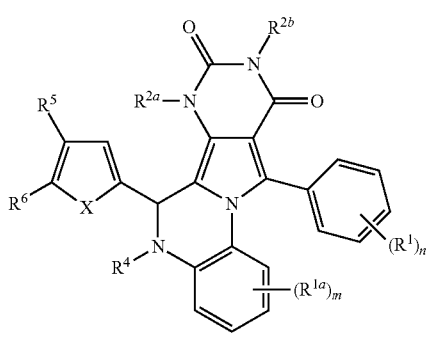

(II)

as an isolated enantiomer or a racemic mixture of enantiomers, or as a pharmaceutically acceptable salt, hydrate, solvate, N-oxide, or prodrug thereof,
wherein:
m is 1, 2, 3, or 4;
n is 1, 2, 3, 4 or 5;
p is an integer from 0 to 4;
q is an integer from 1 to 4;
X is O or S;
$R^1$ at each occurrence is the same or different and independently H, halo, haloalkyl, C$_{1-6}$ alkyl, —(CH$_2$)$_p$—C(O)—R$^{4a}$, —S(O)$_2$R$^{4a}$, —NO$_2$, or tetrazolyl;
$R^{1a}$ at each occurrence is the same or different and independently H, halo, haloalkyl, C$_{1-6}$ alkyl, —(CH$_2$)$_p$—C(O)—R$^{4a}$, —S(O)$_2$R$^{4a}$, —NO$_2$, or tetrazolyl;
$R^{2a}$ and $R^{2b}$ are each the same or different and independently H or C$_{1-6}$ alkyl;
$R^{4a}$ is —OR$^7$, —NR$^7$R$^8$, —O(CH$_2$)$_q$—OC(O)R$^7$, an amino acid residue, or a peptide;
$R^4$ is H, —N(=O), C$_{1-6}$ alkyl, or haloalkyl;
$R^5$ is H, halo, or C$_{1-6}$ alkyl;
$R^6$ is halo, C$_{1-6}$ alkyl, or C$_{1-6}$ haloalkyl; and
$R^7$ and $R^8$ are each the same or different and independently H, C$_{1-20}$ alkyl, a saccharide, an amino acid residue, or a peptide.

with the proviso that the following compounds are excluded:
(a) 7,9-Dimethyl-11-(3-methylphenyl)-6-(5-methylfuran-2-yl)-5,6-dihydro-pyrimido[4',5'-3,4]pyrrolo[1,2-a]quinoxaline-8,10-(7H,9H)-dione;
(b) 7,9-Dimethyl-11-phenyl-6-(5-methylfuran-2-yl)-5,6-dihydro-pyrimido[4',5'-3,4]pyrrolo[1,2-a]quinoxaline-8,10-(7H,9H)-dione;
(c) 7,9-Dimethyl-11-(2-methylphenyl)-6-(5-methylfuran-2-yl)-5,6-dihydro-pyrimido[4',5'-3,4]pyrrolo[1,2-a]quinoxaline-8,10-(7H,9H)-dione;
(d) 2,3,7,9-Tetramethyl-11-phenyl-6-(5-methylfuran-2-yl)-5,6-dihydro-pyrimido[4',5'-3,4]pyrrolo[1,2-a]quinoxaline-8,10-(7H,9H)-dione;
(e) 2,3,7,9-Tetramethyl-11-(2-fluorophenyl)-6-(5-methylfuran-2-yl)-5,6-dihydro-pyrimido[4',5'-3,4]pyrrolo[1,2-a]quinoxaline-8,10-(7H,9H)-dione;
(f) 7,9-Dimethyl-11-(4-methylphenyl)-6-(5-methylfuran-2-yl)-5,6-dihydro-pyrimido[4',5'-3,4]pyrrolo[1,2-a]quinoxaline-8,10-(7H,9H)-dione; and
(g) 7,9-Dimethyl-11-(4-cholophenyl)-6-(5-methylfuran-2-yl)-5,6-dihydro-pyrimido[4',5'-3,4]pyrrolo[1,2-a]quinoxaline-8,10-(7H,9H)-dione.

Embodiment 8. The compound of Embodiment 7, wherein $R^{2a}$ and $R^{2b}$ are each methyl, p is 0, $R^{4a}$ is —OR$^7$, n is 1 and $R^1$ is meta to the linking carbon, and the compound has the following structure (IIA):

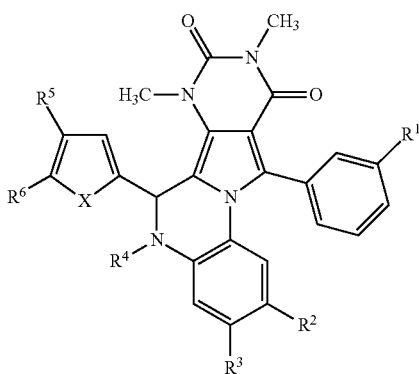

(IIA)

wherein:
X is O or S;
$R^1$ is H, halo, or C$_{1-3}$ alkyl;

$R^2$ is H, halo, —$NO_2$, or —C(=O)$OR^7$;
$R^3$ is H or —$NO_2$;
$R^4$ is —N(=O), $C_{1-3}$ alkyl, or H;
$R^5$ is H or $C_{1-3}$ alkyl;
$R^6$ is $C_{1-6}$ alkyl, $C_{1-6}$ haloalkyl, or halo; and
$R^7$ is H, $C_{1-6}$ alkyl, a saccharide, an amino acid residue, or a peptide with the proviso that the following compounds are excluded:

7,9-Dimethyl-11-(3-methylphenyl)-6-(5-methylfuran-2-yl)-5,6-dihydro-pyrimido[4',5'-3,4]pyrrolo[1,2-a]quinoxaline-8,10-(7H,9H)-dione;

7,9-Dimethyl-11-phenyl-6-(5-methylfuran-2-yl)-5,6-dihydro-pyrimido[4',5'-3,4]pyrrolo[1,2-a]quinoxaline-8,10-(7H,9H)-dione; and 2,3,7,9-Tetramethyl-11-phenyl-6-(5-methylfuran-2-yl)-5,6-dihydro-pyrimido[4',5'-3,4]pyrrolo[1,2-a]quinoxaline-8,10-(7H,9H)-dione.

Embodiment 9. The compound of Embodiment 1, wherein (a) each $R^1$ is H; (b) at least one $R^1$ is methyl or ethyl; (c) at least one $R^1$ is methyl and each remaining $R^1$ is H; or (d) at least one $R^1$ is ethyl and each remaining $R^1$ is H.

Embodiment 10. The compound of either Embodiment 1 or Embodiment 9, wherein m=2 and p=0 and (a) at least one of $R^{1a}$ is halo, —$NO_2$, $C_{1-3}$ alkyl, —C(O)—$R^{4a}$; or (b) each of $R^{1a}$ is H.

Embodiment 11. The compound of Embodiment 5, wherein (a) each $R^1$ is H; (b) at least one $R^1$ is methyl or ethyl; (c) at least one $R^1$ is methyl and each remaining $R^1$ is H; or (d) at least one $R^1$ is ethyl and each remaining $R^1$ is H.

Embodiment 12. The compound of Embodiment 5 or Embodiment 11, wherein m=2 and p=0 and (a) at least one of $R^{1a}$ is halo, —$NO_2$, $C_{1-3}$ alkyl, —C(O)—$R^{4a}$; or (b) each of $R^{1a}$ is H.

Embodiment 13. The compound of Embodiment 6, wherein $R^1$ is H, methyl, or ethyl.

Embodiment 14. The compound of Embodiment 6, wherein (a) $R^2$ is H, halo, —$NO_2$, or —C(=O)$OR^7$, wherein $R^7$ is H or $C_{1-6}$ alkyl; (b) $R^2$ is H, halo, —$NO_2$, or —C(=O)$OR^7$, wherein $R^7$ is H, —$CH_3$, —$CH_2CH_3$, or —$CH_2CH_2CH_3$; (c) $R^2$ is H, chloro, or —$NO_2$; (d) $R^2$ is —C(=O)$OR^7$, wherein $R^7$ is H, —$CH_3$, or —$CH_2CH_3$; or (e) $R^2$ is chloro.

Embodiment 15. The compound of Embodiment 6, wherein $R^3$ is H or —$NO_2$.

Embodiment 16. The compound of any one Embodiments 5, 6, or 11-15, wherein (a) t=2 and each $R^{1b}$ is the same or different and independently H, —OH, halo, —$NO_2$, $C_{1-3}$ alkyl, or $C_{1-3}$ alkoxy; or (b) t=1 and $R^{1b}$ is —OH, halo, —$NO_2$, $C_{1-3}$ alkyl, or $C_{1-3}$ alkoxy.

Embodiment 17. The compound of any one Embodiments 5, 6, or 11-15, wherein (a) t=2 and each $R^{1b}$ is the same or different and independently H, —OH, chloro, fluoro, —$NO_2$, methyl, or methoxy; (b) t=1 and $R^{1b}$ is —OH, chloro, fluoro, —$NO_2$, methyl, or methoxy; or (c) each $R^{1b}$ is H.

Embodiment 18. The compound of Embodiment 8, wherein $R^4$ is H, —N(=O), or methyl.

Embodiment 19. The compound of any one of Embodiments 3, 4, 8, and 18, wherein $R^1$ is H, methyl, or ethyl.

Embodiment 20. The compound of any one of Embodiments 3, 4, 8, 18, and 19 wherein (a) $R^2$ is H, halo, —$NO_2$, or —C(=O)$OR^7$, wherein $R^7$ is H or $C_1$-$C_6$ alkyl; (b) $R^2$ is H, halo, —$NO_2$, or —C(=O)$OR^7$, wherein $R^7$ is H, —$CH_3$, —$CH_2CH_3$, or —$CH_2CH_2CH_3$; (c) $R^2$ is H, chloro, or —$NO_2$; (d) $R^2$ is —C(=O)$OR^7$, wherein $R^7$ is H, —$CH_3$, or —$CH_2CH_3$; or (e) $R^2$ is chloro.

Embodiment 21. The compound of any one of Embodiments 3, 4, 8, 18-20, wherein $R^3$ is H or —$NO_2$.

Embodiment 22. The compound of any one of Embodiments 3, 4, 8, and 18-21, wherein $R^5$ is H or methyl.

Embodiment 23. The compound of any one of Embodiments 3, 4, 8, and 18-22, wherein $R^6$ is $C_{1-3}$ alkyl, $C_{1-3}$ fluoroalkyl, chloro, bromo, iodo, or fluoro.

Embodiment 24. The compound of any one of Embodiments 3, 4, 8, and 18-23, wherein $R^6$ is methyl, ethyl, chloro, bromo, iodo, or trifluoromethyl.

Embodiment 25. The compound of Embodiment 7, wherein $R^4$ is H, —N(=O), or methyl.

Embodiment 26. The compound of any one of Embodiments 2, 7, and 25, wherein (a) each $R^1$ is H; (b) at least one $R^1$ is methyl or ethyl; (c) at least one $R^1$ is methyl and each remaining $R^1$ is H; or (d) at least one $R^1$ is ethyl and each remaining $R^1$ is H.

Embodiment 27. The compound of any one of Embodiments 2, 7, 25, and 26, wherein m=2 and p=0 and (a) at least one of $R^{1a}$ is halo, —$NO_2$, $C_{1-3}$ alkyl, —C(O)—$R^{4a}$; or (b) each of $R^{1a}$ is H.

Embodiment 28. The compound of any one of Embodiments 2, 7, and 25-27, wherein (a) $R^5$ is H or $C_{1-3}$ alkyl; or (b) $R^5$ is H or methyl.

Embodiment 29. The compound of any one of Embodiments 2, 7, and 25-28, wherein (a) $R^6$ is $C_1$-$C_3$ alkyl, $C_1$-$C_3$ fluoroalkyl, chloro, bromo, iodo, or fluoro; or (b) $R^6$ is methyl, ethyl, trifluoromethyl, chloro, bromo, or iodo.

Embodiment 30. The compound of either Embodiment 7 or Embodiment 8, wherein X is O.

Embodiment 31. The compound of any one of Embodiments 1-3, wherein the compound has any one of the following structures:

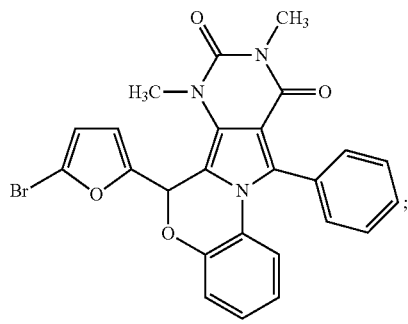

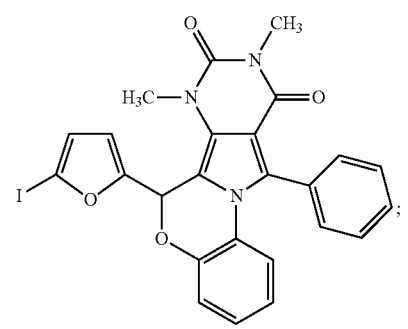

-continued
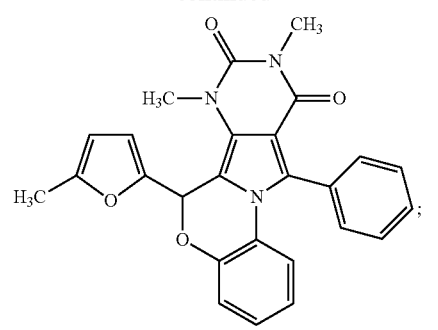
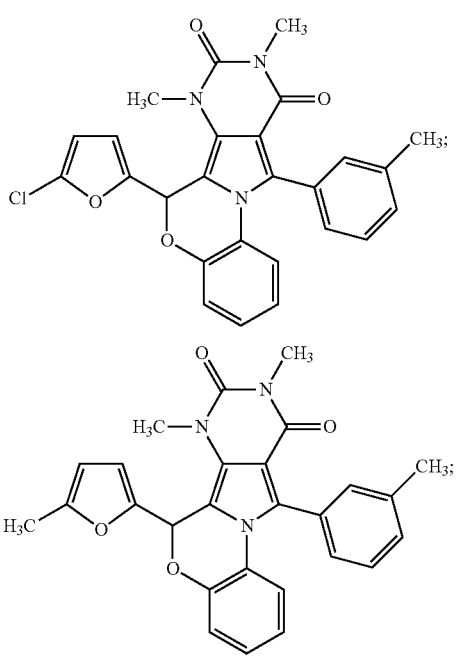
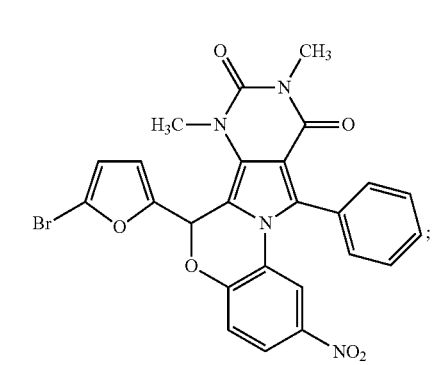
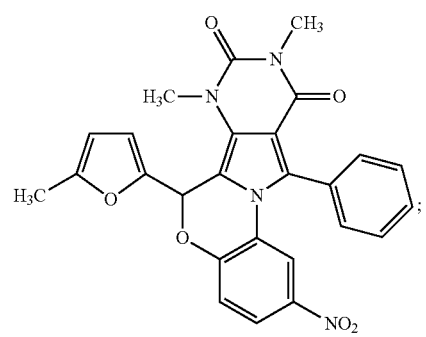
-continued
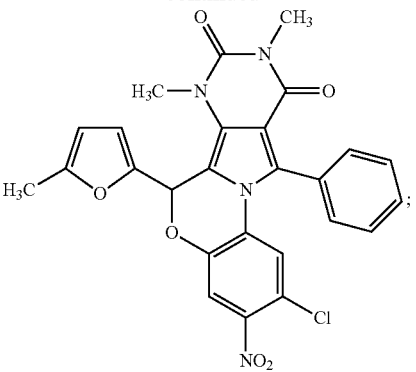
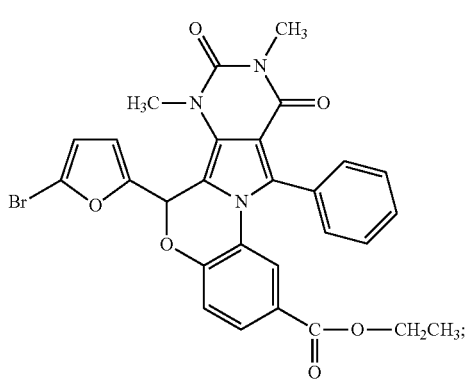
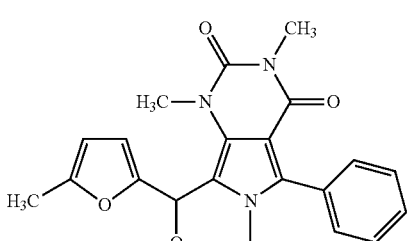
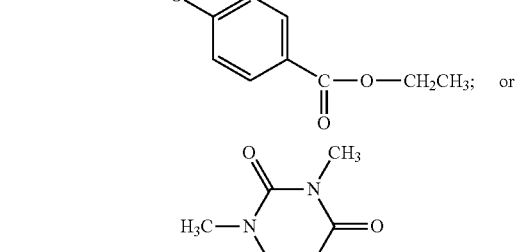
or
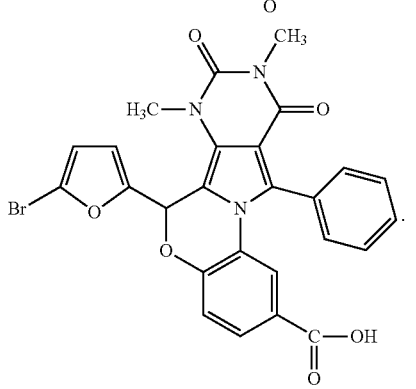
Embodiment 32. The compound of Embodiment 7 or Embodiment 8, wherein the compound has any one of the following structures:

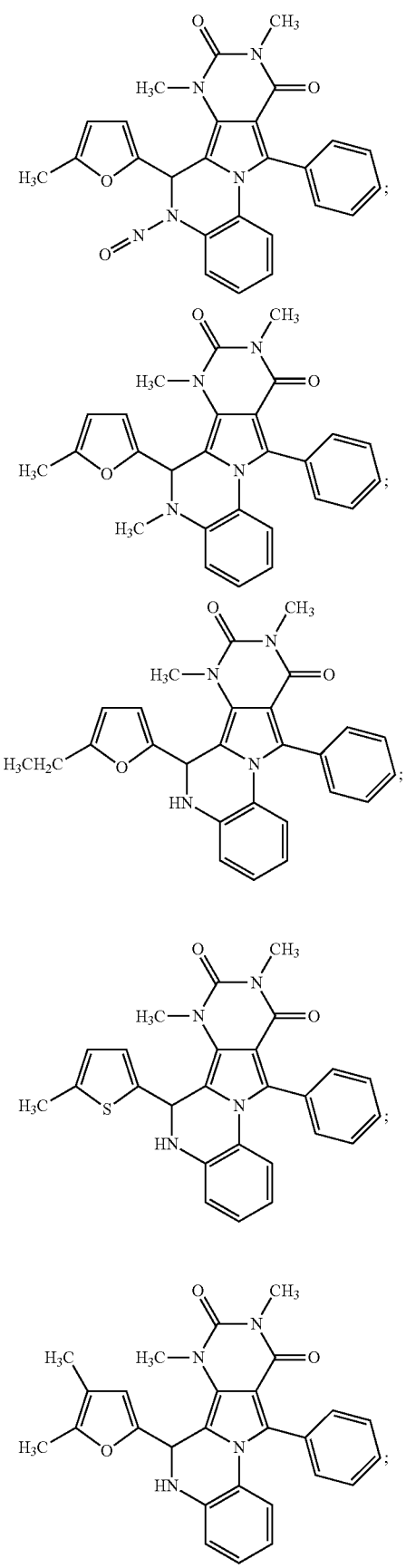
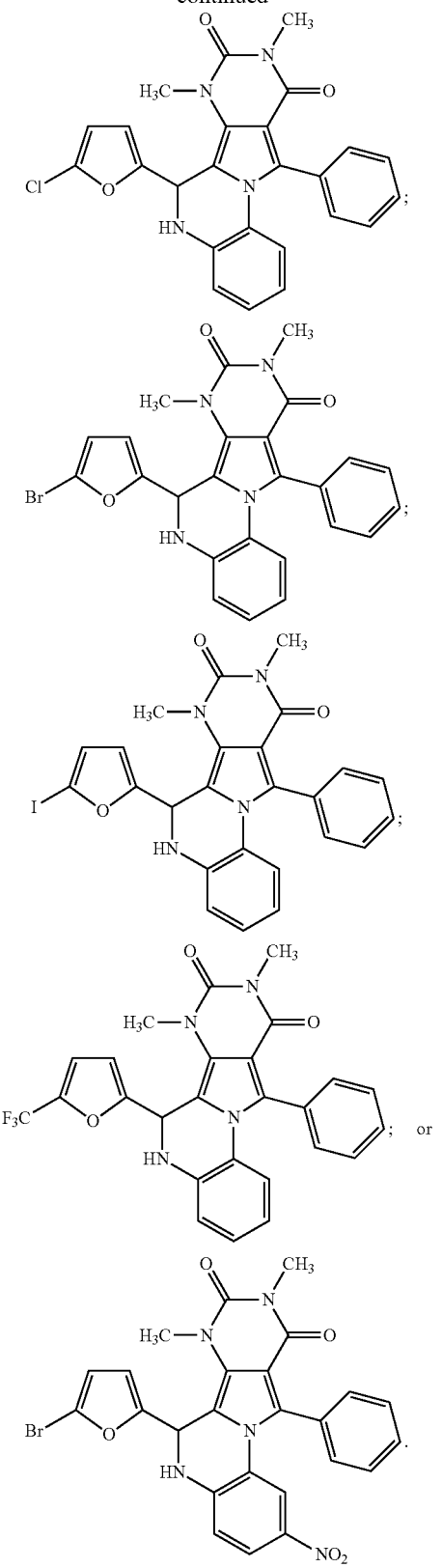
Embodiment 33. The compound of any one of Embodiments 1-32, wherein the compound is an isolated enantiomer in R form.

Embodiment 34. The compound of Embodiment 33 wherein the compound is 6R-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylic acid.

Embodiment 35. The compound of any one of Embodiments 1-32, wherein the compound is an isolated enantiomer in S form.

Embodiment 36. A pharmaceutical composition comprising the compound of any one of Embodiments 1-35 and a pharmaceutically suitable excipient.

Embodiment 37. A method for inhibiting cyst formation or inhibiting cyst enlargement, said method comprising contacting (a) a cell that comprises CFTR and (b) the pharmaceutical composition of Embodiment 36, under conditions and for a time sufficient that permit CFTR and the compound to interact, wherein the compound inhibits CFTR-mediated ion transport.

Embodiment 38. A method for treating polycystic kidney disease comprising administering to a subject the composition of Embodiment 36.

Embodiment 39. The method of Embodiment 38, wherein polycystic kidney disease is autosomal dominant polycystic kidney disease or autosomal recessive polycystic kidney disease.

Embodiment 40. A method for treating a disease, condition, or disorder that is treatable by inhibiting cystic fibrosis transmembrane conductance regulator (CFTR)-mediated ion transport, said method comprising administering to a subject the pharmaceutical composition of Embodiment 36, thereby inhibiting CFTR-mediated ion transport.

Embodiment 41. The method of Embodiment 40, wherein the disease, condition, or disorder is selected from polycystic kidney disease, aberrantly increased intestinal fluid secretion, and secretory diarrhea.

Embodiment 42. The method of Embodiment 41, wherein secretory diarrhea (a) is caused by an enteric pathogen; (b) is induced by an enterotoxin; or (c) is a sequelae of ulcerative colitis, irritable bowel syndrome (IBS), AIDS, chemotherapy, or an enteropathogenic infection.

Embodiment 43. Use of the compound of any one of Embodiments 1-35 for treating a disease, condition, or disorder that is selected from polycystic kidney disease, aberrantly increased intestinal fluid secretion, and secretory diarrhea.

Embodiment 44. Use of the compound of any one of Embodiments 1-35 for the manufacture of a medicament for treating a disease, condition, or disorder that is selected from polycystic kidney disease, aberrantly increased intestinal fluid secretion, and secretory diarrhea.

Embodiment 45. The compound of any one of Embodiments 1-35 for use in treating a disease, condition, or disorder that is selected from polycystic kidney disease, aberrantly increased intestinal fluid secretion, and secretory diarrhea.

As used herein and in the appended claims, the singular forms "a," "and," and "the" include plural referents unless the context clearly dictates otherwise. Thus, for example, reference to "a compound" may refer to one or more compounds, or a plurality of such compounds, and reference to "a cell" or "the cell" includes reference to one or more cells and equivalents thereof (e.g., plurality of cells) known to those skilled in the art, and so forth. Similarly, reference to "a composition" includes a plurality of such compositions, and refers to one or more compositions unless the context clearly dictates otherwise. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

BRIEF DESCRIPTION OF THE DRAWINGS

FIG. 6A presents an LC/MS profile showing PPQ-102 disappearance over 30 min during incubation with microsomes in the presence of NADPH. FIG. 6B indicates the appearance of PPQ-102 metabolites at +14 and +16 daltons. FIG. 6C presents a schematic of potential sites of PPQ-102 metabolism.

FIG. 7A presents data from a fluorescence plate-reader assay of CFTR inhibition. FRT cells expressing human wildtype CFTR and iodide-sensing YFP fluorescent dye were incubated with test compound and CFTR agonists, and then subjected to an inwardly directed iodide gradient. FIG. 7A (top) shows representative data of the kinetics of fluorescence decrease for PPQ-10, following iodide addition (causing YFP fluorescence quenching) in the absence of cAMP agonists and in the presence of cAMP agonists at the indicated concentrations. FIG. 7A (bottom) presents a summary of concentration-inhibition data for the indicated compound (S.E. n=4). FIG. 7B presents data from short-circuit current analysis of CFTR inhibition in CFTR-expressing FRT cells in the presence of a transepithelial chloride gradient and basolateral membrane permeabilization. Where indicated, forskolin (20 µM) was added to activate CFTR chloride conductance, following by indicated concentrations of PPQ-10. FIG. 7C (top) illustrates LC/MS analysis showing disappearance of PPQ-10 and BPO-17 in hepatic microsomes in the presence of NADPH. FIG. 7C (bottom) provides a summary of kinetics of compound disappearance (SEM, n=3). Data for PPQ-102 are shown for comparison.

FIG. 8A presents data from short-circuit current analysis that shows CFTR inhibition by compounds, BPO-21 and BPO-27. FIG. 8B illustrates the stability of the compounds in hepatic microsomes in the presence of NADPH.

FIG. 9A presents transmission light micrographs of E13.5 embryonic kidneys cultured for the indicated days without or in the presence of 100 µM 8-Br-cAMP, and with 0, 0.1, or 1 µM BPO-27. FIG. 9B presents a summary of percent cyst areas at 5 days in cultures (SEM, n=4-6, * P<0.001).

FIG. 10A shows BPO-27 fractions 2 and then 1 (each 100 nM) added where indicated. FIG. 10B shows BPO-27 fraction 1 added at different concentrations. $IC_{50}$ was deduced as approximately 4 nM.

FIG. 11A: In vitro metabolic stability of BPO-27 measured in hepatic microsomes supplemented with NADPH. (left) LC/MS chromatograms of non-metabolized BPO-27 enantiomers at indicated times. (right) Percentage non-metabolized compound remaining (S.E., n=4). FIG. 11B: In vivo pharmacokinetics of BPO-27 in mice following bolus intraperitoneal injection of 300 mg/kg BPO-27. (left) Reference measurement. LC/MS chromatograms in which known amounts of BPO-27 was added to kidney homogenates and then extracted. Inset shows assay linearity. (right) LC/MS chromatograms of kidney homogenates at indicated times after bolus intraperitoneal injection. FIG. 11C: Concentration of BPO-27 measured in kidney, blood and urine following bolus intraperitoneal injection (S.E., n=4).

DETAILED DESCRIPTION

Figure 1:
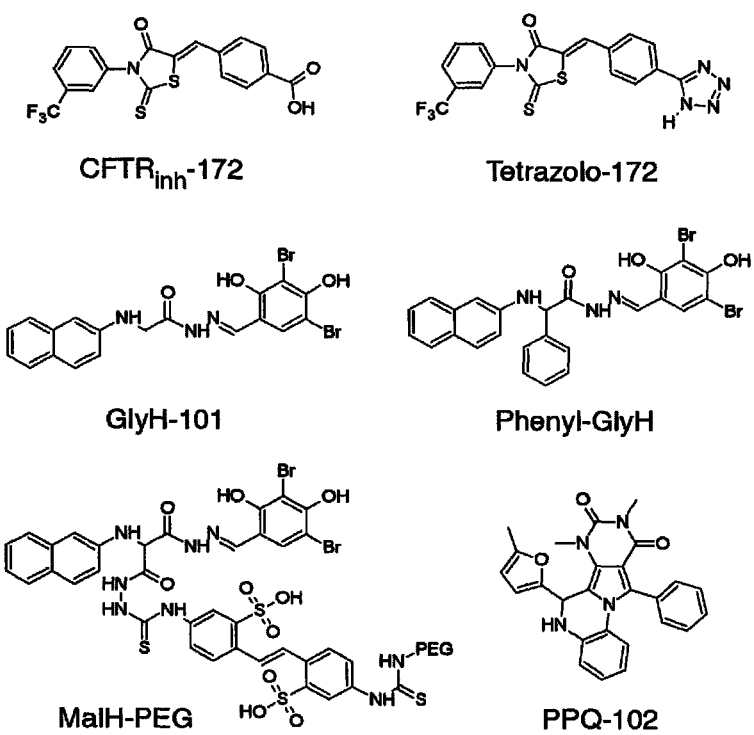
FIG. 1 illustrates the chemical structure of various CFTR inhibitors.

Provided herein are pyrimido-pyrrolo-oxazine-dione (BPO) compounds that inhibit activity of the cystic fibrosis transmembrane conductance regulator (CFTR) chloride channel. Also provided herein are certain pyrimido-pyrrolo-quinoxalinedione (PPQ) compounds that inhibit CFTR. The BPO and PPQ compounds described herein are capable of inhibiting CFTR-mediated ion transport (e.g., CFTR-mediated Cl⁻ transport) (i.e., inhibiting CFTR conductance). The most potent BPO compounds have substantially improved metabolic stability (greater than 10-fold) compared with a previously characterized PPQ compound (called herein PPQ-102; see, e.g., International Patent Application Publication No. WO 2011/019737). These compounds disclosed herein also exhibit greater polarity and potency for inhibiting CFTR chloride conductance in vitro (~10-fold) and renal cystogenesis ex vivo (>5-fold).

The compounds and compositions comprising these compounds are useful for administering to a subject who has or who is at risk of developing a disease, disorder, or condition that is treatable (i.e., administration of the compounds and compositions will provide a therapeutic or prophylactic benefit) by inhibiting CFTR-mediated ion transport. The compounds described herein may therefore be useful for treating diseases, disorders, and conditions including, for example, polycystic kidney disease, secretory diarrhea, and other intestinal secretion conditions, diseases, and disorders characterized by aberrantly increased intestinal fluid secretion.

As noted above, autosomal dominant polycystic kidney disease (ADPKD) is a major health care burden and has a prevalence of 1 in 500 to 1000 individuals (see, e.g., Torres et al., *Lancet* (2007), supra). No FDA-approved drug is available at present that is capable of slowing the progression of renal disease in PKD. Cyst expansion in ADPKD also requires cyst epithelial cell proliferation involving mTor signaling (see, e.g., Lieberthal et al., *J. Am. Soc. Nephrol.* 20:2493-502 (2009); Torres et al., *Clin. J. Am. Soc. Nephrol.* 5: 1312-29 (2010)), which is the basis of several 'anti-proliferative' therapies under development (see, e.g., Belibi et al., *Expert Opin. Investig. Drugs* 19:315-28 (2010); Torres, *Clin. J. Am. Soc. Nephrol.*, 3:1212-18 (2008); Masoumi et al., *Drugs* 67:2495-2510 (2007); Patel et al., *Curr Opin Nephrol Hypertens*. 18:99-106 (2009); Torres, *Adv. Chronic Kidney Dis.* 17:190-204 (2010)). "Anti-secretory" (e.g., CFTR inhibition) therapy is predicted to complement antiproliferative therapy or be effective alone in life-long treatment of ADPKD. The BPO and PPQ compounds described herein are CFTR inhibitors that may be useful as anti-secretory therapy for PKD. An alternative anti-secretory therapy, vasopressin V2 antagonism, is in clinical trials for PKD and is based on the concept that cysts in PKD often express V2 receptors, which when stimulated by antidiuretic hormone, elevate cytoplasmic cAMP and activate both CFTR chloride conductance and mTOR signaling (see, e.g., Belibi et al. (2010), supra; Torres, *Clin. J. Am. Soc. Nephrol.*, 3:1212-18 (2008)). An alternative, V2 receptor-independent strategy has been suggested for reducing cAMP involving small-molecule phosphodiesterase activators, which were shown to resist growth in an in vitro PKD model (see, e.g., Tradtrantip et al., *Mol. Pharmacol.* 75:134-42 (2009)). Pure anti-proliferative therapies, most based on the central role of mTOR signaling in proliferation of cyst-lining epithelial cells, are also in clinical trials, as well as renin-angiotensin inhibitors and statins (see, e.g., Masoumi et al., *Drugs* (2007), supra; Patel et al., (2009), supra; Torres, (2010), supra).

Several classes of small-molecule CFTR inhibitors have been identified by high-throughput screening and characterized (see, e.g., Verkman et al., supra). Exemplary compounds are shown in FIG. 1. Thiazolidinone-class CFTR inhibitors such as $CFTR_{inh}$-172 act on the cytoplasmic side of the plasma membrane at a site near the CFTR pore to block CFTR chloride conductance (see, e.g., Caci et al., *Biochem.* 413: 135-42 (2008); Ma et al., *J. Clin. Invest.* 110:1651-58 (2002); Taddei et al., *FEBS Lett.* 558:52-56 (2004); U.S. Pat. Nos. 7,235,573 and 7,638,543). $CFTR_{inh}$-172 inhibits CFTR with $IC_{50}$ in the range of 300-3000 nM, depending on cell type and membrane potential and has low toxicity and metabolic stability with primarily renal excretion (see, e.g., Ma et al., supra; Sonawane et al., *J. Pharm. Sci.* 94:134-43 (2005)). The tetrazolo-substituted thiazolidinone Tetrazolo-172 (see FIG.

1) had improved water solubility compared to CFTR$_{inh}$-172 (see, e.g., Sonawane et al., *Bioorg. Med. Chem.* 16:8187-95 (2008); International Patent Application Publication No. WO 09/120,803), and reduced cyst expansion in organ culture and mouse models of PKD (see, e.g., Yang et al., *J. Am. Soc. Nephrol.* 19:1300-10 (2008)). A second class of small-molecule CFTR inhibitors, the glycine hydrazides, such as GlyH-101 (see FIG. 1), block CFTR at an external site within the CFTR pore (see, e.g., Muanprasat et al., *J. Gen. Physiol.* 124:125-37 (2004); U.S. Pat. Nos. 7,414,037 and 7,888,332). Membrane-impermeant, non-absorbable conjugates of glycine hydrazides with polyethylene glycols (see FIG. 1) (see, e.g., Sonawane et al., *FASEB J.* 20:130-32 (2006); Sonawane et al., *Chem. Biol.* 15:718-28 (2008); U.S. Pat. Nos. 7,414,037 and 7,888,332; U.S. Application Publication No. US2009/0253799; Int'l Patent Appl. Publication No. WO 09/146,144) and lectins (see, e.g., Sonawane et al., *Gastroenterology* 132: 1234-44 (2007); U.S. Application Publication No. 2008/0171793; Int'l Patent Appl. Publication No. WO 08/079,897) inhibit CFTR with an IC$_{50}$ of 50-100 nM when added at the mucosal cell surface, and were effective in rodent models of secretory diarrheas such as cholera. An absorbable glycine hydrazide, phenyl-GlyH-101 (see FIG. 1), reduced cyst growth in PKD (see, e.g., Yang et al., 2008, supra; Int'l Patent Appl. Publication No. WO 09/120,803).

Additional small molecule screening yielded pyrimido-pyrrolo-quinoxalinedione (PPQ) compounds, which were uncharged, and thus membrane-potential insensitive, CFTR inhibitors, and were very potent CFTR inhibitors (Tradtrantip et al., *J. Med. Chem.* 52, 6447-55 (2009); Int'l Patent Appl. Publication No. WO 2011/019737). One inhibitor, called PPQ-102 (7,9-dimethyl-11-phenyl-6-(5-methyl furan-2-yl)-5,6-dihydro-pyrimido-[4',5'-3,4]pyrrolo[1,2-α]quinoxaline-8,10-(7H,9H)-dione, see FIG. 1) inhibited CFTR chloride current with IC$_{50}$~90 nM, by a mechanism involving stabilization of the channel closed-state. PPQ-102 prevented cyst expansion and reduced the size of pre-formed cysts in an embryonic kidney organ culture model of PKD. However, PPQ-102 has poorer metabolic stability than desired, (precluding animal testing in certain animal models), as well as low polarity and hence low aqueous solubility.

Derivative compounds of PPQ compounds were prepared. The BPO compounds described herein exhibit significantly improved stability, water solubility, and CFTR inhibition potency. The most potent compounds described herein have significantly improved potency more than 10-fold improved metabolic stability, and much greater polarity and thus increased aqueous solubility compared to PPQ-102. As described herein, the improved compounds were effective in preventing renal cyst expansion in a PKD model. By way of example with respect to CFTR inhibitory activity, the compound BPO-27 described herein has an IC$_{50}$ of approximately 8 nM compared with PPQ-102 having an IC$_{50}$ of 100 nM. The PPQ and BPO compounds described herein may also be useful for treating secretory diarrheas and for investigating and elucidating CFTR-dependent cellular and physiological processes.

Pyrimido-Pyrrolo-Oxazine-Dione (BPO) and Pyrimido-Pyrrolo-Quinoxalinedione (PPQ) Compounds Provided herein are compounds that have the capability to inhibit CFTR-mediated ion transport. In one embodiment, a compound is provided that has the following structure (I):

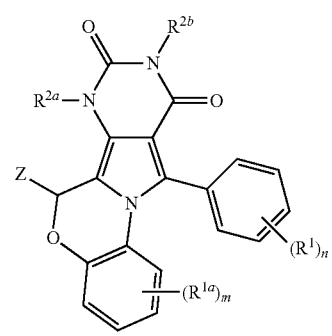

as an isolated enantiomer or a racemic mixture of enantiomers, or as a pharmaceutically acceptable salt, hydrate, solvate, N-oxide, or prodrug thereof,
wherein:
m is 1, 2, 3, or 4;
n is 1, 2, 3, 4 or 5;
p is an integer from 0 to 4;
q is an integer from 1 to 4;
$R^1$ at each occurrence is the same or different and independently H, halo, haloalkyl, $C_{1-6}$ alkyl, —(CH$_2$)—C(O)—$R^{4a}$, —S(O)$_2R^{4a}$, —NO$_2$, or tetrazolyl;
$R^{1a}$ at each occurrence is the same or different and independently H, halo, haloalkyl, $C_{1-6}$ alkyl, —(CH$_2$)$_p$—C(O)—$R^{4a}$, —S(O)$_2R^{4a}$, —NO$_2$, or tetrazolyl;
$R^{2a}$ and $R^{2b}$ are each the same or different and independently H or $C_{1-6}$ alkyl;
$R^{4a}$ is —OR$^7$, —NR$^7$R$^8$, —O(CH$_2$)$_q$—OC(O)R$^7$, an amino acid residue, or a peptide;
$R^7$ and $R^8$ are each the same or different and independently H, $C_{1-20}$ alkyl, a saccharide, an amino acid residue, or a peptide; and
Z is aryl or heteroaryl.

In more particular embodiments of the compound of structure (I), Z is a 5-member, optionally substituted heteroaryl. In other more particular embodiments of the compound of structure (I), Z is optionally substituted phenyl. In certain particular embodiments, Z is optionally substituted furanyl, and in other certain embodiments, Z is optionally substituted thienyl.

In another particular embodiment of the compound of structure (I), n is 1 or 2 and each $R^1$ is the same or different and independently H, halo, haloalkyl, $C_{1-6}$ alkyl, —(CH$_2$)$_p$—C(O)—$R^{4a}$, —S(O)$_2R^{4a}$, —NO$_2$, or tetrazolyl. In other specific embodiments, n is 1 and $R^1$ is unsubstituted $C_1$-$C_6$ alkyl or halo or H. In certain specific embodiments, $R^1$ is H at each occurrence. In other specific embodiments, n is 1 and $R^1$ is unsubstituted $C_1$-$C_6$ alkyl. In a specific embodiment, n is 1 and $R^1$ is $C_1$-$C_3$ alkyl, which in more specific embodiments is unsubstituted. In another embodiment, n is 1 and $R^1$ is halo, which in certain embodiments is chloro (Cl), fluoro (F), iodo (I), or bromo (Br). In one specific embodiment, n is 1, 2, or 3 and each $R^1$ is the same or different and independently halo, methyl, or ethyl. In another particular embodiment, n is 1 and $R^1$ is methyl (—CH$_3$) or ethyl (—CH$_2$CH$_3$). In certain specific embodiments, at least one $R^1$ is methyl or ethyl and the remaining $R^1$ are each H. In still another particular embodiment, n is 1 and $R^1$ is methyl. In still another specific embodiment, n is at least 1 and the at least one $R^1$ is haloalkyl. In still other specific embodiments, n is 1 or 2 and each $R^1$ is haloalkyl. In still another specific embodiments, n is 1 and $R^1$ is $C_1$-$C_6$ haloalkyl. In more specific embodiments, n is 1 and $R^1$ is $C_1$-$C_3$ haloalkyl. In another specific embodiment, n is 1 and $R^1$ is $C_1$-$C_3$ fluoroalkyl. In a more specific embodiment, the fluoroalkyl is a trifluoromethyl ($-CF_3$) or $-CH_2CH_2CF_3$. In another specific embodiment, n is 1 and $R^1$ is trifluoromethyl ($-CF_3$). In still another specific embodiment, n is 1 and $R^1$ is $-CH_2CF_2CF_3$. In other certain embodiments, n is 1 and $R^1$ is $-NO_2$. In still other certain embodiments, n is 1 and $R^1$ is tetrazolyl (e.g., 5-tetrazolyl). In yet other certain embodiments, n is 1 and $R^1$ is $-(CH_2)_p-C(O)-R^{4a}$. In yet other certain embodiments, n is 1 and $R^1$ is $-S(O)_2R^{4a}$.

In still another specific embodiment, n is 1 or 2, and at least one of $R^1$ is $-S(O)_2R^{4a}$ or $-(CH_2)_p-C(O)-R^{4a}$, and $R^{4a}$ is $-OR^7$, $-NR^7R^8$, or $-O(CH_2)_q-OC(O)R^7$. In other certain embodiments, at least one of $R^1$ is $-S(O)_2R^{4a}$ or $-(CH_2)_p-C(O)-R^{4a}$, and $R^{4a}$ is an amino acid residue. In another certain embodiment, at least one of $R^1$ is $-S(O)_2R^{4a}$ or $-(CH_2)_p-C(O)-R^{4a}$, and $R^{4a}$ is a peptide that consists of two (i.e., a dipeptide), three (i.e., a tripeptide), four, five, or six amino acid residues. In particular embodiments, $R^7$ is H or $C_1$-$C_6$ alkyl. In yet another specific embodiment, $R^7$ is $C_1$-$C_3$ alkyl, which in particular embodiments is unsubstituted, and which in other particular embodiments is methyl or ethyl. In still another specific embodiment, $R^7$ is a saccharide. In particular embodiments, $R^8$ is H or $C_1$-$C_6$ alkyl. In yet another specific embodiment, $R^8$ is $C_1$-$C_3$ alkyl, which in particular embodiments is unsubstituted, and which in other particular embodiments is methyl or ethyl. In still another specific embodiment, $R^8$ is a saccharide. In certain embodiments, $R^{4a}$ is $-NR^7R^8$, and each of $R^7$ and $R^8$ is the same or different and independently H or $C_1$-$C_6$ alkyl. In certain embodiments, $R^{4a}$ is $-NR^7R^8$, and each of $R^7$ and $R^8$ is the same or different and independently H, methyl, or ethyl. In other particular embodiments, $R^{4a}$ is $-OR^7$ or $-O(CH_2)_q-OC(O)R^7$ and $R^7$ is an amino acid residue. In still other certain embodiments, $R^{4a}$ is $-OR^7$ or $-O(CH_2)_q-OC(O)R^7$ and $R^7$ is a peptide that consists of two (i.e., a dipeptide), three (i.e., a tripeptide), four, five, or six amino acid residues. In still other certain embodiments, $R^{4a}$ is $-NR^7R^8$ and either $R^7$ or $R^8$ is an amino acid residue. In still other certain embodiments, $R^{4a}$ is $-NR^7R^8$ and either $R^7$ or $R^8$ is a peptide that consists of two (i.e., a dipeptide), three (i.e., a tripeptide), four, five, or six amino acid residues.

In particular embodiments, when $R^1$ is $-(CH_2)_p-C(O)-R^{4a}$, p is 0, 1, or 2. In one specific embodiment, p is 0, and $R^1$ is $-C(O)-R^{4a}$. In yet other certain embodiments, n is 1 and $R^1$ is $-(CH_2)_p-C(O)-R^{4a}$, and $R^{4a}$ is $-OR^7$. In certain particular embodiments, $R^{4a}$ is $-OR^7$, and $R^7$ is hydrogen, $C_1$-$C_{20}$ alkyl, or a saccharide. In other certain embodiments, when $R^1$ is $-(CH_2)_p-C(O)-R^{4a}$, and $R^{4a}$ is $-OR^7$, $R^7$ is hydrogen, methyl, ethyl. In other certain embodiments, when $R^1$ is $-(CH_2)_p-C(O)-R^{4a}$, and $R^{4a}$ is $-OR^7$, $R^7$ is a saccharide. In still other particular embodiments, when $R^1$ is $-(CH_2)_p-C(O)-R^{4a}$, and $R^{4a}$ is $-OR^7$, $R^7$ is an amino acid residue or a peptide (i.e., consisting of 2, 3, 4, 5, or six amino acids).

In another particular embodiment of the compound of structure (I), m is 1 or 2. In another particular embodiment of the compound of structure (I), m is 1 or 2 and each $R^{1a}$ is the same or different and independently H, halo, haloalkyl, $C_1$-$C_6$ alkyl, $-(CH_2)_p-C(O)-R^{4a}$, $-S(O)_2R^{4a}$, $-NO_2$, or tetrazolyl. In certain specific embodiments, $R^{1a}$ is H at each occurrence. In other particular embodiments, m is 1 or 2 and at least one of $R^{1a}$ is halo, which in particular embodiments is I, Cl, or Br. In more specific embodiments, m is 1 or 2 and at least one of $R^{1a}$ is Cl. In yet another specific embodiment, m is 1 and $R^{1a}$ is Cl. In other specific embodiments, $R^{1a}$ is unsubstituted $C_1$-$C_6$ alkyl and m is 1 or 2. In a specific embodiment, m is 1 or 2 and at least one $R^{1a}$ is $C_1$-$C_3$ alkyl, which in more specific embodiments is unsubstituted. In another particular embodiment, m is 1 and $R^{1a}$ is methyl or ethyl. In still another particular embodiment, m is 1 and $R^{1a}$ is methyl. In still other certain embodiments, m is 1 or 2, and at least one $R^{1a}$ is tetrazolyl (e.g., 5-tetrazolyl). In still yet another certain embodiments, m is 1 and $R^{1a}$ is tetrazolyl. In another specific embodiment, m is 1 or 2 and at least one of $R^{1a}$ is $-NO_2$. In another specific embodiment, m is 1 and $R^{1a}$ is $-NO_2$.

In more specific embodiments, m is 1 and $R^{1a}$ is $C_1$-$C_3$ haloalkyl. In another specific embodiment, m is 1 and $R^{1a}$ is $C_1$-$C_3$ fluoroalkyl. In a more specific embodiment, the fluoroalkyl is a trifluoromethyl ($-CF_3$) or $-CH_2CH_2CF_3$. In another specific embodiment, m is 1 and $R^{1a}$ is trifluoromethyl ($-CF_3$). In still another specific embodiment, m is 1 and $R^{1a}$ is $-CH_2CF_2CF_3$.

In still another specific embodiment, m is 1 or 2, and at least one of $R^{1a}$ is $-(CH_2)_p-C(O)-R^{4a}$, and $R^{4a}$ is $-OR^7$, $-NR^7R^8$, or $-O(CH_2)_q-OC(O)R^7$. In particular embodiments, when $R^{1a}$ is $-(CH_2)_p-C(O)-R^{4a}$, p is 0, 1, or 2. In one particular embodiments, m is 2 and p is 0 and at least one of $R^{1a}$ is halo, $-NO_2$, $C_1$-$C_3$ alkyl, $-C(O)-R^{4a}$. In one specific embodiment, p is 0, and $R^1$ is $-C(O)-R^{4a}$, wherein $R^{4a}$ is $-OR^7$ and $R^7$ is H, $-CH_3$, $-CH_2CH_3$, or $-CH_2CH_2CH_3$. In certain particular embodiments, $R^{4a}$ is $-OR^7$, and $R^7$ is hydrogen, $C_1$-$C_{20}$ alkyl, a saccharide, an amino acid residue, or a peptide (i.e., 2-6 amino acids). In other particular embodiments, $R^7$ is H or $C_1$-$C_6$ alkyl. In yet another specific embodiment, $R^7$ is $C_1$-$C_3$ alkyl, which in particular embodiments is unsubstituted, and which in other particular embodiments is methyl or ethyl. In still another specific embodiment, $R^7$ is a saccharide (e.g., a monosaccharide, a disaccharide, a trisaccharide, or polysaccharide). In still other particular embodiments, $R^7$ is an amino acid residue. In still another particular embodiment, $R^7$ is a peptide.

In one embodiment when $R^{1a}$ is $-(CH_2)_p-C(O)-R^{4a}$, $R^{4a}$ is $-OR^7$, and $R^7$ is hydrogen, $C_1$-$C_{20}$ alkyl, or a saccharide. In other particular embodiments, $R^7$ is H or $C_1$-$C_6$ alkyl. In yet another specific embodiment, when $R^{1a}$ is $-(CH_2)_p-C(O)-R^{4a}$, and $R^{4a}$ is $-OR^7$, $R^7$ is $C_1$-$C_3$ alkyl, which in particular embodiments is unsubstituted, and which in other particular embodiments is methyl or ethyl. In still another particular embodiments, when $R^{1a}$ is $-(CH_2)_p-C(O)-R^{4a}$ and $R^{4a}$ is $-OR^7$, $R^7$ is a saccharide. In still another embodiment, $R^7$ is an amino acid residue. In still another particular embodiment, $R^7$ is a peptide (i.e., 2-6 amino acids). In still more specific embodiments, when $R^{1a}$ is $-(CH_2)_p-C(O)-R^{4a}$, $R^{4a}$ is $-OR^7$, p is 0, and $R^7$ is H, methyl, or ethyl.

In still one specific embodiment when $R^{1a}$ is $-(CH_2)_p-C(O)-R^{4a}$, $R^{4a}$ is $-NR^7R^8$, wherein each of $R^7$ and $R^8$ is the same or different and independently hydrogen, $C_1$-$C_6$ alkyl, a saccharide, an amino acid residue or a peptide (i.e., 2-6 amino acids). In certain embodiments, when $R^{4a}$ is $-NR^7R^8$, at least one or both of $R^7$ and $R^8$ is hydrogen. In other certain embodiments, when $R^{4a}$ is $-NR^7R^8$, at least one of $R^7$ and $R^8$ is hydrogen and the other is $C_1$-$C_6$ alkyl. In other certain embodiments, when $R^{4a}$ is $-NR^7R^8$, at least one of $R^7$ and $R^8$ is hydrogen and the other is $C_1$-$C_3$ alkyl, which in particular embodiments is unsubstituted, and which in other particular embodiments is methyl or ethyl. In yet another embodiment when $R^{4a}$ is $-NR^7R^8$, at least one of $R^7$ and $R^8$ is hydrogen and the other is a saccharide. In yet another embodiment when $R^{4a}$ is $-NR^7R^8$, at least one of $R^7$ and $R^8$ is hydrogen and the other is an amino acid residue or a peptide (i.e., 2-6 amino acids).

In still another specific embodiment, when $R^{1a}$ is $-(CH_2)_p-C(O)-R^{4a}$, $R^{4a}$ is $-O(CH_2)_q-OC(O)R^7$ and $R^7$ is hydrogen, $C_1$-$C_{20}$ alkyl, or a saccharide. In particular embodiments, p is 1, 2, or 3; in other particular embodiments, q is 1, 2, or 3. In still other specific embodiments, $R^7$ is H or $C_1$-$C_6$ alkyl. In more specific embodiments, $R^7$ is $C_1$-$C_3$ alkyl, which in particular embodiments is unsubstituted, and which in other particular embodiments $R^7$ is methyl or ethyl. In another embodiment, $R^7$ is a saccharide. In still another embodiment, $R^7$ is an amino acid residue. In still another particular embodiment, $R^7$ is a peptide (i.e., 2-6 amino acids).

In a particular embodiment, at least one of $R^1$ or $R^{1a}$ is a polar group selected from $-NO_2$, tetrazolyl, $-S(O)_2OR^7$, or $-C(=O)OR^7$ (wherein $R^7$ is hydrogen, $C_{1-20}$ alkyl, or a saccharide). In specific embodiments, $R^7$ is H or $C_1$-$C_6$ alkyl. In more specific embodiments, $R^7$ is $C_1$-$C_3$ alkyl, which in particular embodiments is unsubstituted, and which in other particular embodiments is methyl or ethyl. In another embodiment, $R^7$ is a saccharide. In still another embodiment, $R^7$ is an amino acid residue. In still another particular embodiment, $R^7$ is a peptide (i.e., 2-6 amino acids).

In other particular embodiments, $R^{2a}$ or $R^{2b}$ are each the same or different and independently hydrogen or $C_1$-$C_3$ alkyl. In yet another particular embodiments, $R^{2a}$ or $R^{2b}$ are each the same or different and independently hydrogen, methyl, or ethyl. In certain embodiments, $R^{2a}$ and $R^{2b}$ are each H. In other certain embodiments, $R^{2a}$ and $R^{2b}$ are each methyl. In still other certain embodiments, $R^{2a}$ and $R^{2b}$ are each ethyl.

In further particular embodiments, the compound of structure (I) is an isolated R form.

In further particular embodiments, the compound of structure (I) is an isolated S form.

In one specific embodiment of the compound of structure (I), Z is optionally substituted furanyl or optionally substituted thienyl, and the compound has the following structure (Ia(i)) or I(b(i)), respectively.

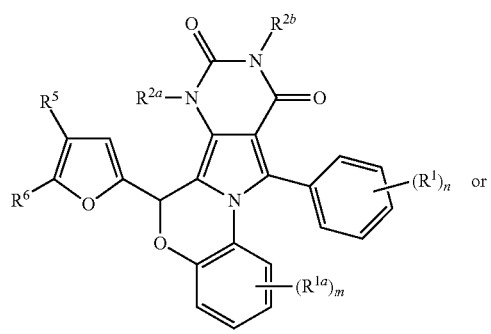

(Ia(i))

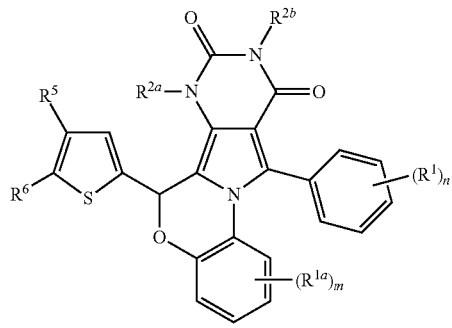

(Ib(i))

as an isolated enantiomer or a racemic mixture of enantiomers, or as a pharmaceutically acceptable salt, hydrate, solvate, N-oxide, or prodrug thereof, wherein each of $R^1$, $R^{1a}$, $R^{2a}$, and $R^{2b}$ are defined as above for a compound of structure (I), and wherein each of $R^5$ and $R^6$ are defined as below for a compound of substructure (IA) or (IB).

In a more specific embodiment of the compound of structure (I), $R^{2a}$ and $R^{2b}$ are each methyl, and Z is optionally substituted furanyl or optionally substituted thienyl, and the compound has the following structure (IA) or (IB), respectively.

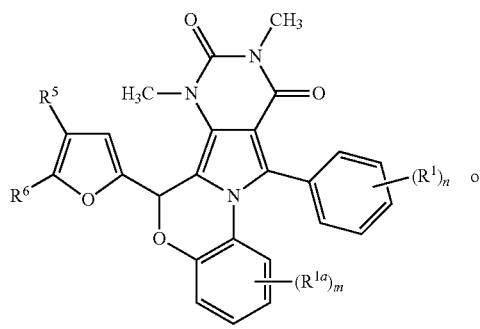

(IA)

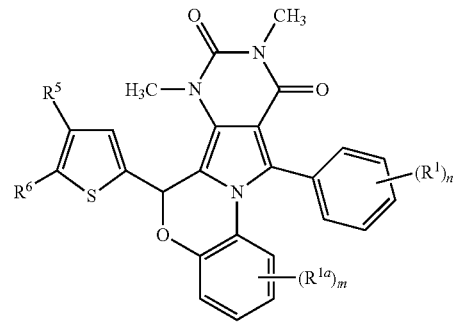

(IB)

as an isolated enantiomer or a racemic mixture of enantiomers, or as a pharmaceutically acceptable salt, hydrate, solvate, N-oxide, or prodrug thereof, wherein:

m is 1, 2, 3, or 4;
n is 1, 2, 3, 4 or 5;
p is an integer from 0 to 4;
q is an integer from 1 to 4;
$R^1$ at each occurrence is the same or different and independently H, halo, haloalkyl, $C_1$-$C_6$ alkyl, $-(CH_2)_p-C(O)-R^{4a}$, $-S(O)_2R^{4a}$, $-NO_2$, or tetrazolyl;
$R^{1a}$ at each occurrence is the same or different and independently H, halo, haloalkyl, $C_1$-$C_6$ alkyl, $-(CH_2)_p-C(O)-R^{4a}$, $-S(O)_2R^{4a}$, $-NO_2$, or tetrazolyl;
$R^{4a}$ is $-OR^7$, $-NR^7R^8$, $-O(CH_2)_q-OC(O)R^7$, an amino acid residue, or a peptide;
$R^5$ is H, halo, or $C_{1-6}$ alkyl;
$R^6$ is H, halo, $C_{1-6}$ alkyl, or $C_1$-$C_6$ haloalkyl; and
$R^7$ and $R^8$ are each the same or different and independently H, $C_1$-$C_{20}$ alkyl, a saccharide, an amino acid residue, or a peptide.

In a particular embodiment of the compound of structure (IA) or (IB), or structure (Ia(i)) or (Ib(i)), n is 1 or 2 and each $R^1$ is the same or different and independently H, halo, haloalkyl, $C_1$-$C_6$ alkyl, $-(CH_2)_p-C(O)-R^{4a}$, $-S(O)_2R^{4a}$, $-NO_2$, or tetrazolyl. In one specific embodiment, n is 1, 2, or 3 and each $R^1$ is the same or different and independently H, halo, methyl, or ethyl. In certain specific embodiments, $R^1$ is H at each occurrence. In other specific embodiments, n is 1 and $R^1$ is unsubstituted $C_1$-$C_6$ alkyl or halo. In other specific embodiments, n is 1 and $R^1$ is unsubstituted $C_1$-$C_6$ alkyl. In a specific embodiment, n is 1 and $R^1$ is $C_1$-$C_3$ alkyl, which in more specific embodiments is unsubstituted. In another embodiment, n is 1 and $R^1$ is halo, which in certain embodiments is chloro, fluoro, iodo, or bromo. In another particular embodiment, n is 1 and $R^1$ is methyl or ethyl. In still another particular embodiment, n is 1 and $R^1$ is methyl. In certain embodiments, at least one $R^1$ is methyl or ethyl and the remaining $R^1$ are each H. In still another specific embodiment n is at least 1 and the at least one $R^1$ is haloalkyl. In still other specific embodiments, n is 1 or 2 and each $R^1$ is haloalkyl. In still another specific embodiment, n is 1 and $R^1$ is $C_1$-$C_6$ haloalkyl. In more specific embodiments, n is 1 and $R^1$ is $C_1$-$C_3$ haloalkyl. In another specific embodiment, n is 1 and $R^1$ is $C_1$-$C_3$ fluoroalkyl. In a more specific embodiment, the fluoroalkyl is a trifluoromethyl ($-CF_3$) or $-CH_2CH_2CF_3$. In another specific embodiment, n is 1 and $R^1$ is trifluoromethyl ($-CF_3$). In still another specific embodiment, n is 1 and $R^1$ is $-CH_2CF_2CF_3$. In other certain embodiments, n is 1 and $R^1$ is $-NO_2$. In still other certain embodiments, n is 1 and $R^1$ is tetrazolyl (e.g., 5-tetrazolyl). In yet other certain embodiments, n is 1 and $R^1$ is $-(CH_2)_p-C(O)-R^{4a}$. In yet other certain embodiments, n is 1 and $R^1$ is $-S(O)_2R^{4a}$.

In still another specific embodiment, n is 1 or 2, and at least one of $R^1$ is $-S(O)_2R^{4a}$ or $-(CH_2)_p-C(O)-R^{4a}$, and $R^{4a}$ is $-OR^7$, $-NR^7R^8$, or $-O(CH_2)_q-OC(O)R^7$. In other certain embodiments, at least one of $R^1$ is $-S(O)_2R^{4a}$ or $-(CH_2)_p-C(O)-R^{4a}$, and $R^{4a}$ is an amino acid residue. In another certain embodiment, at least one of $R^1$ is $-S(O)_2R^{4a}$ or $-(CH_2)_p-C(O)-R^{4a}$, and $R^{4a}$ is a peptide that consists of two (i.e., a dipeptide), three (i.e., a tripeptide), four, five, or six amino acid residues. In particular embodiments, $R^7$ is H or $C_1$-$C_6$ alkyl. In yet another specific embodiment, $R^7$ is $C_1$-$C_3$ alkyl, which in particular embodiments is unsubstituted, and which in other particular embodiments is methyl or ethyl. In still another specific embodiment, $R^7$ is a saccharide. In particular embodiments, $R^8$ is H or $C_1$-$C_6$ alkyl. In yet another specific embodiment, $R^8$ is $C_1$-$C_3$ alkyl, which in particular embodiments is unsubstituted, and which in other particular embodiments is methyl or ethyl. In still another specific embodiment, $R^8$ is a saccharide. In certain embodiments, $R^{4a}$ is $-NR^7R^8$, and each of $R^7$ and $R^8$ is the same or different and independently H or $C_1$-$C_6$ alkyl. In certain embodiments, $R^{4a}$ is $-NR^7R^8$, and each of $R^7$ and $R^8$ is the same or different and independently H, methyl, or ethyl. In other particular embodiments, $R^{4a}$ is $-OR^7$ or $-O(CH_2)_q-OC(O)R^7$ and $R^7$ is an amino acid residue. In still other certain embodiments, $R^{4a}$ is $-OR^7$ or $-O(CH_2)_q-OC(O)R^7$ and $R^7$ is a peptide that consists of two (i.e., a dipeptide), three (i.e., a tripeptide), four, five, or six amino acid residues. In still other certain embodiments, $R^{4a}$ is $-NR^7R^8$ and either $R^7$ or $R^8$ is an amino acid residue. In still other certain embodiments, $R^{4a}$ is $-NR^7R^8$ and either $R^7$ or $R^8$ is a peptide that consists of two (i.e., a dipeptide), three (i.e., a tripeptide), four, five, or six amino acid residues.

In particular embodiments, when $R^1$ is $-(CH_2)_p-C(O)-R^{4a}$, p is 0, 1, or 2. In yet other certain embodiments, n is 1 and $R^1$ is $-(CH_2)_p-C(O)-R^{4a}$, and $R^{4a}$ is $-OR^7$. In certain particular embodiments, $R^{4a}$ is $-OR^7$, and $R^7$ is hydrogen, $C_1$-$C_{20}$ alkyl, or a saccharide. In other certain embodiments, when $R^1$ is $-(CH_2)_p-C(O)-R^{4a}$, and $R^{4a}$ is $-OR^7$, $R^7$ is hydrogen, methyl, ethyl. In other certain embodiments, when $R^1$ is $-(CH_2)_p-C(O)-R^{4a}$, and $R^{4a}$ is $-OR^7$, $R^7$ is a saccharide. In still other particular embodiments, when $R^1$ is $-(CH_2)_p-C(O)-R^{4a}$, and $R^{4a}$ is $-OR^7$, $R^7$ is an amino acid residue or a peptide (i.e., consisting of 2, 3, 4, 5, or six amino acids).

In another particular embodiment of the compound of structure (IA) or (IB), or structure (Ia(i)) or (Ib(i)), m is 1 or 2. In another particular embodiment of the compound of structure (I), m is 1 or 2 and each $R^{1a}$ is the same or different and independently H, halo, haloalkyl, $C_1$-$C_6$ alkyl, $-(CH_2)_p-C(O)-R^{4a}$, $-S(O)_2R^{4a}$, $-NO_2$, or tetrazolyl. In certain specific embodiments, $R^{1a}$ is H at each occurrence. In particular embodiments, m is 1 or 2 and at least one of $R^{1a}$ is halo, which in particular embodiments halo is I, Cl, or Br. In more specific embodiments, m is 1 or 2 and at least one of $R^{1a}$ is Cl. In other specific embodiments, $R^{1a}$ is unsubstituted $C_1$-$C_6$ alkyl and m is 1 or 2. In a specific embodiment, m is 1 or 2 and at least one $R^{1a}$ is $C_1$-$C_3$ alkyl, which in more specific embodiments is unsubstituted. In another particular embodiment, m is 1 and $R^{1a}$ is methyl or ethyl. In still another particular embodiment, m is 1 and $R^{1a}$ is methyl. In certain embodiments, at least one $R^{1a}$ is methyl or ethyl and the remaining $R^{1a}$ are each H. In still other certain embodiments, m is 1 or 2, and at least one $R^{1a}$ is tetrazolyl (e.g., 5-tetrazolyl). In another specific embodiment, m is 1 or 2 and at least one of $R^{1a}$ is $-NO_2$. In more specific embodiments, m is 1 and $R^{1a}$ is $C_1$-$C_3$ haloalkyl. In another specific embodiment, m is 1 and $R^{1a}$ is $C_1$-$C_3$ fluoroalkyl. In a more specific embodiment, the fluoroalkyl is a trifluoromethyl ($-CF_3$) or $-CH_2CH_2CF_3$. In another specific embodiment, m is 1 and $R^{1a}$ is trifluoromethyl ($-CF_3$). In still another specific embodiment, m is 1 and $R^{1a}$ is $-CH_2CF_2CF_3$.

In still another specific embodiment, m is 1 or 2, and at least one of $R^{1a}$ is $-(CH_2)_p-C(O)-R^{4a}$, and $R^{4a}$ is $-OR^7$, $-NR^7R^8$, or $-O(CH_2)_q-OC(O)R^7$. In particular embodiments, when $R^{1a}$ is $-(CH_2)_p-C(O)-R^{4a}$, p is 0, 1, or 2. In one particular embodiment, m is 2 and p is 0 and at least one of $R^{1a}$ is halo, $-NO_2$, $C_1$-$C_3$ alkyl, $-C(O)-R^{4a}$. In certain embodiments, $R^{1a}$ is H at every occurrence. In one embodiment when $R^{1a}$ is $-(CH_2)_p-C(O)-R^{4a}$, $R^{4a}$ is $-OR^7$, and $R^7$ is hydrogen, $C_1$-$C_{20}$ alkyl, a saccharide, an amino acid residue, or a peptide (i.e., 2-6 amino acids). In other particular embodiments, $R^7$ is H or $C_1$-$C_6$ alkyl. In yet another specific embodiment, when $R^{1a}$ is $-(CH_2)_p-C(O)-R^{4a}$, and $R^{4a}$ is $-OR^7$, $R^7$ is $C_1$-$C_3$ alkyl, which in particular embodiments is unsubstituted, and which in other particular embodiments is methyl or ethyl. In still another specific embodiment, when $R^{1a}$ is $-(CH_2)_p-C(O)-R^{4a}$ and $R^{4a}$ is $-OR^7$, $R^7$ is a saccharide. In still more specific embodiments, when $R^{1a}$ is $-(CH_2)_p-C(O)-R^{4a}$, $R^{4a}$ is $-OR^7$, p is 0, and $R^7$ is H, methyl, or ethyl. In still other particular embodiments, $R^7$ is an amino acid residue. In still another particular embodiment, $R^7$ is a peptide.

In still one specific embodiment when $R^{1a}$ is $-(CH_2)_p-C(O)-R^{4a}$, $R^{4a}$ is $-NR^7R^8$, wherein each of $R^7$ and $R^8$ is the same or different and independently hydrogen, $C_1$-$C_6$ alkyl, a saccharide, an amino acid residue, or a peptide (i.e., 2-6 amino acids). In certain embodiments, when $R^{4a}$ is $-NR^7R^8$, at least one or both of $R^7$ and $R^8$ is hydrogen. In other certain embodiments, when $R^{4a}$ is $-NR^7R^8$, at least one of $R^7$ and $R^8$ is hydrogen and the other is $C_1$-$C_6$ alkyl. In other certain embodiments, when $R^{4a}$ is $-NR^7R^8$, at least one of $R^7$ and $R^8$ is hydrogen and the other is $C_1$-$C_3$ alkyl, which in particular embodiments is unsubstituted, and which in other particular embodiments is methyl or ethyl. In yet another embodiment when $R^{4a}$ is $-NR^7R^8$, at least one of $R^7$ and $R^8$ is hydrogen and the other is a saccharide. In yet another embodiment when R$^{4a}$ is —NR$^7$R$^8$, at least one of R$^7$ and R$^8$ is hydrogen and the other is an amino acid residue or a peptide (i.e., 2-6 amino acids).

In still another specific embodiment, when R$^{1a}$ is —(CH$_2$)$_p$—C(O)_R$^{4a}$, R$^{4a}$ is —O(CH$_2$)$_q$—OC(O)R$^7$ and R$^7$ is hydrogen, C$_1$-C$_{20}$ alkyl, or a saccharide. In particular embodiments, p is 1, 2, or 3; in other particular embodiments, q is 1, 2, or 3. In still other specific embodiments, R$^7$ is H or C$_1$-C$_6$ alkyl. In more specific embodiments, R$^7$ is C$_1$-C$_3$ alkyl, which in particular embodiments is unsubstituted, and which in other particular embodiments is methyl or ethyl. In another embodiment, R$^7$ is a saccharide. In still another embodiment, R$^7$ is an amino acid residue. In still another particular embodiment, R$^7$ is a peptide (i.e., 2-6 amino acids).

In a particular embodiment, at least one of R$^1$ or R$^{1a}$ is a polar group selected from —NO$_2$, tetrazolyl, —S(O)$_2$OR$^7$, or —C(=O)OR$^7$ (wherein R$^7$ is hydrogen, C$_{1-20}$ alkyl, a saccharide, an amino acid residue, or a peptide (i.e., 2-6 amino acids). In specific embodiments, R$^7$ is H or C$_1$-C$_6$ alkyl. In more specific embodiments, R$^7$ is C$_1$-C$_3$ alkyl, which in particular embodiments is unsubstituted, and which in other particular embodiments is methyl or ethyl. In another embodiment, R$^7$ is a saccharide. In still other particular embodiments, R$^7$ is an amino acid residue. In still another particular embodiment, R$^7$ is a peptide.

In another specific embodiment of the compound of structure (IA) or (IB), R$^5$ is H or C$_1$-C$_3$ alkyl. In one specific embodiment, R$^5$ is H. In another specific embodiment, R$^5$ is C$_1$-C$_3$ alkyl, which in particular embodiments is unsubstituted. In one embodiment, R$^5$ is H or methyl. In still another specific embodiment, R$^5$ is methyl. In a more specific embodiment, each of R$^5$ and R$^6$ is methyl.

In yet another specific embodiment of the compound of structure (IA) or (IB), R$^6$ is H, C$_1$-C$_3$ alkyl, C$_1$-C$_3$ fluoroalkyl, chloro, bromo, iodo, or fluoro. In another specific embodiment, R$^6$ is methyl, ethyl, trifluoromethyl, chloro, bromo, or iodo. In another specific embodiment, R$^6$ is C$_1$-C$_6$ alkyl. In another more specific embodiment, R$^6$ is C$_1$-C$_3$ alkyl. In more specific embodiments, R$^6$ is unsubstituted C$_1$-C$_6$ alkyl. In yet another specific embodiment, R$^6$ is unsubstituted C$_1$-C$_3$ alkyl (i.e., —CH$_3$, —CH$_2$CH$_3$, or —CH$_2$CH$_2$CH$_3$ (branched or straight chain)). In still more specific embodiments, R$^6$ is methyl or ethyl. In still another more specific embodiment, R$^6$ is methyl. In yet another specific embodiment, R$^6$ is C$_1$-C$_6$ haloalkyl. In more specific embodiments, R$^6$ is C$_1$-C$_3$ haloalkyl. In another specific embodiment, R$^6$ is C$_1$-C$_3$ fluoroalkyl. In a more specific embodiment, the fluoroalkyl is a trifluoromethyl (—CF$_3$) or —CH$_2$CH$_2$CF$_3$. In another specific embodiment, R$^6$ is trifluoromethyl (—CF$_3$). In still another specific embodiment, R$^6$ is —CH$_2$CF$_2$CF$_3$. In yet another particular embodiment, R$^6$ is halo. In a more particular embodiment, R$^6$ is chloro (Cl), bromo (Br), or iodo (I). In still another particular embodiment, R$^6$ is chloro. In yet another specific embodiment, R$^6$ is bromo. In yet another particular embodiment, R$^6$ is iodo.

In a particular embodiment, at least one of R$^1$ or R$^{1a}$ is a polar group selected from —NO$_2$, tetrazolyl, —S(O)$_2$OR$^7$, or —C(=O)OR$^7$ (wherein R$^7$ is hydrogen, C$_1$-C$_{20}$ alkyl, a saccharide, an amino acid residue, or a peptide (i.e., 2-6 amino acids). In specific embodiments, R$^7$ is H or C$_1$-C$_6$ alkyl. In more specific embodiments, R$^7$ is C$_1$-C$_3$ alkyl, which in particular embodiments is unsubstituted, and which in other particular embodiments is methyl or ethyl. In another embodiment, R$^7$ is a saccharide. In still another embodiment, R$^7$ is an amino acid residue. In still another particular embodiment, R$^7$ is a peptide (i.e., 2-6 amino acids).

In further particular embodiments, the compound of structure (IA) or (IB) is an isolated R form.

In further particular embodiments, the compound of structure (IA) or (IB) is an isolated S form.

In another embodiment of the compound of structure (I) and (IA), wherein R$^{2a}$ and R$^{2b}$ are each methyl, p is 0, R$^{4a}$ is —OR$^7$, Z is optionally substituted furanyl, n is 1, and R$^1$ is meta to the linking carbon and the compound has the following structure (IA1):

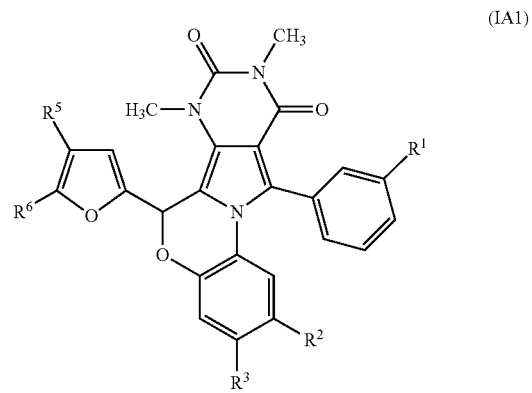

(IA1)

wherein:
R$^1$ is H, halo, or C$_1$-C$_6$ alkyl;
R$^2$ and R$^3$ are each the same or different and independently H, halo, —NO$_2$, C$_1$-C$_6$ alkyl, tetrazolyl, —S(O)$_2$OR$^7$, or —C(=O)OR$^7$;
R$^5$ is H, halo, or C$_1$-C$_6$ alkyl;
R$^6$ is halo, C$_1$-C$_6$ alkyl, or C$_1$-C$_6$ haloalkyl; and
R$^7$ is hydrogen, C$_1$-C$_6$ alkyl, a saccharide, an amino acid residue, or a peptide.

In a more specific embodiment of the compound of structure (IA1), R$^1$ is H, halo, methyl, or ethyl. In a more specific embodiment, R$^1$ is H. In other specific embodiments, R$^1$ is unsubstituted C$_1$-C$_6$ alkyl or halo. In other specific embodiments, R$^1$ is unsubstituted C$_1$-C$_6$ alkyl. In a specific embodiment, R$^1$ is C$_1$-C$_3$ alkyl, which in more specific embodiments is unsubstituted. In another embodiment, R$^1$ is halo, which in certain embodiments is chloro (Cl), fluoro (F), iodo (I), or bromo (Br). In another particular embodiment, R$^1$ is (—CH$_3$) or ethyl (—CH$_2$CH$_3$). In still another particular embodiment, R$^1$ is methyl.

In another particular embodiment of the compound of structure (IA1), R$^2$ is H, halo, —NO$_2$, or —C(=O)OR$^7$, wherein R$^7$ is H or C$_{1-6}$ alkyl. In a particular embodiment, R$^2$ is H. In a more specific embodiment, R$^2$ is H, halo, —NO$_2$, or —C(=O)OR$^7$, wherein R$^7$ is H, —CH$_3$, —CH$_2$CH$_3$, or —CH$_2$CH$_2$CH$_3$. In another embodiment, R$^2$ is H, chloro, —NO$_2$, or —C(=O)OR$^7$, wherein R$^7$ is H, —CH$_3$, or —CH$_2$CH$_3$. In another specific embodiment, R$^2$ is halo, which in particular embodiments is I, Cl, or Br. In more specific embodiments, R$^2$ is Cl. In another specific embodiment, R$^2$ is —NO$_2$. In yet another specific embodiment, R$^2$ is tetrazolyl (e.g., 5-tetrazolyl). In still another specific embodiment, R$^2$ is —C(=O)OR$^7$. In a more particular embodiment, when R$^2$ is —C(=O)OR$^7$, R$^7$ is hydrogen. In another more particular embodiment, R$^2$ is —C(=O)OR$^7$, and R$^7$ is C$_1$-C$_6$ alkyl, which in particular embodiments is unsubstituted. In yet another specific embodiment, R$^2$ is —C(=O)OR$^7$, and R$^7$ is C$_1$-C$_3$ alkyl, which in particular embodiments is unsubstituted. In still another specific embodiment, R$^2$ is —C(=O)

OR$^7$, and R$^7$ is methyl or ethyl. In still other particular embodiments, R$^7$ is an amino acid residue. In still another particular embodiment, R$^7$ is a peptide (i.e., 2-6 amino acids). In yet another embodiment, R$^7$ is a saccharide.

In yet another specific embodiment, R$^2$ is tetrazolyl (e.g., 5-tetrazolyl). In still another particular embodiment, R$^2$ is —S(O)$_2$OR$^7$ and R$^7$ is H or C$_{1-6}$ alkyl. In more specific embodiments, R$^7$ is C$_1$-C$_3$ alkyl, which in particular embodiments is unsubstituted, and which in other particular embodiments is methyl or ethyl. In still another embodiment, R$^7$ is a saccharide. In still other particular embodiments, R$^7$ is an amino acid residue. In still another particular embodiment, R$^7$ is a peptide (i.e., 2-6 amino acids).

In another particular embodiment of the compound of structure (IA1), R$^3$ is H. In another specific embodiment, R$^3$ is —NO$_2$.

In another specific embodiment of the compound of structure (IA1), R$^5$ is H or C$_1$-C$_3$ alkyl. In one specific embodiment, R$^5$ is H. In another specific embodiment, R$^5$ is C$_1$-C$_3$ alkyl, which in particular embodiments is unsubstituted. In one embodiment, R$^5$ is H or methyl. In still another specific embodiment, R$^5$ is methyl (—CH$_3$). In a more specific embodiment, each of R$^5$ and R$^6$ is methyl.

In yet another specific embodiment of the compound of structure (IA1), R$^6$ is C$_1$-C$_3$ alkyl, C$_1$-C$_3$ fluoroalkyl, chloro, bromo, iodo, or fluoro. In another specific embodiment, R$^6$ is methyl, ethyl, trifluoromethyl, chloro, bromo, or iodo. In another specific embodiment, R$^6$ is C$_1$-C$_6$ alkyl. In another more specific embodiment, R$^6$ is C$_1$-C$_3$ alkyl. In more specific embodiments, R$^6$ is unsubstituted C$_1$-C$_6$ alkyl. In yet another specific embodiment, R$^6$ is unsubstituted C$_1$-C$_3$ alkyl (i.e., —CH$_3$, —CH$_2$CH$_3$, or —CH$_2$CH$_2$CH$_3$ (branched or straight chain)). In still more specific embodiments, R$^6$ is methyl (—CH$_3$) or ethyl (—CH$_2$CH$_3$). In still another more specific embodiment, R$^6$ is methyl (—CH$_3$). In yet another specific embodiment, R$^6$ is C$_1$-C$_6$ haloalkyl. In more specific embodiments, R$^6$ is C$_1$-C$_3$ haloalkyl. In another specific embodiment, R$^6$ is C$_1$-C$_3$ fluoroalkyl. In a more specific embodiment, the fluoroalkyl is a trifluoromethyl (—CF$_3$) or —CH$_2$CH$_2$CF$_3$. In another specific embodiment, R$^6$ is trifluoromethyl (—CF$_3$). In still another specific embodiment, R$^6$ is —CH$_2$CF$_2$CF$_3$. In yet another particular embodiment, R$^6$ is halo. In a more particular embodiment, R$^6$ is chloro (Cl), bromo (Br), or iodo (I). In still another particular embodiment, R$^6$ is chloro. In yet another particular embodiment, R$^6$ is bromo. In yet another particular embodiment, R$^6$ is iodo.

In a particular embodiment, at least one of R$^2$ or R$^3$ is a polar group selected from —NO$_2$, tetrazolyl, —S(O)$_2$OR$^7$, or —C(=O)OR$^7$ (wherein R$^7$ is hydrogen, C$_{1-20}$ alkyl, or a saccharide, an amino acid residue, or a peptide (i.e., 2-6 amino acids). In specific embodiments, R$^7$ is H or C$_1$-C$_6$ alkyl. In more specific embodiments, R$^7$ is C$_1$-C$_3$ alkyl, which in particular embodiments is unsubstituted, and which in other particular embodiments is methyl or ethyl. In another embodiment, R$^7$ is a saccharide. In still another embodiment, R$^7$ is an amino acid residue. In still another particular embodiment, R$^7$ is a peptide (i.e., 2-6 amino acids).

In further particular embodiments, the compound of structure (IA1) is an isolated R form.

In further particular embodiments, the compound of structure (IA1) is an isolated S form.

In certain specific embodiments, BPO compounds of structure (I), substructure (Ia(i)), substructure (IA), and substructure (IA1) are as follows.

| Compound Designation | Compound Structure | Compound Name |
|---|---|---|
| BPO-16 | 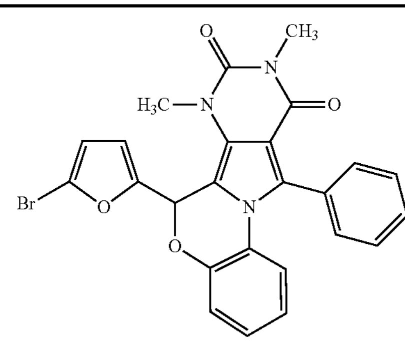 | 6-(5-Bromofuran-2-yl)-7,9-dimethyl-11-phenyl-6H-benzo[b]pyrimido[4',5'-3,4]pyrrolo[1,2-d]oxazine-8,10-(7H,9H)-dione |
| BPO-17 | 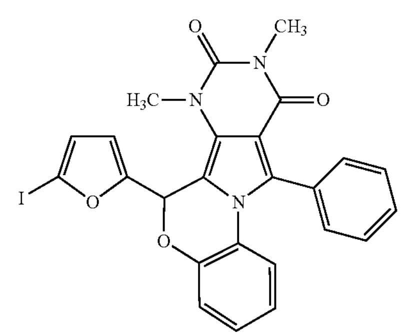 [SMILES: Cn1c(=O)c2c(-c3ccccc3)n3c(c2n(C)c1=O)C(c1ccc(I)o1)Oc1ccccc1-3] | 7,9-Dimethyl-6-(5-iodofuran-2-yl)-11-phenyl-6H-benzo[b]pyrimido[4',5'-3,4]pyrrolo[1,2-d]oxazine-8,10-(7H,9H)-dione |

-continued

| Compound Designation | Compound Structure | Compound Name |
|---|---|---|
| BPO-18 | 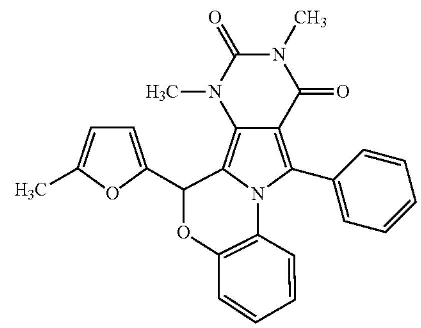 [SMILES: Cc1ccc(C2Oc3ccccc3-n3c(-c4ccccc4)c4c(=O)n(C)c(=O)n(C)c4c32)o1] | 7,9-Dimethyl-6-(5-methylfuran-2-yl)-11-phenyl-6H-benzo[b]pyrimido[4',5'-3,4]pyrrolo[1,2-d]oxazine-8,10-(7H,9H)-dione |
| BPO-19 | 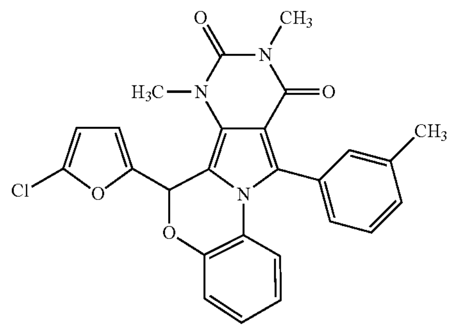 [SMILES: Cc1cccc(-c2c3c(=O)n(C)c(=O)n(C)c3c3n2-c2ccccc2OC3c2ccc(Cl)o2)c1] | 6-(5-Chlorofuran-2-yl)-7,9-dimethyl-11-(m-tolyl)-6H-benzo[b]pyrimido[4',5'-3,4]pyrrolo[1,2-d]oxazine-8,10-(7H,9H)-dione |
| BPO-20 | 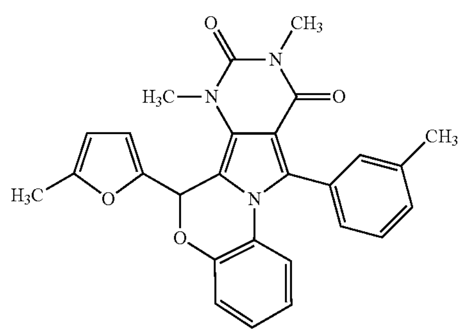 | 7,9-Dimethyl-6-(5-methylfuran-2-yl)-11-(m-tolyl)-6H-benzo[b]pyrimido[4',5'-3,4]pyrrolo[1,2-d]oxazine-8,10-(7H,9H)-dione |
| BPO-21 | 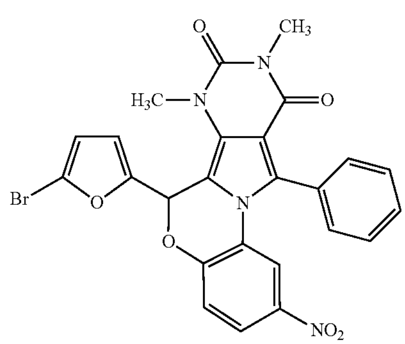 | 6-(5-bromofuran-2-yl)-7,9-dimethyl-2-nitro-11-phenyl-6H-benzo[b]pyrimido[4',5'-3,4]pyrrolo[1,2-d]oxazine-8,10-(7H,9H)-dione |

-continued

| Compound Designation | Compound Structure | Compound Name |
|---|---|---|
| BPO-22 | 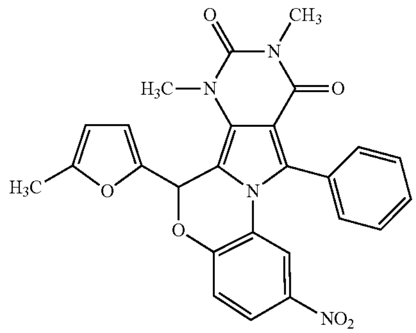 [SMILES: Cc1ccc(C2Oc3ccc([N+](=O)[O-])cc3-n3c(-c4ccccc4)c4c(=O)n(C)c(=O)n(C)c4c32)o1] | 7,9-Dimethyl-6-(5-methylfuran-2-yl)-2-nitro-11-phenyl-6H-benzo[b]pyrimido[4',5'-3,4]pyrrolo[1,2-d]oxazine-8,10-(7H,9H)-dione |
| BPO-24 | 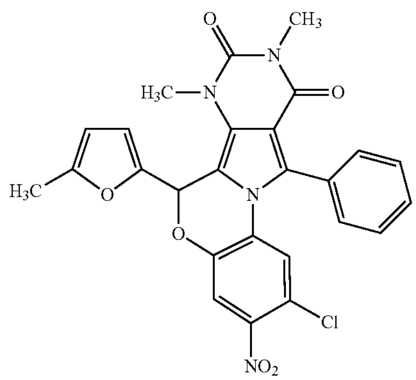 [SMILES: Cc1ccc(C2Oc3cc([N+](=O)[O-])c(Cl)cc3-n3c(-c4ccccc4)c4c(=O)n(C)c(=O)n(C)c4c32)o1] | 2-Chloro-7,9-Dimethyl-6-(5-methylfuran-2-yl)-3-nitro-11-phenyl-6H-benzo[b]pyrimido[4',5'-3,4]pyrrolo[1,2-d]oxazine-8,10-(7H,9H)-dione |
| BPO-25 | 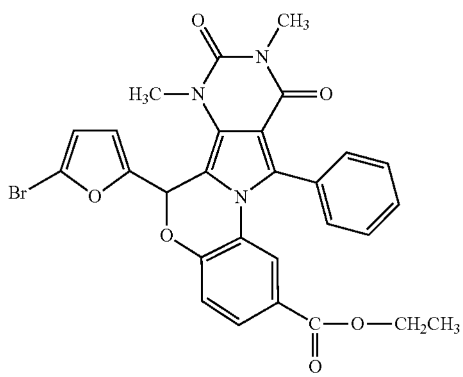 [SMILES: CCOC(=O)c1ccc2c(c1)-n1c(-c3ccccc3)c3c(=O)n(C)c(=O)n(C)c3c1C(c1ccc(Br)o1)O2] | Ethyl 6-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylate |
| (R)-BPO-25 | 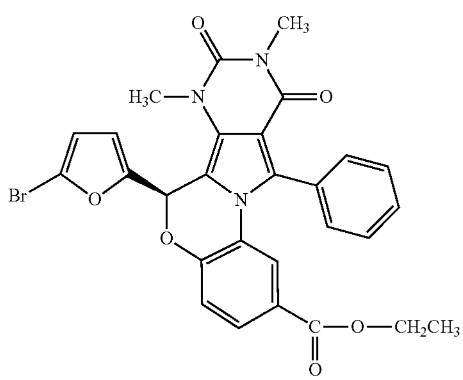 [SMILES: CCOC(=O)c1ccc2c(c1)-n1c(-c3ccccc3)c3c(=O)n(C)c(=O)n(C)c3c1[C@H](c1ccc(Br)o1)O2] | Ethyl 6R-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylate |

| Compound Designation | Compound Structure | Compound Name |
|---|---|---|
| (S)-BPO-25 | 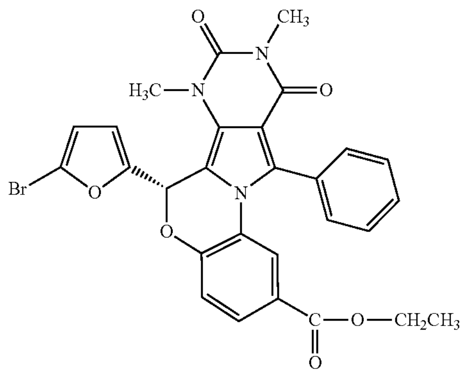 [SMILES: CCOC(=O)c1ccc2c(c1)-n1c(-c3ccccc3)c3c(=O)n(C)c(=O)n(C)c3c1[C@@H](c1ccc(Br)o1)O2] | Ethyl 6S-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylate |
| BPO-26 | 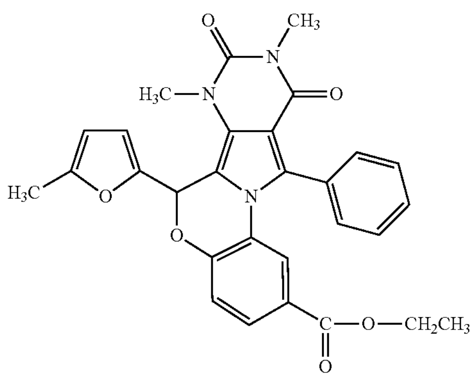 [SMILES: CCOC(=O)c1ccc2c(c1)-n1c(-c3ccccc3)c3c(=O)n(C)c(=O)n(C)c3c1C(c1ccc(C)o1)O2] | Ethyl 7,9-Dimethyl-8,10-dioxo-6-(5-methylfuran-2-yl)-11-phenyl-7,8,9,10-tetrahydro-6H-benzo[b]pyrimido[4',5':3,4]pyrrolo[1,2-d][1,4]oxazine-2-carboxylate |
| BPO-27 | 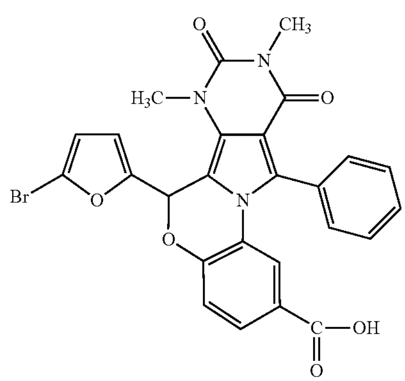 [SMILES: Cn1c(=O)c2c(-c3ccccc3)n3c(c2n(C)c1=O)C(c1ccc(Br)o1)Oc1ccc(C(=O)O)cc1-3] | 6-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylic acid |
| (R)-BPO-27 | 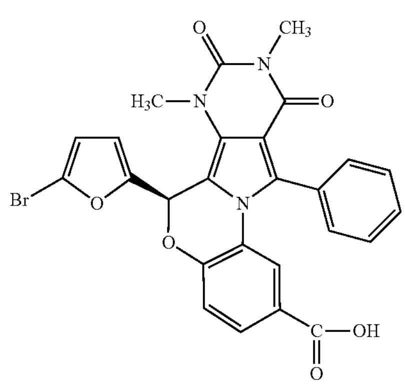 [SMILES: Cn1c(=O)c2c(-c3ccccc3)n3c(c2n(C)c1=O)[C@H](c1ccc(Br)o1)Oc1ccc(C(=O)O)cc1-3] | 6R-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylic acid |

| Compound Designation | Compound Structure | Compound Name |
|---|---|---|
| (S)-BPO-27 | 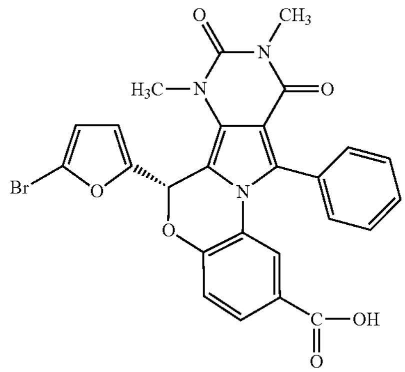 [SMILES: Cn1c(=O)c2c(-c3ccccc3)n3c(c2n(C)c1=O)[C@@H](c1ccc(Br)o1)Oc1ccc(C(=O)O)cc1-3] | 6S-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylic acid |

In another embodiment of the compound of structure (I) and (IB), $R^{2a}$ and $R^{2b}$ are each methyl, p is 0, $R^{4a}$ is —$OR^7$, Z is optionally substituted thienyl, and $R^1$ is meta to the linking carbon the compound has the following structure (IB1):

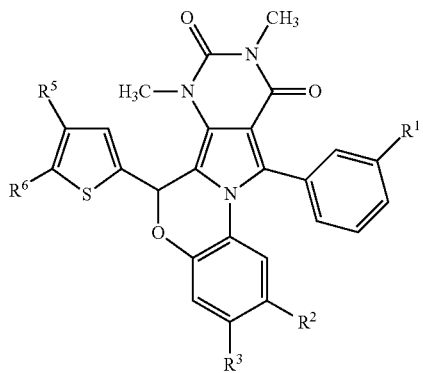

(IB1)

wherein:

$R^1$ is H, halo, or $C_{1-6}$ alkyl;

$R^2$ and $R^3$ are each the same or different and independently H, halo, —$NO_2$, $C_1$-$C_6$ alkyl, tetrazolyl, —$S(O)_2OR^7$, or —$C(=O)OR^7$;

$R^5$ is H, halo, or $C_1$-$C_6$ alkyl;

$R^6$ is halo, $C_1$-$C_6$ alkyl, or $C_1$-$C_6$ haloalkyl; and $R^7$ is H, $C_1$-$C_6$ alkyl, a saccharide, an amino acid residue, or a peptide.

In a more specific embodiment of the compound of structure (IB 1), $R^1$ is H, halo, methyl, or ethyl. In a more specific embodiment, $R^1$ is H. In other specific embodiments, $R^1$ is unsubstituted $C_1$-$C_6$ alkyl or halo. In other specific embodiments, $R^1$ is unsubstituted $C_1$-$C_6$ alkyl. In a specific embodiment, $R^1$ is $C_1$-$C_3$ alkyl, which in more specific embodiments is unsubstituted. In another embodiment, $R^1$ is halo, which in certain embodiments is chloro, fluoro, iodo, or bromo. In another particular embodiment, $R^1$ is methyl or ethyl. In still another particular embodiment, $R^1$ is methyl.

In another particular embodiment of the compound of structure (IB 1), $R^2$ is H, halo, —$NO_2$, or —$C(=O)OR^7$, wherein $R^7$ is H or $C_1$-$C_6$ alkyl. In a particular embodiment, $R^2$ is H. In a more specific embodiment, $R^2$ is H, halo, —$NO_2$, or —$C(=O)OR^7$, wherein $R^7$ is H, —$CH_3$, —$CH_2CH_3$, or —$CH_2CH_2CH_3$. In another embodiment, $R^2$ is H, chloro, —$NO_2$, or —$C(=O)OR^7$, wherein $R^7$ is H, —$CH_3$, or —$CH_2CH_3$. In another specific embodiment, $R^2$ is halo, which in particular embodiments is I, Cl, or Br. In more specific embodiments, $R^2$ is Cl. In another specific embodiment, $R^2$ is —$NO_2$. In still another specific embodiment, $R^2$ is —$C(=O)OR^7$. In a more particular embodiment, $R^2$ is —$C(=O)OR^7$, and $R^7$ is hydrogen. In another more particular embodiment, $R^2$ is —$C(=O)OR^7$, and $R^7$ is $C_1$-$C_6$ alkyl, which in particular embodiments is unsubstituted. In yet another specific embodiment, $R^2$ is —$C(=O)OR^7$, and $R^7$ is $C_1$-$C_3$ alkyl, which in particular embodiments is unsubstituted. In still another specific embodiment, $R^2$ is —$C(=O)OR^7$, and $R^7$ is methyl, or ethyl. In still another specific embodiment, $R^2$ is —$C(=O)OR^7$, and $R^7$ is H. In still another embodiment, $R^7$ is an amino acid residue. In still another particular embodiment, $R^7$ is a peptide (i.e., 2-6 amino acids). In yet another embodiment, $R^7$ is a saccharide.

In yet another specific embodiment, $R^2$ is tetrazolyl (e.g., 5-tetrazolyl). In still another particular embodiment, $R^2$ is —$S(O)_2OR^7$ and $R^7$ is H or $C_1$-$C_6$ alkyl. In more specific embodiments, $R^7$ is $C_1$-$C_3$ alkyl, which in particular embodiments is unsubstituted, and which in other particular embodiments is methyl or ethyl. In still another embodiment, $R^7$ is a saccharide. In still another embodiment, $R^7$ is an amino acid residue. In still another particular embodiment, $R^7$ is a peptide (i.e., 2-6 amino acids).

In another particular embodiment of the compound of structure (IB1), $R^3$ is H. In another specific embodiment, $R^3$ is —$NO_2$.

In another specific embodiment of the compound of structure (IB1), $R^5$ is H or $C_1$-$C_3$ alkyl. In one specific embodiment, $R^5$ is H. In another embodiment, $R^5$ is $C_1$-$C_3$ alkyl, which in particular embodiments is unsubstituted. In one embodiment, $R^5$ is H or methyl. In still another embodiment, $R^5$ is methyl. In a more specific embodiment, each of $R^5$ and $R^6$ is methyl.

In yet another specific embodiment of the compound of structure (IB 1), $R^6$ is $C_1$-$C_3$ alkyl, $C_1$-$C_3$ fluoroalkyl, chloro, bromo, iodo, or fluoro. In another specific embodiment, $R^6$ is methyl, ethyl, trifluoromethyl, chloro, bromo, or iodo. In another specific embodiment, $R^6$ is $C_1$-$C_6$ alkyl. In another more specific embodiment, $R^6$ is $C_1$-$C_3$ alkyl. In more specific embodiments, $R^6$ is unsubstituted $C_1$-$C_6$ alkyl. In yet another specific embodiment, $R^6$ is unsubstituted $C_1$-$C_3$ alkyl (i.e., —CH₃, —CH₂CH₃, or —CH₂CH₂CH₃ (branched or straight chain)). In still more specific embodiments, $R^6$ is methyl or ethyl. In still another more specific embodiment, $R^6$ is methyl. In yet another specific embodiment, $R^6$ is $C_1$-$C_6$ haloalkyl. In more specific embodiments, $R^6$ is $C_1$-$C_3$ haloalkyl. In another specific embodiment, $R^6$ is $C_1$-$C_3$ fluoroalkyl. In a more specific embodiment, the fluoroalkyl is a trifluoromethyl (—CF₃) or —CH₂CH₂CF₃. In another specific embodiment, $R^6$ is trifluoromethyl (—CF₃). In still another specific embodiment, $R^6$ is —CH₂CF₂CF₃. In yet another particular embodiment, $R^6$ is halo. In a more particular embodiment, $R^6$ is chloro, bromo, or iodo. In still another particular embodiment, $R^6$ is chloro. In yet another particular embodiment, $R^6$ is bromo. In yet another particular embodiment, $R^6$ is iodo.

In certain particular embodiments of the compound of structure (IB1), $R^1$ is H, methyl, or ethyl; $R^2$ and $R^3$ are each the same or different and independently H, halo, —NO₂, methyl, ethyl, or —C(=O)OR⁷ wherein $R^7$ is hydrogen, methyl, or ethyl; $R^5$ is H or methyl; and $R^6$ is $C_1$-$C_3$ alkyl, $C_1$-$C_3$ fluoroalkyl, chloro, bromo, iodo, or fluoro.

In a particular embodiment, at least one of $R^2$ or $R^3$ is a polar group selected from —NO₂, tetrazolyl, —S(O)₂OR⁷, or —C(=O)OR⁷ (wherein $R^7$ is hydrogen, $C_1$-$C_{20}$ alkyl, a saccharide, an amino acid residue, or a peptide (i.e., 2-6 amino acids).). In specific embodiments, $R^7$ is H or $C_1$-$C_6$ alkyl. In more specific embodiments, $R^7$ is $C_1$-$C_3$ alkyl, which in particular embodiments is unsubstituted, and which in other particular embodiments is methyl or ethyl. In another embodiment, $R^7$ is a saccharide. In still other particular embodiments, $R^7$ is an amino acid residue. In still another particular embodiment, $R^7$ is a peptide.

In further particular embodiments, the compound of structure (IB1) is an isolated R form.

In further particular embodiments, the compound of structure (IB1) is an isolated S form.

In a more specific embodiment of the compound of structure (I), $R^{2a}$ and $R^{2b}$ are each methyl, and Z is optionally substituted phenyl, and the compound has the following structure (IC).

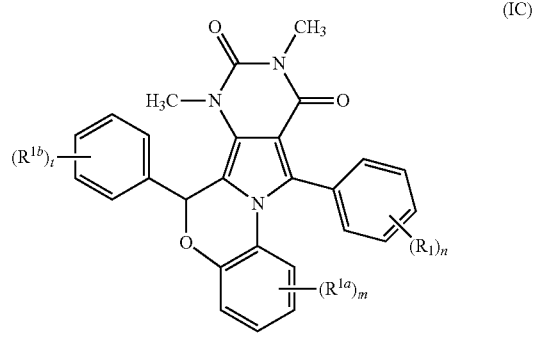

(IC)

as an isolated enantiomer or a racemic mixture of enantiomers, or as a pharmaceutically acceptable salt, hydrate, solvate, N-oxide, or prodrug thereof,
wherein:
m is 1, 2, 3, or 4;
n is 1, 2, 3, 4 or 5;
p is an integer from 0 to 4;
q is an integer from 1 to 4;
t is 1, 2, 3, 4 or 5;
$R^1$ at each occurrence is the same or different and independently H, halo, haloalkyl, $C_1$-$C_6$ alkyl, —(CH₂)ₚ—C(O)—$R^{4a}$, —S(O)₂$R^{4a}$, —NO₂, or tetrazolyl;

$R^{1a}$ at each occurrence is the same or different and independently H, halo, haloalkyl, $C_1$-$C_6$ alkyl, —(CH₂)ₚ—C(O)—$R^{4a}$, —S(O)₂$R^{4a}$, —NO₂, or tetrazolyl;

$R^{1b}$ at each occurrence is the same or different and independently H, halo, $C_1$-$C_6$ alkyl, $C_2$-$C_6$ alkenyl, $C_1$-$C_6$ alkoxy, —NO₂, or —OH;

$R^{4a}$ is –OR⁷, —NR⁷R⁸, —O(CH₂)_q—OC(O)R⁷, an amino acid residue, or a peptide;

$R^7$ and $R^8$ are each the same or different and independently hydrogen, $C_1$-$C_{20}$ alkyl, a saccharide, an amino acid residue, or a peptide.

In another particular embodiment of the compound of substructure (IC), n is 1 or 2 and each $R^1$ is the same or different and independently H, halo, haloalkyl, $C_1$-$C_6$ alkyl, —(CH₂)ₚ—C(O)—$R^{4a}$, —S(O)₂$R^{4a}$, —NO₂, or tetrazolyl. In certain specific embodiments, $R^1$ is H at each occurrence. In one specific embodiment, n is 1, 2, or 3 and each $R^1$ is the same or different and independently H, halo, methyl, or ethyl. In other specific embodiments, n is 1 and $R^1$ is unsubstituted $C_1$-$C_6$ alkyl or halo. In other specific embodiments, $R^1$ is unsubstituted $C_1$-$C_6$ alkyl and n is 1. In a specific embodiment, n is 1 and $R^1$ is $C_1$-$C_3$ alkyl, which in more specific embodiments is unsubstituted. In another embodiment, n is 1 and $R^1$ is halo, which in certain embodiments is chloro, fluoro, iodo, or bromo. In another particular embodiment, n is 1 and $R^1$ is methyl or ethyl. In still another particular embodiment, n is 1 and $R^1$ is methyl. In certain embodiments, at least one $R^1$ is methyl or ethyl and the remaining $R^1$ are each H. In still another specific embodiment n is at least 1 and the at least one $R^1$ is haloalkyl. In still other specific embodiments, n is 1 or 2 and each $R^1$ is haloalkyl. In still another specific embodiment, n is 1 and $R^1$ is $C_1$-$C_6$ haloalkyl. In more specific embodiments, n is 1 and $R^1$ is $C_1$-$C_3$ haloalkyl. In another specific embodiment, n is 1 and $R^1$ is $C_1$-$C_3$ fluoroalkyl. In a more specific embodiment, the fluoroalkyl is a trifluoromethyl (—CF₃) or —CH₂CH₂CF₃. In another specific embodiment, n is 1 and $R^1$ is trifluoromethyl (—CF₃). In still another specific embodiment, n is 1 and $R^1$ is —CH₂CF₂CF₃. In other certain embodiments, n is 1 and $R^1$ is —NO₂. In still other certain embodiments, n is 1 and $R^1$ is tetrazolyl (e.g., 5-tetrazolyl). In yet other certain embodiments, n is 1 and $R^1$ is —(CH₂)ₚ—C(O)—$R^{4a}$. In yet other certain embodiments, n is 1 and $R^1$ is —S(O)₂$R^{4a}$.

In still another specific embodiment, n is 1 or 2, and at least one of $R^1$ is —S(O)₂$R^{4a}$ or —(CH₂)ₚ—C(O)—$R^{4a}$, and $R^{4a}$ is —OR⁷, —NR⁷R⁸, or —O(CH₂)_q—OC(O)R⁷. In other certain embodiments, at least one of $R^1$ is —S(O)₂$R^{4a}$ or —(CH₂)ₚ—C(O)—$R^{4a}$, and $R^{4a}$ is an amino acid residue. In another certain embodiment, at least one of $R^1$ is —S(O)₂$R^{4a}$ or —(CH₂)ₚ—C(O)—$R^{4a}$, and $R^{4a}$ is a peptide that consists of two (i.e., a dipeptide), three (i.e., a tripeptide), four, five, or six amino acid residues. In particular embodiments, $R^7$ is H or $C_1$-$C_6$ alkyl. In yet another specific embodiment, $R^7$ is $C_1$-$C_3$ alkyl, which in particular embodiments is unsubstituted, and which in other particular embodiments is methyl or ethyl. In still another specific embodiment, $R^7$ is a saccharide. In particular embodiments, $R^8$ is H or $C_1$-$C_6$ alkyl. In yet another specific embodiment, $R^8$ is $C_1$-$C_3$ alkyl, which in particular embodiments is unsubstituted, and which in other particular embodiments is methyl or ethyl. In still another specific embodiment, $R^8$ is a saccharide. In certain embodiments, $R^{4a}$ is —NR⁷R⁸, and each of $R^7$ and $R^8$ is the same or different and independently H or $C_1$-$C_6$ alkyl. In certain embodiments, $R^{4a}$ is —NR⁷R⁸, and each of $R^7$ and $R^8$ is the same or different and independently H, methyl, or ethyl. In other particular embodiments, $R^{4a}$ is —OR⁷ or —O(CH₂)_q—OC(O)R⁷ and $R^7$ is an amino acid residue. In still other certain embodiments, $R^{4a}$ is —OR$^7$ or —O(CH$_2$)$_q$—OC(O)R$^7$ and R$^7$ is a peptide that consists of two (i.e., a dipeptide), three (i.e., a tripeptide), four, five, or six amino acid residues. In still other certain embodiments, R$^{4a}$ is —NR$^7$R$^8$ and either R$^7$ or R$^8$ is an amino acid residue. In still other certain embodiments, R$^{4a}$ is —NR$^7$R$^8$ and either R$^7$ or R$^8$ is a peptide that consists of two (i.e., a dipeptide), three (i.e., a tripeptide), four, five, or six amino acid residues.

In particular embodiments, when R$^1$ is —(CH$_2$)$_p$—C(O)—R$^{4a}$, p is 0, 1, or 2. In yet other certain embodiments, n is 1 and R$^1$ is —(CH$_2$)$_p$—C(O)—R$^{4a}$, and R$^{4a}$ is —OR$^7$. In certain particular embodiments, R$^{4a}$ is —OR$^7$, and R$^7$ is hydrogen, C$_1$-C$_{20}$ alkyl, or a saccharide. In other certain embodiments, when R$^1$ is —(CH$_2$)$_p$—C(O)—R$^{4a}$, and R$^{4a}$ is —OR$^7$, R$^7$ is hydrogen, methyl, ethyl. In other certain embodiments, when R$^1$ is —(CH$_2$)$_p$—C(O)—R$^{4a}$, and R$^{4a}$ is —OR$^7$, R$^7$ is a saccharide. In still other particular embodiments, when R$^1$ is —(CH$_2$)$_p$—C(O)—R$^{4a}$, and R$^{4a}$ is —OR$^7$, R$^7$ is an amino acid residue or a peptide (i.e., consisting of 2, 3, 4, 5, or six amino acids).

In another particular embodiment of the compound of structure (IC), m is 1 or 2. In another particular embodiment of the compound of structure (I), m is 1 or 2 and each R$^{1a}$ is the same or different and independently H, halo, haloalkyl, C$_1$-C$_6$ alkyl, —(CH$_2$)$_p$—C(O)—R$^{4a}$, —S(O)$_2$R$^{4a}$, —NO$_2$, or tetrazolyl. In one particular embodiment, m is 2 and p is 0 and at least one of R$^{1a}$ is halo, —NO$_2$, C$_1$-C$_3$ alkyl, —C(O)—R$^{4a}$. In certain embodiments, R$^{1a}$ is H at every occurrence. In particular embodiments, m is 1 or 2 and at least one of R$^{1a}$ is halo, which in particular embodiments halo is I, Cl, or Br. In more specific embodiments, m is 1 or 2 and at least one of R$^h$ is Cl. In other specific embodiments, R$^{1a}$ is unsubstituted C$_1$-C$_6$ alkyl and m is 1 or 2. In a specific embodiment, m is 1 or 2 and at least one R$^{1a}$ is C$_1$-C$_3$ alkyl, which in more specific embodiments is unsubstituted. In another particular embodiment, m is 1 and R$^{1a}$ is methyl or ethyl. In still another particular embodiment, m is 1 and R$^{1a}$ is methyl. In still other certain embodiments, m is 1 or 2, and at least one R$^{1a}$ is tetrazolyl (e.g., 5-tetrazolyl). In another specific embodiment, m is 1 or 2 and at least one of R$^{1a}$ is —NO$_2$. In more specific embodiments, m is 1 and R$^{1a}$ is C$_1$-C$_3$ haloalkyl. In another specific embodiment, m is 1 and R$^{1a}$ is C$_1$-C$_3$ fluoroalkyl. In a more specific embodiment, the fluoroalkyl is a trifluoromethyl (—CF$_3$) or —CH$_2$CH$_2$CF$_3$. In another specific embodiment, m is 1 and R$^{1a}$ is trifluoromethyl (—CF$_3$). In still another specific embodiment, m is 1 and R$^{1a}$ is —CH$_2$CF$_2$CF$_3$.

In still another specific embodiment, m is 1 or 2, and at least one of R$^{1a}$ is —(CH$_2$)$_p$—C(O)—R$^{4a}$, and R$^{4a}$ is —OR$^7$, —NR$^7$R$^8$, or —O(CH$_2$)$_q$—OC(O)R$^7$. In particular embodiments, when R$^{1a}$ is —(CH$_2$)$_p$—C(O)—R$^{4a}$, p is 0, 1, or 2. In one embodiment when R$^{1a}$ is —(CH$_2$)$_p$—C(O)—R$^{4a}$, R$^{4a}$ is —OR$^7$, and R$^7$ is hydrogen, C$_1$-C$_{20}$ alkyl, a saccharide, an amino acid residue, or a peptide (i.e., 2-6 amino acids). In other particular embodiments, R$^7$ is H or C$_1$-C$_6$ alkyl. In yet another specific embodiment, when R$^{1a}$ is —(CH$_2$)$_p$—C(O)—R$^{4a}$, and R$^{4a}$ is —OR$^7$, R$^7$ is C$_1$-C$_3$ alkyl, which in particular embodiments is unsubstituted, and which in other particular embodiments R$^7$ is methyl or ethyl. In still another specific embodiment, when R$^{1a}$ is —(CH$_2$)$_p$—C(O)—R$^{4a}$ and R$^{4a}$ is —OR$^7$, R$^7$ is a saccharide. In still other particular embodiments, R$^7$ is an amino acid residue. In still another particular embodiment, R$^7$ is a peptide. In still more specific embodiments, when R$^{1a}$ is —(CH$_2$)$_p$—C(O)—R$^{4a}$, p is 0, R$^{4a}$ is —OR$^7$, and R$^7$ is H, methyl, or ethyl.

In still one specific embodiment when R$^{1a}$ is —(CH$_2$)$_p$—C(O)—R$^{4a}$, R$^{4a}$ is —NR$^7$R$^8$, wherein each of R$^7$ and R$^8$ is the same or different and independently hydrogen, C$_1$-C$_6$ alkyl, or a saccharide. In certain embodiments, when R$^{4a}$ is —NR$^7$R$^8$, at least one or both of R$^7$ and R$^8$ is hydrogen. In other certain embodiments, when R$^{4a}$ is —NR$^7$R$^8$, at least one of R$^7$ and R$^8$ is hydrogen and the other is C$_1$-C$_6$ alkyl. In other certain embodiments, when R$^{4a}$ is —NR$^7$R$^8$, at least one of R$^7$ and R$^8$ is hydrogen and the other is C$_1$-C$_3$ alkyl, which in particular embodiments is unsubstituted, and which in other particular embodiments is methyl or ethyl. In yet another embodiment when R$^{4a}$ is —NR$^7$R$^8$, at least one of R$^7$ and R$^8$ is hydrogen and the other is a saccharide. In yet another embodiment when R$^{4a}$ is —NR$^7$R$^8$, at least one of R$^7$ and R$^8$ is hydrogen and the other is an amino acid residue or a peptide (i.e., 2-6 amino acids).

In still another specific embodiment, when R$^{1a}$ is —(CH$_2$)$_p$—C(O)—R$^{4a}$, R$^{4a}$ is —O(CH$_2$)$_q$—OC(O)R$^7$ and R$^7$ is hydrogen, C$_1$-C$_{20}$ alkyl, or a saccharide. In particular embodiments, p is 1, 2, or 3; in other particular embodiments, q is 1, 2, or 3. In still other specific embodiments, R$^7$ is H or C$_1$-C$_6$ alkyl. In more specific embodiments, R$^7$ is C$_1$-C$_3$ alkyl, which in particular embodiments is unsubstituted, and which in other particular embodiments is methyl or ethyl. In another embodiment, R$^7$ is a saccharide. In still another embodiment, R$^7$ is an amino acid residue. In still another particular embodiment, R$^7$ is a peptide (i.e., 2-6 amino acids).

In a particular embodiment, at least one of R$^1$ or R$^{1a}$ is a polar group selected from —NO$_2$, tetrazolyl, —S(O)$_2$OR$^7$, or —C(=O)OR$^7$ (wherein R$^7$ is hydrogen, C$_1$-C$_{20}$ alkyl, or a saccharide). In specific embodiments, R$^7$ is H or C$_1$-C$_6$ alkyl. In more specific embodiments, R$^7$ is C$_1$-C$_3$ alkyl, which in particular embodiments is unsubstituted, and which in other particular embodiments is methyl or ethyl. In another embodiment, R$^7$ is a saccharide. In still another embodiment, R$^7$ is an amino acid residue. In still another particular embodiment, R$^7$ is a peptide (i.e., 2-6 amino acids).

In certain embodiments of the compound of substructure (IC), t is 1, 2, or 3. In other particular embodiments, when t is 1, 2, or 3, each R$^{1b}$ is the same or different and independently H, halo, C$_1$-C$_6$ alkyl, C$_2$-C$_6$ alkenyl, C$_1$-C$_6$ alkoxy, nitro (—NO$_2$), or —OH. In other specific embodiments, t=2 and each R$^{1b}$ is the same or different and independently H, —OH, halo, —NO$_2$, C$_1$-C$_3$ alkyl, or C$_1$-C$_3$ alkoxy. In another specific embodiment, t=1 and R$^{1b}$ is —OH, halo, —NO$_2$, C$_1$-C$_3$ alkyl, or C$_1$-C$_3$ alkoxy. In still another specific embodiment, t=1 and R$^{1b}$ is —OH, chloro, fluoro, —NO$_2$, methyl, or methoxy. In yet more specific embodiments, t=2 and each R$^{1b}$ is the same or different and independently H, —OH, chloro, fluoro, —NO$_2$, methyl, or methoxy. In other specific embodiments, R$^{1b}$ is H at each occurrence. In specific embodiments, R$^{1b}$ is halo selected from bromo, chloro, iodo, and fluoro. In more specific embodiments, R$^{1b}$ is chloro. In other particular embodiments, R$^{1b}$ is fluoro. In other specific embodiments, R$^{1b}$ is C$_1$-C$_6$ alkyl. In certain embodiments, R$^{1b}$ is C$_2$-C$_6$ alkenyl, and in other particular embodiments, R$^{1b}$ is C$_1$-C$_6$ alkoxy. In still other embodiments, R$^{1b}$ is C$_1$-C$_3$ alkyl (e.g., methyl, ethyl, propyl). In other embodiments, R$^{1b}$ is C$_1$-C$_3$ alkoxy. In more particular embodiments, R$^{1b}$ is methoxy or ethoxy. In still other embodiments, R$^{1b}$ is hydroxyl (—OH), and in yet another specific embodiment, R$^{1b}$ is —NO$_2$. In other particular embodiments, t is 1 or 2. In still other embodiments, t is 2 and each R$^{1b}$ is the same or different and selected from methyl, chloro, fluoro, methoxy, nitro, and hydroxyl. In a particular embodiment, at least one of R$^1$ or R$^{1a}$ is a polar group selected from —NO$_2$, tetrazolyl, —S(O)$_2$OR$^7$, and —C(=O)OR$^7$ (wherein R$^7$ is hydrogen, C$_{1-20}$ alkyl, or a saccharide). In specific embodiments, R$^7$ is H or C$_1$-C$_6$ alkyl. In more specific embodiments, R$^7$ is C$_1$-C$_3$ alkyl, which in particular embodiments is unsubstituted, and which in other particular embodiments is methyl or ethyl. In another embodiment, $R^7$ is a saccharide. In still another embodiment, $R^7$ is an amino acid residue. In still another particular embodiment, $R^7$ is a peptide (i.e., 2-6 amino acids).

In further particular embodiments, the compound of structure (IC) is an isolated R form.

In further particular embodiments, the compound of structure (IC) is an isolated S form.

In another embodiment of the compound of structure (I) and (IC), wherein $R^{2a}$ and $R^{2b}$ are each methyl, p is 0, $R^{4a}$ is —$OR^7$, n is 1, and R' is meta to the linking carbon and the compound has the following structure:

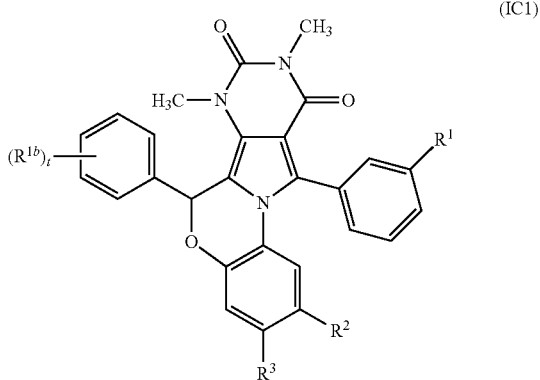

(IC1)

wherein:
$R^1$ is H, halo, or $C_{1-6}$ alkyl;
$R^2$ and $R^3$ are each the same or different and independently H, halo, —$NO_2$, $C_{1-6}$ alkyl, tetrazolyl, —$S(O)_2OR^7$, or —$C(=O)OR^7$;
t is 1, 2, 3, 4 or 5;
$R^{1b}$ at each occurrence is the same or different and independently H, halo, —$NO_2$, $C_{1-6}$ alkoxy, $C_2-C_6$ alkenyl or $C_{1-6}$ alkyl;
$R^7$ is hydrogen, $C_1-C_6$ alkyl, a saccharide, an amino acid residue, or a peptide.

In a more specific embodiment of the compound of structure (IC1), $R^1$ is H, halo, methyl, or ethyl. In a more specific embodiment, $R^1$ is H. In other specific embodiments, $R^1$ is unsubstituted $C_1-C_6$ alkyl or halo. In other specific embodiments, $R^1$ is unsubstituted $C_1-C_6$ alkyl. In a specific embodiment, $R^1$ is $C_1-C_3$ alkyl, which in more specific embodiments is unsubstituted. In another embodiment, $R^1$ is halo, which in certain embodiments is chloro, fluoro, iodo, or bromo. In another particular embodiment, $R^1$ is methyl or ethyl. In still another particular embodiment, $R^1$ is methyl.

In another particular embodiment of the compound of structure (IC1), $R^2$ is H, halo, —$NO_2$, or —$C(=O)OR^7$, wherein $R^7$ is H or $C_{1-6}$ alkyl. In a particular embodiment, $R^2$ is H. In a more specific embodiment, $R^2$ is H, halo, —$NO_2$, or —$C(=O)OR^7$, wherein $R^7$ is H, —$CH_3$, —$CH_2CH_3$, or —$CH_2CH_2CH_3$. In another embodiment, $R^2$ is H, chloro, —$NO_2$, or —$C(=O)OR^7$, wherein $R^7$ is H, —$CH_3$, or —$CH_2CH_3$. In another specific embodiment, $R^2$ is halo, which in particular embodiments is I, Cl, or Br. In more specific embodiments, $R^2$ is Cl. In another specific embodiment, $R^2$ is —$NO_2$. In still another specific embodiment, $R^2$ is —$C(=O)OR^7$. In a more particular embodiment, $R^2$ is —$C(=O)OR^7$, and $R^7$ is hydrogen. In another more particular embodiment, $R^2$ is —$C(=O)OR^7$, and $R^7$ is $C_1-C_6$ alkyl, which in particular embodiments is unsubstituted. In yet another specific embodiment, $R^2$ is —$C(=O)OR^7$, and $R^7$ is $C_1-C_3$ alkyl, which in particular embodiments is unsubstituted. In still another specific embodiment, $R^2$ is —$C(=O)OR^7$, and $R^7$ is methyl or ethyl).

In another particular embodiment of the compound of structure (IC1), $R^3$ is H. In another specific embodiment, $R^3$ is —$NO_2$.

In certain embodiments of the compound of substructure (IC1), t is 1 or 2. In other particular embodiments, when t is 1 or 2, each $R^{1b}$ is the same or different and independently H, halo, $C_1-C_6$ alkyl, $C_2-C_6$ alkenyl, $C_1-C_6$ alkoxy, nitro (—$NO_2$), or —OH. In other specific embodiments, t=2 and each $R^{1b}$ is the same or different and independently H, —OH, halo, —$NO_2$, $C_1-C_3$ alkyl, or $C_1-C_3$ alkoxy. In another specific embodiment, t=1 and $R^{1b}$ is —OH, halo, —$NO_2$, $C_1-C_3$ alkyl, or $C_1-C_3$ alkoxy. In still another specific embodiment, t=1 and $R^{1b}$ is —OH, chloro, fluoro, —$NO_2$, methyl, or methoxy. In yet more specific embodiments, t=2 and each $R^{1b}$ is the same or different and independently H, —OH, chloro, fluoro, —$NO_2$, methyl, or methoxy. In other specific embodiments, $R^{1b}$ is H at each occurrence. In specific embodiments, at least one $R^{1b}$ is halo selected from bromo, chloro, iodo, and fluoro. In more specific embodiments, at least one $R^{1b}$ is chloro. In other particular embodiments, at least one $R^{1b}$ is fluoro. In other specific embodiments, at least one $R^{1b}$ is $C_1-C_6$ alkyl. In certain embodiments, at least one $R^{1b}$ is $C_1-C_6$ alkoxy. In still other specific embodiments, the at least one $R^{1b}$ is $C_1-C_3$ alkyl (e.g., methyl, ethyl, propyl). In other specific embodiments, at least one $R^{1b}$ is $C_1-C_3$ alkoxy. In more particular embodiments, at least one $R^{1b}$ is methoxy or ethoxy. In still other embodiments, at least one $R^{1b}$ is hydroxyl (—OH), and in yet another specific embodiment, at least one $R^{1b}$ is —$NO_2$. In certain embodiments, t is 2 and each $R^{1b}$ is the same or different and selected from methyl, chloro, fluoro, methoxy, nitro, and hydroxyl. In certain particular embodiments, t is 1 and $R^{1b}$ is selected from methyl, chloro, fluoro, methoxy, nitro, and hydroxyl.

In further particular embodiments, the compound of structure (IC1) is an isolated R form.

In further particular embodiments, the compound of structure (IC1) is an isolated S form.

In a further embodiment, a compound is provided that has the following structure (II):

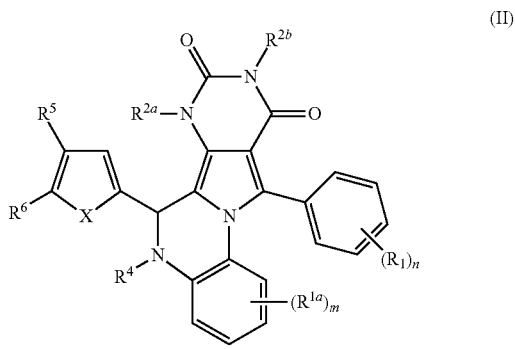

(II)

as an isolated enantiomer or a racemic mixture of enantiomers, or as a pharmaceutically acceptable salt, hydrate, solvate, N-oxide, or prodrug thereof,
wherein:
m is 1, 2, 3, or 4;
n is 1, 2, 3, 4 or 5;
p is an integer from 0 to 4;

q is an integer from 1 to 4;

X is O or S;

$R^1$ at each occurrence is the same or different and independently H, halo, haloalkyl, $C_{1-6}$ alkyl, —$(CH_2)_p$—C(O)—$R^{4a}$, —$S(O)_2R^{4a}$, —$NO_2$, or tetrazolyl;

$R^{1a}$ at each occurrence is the same or different and independently H, halo, haloalkyl, $C_1$-$C_6$ alkyl, —$(CH_2)_p$—C(O)—$R^{4a}$, —$S(O)_2R^{4a}$, —$NO_2$, or tetrazolyl;

$R^{2a}$ and $R^{2b}$ are each the same or different and independently H or $C_{1-6}$ alkyl;

$R^{4a}$ is —$OR^7$, —$NR^7R^8$, —$O(CH_2)_q$—$OC(O)R^7$, an amino acid residue, or a peptide;

$R^4$ is hydrogen, —N(=O), $C_{1-6}$ alkyl, or haloalkyl;

$R^5$ is H, halo, or $C_{1-6}$ alkyl;

$R^6$ is halo, $C_{1-6}$ alkyl, or $C_{1-6}$ haloalkyl; and $R^7$ and $R^8$ are each the same or different and independently hydrogen, $C_{1-20}$ alkyl, a saccharide, an amino acid residue, or a peptide.

with the proviso that the following compounds are excluded:

(a) 7,9-Dimethyl-11-(3-methylphenyl)-6-(5-methylfuran-2-yl)-5,6-dihydro-pyrimido[4',5'-3,4]pyrrolo[1,2-a]quinoxaline-8,10-(7H,9H)-dione;

(b) 7,9-Dimethyl-11-phenyl-6-(5-methylfuran-2-yl)-5,6-dihydro-pyrimido[4',5'-3,4]pyrrolo[1,2-a]quinoxaline-8,10-(7H,9H)-dione;

(c) 7,9-Dimethyl-11-(2-methylphenyl)-6-(5-methylfuran-2-yl)-5,6-dihydro-pyrimido[4',5'-3,4]pyrrolo[1,2-a]quinoxaline-8,10-(7H,9H)-dione;

(d) 2,3,7,9-Tetramethyl-11-phenyl-6-(5-methylfuran-2-yl)-5,6-dihydro-pyrimido[4',5'-3,4]pyrrolo[1,2-a]quinoxaline-8,10-(7H,9H)-dione;

(e) 2,3,7,9-Tetramethyl-11-(2-fluorophenyl)-6-(5-methylfuran-2-yl)-5,6-dihydro-pyrimido[4',5'-3,4]pyrrolo[1,2-a]quinoxaline-8,10-(7H,9H)-dione;

(f) 7,9-Dimethyl-11-(4-methylphenyl)-6-(5-methylfuran-2-yl)-5,6-dihydro-pyrimido[4',5'-3,4]pyrrolo[1,2-a]quinoxaline-8,10-(7H,9H)-dione; and (g) 7,9-Dimethyl-11-(4-cholophenyl)-6-(5-methylfuran-2-yl)-5,6-dihydro-pyrimido[4',5'-3,4]pyrrolo[1,2-a]quinoxaline-8,10-(7H,9H)-dione.

The chemical structures of the excluded compounds are set forth in Table A below.

TABLE A

PPQ-101

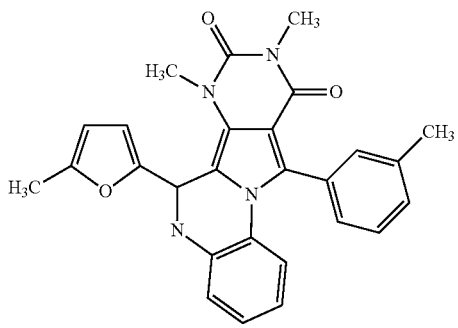

(a) 7,9-Dimethyl-11-(3-methylphenyl)-6-(5-methylfuran-2-yl)-5,6-dihydro-pyrimido[4',5'-3,4]pyrrolo[1,2-a]quinoxaline-8,10-(7H,9H)-dione

PPQ-102

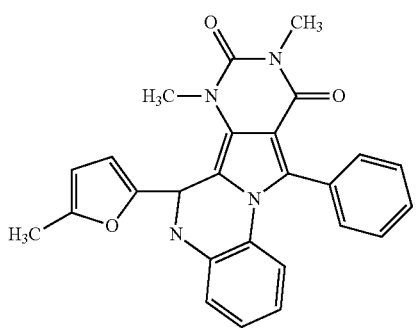 [SMILES: Cc1ccc(C2Nc3ccccc3-n3c(-c4ccccc4)c4c(=O)n(C)c(=O)n(C)c4c32)o1]

(b) 7,9-Dimethyl-11-phenyl-6-(5-methylfuran-2-yl)-5,6-dihydro-pyrimido[4',5'-3,4]pyrrolo[1,2-a]quinoxaline-8,10-(7H,9H)-dione

PPQ-103

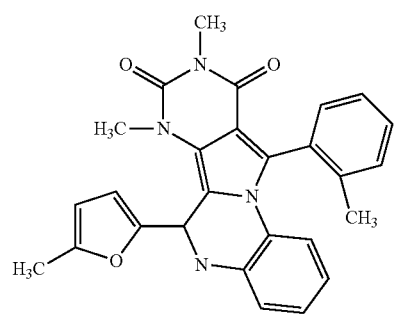 [SMILES: Cc1ccc(C2Nc3ccccc3-n3c(-c4ccccc4C)c4c(=O)n(C)c(=O)n(C)c4c32)o1]

(c) 7,9-Dimethyl-11-(2-methylphenyl)-6-(5-methylfuran-2-yl)-5,6-dihydro-pyrimido[4',5'-3,4]pyrrolo[1,2-a]quinoxaline-8,10-(7H,9H)-dione TABLE A-continued

| ID | Structure | Name |
|---|---|---|
| PPQ-104 | 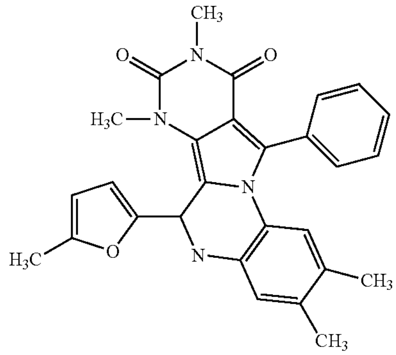 [SMILES: Cc1ccc(C2Nc3cc(C)c(C)cc3-n3c(-c4ccccc4)c4c(=O)n(C)c(=O)n(C)c4c32)o1] | (d) 2,3,7,9-Tetramethyl-11-phenyl-6-(5-methylfuran-2-yl)-5,6-dihydro-pyrimido[4',5'-3,4]pyrrolo[1,2-a]quinoxaline-8,10-(7H,9H)-dione |
| PPQ-105 | 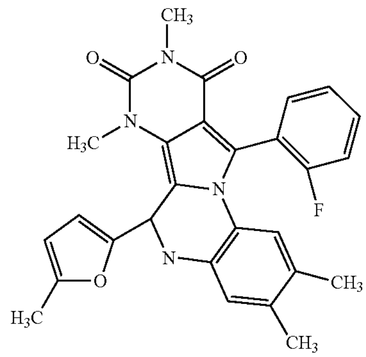 [SMILES: Cc1ccc(C2Nc3cc(C)c(C)cc3-n3c(-c4ccccc4F)c4c(=O)n(C)c(=O)n(C)c4c32)o1] | (e) 2,3,7,9-Tetramethyl-11-(2-fluorophenyl)-6-(5-methylfuran-2-yl)-5,6-dihydro-pyrimido[4',5'-3,4]pyrrolo[1,2-a]quinoxaline-8,10-(7H,9H)-dione |
| PPQ-110 | 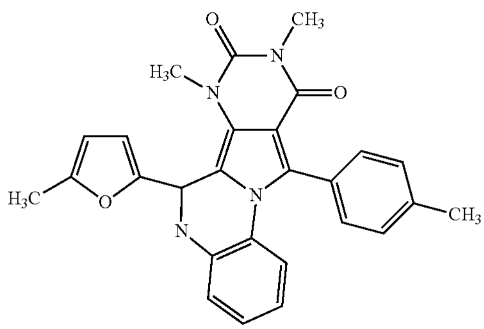 | (f) 7,9-Dimethyl-11-(4-methylphenyl)-6-(5-methylfuran-2-yl)-5,6-dihydro-pyrimido[4',5'-3,4]pyrrolo[1,2-a]quinoxaline-8,10-(7H,9H)-dione |
| PPQ-111 | 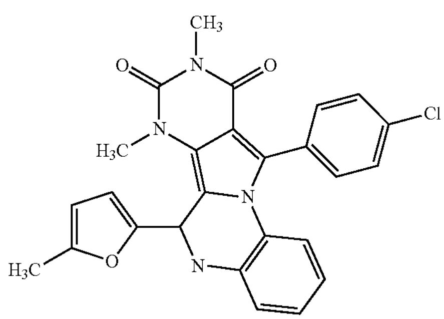 [SMILES: Cc1ccc(C2Nc3ccccc3-n3c(-c4ccc(Cl)cc4)c4c(=O)n(C)c(=O)n(C)c4c32)o1] | (g) 7,9-Dimethyl-11-(4-cholophenyl)-6-(5-methylfuran-2-yl)-5,6-dihydro-pyrimido[4',5'-3,4]pyrrolo[1,2-a]quinoxaline-8,10-(7H,9H)-dione |

In certain embodiments of the compound of structure (II), X is O. In other certain embodiments of the compound of structure (II), X is S.

In a particular embodiment of the compound of structure (II), n is 1 or 2 and each $R^1$ is the same or different and independently H, halo, haloalkyl, $C_1$-$C_6$ alkyl, —$(CH_2)_p$—C(O)—$R^{4a}$, —$S(O)_2R^{4a}$, —$NO_2$, or tetrazolyl. In one specific embodiment, n is 1, 2, or 3 and each $R^1$ is the same or different and independently H, halo, methyl, or ethyl. In certain specific embodiments, $R^1$ is H at each occurrence. In other specific embodiments, n is 1 and $R^1$ is unsubstituted $C_1$-$C_6$ alkyl or halo. In other specific embodiments, $R^1$ is unsubstituted $C_1$-$C_6$ alkyl and n is 1. In a specific embodiment, n is 1 and $R^1$ is $C_1$-$C_3$ alkyl, which in more specific embodiments is unsubstituted. In another embodiment, n is 1 and $R^1$ is halo, which in certain embodiments is chloro, fluoro, iodo, or bromo. In another particular embodiment, n is 1 and $R^1$ is methyl or ethyl. In still another particular embodiment, n is 1 and $R^1$ is methyl. In certain embodiments, at least one $R^1$ is methyl or ethyl and the remaining $R^1$ are each H. In still another specific embodiment n is at least 1 and the at least one $R^1$ is haloalkyl. In still other specific embodiments, n is 1 or 2 and each $R^1$ is haloalkyl. In still another specific embodiment, n is 1 and $R^1$ is $C_1$-$C_6$ haloalkyl. In more specific embodiments, n is 1 and $R^1$ is $C_1$-$C_3$ haloalkyl. In another specific embodiment, n is 1 and $R^1$ is $C_1$-$C_3$ fluoroalkyl. In a more specific embodiment, the fluoroalkyl is a trifluoromethyl (—$CF_3$) or —$CH_2CH_2CF_3$. In another specific embodiment, n is 1 and $R^1$ is trifluoromethyl (—$CF_3$). In still another specific embodiment, n is 1 and $R^1$ is —$CH_2CF_2CF_3$. In other certain embodiments, n is 1 and $R^1$ is —$NO_2$. In still other certain embodiments, n is 1 and $R^1$ is tetrazolyl (e.g., 5-tetrazolyl). In yet other certain embodiments, n is 1 and $R^1$ is —$(CH_2)_p$—C(O)—$R^{4a}$. In yet other certain embodiments, n is 1 and $R^1$ is —$S(O)_2R^{4a}$.

In still another specific embodiment, n is 1 or 2, and at least one of $R^1$ is —$S(O)_2R^{4a}$ or —$(CH_2)_p$—C(O)—$R^{4a}$, and $R^{4a}$ is —$OR^7$, —$NR^7R^8$, or —$O(CH_2)_q$—$OC(O)R^7$. In other certain embodiments, at least one of $R^1$ is —$S(O)_2R^{4a}$ or —$(CH_2)_p$—C(O)—$R^{4a}$, and $R^{4a}$ is an amino acid residue. In another certain embodiment, at least one of $R^1$ is —$S(O)_2R^{4a}$ or —$(CH_2)_p$—C(O)—$R^{4a}$, and $R^{4a}$ is a peptide that consists of two (i.e., a dipeptide), three (i.e., a tripeptide), four, five, or six amino acid residues. In particular embodiments, $R^7$ is H or $C_1$-$C_6$ alkyl. In yet another specific embodiment, $R^7$ is $C_1$-$C_3$ alkyl, which in particular embodiments is unsubstituted, and which in other particular embodiments is methyl or ethyl. In still another specific embodiment, $R^7$ is a saccharide. In particular embodiments, $R^8$ is H or $C_1$-$C_6$ alkyl. In yet another specific embodiment, $R^8$ is $C_1$-$C_3$ alkyl, which in particular embodiments is unsubstituted, and which in other particular embodiments is methyl or ethyl. In still another specific embodiment, $R^8$ is a saccharide. In certain embodiments, $R^{4a}$ is —$NR^7R^8$, and each of $R^7$ and $R^8$ is the same or different and independently H or $C_1$-$C_6$ alkyl. In certain embodiments, $R^{4a}$ is —$NR^7R^8$, and each of $R^7$ and $R^8$ is the same or different and independently H, methyl, or ethyl. In other particular embodiments, $R^{4a}$ is —$OR^7$ or —$O(CH_2)_q$—$OC(O)R^7$ and $R^7$ is an amino acid residue. In still other certain embodiments, $R^{4a}$ is —$OR^7$ or —$O(CH_2)_q$—$OC(O)R^7$ and $R^7$ is a peptide that consists of two (i.e., a dipeptide), three (i.e., a tripeptide), four, five, or six amino acid residues. In still other certain embodiments, $R^{4a}$ is —$NR^7R^8$ and either $R^7$ or $R^8$ is an amino acid residue. In still other certain embodiments, $R^{4a}$ is —$NR^7R^8$ and either $R^7$ or $R^8$ is a peptide that consists of two (i.e., a dipeptide), three (i.e., a tripeptide), four, five, or six amino acid residues.

In particular embodiments, when $R^1$ is —$(CH_2)_p$—C(O)—$R^{4a}$, p is 0, 1, or 2. In yet other certain embodiments, n is 1 and $R^1$ is —$(CH_2)_p$—C(O)—$R^{4a}$, and $R^{4a}$ is —$OR^7$. In certain particular embodiments, $R^{4a}$ is —$OR^7$, and $R^7$ is hydrogen, $C_1$-$C_{20}$ alkyl, or a saccharide. In other certain embodiments, when $R^1$ is —$(CH_2)_p$—C(O)—$R^{4a}$, and $R^{4a}$ is —$OR^7$, $R^7$ is hydrogen, methyl, ethyl. In other certain embodiments, when $R^1$ is —$(CH_2)_p$—C(O)—$R^{4a}$, and $R^{4a}$ is —$OR^7$, $R^7$ is a saccharide. In still another embodiment, $R^7$ is an amino acid residue. In still another particular embodiment, $R^7$ is a peptide (i.e., 2-6 amino acids).

In another particular embodiment of the compound of structure (II), m is 1 or 2. In another particular embodiment of the compound of structure (I), m is 1 or 2 and each $R^{1a}$ is the same or different and independently H, halo, haloalkyl, $C_1$-$C_6$ alkyl, —$(CH_2)_p$—C(O)—$R^{4a}$, —$S(O)_2R^{4a}$, —$NO_2$, or tetrazolyl. In one particular embodiment, m is 2 and p is 0 and at least one of $R^{1a}$ is halo, —$NO_2$, $C_1$-$C_3$ alkyl, —C(O)—$R^{4a}$. In certain embodiments, $R^{1a}$ is H at every occurrence. In particular embodiments, m is 2 and at least one of $R^{1a}$ is halo, which in particular embodiments halo is I, Cl, or Br. In more specific embodiments, m is 1 or 2 and at least one of $R^{1a}$ is Cl.

In other specific embodiments, m is 1 or 2 and $R^{1a}$ is unsubstituted $C_1$-$C_6$ alkyl. In a specific embodiment, m is 1 or 2 and at least one $R^{1a}$ is $C_1$-$C_3$ alkyl, which in more specific embodiments is unsubstituted. In another particular embodiment, m is 1 and $R^{1a}$ is methyl or ethyl. In still another particular embodiment, m is 1 and $R^{1a}$ is methyl. In still other certain embodiments, m is 1 or 2, and at least one $R^{1a}$ is tetrazolyl (e.g., 5-tetrazolyl). In another specific embodiment, m is 1 or 2 and at least one of $R^{1a}$ is —$NO_2$. In more specific embodiments, m is 1 and $R^{1a}$ is $C_1$-$C_3$ haloalkyl. In another specific embodiment, m is 1 and $R^{1a}$ is $C_1$-$C_3$ fluoroalkyl. In a more specific embodiment, the fluoroalkyl is a trifluoromethyl (—$CF_3$) or —$CH_2CH_2CF_3$. In another specific embodiment, m is 1 and $R^{1a}$ is trifluoromethyl (—$CF_3$). In still another specific embodiment, m is 1 and $R^{1a}$ is —$CH_2CF_2CF_3$.

In still another specific embodiment, m is 1 or 2, and at least one of $R^{1a}$ is —$(CH_2)_p$—C(O)—$R^{4a}$, and $R^{4a}$ is —$OR^7$, —$NR^7R^8$, or —$O(CH_2)_q$—$OC(O)R^7$. In particular embodiments, when $R^{1a}$ is —$(CH_2)_p$—C(O)—$R^{4a}$, p is 0, 1, or 2. In one embodiment when $R^{1a}$ is —$(CH_2)_p$—C(O)—$R^{4a}$, $R^{4a}$ is —$OR^7$, and $R^7$ is hydrogen, $C_1$-$C_{20}$ alkyl, a saccharide, an amino acid residue, or a peptide (i.e., 2-6 amino acids). In other particular embodiments, $R^7$ is H or $C_1$-$C_6$ alkyl. In yet another specific embodiment, when $R^{1a}$ is —$(CH_2)_p$—C(O)—$R^{4a}$, and $R^{4a}$ is $R^7$ is $C_1$-$C_3$ alkyl, which in particular embodiments is unsubstituted, and which in other particular embodiments is methyl or ethyl. In still another specific embodiment, when $R^{1a}$ is —$(CH_2)_p$—C(O)—$R^{4a}$ and $R^{4a}$ is –$OR^7$, $R^7$ is a saccharide. In still other particular embodiments, $R^7$ is an amino acid residue. In still another particular embodiment, $R^7$ is a peptide. In still more specific embodiments, when $R^{1a}$ is —$(CH_2)_p$—C(O)—$R^{4a}$, $R^{4a}$ is —$OR^7$, p is 0, and $R^7$ is H, methyl, or ethyl.

In still one specific embodiment when $R^{1a}$ is —$(CH_2)_p$—C(O)—$R^{4a}$, $R^{4a}$ is —$NR^7R^8$, wherein each of $R^7$ and $R^8$ is the same or different and independently hydrogen, $C_1$-$C_6$ alkyl, or a saccharide. In certain embodiments, when $R^{4a}$ is —$NR^7R^8$, at least one or both of $R^7$ and $R^8$ is hydrogen. In other certain embodiments, when $R^{4a}$ is —$NR^7R^8$, at least one of $R^7$ and $R^8$ is hydrogen and the other is $C_1$-$C_6$ alkyl. In other certain embodiments, when $R^{4a}$ is —$NR^7R^8$, at least one of $R^7$ and $R^8$ is hydrogen and the other is $C_1$-$C_3$ alkyl, which in particular embodiments is unsubstituted, and which in other particular embodiments is methyl or ethyl. In yet another embodiment when $R^{4a}$ is —$NR^7R^8$, at least one of $R^7$ and $R^8$ is hydrogen and the other is a saccharide. In still other particular embodiments, $R^7$ is an amino acid residue. In still another particular embodiment, $R^7$ is a peptide (i.e., consisting of 2, 3, 4, 5, or six amino acids).

In still another specific embodiment, when $R^{1a}$ is —$(CH_2)_p$—C(O)—$R^{4a}$, $R^{4a}$ is —$O(CH_2)_q$—$OC(O)R^7$ and $R^7$ is hydrogen, $C_1$-$C_{20}$ alkyl, or a saccharide. In particular embodiments, p is 1, 2, or 3; in other particular embodiments, q is 1, 2, or 3. In still other specific embodiments, $R^7$ is H or $C_1$-$C_6$ alkyl. In more specific embodiments, $R^7$ is $C_1$-$C_3$ alkyl, which in particular embodiments is unsubstituted, and which in other particular embodiments is methyl or ethyl. In another embodiment, $R^7$ is a saccharide. In still other particular embodiments, $R^7$ is an amino acid residue. In still another particular embodiment, $R^7$ is a peptide (i.e., consisting of 2, 3, 4, 5, or six amino acids).

In a particular embodiment, at least one of $R^1$ or $R^{1a}$ is a polar group selected from —$NO_2$, tetrazolyl, —$S(O)_2OR^7$, or —C(=O)$OR^7$ (wherein $R^7$ is hydrogen, $C_{1-20}$ alkyl, or a saccharide). In specific embodiments, $R^7$ is H or $C_1$-$C_6$ alkyl. In more specific embodiments, $R^7$ is $C_1$-$C_3$ alkyl, which in particular embodiments is unsubstituted, and which in other particular embodiments is methyl or ethyl. In another embodiment, $R^7$ is a saccharide. In still other particular embodiments, $R^7$ is an amino acid residue. In still another particular embodiment, $R^7$ is a peptide.

In other particular embodiments, $R^{2a}$ or $R^{2b}$ are each the same or different and independently hydrogen or $C_1$-$C_3$ alkyl. In yet another particular embodiments, $R^{2a}$ or $R^{2b}$ are each the same or different and independently hydrogen, methyl, or ethyl. In certain embodiments, $R^{2a}$ and $R^{2b}$ are each H. In other certain embodiments, $R^{2a}$ and $R^{2b}$ are each methyl. In still other certain embodiments, $R^{2a}$ and $R^{2b}$ are each ethyl.

In still another embodiment of the compound of structure (II), $R^4$ is H, —N(=O), or unsubstituted $C_{1-6}$ alkyl. In another specific embodiment, $R^4$ is H, —N(=O), or methyl. In another specific embodiment of the compound of structure (II), $R^4$ is H. In another specific embodiment, $R^4$ is —N(=O). In another specific embodiment, $R^4$ is $C_1$-$C_3$ alkyl. In yet another specific embodiment, $R^4$ is methyl (—CH$_3$) or ethyl (—CH$_2$CH$_3$). In still another specific embodiment, $R^4$ is methyl.

In another specific embodiment of the compound of structure (II), $R^5$ is H. In another specific embodiment, $R^5$ is $C_1$-$C_3$ alkyl, which in particular embodiments is unsubstituted. In one embodiment, $R^5$ is H or methyl. In still another specific embodiment, $R^5$ is methyl. In a more specific embodiment, each of $R^5$ and $R^6$ is methyl.

In yet another specific embodiment of the compound of structure (II), $R^6$ is $C_1$-$C_3$ alkyl, $C_1$-$C_3$ fluoroalkyl, chloro, bromo, iodo, or fluoro. In another specific embodiment, $R^6$ is methyl, ethyl, trifluoromethyl, chloro, bromo, or iodo. In another specific embodiment, $R^6$ is $C_1$-$C_6$ alkyl. In another more specific embodiment, $R^6$ is $C_1$-$C_3$ alkyl. In more specific embodiments, $R^6$ is unsubstituted $C_1$-$C_6$ alkyl. In yet another specific embodiment, $R^6$ is unsubstituted $C_1$-$C_3$ alkyl (i.e., —CH$_3$, —CH$_2$CH$_3$, or —CH$_2$CH$_2$CH$_3$ (branched or straight chain)). In still more specific embodiments, $R^6$ is methyl or ethyl. In still another more specific embodiment, $R^6$ is methyl. In yet another specific embodiment, $R^6$ is $C_1$-$C_6$ haloalkyl. In more specific embodiments, $R^6$ is $C_1$-$C_3$ haloalkyl. In another specific embodiment, $R^6$ is $C_1$-$C_3$ fluoroalkyl. In a more specific embodiment, the fluoroalkyl is a trifluoromethyl (—CF$_3$) or —CH$_2$CH$_2$CF$_3$. In another specific embodiment, $R^6$ is trifluoromethyl (—CF$_3$). In still another specific embodiment, $R^6$ is —CH$_2$CF$_2$CF$_3$. In yet another particular embodiment, $R^6$ is halo. In a more particular embodiment, $R^6$ is chloro, bromo, or iodo. In still another particular embodiment, $R^6$ is chloro. In yet another particular embodiment, $R^6$ is bromo. In yet another particular embodiment, $R^6$ is iodo.

With respect to the embodiments of structure (II) described above, when $R^4$ is H, $R^6$ is ethyl. In certain particular embodiments of the compound of structure (II), when $R^4$ is H, $R^6$ is ethyl. In certain embodiments, when $R^4$ is H, $R^6$ is halo, which in particular embodiments is Cl, Br, or I. In other particular embodiments, when $R^4$ is H, $R^6$ is a trihaloalkyl, which in certain embodiments, is a trifluoroalkyl. In more specific embodiments, when $R^4$ is H, $R^6$ is trifluoromethyl (—CF$_3$).

In other certain embodiments of the compound of structure (II), when $R^4$ is H, and $R^6$ is methyl, then X is S. In still other certain embodiments, when $R^4$ is H, and $R^6$ is methyl, then $R^5$ is also methyl.

In specific embodiments when $R^6$ is —CH$_3$, then (i) $R^4$ is —N(=O) or —CH$_3$; (ii) $R^5$ is halo or $C_1$-$C_6$ alkyl; or (iii) X is S. In another specific embodiment when X is O, and each of $R^4$ and $R^5$ is H, then $R^6$ is $C_2$-$C_6$ alkyl, halo, or $C_1$-$C_6$ haloalkyl.

In further particular embodiments, the compound of structure (II) is an isolated R form.

In further particular embodiments, the compound of structure (II) is an isolated S form.

In another embodiment, the compound of structure II has the following substructure, wherein $R^{2a}$ and $R^{2b}$ are each methyl, p is 0, $R^{4a}$ is —OR$^7$, n is 1, and $R^1$ is meta to the linking carbon, and the compound has the following structure (IIA):

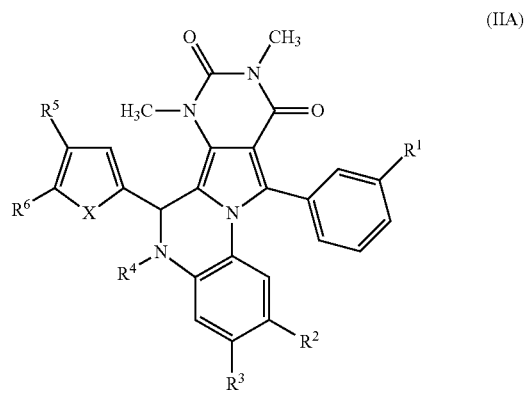

wherein:
X is O or S;
$R^1$ is H, halo, or $C_1$-$C_3$ alkyl;
$R^2$ is H, halo, —NO$_2$, or —C(=O)OR$^7$;
$R^3$ is H or NO$_2$;
$R^4$ is —N(=O), $C_1$-$C_3$ alkyl, or H;
$R^5$ is H or $C_1$-$C_3$ alkyl;
$R^6$ is $C_1$-$C_6$ alkyl, $C_1$-$C_6$ haloalkyl, or halo; and
$R^7$ is H, $C_1$-$C_6$ alkyl, a saccharide, or an amino acid residue, or a peptide.

The following compounds as shown in Table A are excluded from the compounds that have the structure (IIA):
(a) 7,9-Dimethyl-11-(3-methylphenyl)-6-(5-methylfuran-2-yl)-5,6-dihydro-pyrimido[4',5'-3,4]pyrrolo[1,2-a]quinoxaline-8,10-(7H,9H)-dione;
(b) 7,9-Dimethyl-11-phenyl-6-(5-methylfuran-2-yl)-5,6-dihydro-pyrimido[4',5'-3,4]pyrrolo[1,2-a]quinoxaline-8,10-(7H,9H)-dione; and
(d) 2,3,7,9-Tetramethyl-11-phenyl-6-(5-methylfuran-2-yl)-5,6-dihydro-pyrimido[4',5'-3,4]pyrrolo[1,2-a]quinoxaline-8,10-(7H,9H)-dione.

In certain embodiments of the compound of structure (IIA), X is O. In other certain embodiments of the compound of structure (IIA), X is S.

In more specific embodiments of the compound of structure (IIA), $R^1$ is H, —CH$_3$, or —CH$_2$CH$_3$. In a more particular embodiment, $R^1$ is H or —CH$_3$. In other particular embodiments, $R^1$ is H. In still another embodiment, $R^1$ is —CH$_3$. In yet another embodiment, $R^1$ is —CH$_2$CH$_3$. In still another specific embodiment, $R^1$ is halo, which in particular embodiments is any one of Cl, F, I, or Br.

In more specific embodiments of the compound of structure (IIA), $R^2$ is H, chloro, —NO$_2$, or —C(=O)OR$^7$, wherein $R^7$ is H or $C_1$-$C_6$ alkyl. In still another specific embodiment, $R^2$ is H, chloro, —NO$_2$, or —C(=O)OR$^7$, wherein $R^7$ is H, —CH$_3$, —CH$_2$CH$_3$, or —CH$_2$CH$_2$CH$_3$. In one particular embodiment, $R^2$ is H, chloro, or —NO$_2$. In another particular embodiment, $R^2$ is or —C(=O)OR$^7$, wherein $R^7$ is H, —CH$_3$, —CH$_2$CH$_3$, or —CH$_2$CH$_2$CH$_3$. In a particular embodiment, $R^2$ is H. In another embodiment, $R^2$ is H, chloro, —NO$_2$, or —C(=O)OR$^7$, wherein R$^7$ is H, —CH$_3$, or —CH$_2$CH$_3$. In another specific embodiment, R$^2$ is halo, which in particular embodiments is I, Cl, or Br. In more specific embodiments, R$^2$ is Cl. In another specific embodiment, R$^2$ is —NO$_2$. In still another specific embodiment, R$^2$ is —C(=O)OR$^7$ and R$^7$ is methyl. In a more particular embodiment, R$^2$ is —C(=O)OR$^7$, and R$^7$ is H. In still another specific embodiment, R$^2$ is —C(=O)OR$^7$, and R$^7$ is ethyl. In still other particular embodiments, R$^7$ is an amino acid residue. In still another particular embodiment, R$^7$ is a peptide (i.e., consisting of 2, 3, 4, 5, or six amino acids). In yet another embodiment, R$^7$ is a saccharide.

In another particular embodiment of the compound of structure (IIA), R$^3$ is H. In another specific embodiment, R$^3$ is —NO$_2$.

In another specific embodiment of the compound of structure (IIA), R$^4$ is H, methyl, or —N(=O). In another specific embodiment R$^4$ is H. In another specific embodiment, R$^4$ is —N(=O). In one specific embodiment, R$^4$ is ethyl. In yet another specific embodiment, R$^4$ is —CH$_3$.

In another specific embodiment of the compound of structure (IIA), R$^5$ is H. In another specific embodiment, R$^5$ is C$_1$-C$_3$ alkyl, which in particular embodiments is unsubstituted. In one embodiment, R$^5$ is H or methyl. In still another specific embodiment, R$^5$ is methyl (—CH$_3$). In a more specific embodiment, each of R$^5$ and R$^6$ is methyl.

In yet another specific embodiment of the compound of structure (IIA), R$^6$ is C$_1$-C$_3$ alkyl, C$_1$-C$_3$ fluoroalkyl, chloro, bromo, iodo, or fluoro. In another specific embodiment, R$^6$ is methyl, ethyl, trifluoromethyl, chloro, bromo, or iodo. In another specific embodiment, R$^6$ is C$_1$-C$_6$ alkyl. In another more specific embodiment, R$^6$ is C$_1$-C$_3$ alkyl. In more specific embodiments, R$^6$ is unsubstituted C$_1$-C$_6$ alkyl. In yet another specific embodiment, R$^6$ is unsubstituted C$_1$-C$_3$ alkyl (i.e., —CH$_3$, —CH$_2$CH$_3$, or —CH$_2$CH$_2$CH$_3$ (branched or straight chain)). In still more specific embodiments, R$^6$ is methyl or ethyl. In still another more specific embodiment, R$^6$ is methyl. In yet another specific embodiment, R$^6$ is C$_1$-C$_6$ haloalkyl. In more specific embodiments, R$^6$ is C$_1$-C$_3$ haloalkyl. In another specific embodiment, R$^6$ is C$_1$-C$_3$ fluoroalkyl. In a more specific embodiment, the fluoroalkyl is a trifluoromethyl (—CF$_3$) or —CH$_2$CH$_2$CF$_3$. In another specific embodiment, R$^6$ is trifluoromethyl (—CF$_3$). In still another specific embodiment, R$^6$ is —CH$_2$CF$_2$CF$_3$. In yet another particular embodiment, R$^6$ is halo. In a more particular embodiment, R$^6$ is chloro, bromo, or iodo. In still another particular embodiment, R$^6$ is chloro. In yet another particular embodiment, R$^6$ is bromo. In yet another particular embodiment, R$^6$ is iodo.

In further particular embodiments, the compound of structure (IIA) is an isolated R form.

In further particular embodiments, the compound of structure (IIA) is an isolated S form.

In certain specific embodiments, PPQ compounds of structure (II), substructure (IIA), are as follows:

| Compound Designation | Compound Structure | Compound Name |
|---|---|---|
| PPQ-4 | 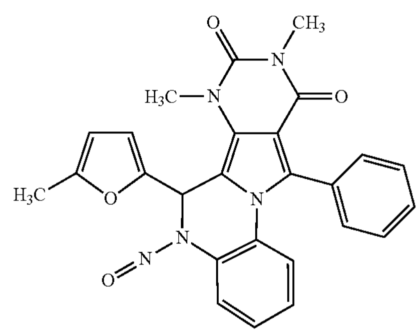 [SMILES: Cc1ccc(C2c3c4c(c(-c5ccccc5)n3-c3ccccc3N2N=O)c(=O)n(C)c(=O)n4C)o1] | 7,9-Dimethyl-6-(5-methylfuran-2-yl)-5-nitroso-11-phenyl-5,6-dihydropyrimido[4',5'-3,4] pyrrolo[1,2-a]quinoxaline-8,10-(7H,9H)-dione |
| PPQ-5 | 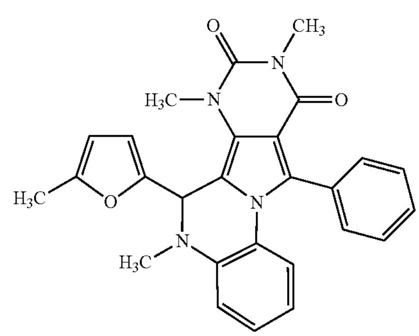 [SMILES: Cc1ccc(C2c3c4c(c(-c5ccccc5)n3-c3ccccc3N2C)c(=O)n(C)c(=O)n4C)o1] | 5,7,9-Trimethyl-6-(5-methylfuran-2-yl)-11-phenyl-5,6-dihydropyrimido [4',5'-3,4] pyrrolo[1,2-a]quinoxaline-8,10-(7H,9H)-dione |

-continued

| Compound Designation | Compound Structure | Compound Name |
|---|---|---|
| PPQ-6 | 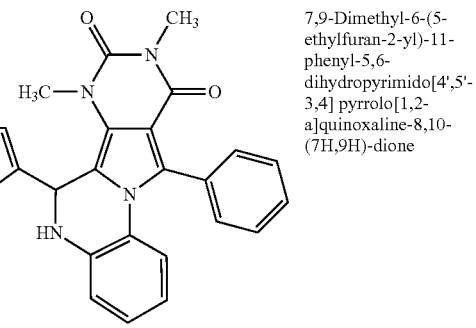 | 7,9-Dimethyl-6-(5-ethylfuran-2-yl)-11-phenyl-5,6-dihydropyrimido[4',5'-3,4] pyrrolo[1,2-a]quinoxaline-8,10-(7H,9H)-dione |
| PPQ-7 | 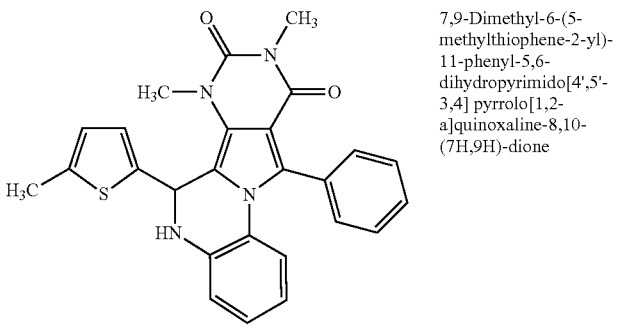 | 7,9-Dimethyl-6-(5-methylthiophene-2-yl)-11-phenyl-5,6-dihydropyrimido[4',5'-3,4] pyrrolo[1,2-a]quinoxaline-8,10-(7H,9H)-dione |
| PPQ-8 | 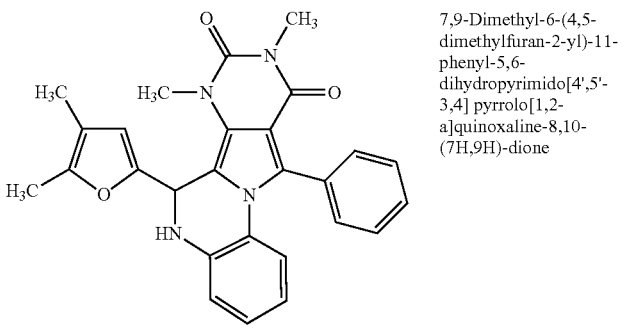 | 7,9-Dimethyl-6-(4,5-dimethylfuran-2-yl)-11-phenyl-5,6-dihydropyrimido[4',5'-3,4] pyrrolo[1,2-a]quinoxaline-8,10-(7H,9H)-dione |
| PPQ-9 | 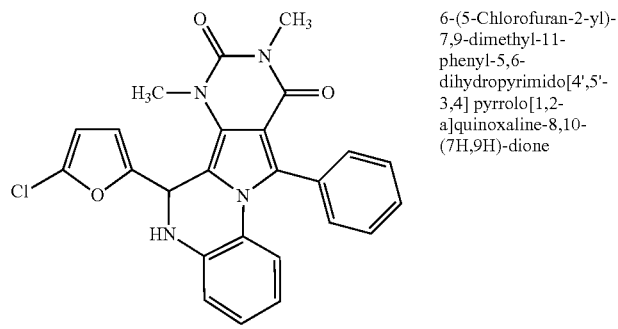 | 6-(5-Chlorofuran-2-yl)-7,9-dimethyl-11-phenyl-5,6-dihydropyrimido[4',5'-3,4] pyrrolo[1,2-a]quinoxaline-8,10-(7H,9H)-dione |

-continued

| Compound Designation | Compound Structure | Compound Name |
|---|---|---|
| PPQ-10 | 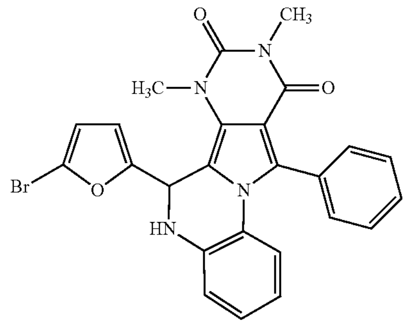 [SMILES: Cn1c(=O)c2c(-c3ccccc3)n3c(c2n(C)c1=O)C(c1ccc(Br)o1)Nc1ccccc1-3] | 6-(5-Bromofuran-2-yl)-7,9-dimethyl-11-phenyl-5,6-dihydropyrimido[4',5'-3,4] pyrrolo[1,2-a]quinoxaline-8,10-(7H,9H)-dione |
| PPQ-11 | 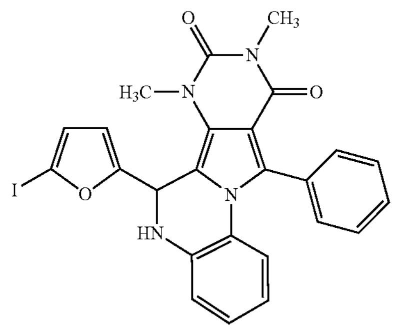 | 7,9-Dimethyl-6-(5-iodofuran-2-yl)-11-phenyl-5,6-dihydropyrimido[4',5'-3,4]pyrrolo[1,2-a]quinoxaline-8,10-(7H,9H)-dione |
| PPQ-12 | 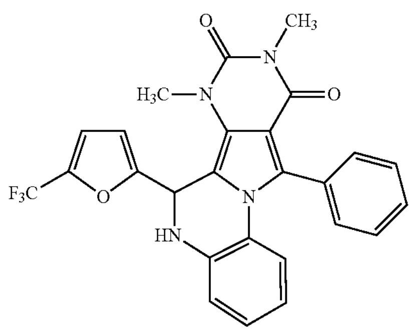 [SMILES: Cn1c(=O)c2c(-c3ccccc3)n3c(c2n(C)c1=O)C(c1ccc(C(F)(F)F)o1)Nc1ccccc1-3] | 7,9-Dimethyl-11-phenyl-6-(5-trifluoromethylfuran-2-yl)-5,6-dihydropyrimido[4',5'-3,4] pyrrolo[1,2-a]quinoxaline-8,10-(7H,9H)-dione |
| PPQ-23 | 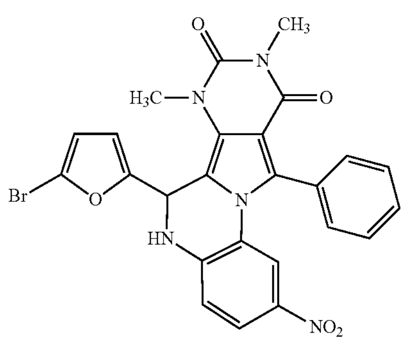 [SMILES: Cn1c(=O)c2c(-c3ccccc3)n3c(c2n(C)c1=O)C(c1ccc(Br)o1)Nc1ccc([N+](=O)[O-])cc1-3] | 6-(5-Bromofuran-2-yl)-7,9-dimethyl-2-nitro-11-phenyl-5,6-dihydropyrimido[4',5'-3,4] pyrrolo[1,2-a]quinoxaline-8,10-(7H,9H)-dione |

As discussed in greater detail herein, also provided are pharmaceutical compositions comprising any one or more of the above-described BPO (i.e., the compounds of structure I and substructures (Ia(i)), (Ib(i)), (IA), (IA1), (IB), (IB 1), (IC), (IC1), and specific compounds) and PPQ compounds (i.e., the compounds of structure (II), substructure IIA, and specific compounds) and a pharmaceutically (i.e., physiologically) suitable (i.e., acceptable) excipient (such as a diluent, carrier, or adjuvant). The BPO and PPQ compounds having the structures described herein are capable of inhibiting (i.e., slowing, retarding, decreasing, reducing) CFTR-mediated ion transport (i.e., inhibiting in a statistically significant, clinically significant, and/or biologically significant manner), for example, inhibiting CFTR-mediated chloride ion (i.e., Cl−) transport. In other embodiments provided herein, the BPO and PPQ compounds and compositions comprising these compounds described above and herein may be used in methods for treating a disease, condition, or disorder that is treatable by inhibiting CFTR-mediated ion transport. Exemplary diseases, conditions, and disorders include, but are not limited to, polycystic kidney disease (PKD or PCKD) (including autosomal dominant PKD and autosomal recessive PKD), aberrantly increased intestinal fluid secretion, and secretory diarrhea. In particular embodiments, the BPO and PPQ compounds and compositions comprising any one or more of the BPO and PPQ compounds may be used in methods for inhibiting (i.e., preventing, delaying, slowing, retarding) cyst formation (i.e., reducing the likelihood of occurrence of one or more cysts forming) and/or inhibiting cyst enlargement or expansion (i.e., slowing, reducing, preventing, retarding, reversing, decreasing cyst enlargement or expansion), particularly inhibiting cyst formation or inhibiting cyst enlargement in one or both kidneys of a human or non-human animal. Inhibiting cyst enlargement or expansion may thus reduce or decrease the volume of one or more fluid-filled cysts. Each of these methods and uses is described in greater detail herein.

Definitions

Certain chemical groups named herein are preceded by a shorthand notation indicating the total number of carbon atoms that are to be found in the indicated chemical group. For example, $C_{1-6}$ alkyl (or $C_1$-$C_6$ alkyl) describes an alkyl group, as defined below, has a total of 1, 2, 3, 4, 5, or 6 carbon atoms. Similarly, $C_{1-3}$ alkyl (or $C_1$-$C_3$ alkyl) describes an alkyl group, as defined below, has a total of 1, 2, or 3 carbon atoms. By way of additional example, $C_{1-20}$ alkyl (or $C_1$-$C_{20}$ alkyl) describes an alkyl group, as defined below, has a total of any number of carbon atoms between 1 and 20 (i.e., 1, 2, 3, 4, 5, 6, 7, 8, 9, 10, 11, 12, 13, 14 15, 16, 17, 18, 19, or 20 carbon atoms). The total number of carbons in the shorthand notation does not include carbons that may exist in substituents of the group described. In addition to the foregoing, as used herein, unless specified to the contrary, the following terms have the meaning indicated.

"Alkyl" means a straight chain or branched, noncyclic or cyclic, saturated aliphatic hydrocarbon containing from 1 to 20 carbon atoms, while the terms "$C_{1-6}$ alkyl" and "$C_{1-3}$ alkyl" have the same meaning as alkyl but contain from 1 to 6 carbon atoms or 1 to 3 carbon atoms, respectively. Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, isopentyl, and the like. Representative saturated cyclic alkyls (e.g., $C_{3-20}$ cycloalkyl) include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like. Cyclic alkyls, also referred to as "homocyclic rings," include di- and poly-homocyclic rings such as decalin and adamantyl. A straight or branched hydrocarbon chain radical group may contain at least one double or triple bond between adjacent carbon atoms (referred to as an "alkenyl" or "alkynyl," respectively). Representative straight chain and branched alkenyls (e.g., $C_{2-6}$ alkenyl) include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; representative straight chain and branched alkynyls include acetylenyl, propynyl, 1-butynyl, 2-butynyl, 1-pentynyl, 2-pentynyl, 3-methyl-1 butynyl, and the like. Unless otherwise specified, it is understood that within the context of the current disclosure, the term "alkyl" can be optionally substituted, i.e., "optionally substituted alkyl" encompasses unsubstituted alkyl and substituted alkyl as defined herein.

As used herein, the term "substituted" in the context of alkyl, alkenyl, aryl, heteroaryl, and alkoxy means that at least one hydrogen atom of the alky, aryl, and heteroaryl moiety is replaced with a substituent. In the instance of an oxo substituent ("=O") two hydrogen atoms are replaced. A "substituent" as used within the context of this disclosure includes oxo, halogen, hydroxy, cyano, nitro, amino, alkylamino, dialkylamino, alkyl, alkoxy, thioalkyl, haloalkyl, substituted alkyl, heteroalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$ —NR$_a$S(=O)$_2$R$_b$, —OR$_a$, —C(=O) R$_a$—C(=O)OR$_a$, —C(=O)NR$_a$R$_b$, —OCH$_2$C(=O) NR$_a$R$_b$, —OC(=O)NR$_a$R$_b$, —SH, —SR$_a$, —SOR$_a$, —S(=O)$_2$NR$_a$R$_b$, —S(=O)$_2$R$_a$, —SR$_a$C(=O)NR$_a$R$_b$, —OS(=O)$_2$R$_a$ and —S(=O)$_2$OR$_a$, wherein R$_a$ and R$_b$ are the same or different and independently hydrogen, alkyl, haloalkyl, substituted alkyl, alkoxy, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl. As used herein and according to chemistry convention, the formula —C(=O)— may also be represented as —C(O)—, or —S(=O)$_2$— may be represented as —S(O)$_2$—. By way of example, —C(=O)R$_a$ has the same meaning as —C(O)R$_a$.

Representative substituents include (but are not limited to) alkoxy (i.e., alkyl-O—, e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, alkyloxycarbonyloxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonyl-phenylthio), amino (e.g., amino, mono- and di- $C_{1-3}$ alkanylamino, methylphenylamino, methylbenzylamino, $C_{1-3}$ alkanylamido, acylamino, carbamamido, ureido, guanidino, nitro and cyano). Moreover, any substituent may have from 1-5 further substituents attached thereto.

"Alkenyl" refers to a straight or branched, noncyclic or cyclic, hydrocarbon radical group consisting solely of carbon and hydrogen atoms, containing at least one double bond, and having from two to twelve carbon atoms. In certain embodiments, an alkenyl may comprise two to eight carbon atoms. In other embodiments, an alkenyl may comprise two to six carbon atoms (i.e., $C_2$-$C_6$ alkenyl). In other embodiments, an alkenyl may comprise two to four carbon atoms. The alkenyl is connected to the rest of the molecule by a single bond, for example, ethenyl (i.e., vinyl), prop-1-enyl (i.e., allyl), but-1-enyl, pent-1-enyl, penta-1,4-dienyl, and the like. Representative straight chain and branched alkenyls (e.g., $C_{2-6}$ alkenyl) include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. Representative unsaturated cyclic alkyls include cyclopentenyl and cyclohexenyl, and the like. Unless otherwise specified, it is understood that within the context of the current disclosure, the term "alkenyl" can be optionally substituted, i.e., "optionally substituted alkenyl" encompasses unsubstituted alkyl and substituted alkenyl as defined herein.

"Aryl" refers to aromatic monocyclic or multicyclic hydrocarbon ring system consisting only of hydrogen and carbon and containing from six to eighteen carbon atoms, where the ring system may be partially or fully saturated. Aryl groups include, but are not limited to, groups such as fluorenyl, phenyl and naphthyl. Unless otherwise specified, it is understood that within the context of the current disclosure, the term "aryl" can be optionally substituted, i.e., "optionally substituted aryl" encompasses unsubstituted aryl and substituted aryl (e.g., substituted phenyl) as defined herein.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heteroaryl" means an aromatic heterocycle ring of 5- to 10 members and having at least one heteroatom selected from nitrogen, oxygen and sulfur, and containing at least 1 carbon atom, including monocyclic, bicyclic and tricyclic ring systems. A fused heteroaryl (e.g., a bicyclic heteroaryl) contains at least one aromatic ring, which may be a benzo ring (e.g., benzofuranyl, 1,3-benzodioxolyl or indolyl). Representative heteroaryls are furanyl, benzofuranyl, thienyl, benzothienyl, 1,3-benzodioxolyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. Unless otherwise specified, it is understood that within the context of the current disclosure, the term "heteroaryl" can be optionally substituted, i.e., "optionally substituted heteroaryl" encompasses unsubstituted heteroaryl and substituted heteroaryl (e.g., substituted furanyl) as defined herein.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Halogen" or "halo" means fluoro (F), chloro (Cl), bromo (B), and iodo (I).

"Alkoxy" refers to the radical: —O-alkyl, such as methoxy, ethoxy, and the like. $C_{1-6}$alkoxy means that the alkyl moiety is $C_{1-6}$ alkyl.

A saccharide includes any monosaccharide, disaccharide, trisaccharide, or polysaccharide. In particular embodiments, such a saccharide contributes to the polarity of the compound. Exemplary saccharides include those to which a host is commonly exposed and thereby has reduced immunogenicity in the host subject.

"Amino acid residue" refers to the portion of an amino acid that remains after losing a water molecule (or alcohol) when the amino acid is condensed with a molecule. Typically, an amino acid is condensed with a molecule, including a compound of any of structure (I) or (II) (or substructures or specific structures), by forming a peptide bond. In certain embodiments, the amino functional group of the amino acid can be condensed with a carboxylic acid group or its reactive equivalent (e.g., carboxylic anhydride) of the molecule. In other embodiments, the carboxylic acid functional group of the amino acid can be condensed with an amine group of the molecule. Typically, a molecule of water is lost during the formation of the peptide bond. Examples of the "amino acid residues" include, but are not limited to, residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine, 3,5-diiodotyrosine, glycosylated threonine, glycosylated serine, and glycosylated asparagine. A "peptide" as used herein consists of any number of amino acids between 2 and 6 (i.e., 2, 3, 4, 5, or 6 amino acids) linked together by peptide bonds. At least one terminal end of the peptide has an amino acid residue as defined above that is capable of being covalently linked to the compound. As commonly used in the art, the term "dipeptide" refers to a peptide that has two amino acids, and "tripeptide" refers to a peptide that has three amino acids. A single amino acid residue or peptide may be bonded to any compound described herein to facilitate (i.e., promote) or to improve the capability of the compound to enter a cell (e.g., an enterocyte). In other words the amino acid residue or peptide may bind to a molecule (e.g., a cell receptor) that is present on the outer cell membrane and which may facilitate (i.e., promote) uptake or enhance uptake of the compound.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of compounds of Structures I and II and substructures thereof, as well as any and all substructures and specific compounds described herein is intended to encompass any and all pharmaceutically suitable salt forms.

Compounds of Structures I and II and substructures thereof may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt.

"Prodrug" is meant to indicate a compound that may be converted under physiological conditions or by solvolysis to a biologically active compound as described herein. Thus, the term "prodrug" refers to a metabolic precursor of a BPO or PPQ compound that is pharmaceutically acceptable. A prodrug may be inactive when administered to a subject in need thereof, but is converted in vivo to an active compound. Prodrugs are typically rapidly transformed in vivo to yield the parent compound, for example, by hydrolysis in blood. The prodrug compound often offers advantages of solubility, druggability, tissue compatibility or delayed release in a mammalian organism (see, e.g., Bundgard, H., Design of Prodrugs (1985), pp. 7-9, 21-24 (Elsevier, Amsterdam).

A discussion of prodrugs is also provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a subject. Prodrugs of a compound described herein may be prepared by modifying functional groups present in the compound in such a way that the modifications are cleaved, either in routine manipulation or in vivo, to the parent compound. Prodrugs include compounds described herein, wherein a hydroxy, amino, or mercapto group is bonded to any group that, when the prodrug of the compound is administered to a subject, cleaves to form a free hydroxy, free amino, or free mercapto group, respectively. Examples of prodrugs include, but are not limited to, acetate, formate, and benzoate derivatives of alcohol or amine functional groups in the compounds and the like.

With regard to stereoisomers, the compounds of structure (I) and structure (II), as well as any sub-structure herein (e.g., IA, IB, IC, IIA and other substructures), may have one or more chiral (or asymmetric) centers, for example, at the 6 position of the pyrimido[4',5'-3,4]pyrrolo[1,2-a]quinoxaline ring system, and may thus give rise to enantiomers, diastereomers, and other stereoisomeric forms that may be defined, in terms of absolute stereochemistry, as (R)— or (S)—, at a given chiral center.

Using structure (I) as an example, unless otherwise specified, the compounds of structure (I) (and Structure (II)) are not limited to any absolute stereochemistry. Thus, all possible isomers, including diastereomers and racemates, as well as optically pure forms (as isolated R or S form), and all tautomeric forms are intended to be included.

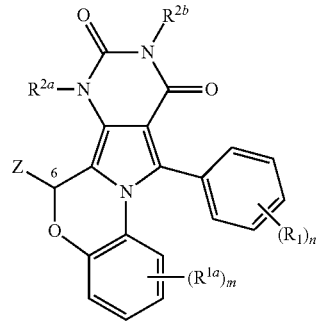

Structure (I)

It is further specifically contemplated that "enantiomers," which refers to two stereoisomers whose molecules are non-superimposeable mirror images of one another, may be isolated in either R or S form (shown below). As used herein, an isolated enantiomer (i.e., an isolated R or S form) has an enantiomeric excess, which is defined as the absolute difference between the mole fraction of the isolated enantiomer and its opposite enantiomer, wherein the mole fraction of the isolated enantiomer is of at least 85%, at least 90%, at least 95%, at least 98%, or at least 99%, or 100%.

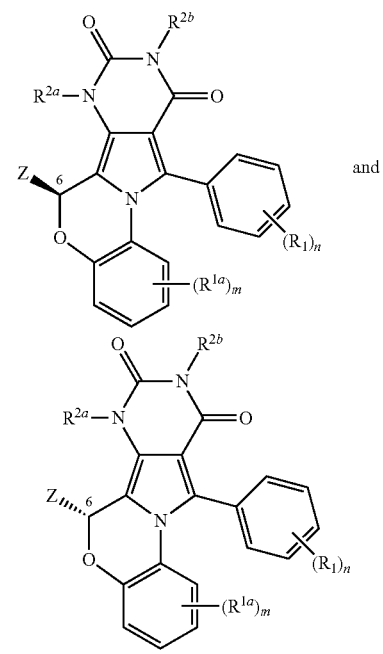

Structure (I) as Isolated Enantiomers

When the compounds described herein contain olefinic double bonds or other centers of geometric asymmetry, and unless specified otherwise, it is intended that the compounds may be an isolated E or an isolated Z or a mixture of both E and Z geometric isomers (e.g., cis or trans).

Furthermore, some of the crystalline forms of any compound described herein may exist as polymorphs, which are also included and contemplated by the present disclosure. In addition, some of the compounds may form solvates with water or other organic solvents. Such solvates are similarly included within the scope of compounds and compositions described herein.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomon, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

Preparation of the BPO Compounds

The following General Reaction Schemes illustrate methods to make compounds of this disclosure, i.e., compounds of structures (I), (Ia(i)), (Ib(i)), (IA), (IB), (IC),

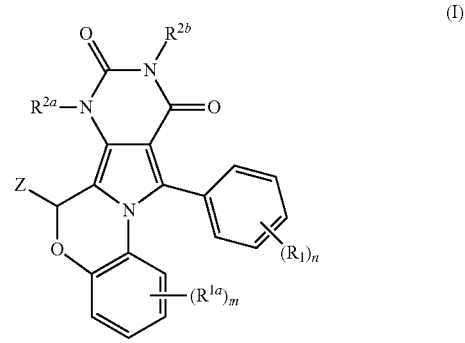

(I)

wherein $R^1$, $R^{1a}$, $R^{2a}$, $R^{2b}$, $R^{4a}$, $R^7$, Z are described above, as an isolated enantiomer or a racemic mixture thereof, or a pharmaceutically acceptable salt thereof. It is understood that in the following Reaction Schemes, combinations of substituents and/or variables of the depicted structures are permissible only if such contributions result in stable compounds.

General Reaction Scheme (I)

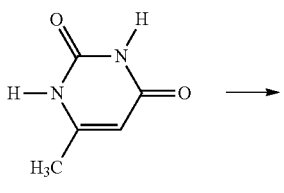

1

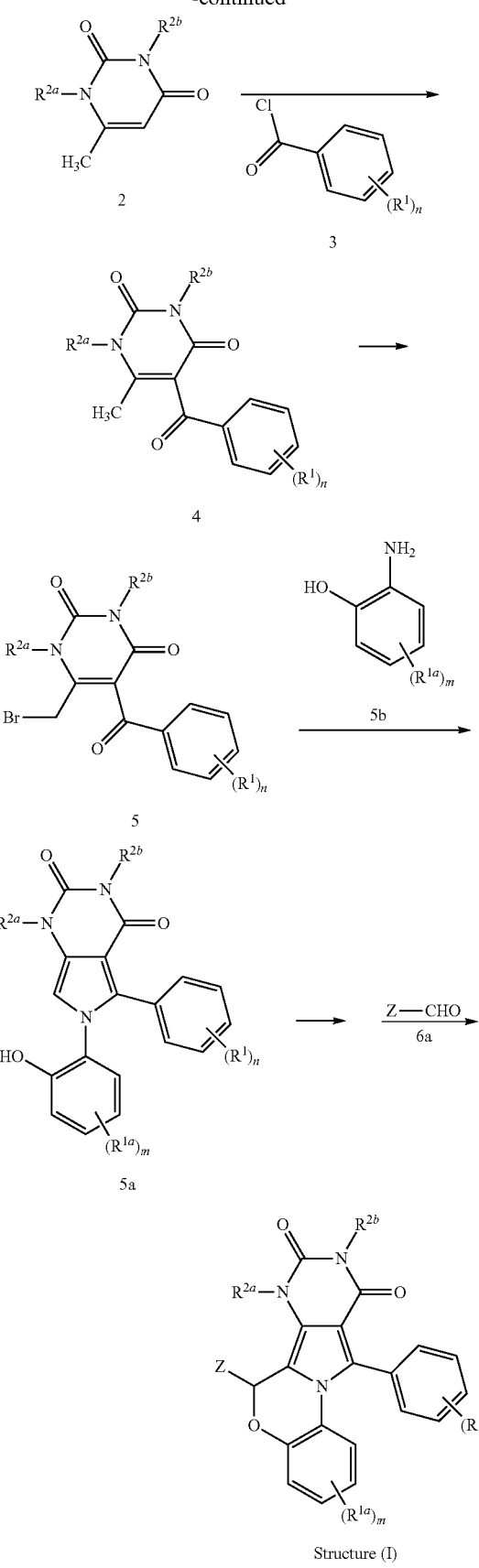

Structure (I)

Generally speaking, commercially available 6-methyluracil (1) can be first alkylated to provide 1,3-dialkyl6-methyluracil (2). Suitable alkylating agents include, for example, alkylsulfate, etc. In particular embodiments, the alkylation is methylation and the exemplary alkylating agents include dimethylsulfate, iodomethane, etc. Thereafter, 1,3-dialkyl-6-methyluracil (2) is further acylated to provide ketone 4 via, e.g., a Friedel-Crafts mechanism, in the presence of an appropriately substituted benzoyl chloride (3) and a Lewis acid catalyst (e.g., ZnCl). Ketone (4) can then be brominated to provide compound (5). Reaction of compound (5) and an appropriately substituted 2-aminophenol (5b) provides a ring-condensed product (5a). Compound (5a) can be combined with a formyl-substituted heteroaryl (furanyl or thienyl group) or a formyl-substituted aryl (6a) to produce a ring-condensed product represented by Structure (I).

In certain embodiments, the ring-condensed product is a racemic mixture of enantiomers. Separation of the enantiomers may be carried out by chiral Supercritical Fluid Chromatography (SFC). The isolated enantiomer may be amorphous and can be further crystallized according to known methods in the art. The absolute enantiomer structure can be determined by X-ray crystallography. For compounds having a carboxylic acid substituent (e.g., BPO-27), a suitable salt, amide or ester may be formed prior to crystallization in order to obtain crystals of sufficient quality for X-ray crystallography.

Preparation of the PPQ Compounds

The following General Reaction Schemes illustrate methods to make compounds of this disclosure, i.e., compounds of structures (II) and (IIA):

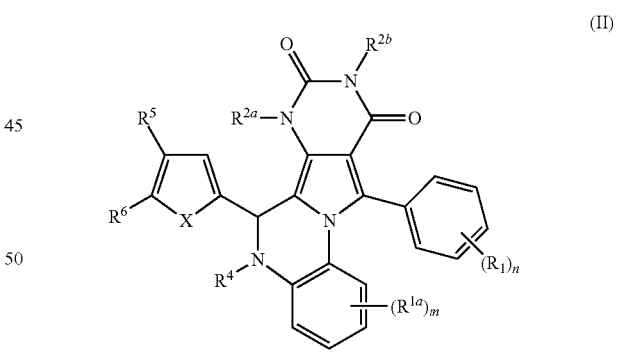

wherein $R^1$, $R^{1a}$, $R^{2a}$, $R^{2b}$, $R^{4a}$, $R^5$, $R^6$, $R^7$, and X are described above in the Brief Summary, as an isolated enantiomer or a racemic mixture thereof, or a pharmaceutically acceptable salt thereof. It is understood that in the following Reaction Schemes, combinations of substituents and/or variables of the depicted structures are permissible only if such contributions result in stable compounds.

General Reaction Scheme (II)

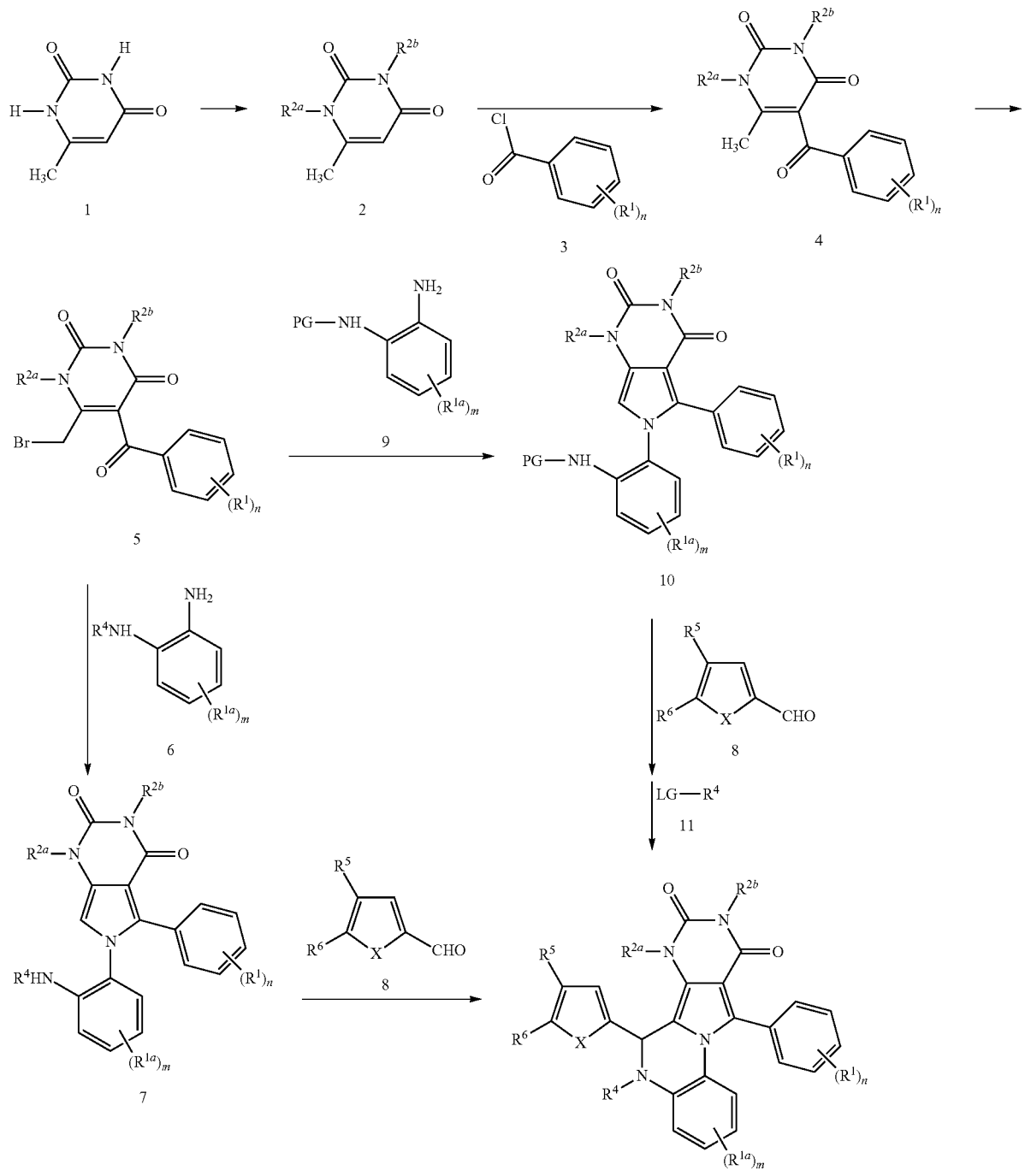

PG = hydrogen or protecting group
LG = leaving group

Generally speaking, commercially available 6-methyluracil (1) can be first alkylated to provide 1,3-dialkyl6-methyluracil (2). Suitable alkylating agents include, for example, alkylsulfate, etc. In particular embodiments, the alkylation is methylation and the exemplary alkylating agents include dimethylsulfate, iodomethane, etc. Thereafter, 1,3-dialkyl-6-methyluracil (2) is further acylated to provide ketone (4) via, e.g., a Friedel-Crafts mechanism, in the presence of an appropriately substituted benzoyl chloride (3) and a Lewis acid catalyst (e.g., ZnCl). Ketone (4) can then be brominated to provide compound (5).

Reaction of compound (5) and an appropriately substituted (including N-substituted) phenylenediamine (6) provides compound (7) following a ring-closure step. Compound (7)

may further react with a formyl-substituted furanyl or thienyl compound (8) to provide a compound of Structure (II).

Alternatively, compound (5) may undergo a ring-closure step by first reacting with an optionally protected phenylenediamine (9) to provide compound (10). If protected, the amino group of (10) may be deprotected through conventional methods (e.g., hydrolysis) prior to reacting with a formyl-substituted furanyl or thienyl group (8). Thereafter, an $R^4$ group (e.g., alkyl, nitroso) may be introduced in the form of $R^4$-LG (LG being a leaving group) to produce a ring-condensed product represented by Structure (II).

Methods of Using and Characterizing BPO and PPQ Compounds and Compositions Comprising the Compounds As described in greater detail herein, pharmaceutical compositions are provided, wherein the pharmaceutical compositions comprise a pharmaceutically suitable excipient (i.e., a pharmaceutically acceptable excipient or a physiologically suitable or acceptable excipient) and at least one of the BPO or PPQ compounds of any one of the structures, substructures, and specific structures described herein, including a compound of structure I and substructures (Ia(i)), (Ib(i)), (IA), (IA1), (IB), (IB1), (IC), (IC1), and specific compounds, and/or a compound of structure (II), substructure IIA, and specific compounds. The BPO and PPQ compounds described herein are capable of inhibiting CFTR activity (i.e., inhibiting, reducing, decreasing, or blocking transport of chloride ion in the CFTR channel or pore in a statistically, clinically and/or biologically significant manner) in a cell and therefore may be used for treating diseases, disorders, and conditions that are treatable by inhibiting CFTR activity. Such diseases, disorder, and conditions include those that result from or are related to aberrantly increased CFTR activity. Accordingly, methods of inhibiting ion transport (e.g., inhibiting chloride ion transport) by CFTR are provided herein.

Also as described herein, the BPO and PPQ compounds of structure I or structure II (and substructures thereof) that are CFTR inhibitors are useful in the treatment of a CFTR-mediated or -associated condition, i.e., any condition, disorder, or disease, that results from activity of CFTR, such as CFTR-mediated ion transport. The condition, disorder, or disease may result from aberrantly increased CFTR activity, particularly aberrantly increased CFTR-mediated ion transport. These conditions, disorders, and diseases, are thus amenable to treatment by inhibiting CFTR activity, e.g., inhibiting CFTR-mediated ion, such as chloride ion, transport.

Accordingly, methods are provided for treating a disease, disorder, or condition that is treatable by inhibiting CFTR-mediated ion transport. In certain embodiments, methods are provided for inhibiting cyst formation and/or cyst enlargement, particularly kidney cyst formation or enlargement. These methods are described in greater detail below and herein.

The BPO and PPQ compounds described herein are capable of blocking or impeding the CFTR pore or channel and inhibiting ion transport (e.g., inhibiting chloride ion (Cl⁻) transport (also referred to as inhibiting chloride ion conductance)) by CFTR, which is located in the outer cell membrane of a cell. Provided herein are methods of inhibiting ion transport by CFTR, which methods comprise contacting a cell that has CFTR located in its outer membrane with any one or more of the BPO or PPQ compounds described herein, thus permitting CFTR and the compound or compounds to interact. Interaction of a BPO or PPQ compound described herein results in binding to CFTR, thereby inhibiting chloride ion transport.

In one embodiment, a method is provided for inhibiting (i.e., preventing, retarding, slowing, impeding) cyst formation and/or for inhibiting (i.e., preventing, retarding, slowing, impeding) or reducing cyst enlargement, or reducing the size and/or volume of one or more cysts, which method comprises contacting (a) a cell that comprises CFTR and (b) at least one BPO or PPQ compound as described herein, under conditions and for a time sufficient for CFTR and the compound to interact, wherein the compound inhibits ion (e.g., chloride ion) transport by CFTR, (i.e., the compound inhibits CFTR-mediated ion transport in a statistically significant, clinically significant, and/or biologically significant manner). In particular embodiments, the cyst formation or cyst enlargement that is inhibited is kidney cyst formation or kidney cyst enlargement (i.e., cyst formation or cyst enlargement in at least one kidney is inhibited).

Inhibiting kidney cyst formation and/or cyst enlargement by the BPO and PPQ compounds described herein is useful for treating a patient who has been diagnosed with or who is at risk of developing polycystic kidney disease. Accordingly, methods are provided herein for treating polycystic kidney disease, which methods comprise administering to a subject in need thereof (a) a pharmaceutically suitable excipient and (b) at least one of the BPO or PPQ compounds (i.e., the compounds of structure I and substructures (Ia(i)), (Ib(i)), (IA), (IA1), (IB), (IB1), (IC), (IC1), and specific compounds and the compounds of structure (II), substructures IIA, and specific compounds) as described herein (i.e., a pharmaceutical composition as described herein). In a specific embodiment, polycystic kidney disease is autosomal dominant polycystic kidney disease. In another specific embodiment, polycystic kidney disease is autosomal recessive polycystic kidney disease.

In another embodiment, a method for treating a disease, disorder, or condition that is treatable by inhibiting CFTR-mediated ion transport includes a disease, disorder, or condition that is associated with aberrantly increased CFTR-mediated ion transport. Accordingly, in a specific embodiment, a method is provided for treating a disease, condition, or disorder associated with aberrantly increased ion transport by cystic fibrosis transmembrane conductance regulator (CFTR), wherein the method comprises administering to a subject in need thereof a pharmaceutically suitable excipient and at least one of the BPO or PPQ compounds described herein (i.e., a pharmaceutical composition as described herein), wherein ion transport mediated by CFTR is inhibited. In a specific embodiment, the disease, condition, or disorder is aberrantly increased intestinal fluid secretion, which may be acute aberrantly increased intestinal fluid secretion.

In another embodiment, the BPO and PPQ compounds of structure I and structure II, respectively (and substructures and specific compounds thereof) are used in the treatment of conditions associated with aberrantly increased intestinal fluid secretion, particularly acute aberrantly increased intestinal fluid secretion, including secretory diarrhea. Diarrhea amenable to treatment using any one of the BPO or PPQ compounds described herein can result from exposure to a variety of agents or pathogens, including those that cause an enteropathogenic infection. In a more specific embodiment, secretory diarrhea is caused by an enteric pathogen. Exemplary enteric pathogens include without limitation, *Vibrio cholerae, Escherichia coli*, (particularly enterotoxigenic *E. coli* (ETEC)), *Shigella, Salmonella, Campylobacter* (including *Campylobacter jejuni*), *Clostridium difficile*, parasites (e.g., *Giardia* (e.g., *Giardia lamblia*), *Entamoeba histolytica, Cryptosporidium, Cyclospora*), or diarrheal viruses (e.g., rotavirus). Secretory diarrhea resulting from increased intestinal fluid secretion mediated by CFTR may also be a disorder or sequelae associated with food poisoning, or exposure to a toxin including but not limited to a bacterial enterotoxin such as cholera toxin (*V. cholera*), a *E. coli* toxin, a *Salmonella* toxin, a *Campylobacter* toxin, or a *Shigella* toxin, or any other bacterial toxin that causes aberrantly increased intestinal fluid secretion.

Other secretory diarrheas that may be treated by administering any one or more of the BPO and PPQ compounds described herein include diarrhea associated with or that is a sequelae of AIDS; diarrhea that is a condition related to the effects of anti-AIDS medications such as protease inhibitors; diarrhea that is a condition of or is related to administration of chemotherapeutic compounds; inflammatory gastrointestinal disorders, such as ulcerative colitis, inflammatory bowel disease (IBD), Crohn's disease, diverticulosis, and the like. Intestinal inflammation modulates the expression of three major mediators of intestinal salt transport and may contribute to diarrhea in ulcerative colitis both by increasing transepithelial Cl⁻ secretion and by inhibiting the epithelial NaCl absorption (see, e.g., Lohi et al., *Am. J. Physiol. Gastrointest. Liver Physiol.* 283:G567-75 (2002)). Thus, one or more of the BPO and PPQ compounds of structure I or structure II and substructures thereof, and specific structures as described herein, may be administered in an amount effective to inhibit CFTR ion transport and, thus, decrease intestinal fluid secretion.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide the BPO and/or PPQ compound in an amount sufficient to provide therapeutic and/or prophylactic benefit. Therapeutic and/or prophylactic benefit resulting from therapeutic treatment and/ or prophylactic or preventative measures includes, for example, an improved clinical outcome, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder, and those in which the disease, condition, or disorder is to be prevented (i.e., decreasing the likelihood of occurrence of the disease, disorder, or condition).

Other embodiments provided herein include use of at least one of the BPO and PPQ compounds of structure I, structure II, substructures, and specific structures as described herein for treating any one of the diseases or disorders described herein (e.g., polycystic kidney disease, aberrantly increased intestinal fluid secretion, secretory diarrhea) that is treatable by inhibiting ion transport (e.g., chloride ion transport) by CFTR. In one embodiment, a use is provided for the preparation of a medicament for treating any one of the diseases, conditions or disorders described herein (e.g., polycystic kidney disease, aberrantly increased intestinal fluid secretion, secretory diarrhea) that is treatable by inhibiting ion transport (e.g., chloride ion transport) by CFTR.

In other embodiments, methods are provided for treating a disease, disorder, or condition described herein (including but not limited to PCKD, secretory diarrhea or other condition associated with aberrantly increased intestinal fluid secretion). Such methods comprise administering the compound or a pharmaceutical composition that comprises at least one BPO or PPQ compound and a pharmaceutically suitable (i.e., pharmaceutically acceptable, or physiologically suitable or acceptable) excipient in combination with, either in the same composition or in a separate (or second) composition, at least one thiazolidinone compound and/or at least one glycine hydrazide compound that inhibit CFTR-mediated ion transport (see, e.g., U.S. Pat. Nos. 7,235,573; 7,414,037; U.S. Patent Application Publication No. 2008/0064666; International Patent Application Publication No. WO 2008/079897; U.S. Patent Application Publication No. US2009/0253799; International Patent Application No. PCT/US2009/038292, which are hereby incorporated by reference in their entireties) for treating any one of the diseases or disorders described herein that is treatable by inhibiting ion transport (e.g., chloride ion transport) by CFTR. When a first composition comprising at least one BPO or PPQ compound described herein and a second composition comprising at least one thiazolidinone compound and/or at least one glycine hydrazide compound is administered to a subject in need thereof, the first composition may be administered prior to, concurrently with, or subsequent to administration of the second composition.

In particular embodiments of the methods described herein, the subject is a human or non-human animal. A subject in need of the treatments described herein may exhibit symptoms or sequelae of a disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

In another embodiment, a method is provided for inhibiting ion transport by a cystic fibrosis transmembrane conductance regulator (CFTR) comprising contacting (a) a cell that comprises CFTR and (b) at least one of the compounds of structure I or structure II, substructures, and specific structures described herein, under conditions and for a time sufficient that permit CFTR and the compound to interact, thereby inhibiting ion transport (e.g., chloride ion transport) by CFTR, that is, inhibiting CFTR-mediated ion transport.

In another embodiment, a method is provided for treating secretory diarrhea comprising administering to a subject in need thereof a pharmaceutically acceptable excipient and at least one of the compounds of structure I or structure II, substructures, and specific structures described herein (i.e., a pharmaceutical composition as described herein). In a particular embodiment, the subject is a human or non-human animal.

The pharmaceutical compositions and methods of using the PPQ compounds and compositions comprising these compounds are described in greater detail herein.

Methods for Characterizing and Using the BPO and PPQ Compounds

Also provided herein are methods that are useful, for example, for characterizing the potency of BPO and PPQ compounds (and derivatives and analogs thereof) to inhibit CFTR-mediated ion transport (particularly CFTR-mediated chloride ion transport); for monitoring the level (i.e., for example, concentration level, mass level, or $IC_{50}$ level) of a BPO or PPQ compound that has been administered to a subject; and examining disease pathogenesis in cystic fibrosis by blocking or inhibiting CFTR function as models for cystic fibrosis disease, such as in ex vivo tissues (e.g., human tissues) and in animals.

In certain embodiments, these methods may be performed in vitro, such as with using a biological sample as described herein that comprises, for example, cells obtained from a tissue, body fluid, or culture-adapted cell line, or other biological source as described in detail herein below. The step of contacting refers to combining, mixing, or in some manner familiar to persons skilled in the art that permits the compound and the cell to interact such that any effect of the compound on CFTR activity (e.g., the capability of a BPO or PPQ compound to inhibit CFTR ion transport or the level to which the compound inhibits CFTR ion transport) can be measured according to methods described herein and routinely practiced in the art. Methods described herein for inhibiting ion transport by CFTR are understood to be performed under conditions and for a time sufficient that permit the CFTR and the compound to interact. Additional BPO and PPQ compounds may be identified and/or characterized by such a method of inhibiting ion transport by CFTR, performed with isolated cells in vitro. Conditions for a particular assay include temperature, buffers (including salts, cations, media), and other components that maintain the integrity of the cell and the compound, which a person skilled in the art will be familiar and/or which can be readily determined. A person skilled in the art also readily appreciates that appropriate controls can be designed and included when performing the in vitro methods and in vivo methods described herein.

In secretory epithelia, fluid secretion occurs by primary chloride exit across the cell apical membrane, which secondarily drives transepithelial sodium and water secretion (see, e.g., Barrett et al., *Annu. Rev. Physiol.* 62:535-72 (2000)). In renal cells, lumenal fluid accumulation causes progressive cyst expansion directly by net water influx into the cyst lumen, and indirectly by stretching cyst wall epithelial cells to promote their division and thinning (Ye et al., *N Engl. J. Med.* 329:310-13 (1993); Sullivan et al., *Physiol. Rev.* 78:1165-91 (1998); Tanner et al., *J. Am. Soc. Nephrol.* 6:1230-41 (1995)). Without wishing to be bound by any particular theory, CFTR inhibition interferes with fluid secretion at the apical chloride exit step.

Methods for characterizing the compounds described herein, for determining an effective concentration to achieve a therapeutic benefit, for monitoring the level of a BPO or PPQ compound in a biological sample, and for other purposes as described herein and apparent to a person skilled in the art, may be performed using techniques and procedures described herein and routinely practiced by a person skilled in the art. Exemplary methods include, but are not limited to, fluorescence cell-based assays of CFTR inhibition (see, e.g., Galietta et al., *J. Physiol.* 281:C1734-C1742 (2001); Ma et al., *J. Clin. Invest.* 110:1651-58 (2002)), short circuit apical chloride ion current measurements and patch-clamp analysis (see, e.g., Muanprasat et al., *J. Gen. Physiol.* 124:125-37 (2004); Ma et al., *J. Clin. Invest.* (2002), supra; Sonawane et al., *FASEB J.* 20:130-32 (2006); see also, e.g., Carmeliet, *Verh. K Acad. Geneeskd. Belg.* 55:5-26 (1993); Hamill et al., *Pflugers Arch.* 391:85-100 (1981)).

Methods that may be used to characterize a BPO or a PPQ compound, including those described herein, and to determine effectiveness of the compound for reducing, inhibiting, or preventing cyst enlargement and/or preventing or inhibiting cyst formation, and which compound is therefore useful for treating a subject who has or who is at risk of developing PKD, include methods described in the art and herein. The PPQ compounds may be analyzed in models using embryonic or neonatal kidney organ cultures, for example (see, e.g., Yang et al., *J. Am. Soc. Nephrol.* 19:1300-1310 (2008); Magenheimer et al., *J. Am. Soc. Nephrol.* 17:3424-37 (2006); Tradtrantip et al., *J. Med. Chem.* 52:6447-55 (2009)). Without wishing to be bound by any particular theory, certain scientific observations support use of CFTR inhibitors to slow cyst growth in autosomal dominant PKD (ADPKD): (a) CFTR is expressed strongly in epithelial cells lining cysts in ADPKD; (b) cystic fibrosis (CFTR-deficient) mice are resistant to cyst formation; (c) CFTR inhibitors block cyst formation in cell/organ culture and in vivo models; and (d) in some families affected with ADPKD and cystic fibrosis, individuals with both ADPKD and CF have less severe renal disease than those with ADPKD only (see, e.g., O'Sullivan et al., *Am. J. Kidney Dis.* 32:976-983 (1998); Cotton et al., *Am. J. Kidney Dis.* 32:1081-1083 (1998); Xu et al., *J. Nephrol.* 19:529-34 (2006)). Intact kidney models to study cystogenesis are useful for recapitulating native kidney anatomy and cellular phenotype (see, e.g., Magenheimer et al., *J. Am. Soc. Nephrol.* 17:3424-3437 (2006)).

An additional example of a cell culture model for determining whether a compound inhibits cyst formation or enlargement includes an MDCK cell (Madin-Darby Canine Kidney Epithelial Cell) model of PKD (Li et al., *Kidney Int* 66:1926-38 (2004); see also, e.g., Neufeld et al., *Kidney Int.* 41:1222-36 (1992); Mangoo-Karim et al., *Proc. Natl. Acad. Sci. USA* 86:6007-6011 (1989); Mangoo-Karim et al., *FASEB J.* 3:2629-32 (1989); Grantham et al., *Trans. Assoc. Am. Physic.* 102:158-62 (1989); Mohamed et al., *Biochem. J.* 322:259-65 (1997)). See also, e.g., Murcia et al., *Kidney Int.* 55:1187-97 (1999); Igarishi et al., *J. Am. Soc. Nephrol.* 13:2384-88 (2002)). Accordingly, provided herein are methods for identifying and/or characterizing BPO and PPQ compounds of structure I or structure II (and substructures and specific structures thereof) by determining the capability of the compound to inhibit cyst enlargement or prevent or inhibit cyst formation in an in vitro cell culture model.

The MDCK cell line may also be used in methods and techniques for determining that a compound lacks cytotoxicity, for example, by evaluating cell viability (e.g., by any one of numerous cell staining methods and microscopy methods routinely practiced in the art), cell proliferation (e.g., by determining the level of incorporation of nucleotide analogs and other methods for measuring division of cells), and/or apoptosis by using any one of a number of techniques and methods known in the art and described herein. Other methods for determining or quantifying the capability of a compound described herein to inhibit or reverse cyst enlargement or expansion and/or to inhibit or prevent cyst formation and/or to reduce the number of cysts formed include an embryonic kidney organ culture model, which is practiced in the art and described herein (see, e.g., Magenheimer et al., *J. Am. Soc. Nephrol.* 17: 3424-37 (2006); Steenhard et al., *J. Am. Soc. Nephrol.* 16:1623-1631 (2005); Yang et al., *J. Am. Soc. Nephrol.* 19:1300-1310 (2008)). In such an embryonic kidney culture model, organotypic growth and differentiation of renal tissue can be monitored in defined media in the absence of any effect or influence by circulating hormones and glomerular filtration (Magenheimer et al., supra; Gupta et al., *Kidney Int* 63:365-376 (2003)). In metanephric organ culture, the early mouse kidney tubule has an intrinsic capacity to secrete fluid by a CFTR-dependent mechanism in response to cAMP (Magenheimer et al., supra).

Persons skilled in the art may also use animal models to characterize a BPO or PPQ compound, including those described herein, and to determine effectiveness of the compound for reducing, inhibiting, reversing, or preventing cyst enlargement and/or preventing or inhibiting cyst formation thereby reducing the number of cysts formed, and to determine the usefulness of such compounds for treating a subject who has or who is at risk of developing MD. By way of example, Pkd1$^{flox}$ mice and Ksp-Cre transgenic mice in a C57BL/6 background may be generated as described and practiced in the art (see, e.g., Shibazaki et al., *J. Am. Soc. Nephrol.* 13:10-11 (2004) (abstract); Shao et al., *J. Am. Soc. Nephrol.* 13:1837-46 (2002)). Ksp-Cre mice express Cre recombinase under the control of the Ksp-cadherin promoter (see, e.g., Shao et al., supra). Pkd1$^{flox/-}$; Ksp-Cre mice may be generated by cross-breeding Pkd1$^{flox/flox}$ mice with Pkd1$^{+/-}$: Ksp-Cre mice. The effect of a test compound may be determined by quantifying cyst size and growth in metanephroi and kidney sections, histological analyses of tissues and cells, and delay or prevention of renal failure and death (see, e.g., Tradtrantip et al., *J. Med. Chem.*, supra; Shibazaki et al., supra).

The BPO and PPQ compounds may also be analyzed in animal models that are art-accepted animal models for increased intestinal fluid secretion. By way of example, a closed intestinal loop model of cholera, suckling mouse model of cholera, and in vivo imaging of gastrointestinal transit may be used for characterizing the BPO and PPQ compounds described herein (see, e.g., Takeda et al., *Infect. Immun.* 19:752-54 (1978); see also, e.g., Spira et al., *Infect. Immun.* 32:739-747 (1981)). Animal models of secretory diarrheas have been useful for determining efficacy of thiazolidinone (see, e.g., Thiagarajah et al., *Gastroenterology.* 126:511-19 (2004)) and glycine hydrazide CFTR inhibitors (see, e.g., Sonawane et al., *Chem. Biol.* 15:718-28 (2008); Sonawane et al., *Gastroenterology* 132:1234-44 (2007)) and may be employed for testing the BPO and PPQ compounds described herein.

The BPO and PPQ compounds described herein may also be useful for establishing animal models that may be used as cystic fibrosis models. The CF phenotype (in the absence of the CF genotype) may be established by administering any one or more of the BPO and PPQ compounds described herein. CFTR inhibitors are also useful to create the CF phenotype in ex vivo human and animal tissues, as has been done, for example, in studies of the role of CFTR in airway submucosal gland fluid secretion (see, e.g., Thiagarajah et al., *FASEB J.* 18:875-77 (2004)). Finally, though mouse, pig and ferret models of CFTR gene deletion exist, pharmacological creation of the CFTR phenotype in animals by CFTR inhibitors might provide complementary data on CFTR function in the absence of compensatory phenomena that can occur in transgenic animal models.

Methods of inhibiting CFTR-mediated ion transport include in vitro methods that comprise contacting a cell with any one or more of the BPO and/or PPQ compounds of structure I or structure II (and substructures and specific structures thereof) as described herein, under conditions and for a time sufficient for CFTR present in the outer membrane of the cell and the compound to interact. Cells (or cell lines) that may be used in such methods are cells that express CFTR and have channels or pores formed by CFTR in the cell membrane. Exemplary cells and cell lines include without limitation a Fischer rat thyroid (FRT) cell (including a FRT cell that co-expresses human or other animal wildtype CFTR and the halide indicator YFP-H148Q or other comparable yellow fluorescent protein); a cultured human bronchial epithelial cell; and a gastrointestinal cell (such as T84 human intestinal epithelial cells)) that comprises CFTR in the outer membrane of the cell. Such methods are useful for identifying analogs of the BPO and PPQ compounds (i.e., species of structure I or structure II, including species of substructures described herein) and for characterizing the BPO and PPQ compounds described herein.

In certain embodiments, the cell is contacted in an in vitro assay, and the cell may be obtained from a subject or from a biological sample. A biological sample may be a blood sample (from which serum or plasma may be prepared and cells isolated), biopsy specimen, body fluids (e.g., urine, lung lavage, ascites, mucosal washings, synovial fluid), bone marrow, lymph nodes, tissue explant (e.g., kidney cells), organ culture (e.g., kidney), or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., a primary kidney cell culture or primary intestinal epithelial cell culture), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

The BPO and PPQ compounds described herein may also be used in any one or more of the assays described above and herein for in vitro screening methods. By way of non-limiting examples, the compounds may be used as controls for comparing the potency, polarity, solubility, or other properties of compounds in compound libraries when screening assays are performed to identify and characterize compounds that inhibit CFTR activity.

Pharmaceutical Compositions and Methods of Using Pharmaceutical Compositions

Also provided herein are pharmaceutical compositions comprising any one or more of the BPO and PPQ compounds of structure I or structure II (and substructures and specific structures thereof). The compounds described herein may be formulated in a pharmaceutical composition for use in treatment or preventive (or prophylactic) treatment (e.g., reducing the likelihood of occurrence of cyst formation), of polycystic kidney disease (PKD), which includes autosomal dominant PKD (ADPKD) and autosomal recessive PKD (ARPKD). In other embodiments, a pharmaceutical composition comprising at least one BPO or PPQ compound may be formulated for use in treatment or preventive treatment (i.e., for reducing the likelihood of occurrence) of a disease, condition, or disorder manifested by increased intestinal fluid secretion, such as secretory diarrhea.

In pharmaceutical dosage forms, any one or more of the BPO and PPQ compounds of structure I, substructures, and specific structures or structure II, substructures, and specific structures described herein may be administered in the form of a pharmaceutically acceptable derivative, such as a salt, or they may also be used alone or in appropriate association, as well as in combination, with other pharmaceutically active compounds. The methods and excipients described herein are merely exemplary and are in no way limiting.

Optimal doses may generally be determined using experimental models and/or clinical trials. The optimal dose may depend upon the body mass, weight, or blood volume of the subject. In general, the amount of a BPO or PPQ compound of structure I or structure II (and substructures and specific structures thereof) described herein, that is present in a dose, ranges from about 0.01 µg to about 1000 µg per kg weight of the host. The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and are described herein. The level of a compound that is administered to a subject may be monitored by determining the level of the compound in a biological fluid, for example, in the blood, blood fraction (e.g., serum), and/or in the urine, and/or other biological sample from the subject. Any method practiced in the art to detect the compound may be used to measure the level of compound during the course of a therapeutic regimen.

The dose of a composition comprising at least one of the BPO or PPQ compounds described herein for treating PCKD may depend upon the subject's condition, that is, stage of the disease, renal function, severity of symptoms caused by enlarged cysts, general health status, as well as age, gender, and weight, and other factors apparent to a person skilled in the medical art. Similarly, the dose of the BPO or PPQ compound for treating a disease or disorder associated with aberrantly increased CFTR function, including but not limited to intestinal fluid secretion, secretory diarrhea, such as a toxin-induced diarrhea, or secretory diarrhea associated with or a sequelae of an enteropathogenic infection, Traveler's diarrhea, ulcerative colitis, irritable bowel syndrome (IBS), AIDS, chemotherapy and other diseases or conditions described herein may be determined according to parameters understood by a person skilled in the medical art. Accordingly, the appropriate dose may depend upon the subject's condition, that is, stage of the disease, general health status, as well as age, gender, and weight, and other factors considered by a person skilled in the medical art.

Pharmaceutical compositions may be administered in a manner appropriate to the disease or disorder to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose (or effective dose) and treatment regimen provides the composition(s) comprising at least one BPO or PPQ compound (as described herein) in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above). When a subject is treated for aberrantly increased intestinal fluid secretion, clinical assessment of the level of dehydration and/or electrolyte imbalance may be performed to determine the level of effectiveness of a compound and whether dose or other administration parameters (such as frequency of administration or route of administration) should be adjusted.

Polycystic kidney disease (PKD) (or PCKD) and polycystic renal disease are used interchangeably herein, and refer to a group of disorders characterized by a large number of cysts distributed throughout enlarged kidneys. The resultant cyst development leads to impairment of kidney function and can eventually cause kidney failure. PKD includes autosomal dominant polycystic kidney disease (ADPKD) and recessive autosomal recessive polycystic kidney disease (ARPKD), in all stages of development, regardless of the underlying etiology or cause. Effectiveness of a treatment for PKD may be monitored by one or more of several methods practiced in the medical art including, for example, by monitoring renal function by standard measurements, and by radiologic investigations that are performed with ultrasounds, computerized tomography (CT), or magnetic resonance imaging, which are useful for evaluating renal cyst morphology and volume and estimating the amount of residual renal parenchyma.

To evaluate and to monitor the effectiveness of any one of the BPO or PPQ compounds described herein to treat PKD or a related disease or condition, one or more of several clinical assay methods may be performed that are familiar to a person skilled in the clinical art. For example, a clinical method called a urea clearance test may be performed. A blood sample is obtained from a subject to whom the compound is being administered so that the amount of urea in the bloodstream can be determined. In addition, a first urine sample is collected from the subject and at least one hour later, a second urine sample is collected. The amount of urea quantified in the urine indicates the amount of urea that is filtered, or cleared by the kidneys into the urine. Another clinical assay method measures urine osmolality (i.e., the amount of dissolved solute particles in the urine). Inability of the kidneys to concentrate the urine in response to restricted fluid intake, or to dilute the urine in response to increased fluid intake during osmolality testing may indicate decreased kidney function.

Urea is a by-product of protein metabolism and is formed in the liver. Urea is then filtered from the blood and excreted in the urine by the kidneys. The BUN (blood urea nitrogen) test measures the amount of nitrogen contained in the urea. High BUN levels may indicate kidney dysfunction, but because blood urea nitrogen is also affected by protein intake and liver function, the test is usually performed in conjunction with determination of blood creatinine, which is considered a more specific indicator of kidney function. Low clearance values for creatinine and urea indicate diminished ability of the kidneys to filter these waste products from the blood and excrete them in the urine. As clearance levels decrease, blood levels of creatinine and urea nitrogen increase. An abnormally elevated blood creatinine, a more specific and sensitive indicator of kidney disease than the BUN, is diagnostic of impaired kidney function.

The pharmaceutical compositions described herein that comprise at least one BPO or PPQ compound may be administered to a subject in need by any one of several routes that effectively deliver an effective amount of the compound. Such administrative routes include, for example, oral, parenteral, enteral, rectal, intranasal, buccal, sublingual, intramuscular, and transdermal. By way of example, at least one or more of the compounds may be administered to a mucosal surface of the gastrointestinal tract (e.g., by an enteral route, which includes administration directly to the tract via a tube inserted into the nose, stomach, or small intestine) or to a mucosal surface of the oral or nasal cavities, or (e.g., intranasal, buccal, sublingual, and the like). These administrative methods and additional methods are discussed in greater detail herein.

A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, 21$^{st}$ Ed. Mack Pub. Co., Easton, Pa. (2005)). In general, the type of excipient is selected based on the mode of administration, as well as the chemical composition of the active ingredient(s). Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

A composition comprising any one of the compounds of structure (I) or structure (II), substructures, and specific structures described herein may be formulated for sustained or slow release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

For oral formulations, a BPO or PPQ compound of structure (I) and substructures and specific structures or of structure (II) and substructures and specific structures described herein can be used alone or in combination with appropriate additives to make tablets, powders, granules or capsules, for example, with conventional additives, such as lactose, mannitol, corn starch or potato starch; with binders, such as starch, gelatin, natural sugars such as glucose or beta-lactose, corn sweeteners, natural and synthetic gums such as acacia, tragacanth, or sodium alginate, carboxymethylcellulose, polyethylene glycol, waxes, crystalline cellulose, cellulose derivatives, and acacia; with disintegrators, such as corn starch, potato starch or sodium carboxymethylcellulose, methyl cellulose, agar, bentonite, or xanthan gum; with lubricants, such as talc, sodium oleate, magnesium stearate sodium stearate, sodium benzoate, sodium acetate, or sodium chloride; and if desired, with diluents, buffering agents, moistening agents, preservatives, coloring agents, and flavoring agents. The compounds may be formulated with a buffering agent to provide for protection of the compound from low pH of the gastric environment and/or an enteric coating. A BPO or PPQ compound may be formulated for oral delivery with a flavoring agent, e.g., in a liquid, solid or semi-solid formulation and/or with an enteric coating.

Oral formulations may be provided as gelatin capsules, which may contain the active compound along with powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and/or flavoring agents to increase acceptance of the compound by the subject.

The BPO and PPQ compounds of structure I or structure II (and substructures and specific structures thereof) described herein can be made into suppositories by mixing with a variety of bases such as emulsifying bases or water-soluble bases. These compounds may be administered rectally via a suppository. The suppository can include vehicles such as cocoa butter, carbowaxes and polyethylene glycols, which melt at body temperature, yet are solidified at room temperature.

The BPO and PPQ compounds of structure I or structure II (and substructures and specific structures thereof) described herein may be used in aerosol formulation to be administered via inhalation. The compounds may be formulated into pressurized acceptable propellants such as dichlorodifluoromethane, propane, nitrogen and the like.

Any one or more of the BPO and PPQ compounds of structure I or structure II (and substructures and specific structures thereof) described herein may be administered topically (e.g., by transdermal administration). Topical formulations may be in the form of a transdermal patch, ointment, paste, lotion, cream, gel, and the like. Topical formulations may include one or more of a penetrating agent, thickener, diluent, emulsifier, dispersing aid, or binder. When a BPO or PPQ compound is formulated for transdermal delivery, the compound may be formulated with or for use with a penetration enhancer. Penetration enhancers, which include chemical penetration enhancers and physical penetration enhancers, facilitate delivery of the compound through the skin, and may also be referred to as "permeation enhancers" interchangeably. Physical penetration enhancers include, for example, electrophoretic techniques such as iontophoresis, use of ultrasound (or "phonophoresis"), and the like. Chemical penetration enhancers are agents administered either prior to, with, or immediately following compound administration, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneruas et al., *J. Pharm. Pharmacol.* 2002; 54(4):499-508; Karande et al., *Pharm. Res.* 2002; 19(5):655-60; Vaddi et al., *Int. J. Pharm.* 2002 July; 91(7):1639-51; Ventura et al., *J. Drug Target* 2001; 9(5):379-93; Shokri et al., *Int. J. Pharm.* 2001; 228(1-2):99-107; Suzuki et al., *Biol. Pharm. Bull.* 2001; 24(6):698-700; Alberti et al., *J. Control Release* 2001; 71(3):319-27; Goldstein et al., *Urology* 2001; 57(2):301-5; Kiijavainen et al., *Eur. J. Pharm. Sci.* 2000; 10(2):97-102; and Tenjarla et al., *Int. J. Pharm.* 1999; 192(2): 147-58.

When a BPO or PPQ compound of structure I or structure II (and substructures and specific structures thereof) is formulated with a chemical penetration enhancer, the penetration enhancer is selected for compatibility with the compound, and is present in an amount sufficient to facilitate delivery of the compound through skin of a subject, e.g., for delivery of the compound to the systemic circulation. The BPO and PPQ compounds of structure I or structure II (and substructures and specific structures thereof) may be provided in a drug delivery patch, e.g., a transmucosal or transdermal patch, and can be formulated with a penetration enhancer. The patch generally includes a backing layer, which is impermeable to the compound and other formulation components, a matrix in contact with one side of the backing layer, which matrix provides for sustained release, which may be controlled release, of the compound, and an adhesive layer, which is on the same side of the backing layer as the matrix. The matrix can be selected as is suitable for the route of administration, and can be, for example, a polymeric or hydrogel matrix.

In one embodiment, the BPO and PPQ compounds of structure I or structure II (and substructures and specific structures thereof) are delivered to the gastrointestinal tract of the subject to provide for decreased fluid secretion. Suitable formulations for this embodiment include any formulation that provides for delivery of the compound to the gastrointestinal surface, particularly an intestinal tract surface.

For use in the methods described herein, one or more of the BPO and PPQ compounds of structure I or structure II (and substructures and specific structures thereof) described herein may be formulated with other pharmaceutically active agents or compounds, including other CFTR-inhibiting agents and compounds or agents and compounds that block intestinal chloride channels (e.g., a glycine hydrazide compound or thiazolidinone compound as discussed herein). Similarly, one or more of the BPO and PPQ compounds of structure I or structure II (and substructures and specific structures thereof) described herein may be formulated with other pharmaceutically active agents or compounds, including other CFTR-inhibiting agents and compounds, or other agents and compounds that are administered to a subject for treating PKD.

Kits with unit doses of a BPO or PPQ compound of structure I or structure II (and substructures and specific structures thereof) described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

Also provided herein are methods of manufacturing the pharmaceutical compositions described herein that comprise at least one of the BPO and PPQ compounds of structure I or structure II, and substructures and specific structures thereof, as described herein. In one embodiment, the method of manufacture comprises synthesis of the compound. Synthesis of one of more of the compounds described herein may be performed according to methods described herein and practiced in the art. In another method of manufacture, the method comprises comprise formulating (i.e., combining, mixing) at least one of the compounds disclosed herein with a pharmaceutically suitable excipient. These methods are performed under conditions that permit formulation and/or maintenance of the desired state (i.e., liquid or solid, for example) of each of the compound and excipient. A method of manufacture may comprise one or more of the steps of synthesizing the at least one compound, formulating the compound with at least one pharmaceutically suitable excipient to form a pharmaceutical composition, and dispensing the formulated pharmaceutical composition in an appropriate vessel (i.e., a vessel appropriate for storage and/or distribution of the pharmaceutical composition).

Other embodiments and uses will be apparent to one skilled in the art in light of the present disclosures. The following examples are provided merely as illustrative of various embodiments and shall not be construed to limit the claims in any way.

EXAMPLES

Example 1

Overview of Chemistry Procedures

Synthesis Overview: NMR spectra ($^1$H at 600 MHz; $^{13}$C at 150 MHz) were obtained in methylene chloride ($CD_2Cl_2$), chloroform ($CDCl_3$), acetonitrile ($CD_3CN$) or dimethyl sulfoxide (DMSO-$d_6$) using a 600-MHz Varian Spectrometer. Chemical shifts are expressed in parts per million relative to the solvent. NMR spectra for PPQ and BPO compounds were acquired at −20° C. due to excessive broadening of the 11-phenyl protons at ambient temperature. NMR spectra for the intermediates were obtained at ambient temperature. Mass spectrometry was done using a Waters LC/MS instrument with MS: electrospray (+) ionization, mass ranging from 100 to 900 Da, 20-V cone voltage; LC: Xterra MS $C_{18}$ column (2.1 mm×50 mm×3.5 µm), 0.2 mL/min water/acetonitrile (containing 0.1% TFA). Purity was judged by the peak area percentage of the UV absorbance signal. Compound purities by RP-HPLC were >98%. Flash chromatography was done using EM silica gel (230-400 mesh), and thin-layer chromatography was done on EMD silica gel 60 F254 plates (Darmstadt, Germany). Melting points are uncorrected.

Figure 2:
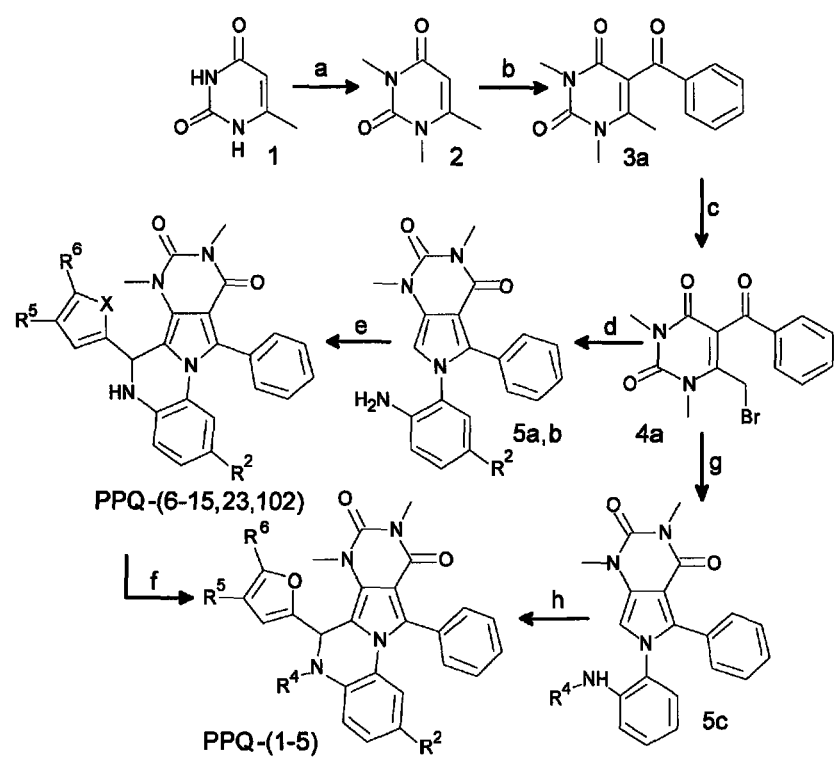
FIG. 2 presents a schematic of a representative synthesis procedure for preparing PPQ compounds as described in Example 1 herein. Reagents: (a) NaOH, $H_2O$, dimethylsulfate, r.t. 3 days; (b) benzoyl chloride, $ZnCl_2$, chlorobenzene, reflux; (c) $Br_2$, $CH_2Cl_2$, cat. $H_2O$, reflux; (d) 4-$R^2$-1,2-phenylenediamine, EtOH, reflux; (e) $R^2$=H, 4-$R^5$-5-$R^6$-furfural, 1,2-dichloroethane, TsOH, reflux; X=S, 5-methylthiophene carbaldehyde, 1,2-dichloroethane, cat. TsOH, reflux; $R^2$=$NO_2$, 5-bromo-2-furaldehyde $CHCl_3$, cat. TFA, reflux; (f) $R^4$=$CH_3SO_2$—, methanesulfonyl chloride, DCM, $Et_3N$; $R^4$=$CF_3CO$—, TFA anhydride, DCM, $Et_3N$; $R^4$=$CH_3CO$—, acetic anhydride, DMAP, 100° C.; $R_4$=NO, t-butyl nitrite, DCM; (g) N-methyl-1,2-phenylenediamine, EtOH, reflux; (h) 5-methylfurfural, 1,2-dichloroethane, cat. TsOH, reflux.
Figure 3:
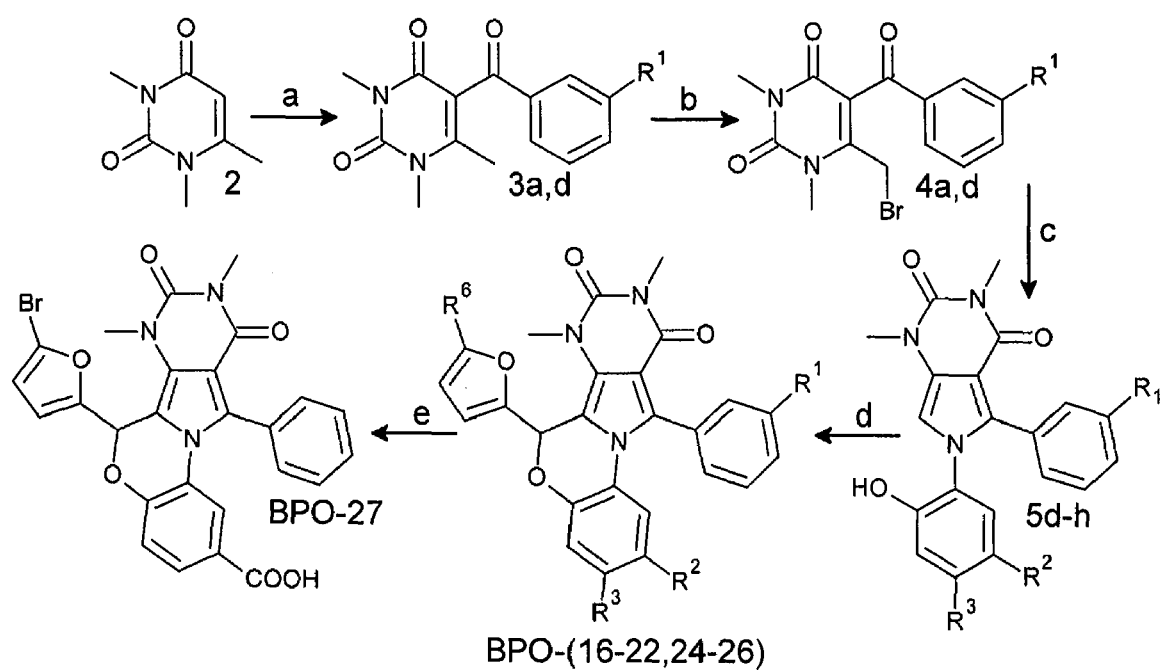
FIG. 3 presents a schematic of a representative synthesis procedure for preparing BPO compounds as described in Example 1 herein. Reagents: (a) $R^1$=H, benzoyl chloride, $ZnCl_2$, chlorobenzene, reflux; $R^1$=Me, m-tolyl chloride, $ZnCl_2$, chlorobenzene, reflux; (b) $Br_2$, $CH_2Cl_2$, cat. $H_2O$, reflux; (c) 2-amino-3-$R^2$-4-$R^3$-phenol, EtOH, reflux; (d) 5-$R^6$-furfural, cat. TFA, $CHCl_3$ or 1,2-dichloroethane, 150° C.; (e) KOH, THF, $H_2O$, HCl workup.

FIG. 2 presents Scheme 1, illustrating synthesis of dihydroquinoxoline PPQ compounds, and FIG. 3 presents Scheme 2, illustrating synthesis of benzoxazine BPO compounds.

Efforts were undertaken to improve methods for synthesizing PPQ-102 because the original synthesis method developed had low yield (see, e.g., Tradtrantip et al., *J. Med. Chem.* 52:6447-55 (2009); Int'l Patent Appl. Publication No. WO 2011/019737). As shown in Scheme 1, 6-methyluracil 1 was exhaustively alkylated using dimethyl sulfate to give 1,3,6-trimethyluracil 2 in 98% yield. 1,3,6-Trimethyluracil 2 was subject to Friedel-Crafts acylation utilizing benzoyl chloride and anhydrous zinc chloride to give ketone 3a in 66% yield. Bromination of ketone 3a gave 4a in quantitative yield. At the first point of diversification, 4a was reacted with substituted 1,2-phenylenediamines (2 eq) to give pyrroles 5a-c in 97% ($R^2$=H), 89% ($R^2$=$NO_2$), and 83% ($R^3$=Me) yields. Pyrroles 5a-c were condensed with the appropriately substituted furfural or thiophene carbaldehyde using catalytic acid to give PPQ-(5-15, 23) with yields of 57-98%. PPQ-102 was obtained on a gram scale in 83% yield. Amide analogs were synthesized from PPQ-102 and acid halides or anhydrides to give PPQ-(1-3), in 73%, 80% and 79% yields, respectively. The nitrosamine PPQ-4 was synthesized from PPQ-102 and t-butyl nitrite in 79% yield.

Scheme 2 shows the synthesis of benzoxazine BPO compounds. Ketone 3d ($R^1$=Me) was synthesized from 2 by Friedel-Crafts acylation utilizing m-tolyl chloride in 26% yield, and subsequently brominated to give 4d in 93% yield. The condensation of substituted 2-aminophenols with 4a,d in ethanol gave pyrroles 5d-h in 96% ($R^1$=$CH_3$, $R^2$=$R^3$=H), 96% ($R^1$=$R^2$=$R^3$=H), 88% ($R^1$=H, $R^2$=Cl, $R^3$=$NO_2$), 94% ($R^1$=$R^3$=H, $R^2$=$NO_2$) and 98% ($R^1$=$R^3$=H, $R^2$=COOEt) yields, respectively. Pyrroles 5d-h were then condensed with substituted furfurals using catalytic acid at 150° C. to give BPO-(16-22, 24-26) in yields of 43-84%. BPO-25 was saponified utilizing KOH in THF and water to give BPO-27 in 83% yield after acid work-up.

In an experiment intended to improve yield, bromination of ketone 3a was conducted under strict anhydrous conditions. Ketone 3a was refluxed in $CH_2Cl_2$ and bromine (1 eq), but after several hours TLC showed little product. Serendipitously, when several drops of wet $CH_2Cl_2$ were added to the reaction, a remarkably rapid discharge of the bromine color and evolution of fuming HBr gas occurred. After several minutes TLC indicated a near quantitative yield of 4a, which spontaneously crystallized when dried in vacuo. When 4a was condensed with N-methyl-1,2-phenylenediamine, the more reactive secondary amine can undergo alkylation by displacement of the readily accessible bromide of 4a. The high regioselectivity evident in the 83% isolated yield of 5c suggests that the formation of the pyrrole ring in the initial reaction is one of imine formation rather than alkylation, despite the crowded reaction center.

The analogs were efficiently synthesized in 5-6 steps with 11-61% overall yield.

Example 2

Synthesis of BPO-27

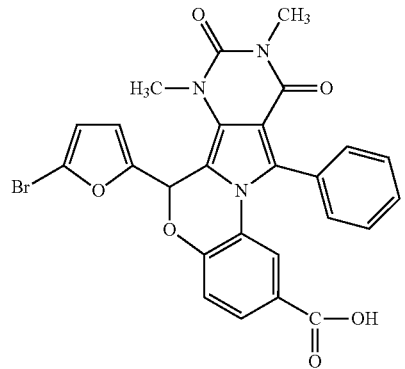 [SMILES: Cn1c(=O)c2c(-c3ccccc3)n3c(c2n(C)c1=O)C(c1ccc(Br)o1)Oc1ccc(C(=O)O)cc1-3]

Modification of PPQ-102 by bromine substitution at the 5-position of the furan ring, replacement of the secondary amine with an ether bridge, and carboxylation, gave BPO-27. Synthesis of BPO-27 is described below.

1,3,6-Trimethyl-1H,3H-pyrimidine-2,4-dione (2) See, e.g., Azas et al., *Farmaco.* 58:1263-70 (2003). In a 250 mL round bottom flask, 6-methyluracil (1; 15.0 g, 119 mmol) and NaOH (9.55 g, 239 mmol) were dissolved in water (150 mL) at low heat. The solution was brought to 25° C. in an ice bath and maintained at 25° C. while dimethyl sulfate (23 mL, 30.59 g, 243 mmol) was added dropwise over 20 min with vigorous stirring. After 22 h, the reaction mixture contained a white precipitate and had pH 9. NaOH (5.0 g, 125 mmol) was added to make the solution homogenous, and an ice bath was used to maintain a temperature of 25° C. while dimethyl sulfate (12 ml, 15.96 g, 127 mmol) was added dropwise over 10 min. The reaction was stirred for 72 h, then NaOH (2 g, 50 mmol) was added and the reaction extracted with $CHCl_3$ (5×50 mL). The chloroform extracts were pooled, dried over $Na_2SO_4$, and concentrated in vacuo to yield 2 (18 g, 98% yield); mp 114-115° C. $^1$H NMR (600 MHz, $CDCl_3$) δ 5.67 (s, 1H), 3.45 (s, 3H), 3.35 (s, 3H), 2.29 (s, 3H). $^{13}$C NMR (151 MHz, $CDCl_3$) δ 162.62, 152.53, 151.81, 101.16, 31.89, 28.11, 20.58. MS (ES+) (m/z): $[M+1]^+$ calculated for $C_7H_{11}N_2O_2$, 155.17. found 155.14.

5-Benzoyl-1,3,6-trimethylpyrimidine-2,4(1H,3H)-dione (3a) See, e.g., Tsupak et al., *Chem. Heterocycl. Comp.* 39:953-959 (2003). In a 100 mL round bottom flask equipped with a condenser and an air lock was added 2 (5.00 g, 32.4 mmol); anhydrous zinc chloride (see, e.g., Pray in *Inorganic Syntheses*, J. Wiley & Sons: New York, 1990; Vol. XXVIII, pp 321-22) (freshly dried, 4.45 g, 32.6 mmol); dry chlorobenzene (20 mL); and benzoyl chloride (freshly distilled, 4 ml, 4.84 g, 34.4 mmol). The reaction was refluxed in an oil bath equipped with an air lock and vigorously stirred for 3 h. The reaction was allowed to cool and the condenser arranged for distillation. Water (40 mL) was added dropwise at first and then with increasing speed. Chlorobenzene (30 mL) and water were distilled off and the mixture was cooled on ice. Diethyl ether (30 ml) was added while stirring causing a precipitate to form. The precipitate was collected by filtration and recrystallized from 2-propanol (50 mL) to yield 3a (5.53 g, 66%); mp 143.2-143.7° C. $^1$H NMR (600 MHz, CD$_3$CN) δ 8.74 (d, J=7.1, 2H), 8.46 (t, J=6.0, 1H), 8.37-8.29 (m, 2H), 4.25 (s, 3H), 4.07 (s, 3H), 2.99 (s, 3H). $^{13}$C NMR (151 MHz, CD$_3$CN) δ 195.15, 162.17, 153.72, 153.16, 139.21, 134.93, 130.49, 130.04, 113.43, 32.82, 28.61, 18.26. MS (ES+) (m/z): [M+1]$^+$ calculated for C$_{14}$H$_{15}$N$_2$O$_3$, 259.28. found 259.11.

5-Benzoyl-6-(bromomethyl)-1,3-dimethylpyrimidine-2,4(1H,3H)-dione (4a).

See, e.g., Tsupak et al., supra. In a 50 mL round bottom flask 3a (1.00 g, 38.7 mmol) was dissolved in CCl$_4$ (5 mL) and CH$_2$Cl$_2$ (4 mL) at 50° C. The starting material was poorly soluble in CCl$_4$, and CH$_2$Cl$_2$ can be substituted entirely. The reaction under anhydrous conditions was slow although the addition of a few drops of wet solvent resulted in quantitative yield in a few minutes. Bromine (200 μL, 0.621 g, 38.8 mmol) was mixed with CCl$_4$ (5 mL) and CH$_2$Cl$_2$ (5 mL) in an addition funnel and added dropwise to the solution of 3a such that the brown color disappeared between drops. The last few drops caused the reaction to remain brown. The reaction was then brought to reflux for 10 min before the brown color was discharged by the addition of a few drops of acetone. The reaction was refluxed for 30 min to remove HBr. The reaction was quantitative by TLC and the product crystallized when concentrated in vacuo to yield 4a (1.305 g, 100%). The product was recrystallized from 2-propanol as colorless needles; mp 171.0-171.7° C. $^1$H NMR (600 MHz, CD$_2$Cl$_2$) δ 7.88-7.80 (m, 2H), 7.65-7.60 (m, 1H), 7.52-7.45 (m, 2H), 4.24 (s, 2H), 3.59 (s, 3H), 3.31 (s, 3H). $^{13}$C NMR (151 MHz, CD$_2$Cl$_2$) δ 192.89, 160.94, 152.01, 149.58, 137.79, 134.46, 129.78, 129.15, 114.75, 31.96, 28.59, 23.67. MS (ES+) (m/z): [M+1]$^+$ calculated for C$_{14}$H$_{14}$BrN$_2$O$_3$, 338.18. found 338.81.

Ethyl 3-amino-4-hydroxybezoate. In a 300 mL round bottom flask was placed, 3-amino-4-hydroxybezoic acid (5.50 g, 35.9 mmol), ethanol (200 mL), and a magnetic stir bar. The mixture was cooled in an ice bath to 10° C. and anhydrous HCl gas was bubbled through the stirred mixture until homogenous. The round bottom flask was then equipped with a condenser and the solution refluxed. After 1 hour the condensor was rearranged for distillation and 125 mL of ethanol was distilled off. The resulting solution was then dried in vacuo to give crude ethyl 3-amino-4-hydroxybezoate hydrochloride (7.73 g 35.5 mmol). Water (125 mL) containing NaHCO$_3$ (3.0 g 35.7 mmol) was slowly added to the crude HCl salt and the resulting mixture was extracted 3×100 mL EtOAc. The EtOAc extracts were pooled, washed with brine, and then dried over NaSO$_4$. The EtOAc was removed in vacuo to give ethyl 3-amino-4-hydroxybezoate (5.08 g, 78.0%) as a viscous oil which crystallized on standing. $^1$H NMR (600 MHz, CD$_2$Cl$_2$) δ 7.42 (d, J=2.0, 1H), 7.37 (dd, J=2.0, 8.2, 1H), 6.76 (d, J=8.2, 1H), 5.56-5.37 (s, 1H), 4.28 (q, J=7.1, 2H), 3.76 (s, 2H), 1.34 (t, J=7.1, 3H). $^{13}$C NMR (151 MHz, CD$_2$Cl$_2$) δ 167.79, 149.37, 134.83, 123.28, 122.37, 117.91, 114.98, 61.48, 14.63. MS (ES+) (m/z): [M+1]$^+$ calculated for C$_9$H$_{12}$NO$_3$, 182.08. found 182.09.

Ethyl 3-(1,3-dimethyl-2,4-dioxo-5-phenyl-3,4-dihydro-1H-pyrrolo[3,4-d]pyrimidin-6(2H)-yl)-4-hydroxybenzoate (5h). In a 100 mL round bottom flask ethyl 3-amino-4-hydroxybezoate (1.10 g, 6.07 mmol) and 4a (1.00 g, 2.98 mmol) were refluxed in ethanol (50 mL). After 2 h, the condenser was rearranged for distillation and ethanol (25 mL) was distilled off. The resulting solution was slowly poured into a vigorously stirred solution of ice cold water (200 mL) and citric acid (50 mg) giving a pink solid precipitate. The mixture was stirred for 10 min and then the solid was collected by filtration and rinsed with cold water to give 5h (1.23 g, 98.5%) after drying. The product was recrystallized from ethanol to give pale pink needles; m.p. 129.2-130° C. $^1$H NMR (600 MHz, CD$_2$Cl$_2$) δ 8.58 (s, 1H), 7.89 (dd, J=2.1, 8.7, 1H), 7.67 (d, J=2.1, 1H), 7.36-7.29 (m, 2H), 7.28-7.18 (m, 3H), 6.97 (d, J=8.7, 1H), 4.25 (q, J=7.1, 2H), 3.27 (s, 3H), 3.17 (s, 3H), 1.30 (t, J=7.1, 3H). $^{13}$C NMR (151 MHz, CD$_2$Cl$_2$) δ 165.40, 159.72, 156.82, 151.91, 136.06, 132.09, 130.86, 130.65, 129.49, 128.99, 128.83, 127.84, 125.70, 122.92, 117.65, 104.70, 103.11, 61.23, 32.02, 28.08, 14.24. MS (ES+) (m/z): [M+1]$^+$ calculated for C$_{23}$H$_{22}$N$_3$O$_5$, 420.16. found 420.13.

Ethyl 6-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylate (BPO-25). Pyrrole 5h (500 mg, 1.19 mmol), 5-bromofurfural (240 mg, 1.37 mmol), chloroform (7 mL), TFA (10 μL, 14.8 mg, 130 μmol), and 3 Å molecular sieves (2.0 g, 8-12 mesh beads), and a stir bar were sealed in an Emrys 10-20 mL process vial and submerged to the level of solvent in an oil bath at 150° C. (The formation of the oxazine ring produces water that collects as beads at or near the top of the tube during the reaction. If the reaction were scaled up such that the beads became large enough to drip back into the reaction mixture, the yield was diminished. The addition of molecular sieves reduced this problem for reactions containing less than 500 mg of the starting pyrrole.) The reaction was stirred for 24 min then removed from the oil bath. Once the internal pressure had dropped the reaction vial was rapidly cooled in water. After cooling, the reaction was filtered through celite into a 50 mL recovery flask and the dried in vacuo. The residue was dissolved in a minimum amount of CH$_2$Cl$_2$ and quickly diluted with warm ethanol (25 mL). Fine crystals began to form immediately. The mixture was then placed on a rotary evaporator and the CH$_2$Cl$_2$ was removed to increase the quantity of crystals. The mixture was then chilled, filtered, and the crystals rinsed with cold ethanol to give BPO-25 (0.500 g, 76.4%) as fine white needle like crystals. No m.p. (slow decomposition). $^1$H NMR (600 MHz, CD$_2$Cl$_2$) δ 7.81 (d, J=7.7, 1H), 7.68 (dd, J=1.9, 8.4, 1H), 7.63 (t, J=7.5, 1H), 7.52 (t, J=7.5, 1H), 7.34 (t, J=7.5, 1H), 7.23 (d, J=1.8, 1H), 7.09 (d, J=8.4, 1H), 7.06 (d, J=7.7, 1H), 6.86 (s, 1H), 6.14 (d, J=3.4, 1H), 5.98 (d, J=2.9, 1H), 4.11 (dq, J=7.2, 10.7, 1H), 4.00 (dq, J=7.1, 10.7, 1H), 3.48 (s, 3H), 3.26 (s, 3H), 1.14 (t, J=7.1, 3H). $^{13}$C NMR (151 MHz, CD$_2$Cl$_2$) δ 165.03, 159.26, 151.87, 151.79, 149.08, 131.78, 131.27, 130.00, 129.80, 129.68, 128.84, 128.81, 128.29, 125.40, 124.69, 124.47, 124.42, 121.57, 119.64, 114.91, 112.43, 105.93, 105.67, 68.40, 61.28, 32.38, 27.95, 14.20. MS (ES+) (m/z): [M+1]$^+$ calculated for C$_{28}$H$_{23}$BrN$_3$O$_6$, 576.08. found 576.04.

An Emrys process vial is a commercially available thick walled vessel much like a test tube typically used for microwave reactions that may be sealed using a disposable plastic-lined metal cap. Precautions should be taken because the reaction vessel is under pressure when heated.

6-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylic acid (BPO-27). In a 500 mL round bottom flask equipped with stir bar, BPO-25 (1.00 g, 1.73 mmol) was dissolved in THF (100 mL) with gentle heat and then allowed to cool. A mixture of water (70 mL) and KOH (768 mg, 13.7 mmol) was quickly added to the vigorously stirred solution which formed a white suspension. After 3 days the mixture was a homogenous yellow solution free of BPO-25 as determined by LC/MS. The THF was removed using a rotary evaporator and warm water bath leaving behind a viscous aqueous solution. The solution was made strongly acidic to litmus using 1% aq. HCl while stirring vigorously with a glass rod. The resulting gel was shaken with EtOAc (125 mL) and then quickly poured into a 1 liter separatory funnel where a precipitate formed in the organic layer. The 500 mL flask was rinsed with additional EtOAc (125 mL), and this EtOAc rinse was also added to the separatory funnel. Additional EtOAc (400 mL) was added to the funnel, and the mixture was vigorously shaken until all solids dissolved. After settling, the lower yellow aqueous layer was discarded. The EtOAc layer was washed with brine, dried over $Na_2SO_4$ and dried on a rotary evaporator. The resulting slightly yellow amorphous powder was loosened by swirling with $CH_2Cl_2$ (15 mL) and then diluted with diethyl ether (15 mL). The solids were collected by filtration and rinsed with $CH_2Cl_2$:$Et_2O$ (1:1') to give BPO-27 (791 mg, 83.2%) as a white solid. No m.p. (slow decomposition). $^1$H NMR (600 MHz, 91% $CD_2Cl_2$, 9% DMSO-$d_6$) δ 12.30 (s, 1H), 7.79 (d, J=7.7, 1H), 7.63 (dd, J=1.9, 8.4, 1H), 7.58 (t, J=7.6, 1H), 7.46 (t, J=7.5, 1H), 7.29 (t, J=7.5, 1H), 7.17 (d, J=1.7, 1H), 7.04 (d, J=8.4, 1H), 7.01 (d, J=7.7, 1H), 6.89 (s, 1H), 6.12 (d, J=3.4, 1H), 5.96 (d, J=3.3, 1H), 3.44 (s, 3H), 3.21 (s, 3H). $^{13}$C NMR (151 MHz, 91% $CD_2Cl_2$, 9% DMSO-$d_6$) δ 166.69, 159.13, 151.86, 151.62, 148.96, 131.75, 131.00, 129.74, 129.65, 129.45, 128.59, 128.53, 128.45, 125.33, 125.23, 124.38, 124.20, 121.86, 119.42, 114.84, 112.34, 105.95, 105.66, 68.20, 32.28, 27.84. MS (ES+) (m/z): $[M+1]^+$ calculated for $C_{26}H_{19}BrN_3O_6$, 548.05. found 548.00.

Example 2A

Separation of Enantiomers of BPO-27

Figure 4:
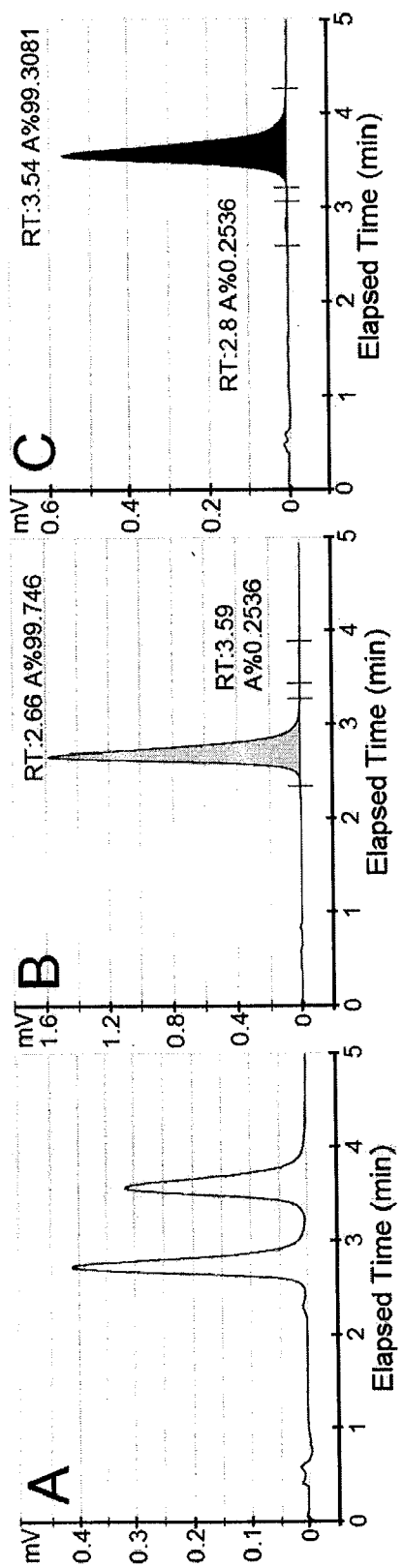
FIG. 4 shows chromatograms of purified BPO-27 enantiomers following chiral HPLC separation. (A). Analytical chromatogram following preparation separation of approximately 1 g BPO-27. (B). Chromatogram of fraction 1 analytical chromatograph showing the retention time (RT) and % area (A %) of peaks. (C). Analytical chromatogram of fraction #2.

Separation of Enantiomers—Separation of approximately 1.0 gram of racemic BPO-27 was carried out by Averica Discovery Services Inc. Preparative scale chiral SFC was carried out on a RegisCell 3.0×25.0 cm column using an isocratic method: 75% $CO_2$, and 25% ethanol containing 1% isopropylamine, 80 mL/min, 100 bar, 25° C. Analysis of the separated enantiomers was carried out on a RegisCell 4.6× 100 mm column, using an isocratic method: 75% $CO_2$, 25% ethanol with 0.1% isopropylamine, 4 mL/min, 100 bar, 25° C. Two distinct peaks were seen following chromatography (FIG. 4A). Fraction 1 contained 413 mg with 99.5% e.e. (FIG. 4B), and fraction 2 contained 396 mg with 98.6% e.e. (FIG. 4C).

Figure 5:
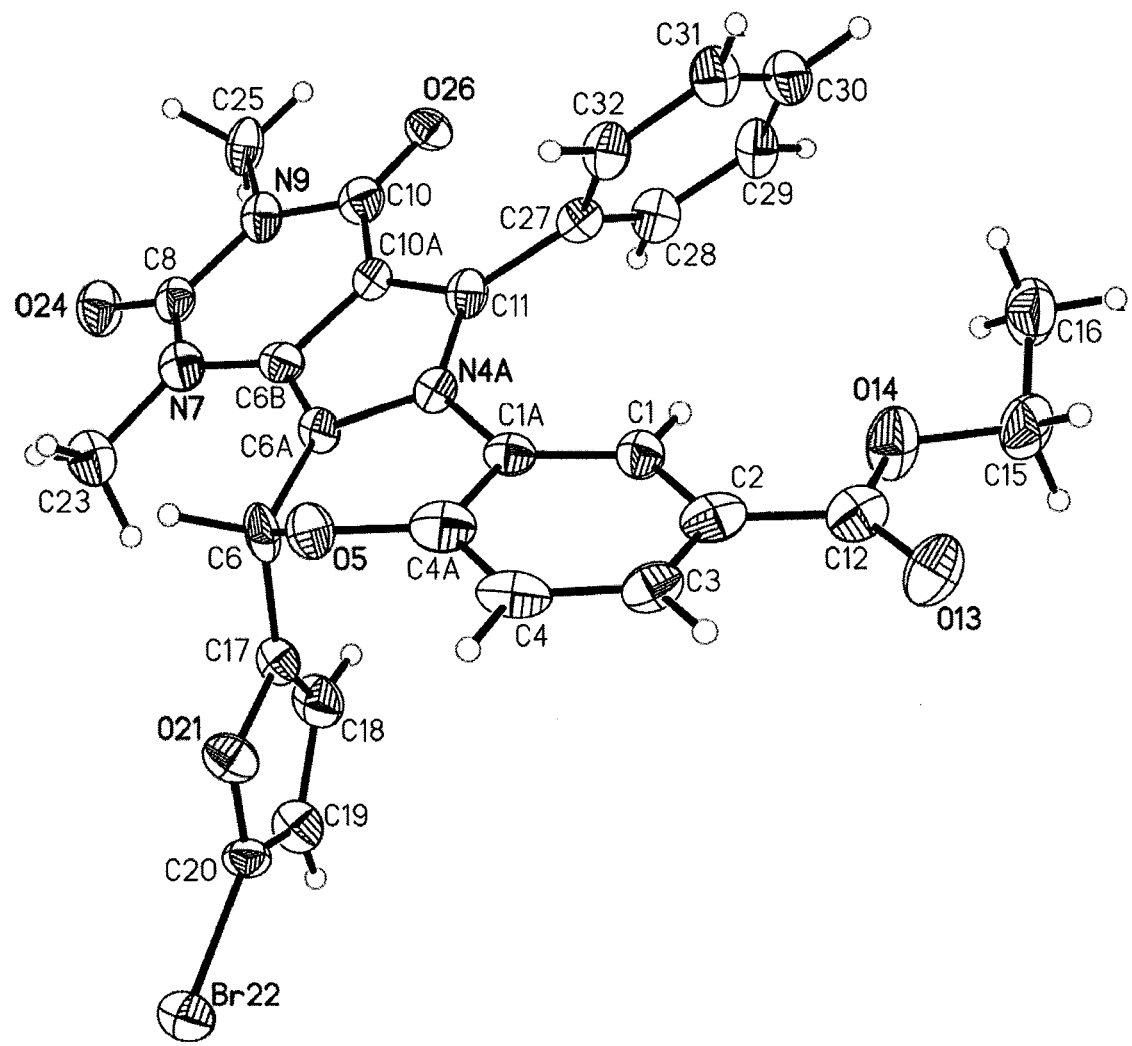
FIG. 5 shows the X-ray crystal structure and absolute stereochemistry of a compound of structure (I), BPO-25(S).

Crystal Preparation—Fraction 1, BPO-27 isopropylamine carboxylate (30 mg, 49 mmol) was placed in a 75 ml separatory funnel filled with very dilute HCl (aq) (20 ml) and EtOAc (20 ml). The mixture was shaken vigorously until no undissolved solids remained. The EtOAc layer was collected and extracted with brine and then dried over $Na_2SO_4$. The EtOAc was evaporated in a 50 ml recovery flask on a rotory evaporator and then dried under high vacuum to give a white solid (24 mg, 44 mmol, yield 89%). To the recovery flask was added a magnetic stir bar, DMAP (1 mg, 8 mmol), EDAC (9 mg, 47 mmol) and finally dry DCM (15 ml). Once the stirred solution became homogenous, dry ethanol (10 μL, 7.9 mg, 172 mmol) was added and the reaction was stirred for 24 h sealed with a rubber septum. The reaction mixture was then transferred to a separatory funnel and extracted with dilute citric acid (10 ml). The organic layer was collected in a 50 ml beaker, dried over $Na_2SO_4$ and then evaporated in a 50 ml recovery flask on a rotary evaporator. The residue, which shared the same $R_f$ value as racemic BPO-25 (BPO-27 ethyl ester) on TLC, was purified by flash chromatography (EtOAc: hexanes, 2:3) to give a clear residue (20 mg, 35 mmol, yield 79%). The residue was dissolved in 0.5 ml toluene and placed in a 1 dram vial. The vial was placed upright in a jar filled with 3-4 mm of mixed hexanes and then sealed. The setup was placed for 6 d in a quiet, vibration-free room, yielding diffraction-quality crystals, which by x-ray analysis, revealed the compound to be (S)-BPO-27 ethyl ester [(S)-BPO-25]. See FIG. 5.

X-Ray Crystallography—Optically centered on a Bruker Duo APEXII CCD system a colorless crystalline needle of fraction 2 BPO-27 ethyl ester with approximate orthogonal dimensions 0.31×0.04×0.04 mm³ was cooled to −183° C. (90° K). Indexing of the unit cell used a random set of reflections collected from three series of 0.5° wide co-scans, 10 s per frame, and 30 frames per series that were well distributed in reciprocal space. Data were collected [CuKα] with 0.5° wide scans, variable time per frame dependent upon detector 2θ angle and varying φ and omega angles such that nearly all unique reflections were collected at least once. The crystal to detector distance was 4.96 cm, thus providing a complete sphere of data to $2\theta_{max}$136.52. Crystallographic calculations were performed on an iMac with 2.80 GHz quad core processor and 8 GB of extended memory. A total of 18750 reflections were collected and corrected for Lorentz and polarization effects with SAINT and absorption using crystal faces and Blessing's method as incorporated into the program SADABS (Blessings, R. H. An empirical Correction for Absorption Anisotropy. Acta Cryst, 1995, A51, 33-38; Sheldrick, G. M. (2002) SHELXTL. Version 2008/1, 'Siemens Area Detector Absotion Correction' Universitat Gottingen: Gottingen, Germany) with 4943 unique for point group 222. The SHELXTL program package was implemented to determine the probable space group and set up the initial files. System symmetry, systematic absences, and intensity statistics indicated the non-centrosymmetric orthorhombic space group $P2_12_12_1$ (no. 19). The structure was determined by direct methods with the successful location of a majority of the main molecule using the program XS (Sheldrick, G. M. (1997) SHELXS97 and SHELXL97. Universität Göttingen: Göttingen, Germany). The structure was refined with XL (Sheldrick, G. M. (1997) SHELXS97 and SHELXL97. Universitat Göttingen: Göttingen, Germany). The data collected were merged for least squares refinement to 4752 unique data [R(int)=0.0925]. A series of least-squares difference-Fourier cycles were required to locate the remaining non-hydrogen atoms and optimize the full occupancy, disordered solvent toluene molecule. All non-hydrogen atoms were refined anisotropically. Hydrogen atoms were idealized throughout the final refinement stages. The final structure was refined to convergence with R(F)=9.09%, wR(F2)=22.64%, GOF=1.128 for all 4752 unique reflections [R(F)=8.86, wR(F2)=22.46% for those 4529 data with Fo >4σ(Fo)]. The final difference-Fourier map was featureless indicating that the structure is both correct and complete. An empirical correction for extinction was also attempted and found to be negative and therefore not applied. The absolute structure parameters, Flack(x) (Flack, Acta Cryst. 1983, A39, 876-881), was refined and found to be −0.08(4) while the Hooft (Hooft, R. W. W, Strayer, L. H. & Spek, A. L. J. Appl, Cryst. (2008), 41, 96-103) parameter is −0.085(18) indicating that the structure's absolute configuration has been reliably determined. Table C shows the Crystal data and structure refinement for BPO-25 $[C_{28}H_{22}N_3O_6Br][C_7H_8]_{0.5}$.

TABLE C

| Identification code | jfZ111of |
|---|---|
| Empirical formula | C31.50 H26 Br N3 O6 |
| Formula weight | 622.46 |
| Temperature | 90(2) K |
| Wavelength | 1.54178 Å |
| Crystal system | Orthorhombic |

TABLE C-continued

| | |
|---|---|
| Space group | P 2₁2₁2₁ |
| Unit cell dimensions | a = 5.7866(4) Å    α = 90°. |
| | b = 20.7586(14) Å   β = 90°. |
| | c = 22.5740(14) Å   γ = 90°. |
| Volume | 2711.6(3) Å$^3$ |
| Z | 4 |
| Density (calculated) | 1.525 Mg/m$^3$ |
| Absorption coefficient | 2.507 mm$^{-1}$ |
| F(000) | 1276 |
| Crystal size | 0.31 × 0.04 × 0.04 mm$^3$ |
| Crystal color and habit | Colorless Needle |
| Diffractometer | Bruker APEX-II CCD |
| Theta range for data collection | 2.89 to 66.59°. |
| Index ranges | −6 <= h <= 6, −24 <= k <= 24, −26 <= l <= 26 |
| Reflections collected | 18348 |
| Independent reflections | 4752 [R(int) = 0.0925] |
| Observed reflections (I > 2sigma(I)) | 4529 |
| Completeness to theta = 66.59° | 99.7% |
| Absorption correction | Numerical |
| Max. and min. transmission | 0.9130 and 0.5123 |
| Solution method | SHELXS-97 (Sheldrick, 2008) |
| Refinement method | SHELXL-97 (Sheldrick, 2008) |
| Data/restraints/parameters | 4752/2/420 |
| Goodness-of-fit on F$^2$ | 1.128 |
| Final R indices [I > 2sigma(I)] | R1 = 0.0886, wR2 = 0.2246 |
| R indices (all data) | R1 = 0.0909, wR2 = 0.2264 |
| Absolute structure parameters; Flack, Hooft. | −0.08(4), −0.085(18) |
| Largest diff. peak and hole | 1.730 and −0.810 e.Å$^{-3}$ |

Example 3

Synthesis of PPQ-102

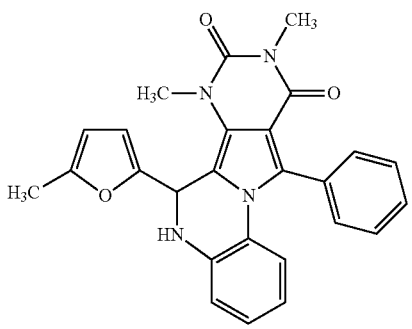 [SMILES: Cc1ccc(C2Nc3ccccc3-n3c(-c4ccccc4)c4c(=O)n(C)c(=O)n(C)c4c32)o1]

Synthesis of 2, 3a, and 4a was performed as described in Example 2. Synthesis of intermediate 5a was performed as follows.

6-(2-Aminophenyl)-1,3-dimethyl-5-phenyl-1H-pyrrolo[3,4-d]pyrimidine-2,4(3H,6H)-dione (5a). 1,2-Phenylenediamine (1.320 g, 12.2 mmol) in absolute EtOH (25 mL) was stirred in a 50 mL round bottom flask. The mixture was warmed on an oil bath until homogenous, and then 4a (2.055 g, 6.1 mmol) was added with the aid of a powder funnel and EtOH (5 mL). The solution was stirred vigorously at refluxed for 1 h, during which a white precipitate formed. The reaction was then cooled in an ice bath, filtered, and the precipitate washed with cold ethanol to yield 5a (2.0357 g, 96.5%) as a white powder. $^1$H NMR (600 MHz, DMSO-d6) δ 7.37-7.31 (m, 2H), 7.25-7.19 (m, 3H), 7.08-7.02 (m, 1H), 6.92 (s, 1H), 6.83 (dd, J=1.3, 7.8, 1H), 6.75 (d, J=8.1, 1H), 6.48-6.43 (m, 1H), 5.08 (s, 2H), 3.33 (s, 3H), 3.19 (s, 3H). $^{13}$C NMR (151 MHz, DMSO-d₆) δ 159.07, 150.89, 144.76, 133.51, 130.42, 129.49, 129.36, 129.05, 128.64, 127.89, 127.13, 123.10, 115.65, 115.46, 105.49, 102.23, 31.50, 27.40. MS (ES+) (m/z): [M+1]$^+$ calculated for C$_{20}$H$_{19}$N$_4$O$_2$, 347.39. found 347.05.

7,9-Dimethyl-6-(5-methylfuran-2-yl)-11-phenyl-5,6-dihydropyrimido[4',5'-3,4]pyrrolo[1,2-a]quinoxaline-8,10-(7H,9H)-dione (PPQ-102)

In a 25 mL pear shaped flask was placed 5a (1.00 g, 2.89 mmol), 5-methylfurfural (332 mg, 0.30 mL, 3.02 mmol), a small crystal of p-toluene-sulfonic acid and 1,2-dichloroethane (10 mL). The mixture was stirred at reflux for 5 min until homogenous, and then concentrated in vacuo to yield a brown sold. The solid was then recrystallized from ethanol to yield PPQ-102 (1.05 g, 83%) as slightly yellow crystals. The product was recrystallized to give white crystals; m.p. 245-246° C. $^1$H NMR (600 MHz, CD$_2$Cl$_2$) δ 7.81 (d, J=7.6, 1H), 7.56 (t, J=7.5, 1H), 7.45 (t, J=7.5, 1H), 7.29 (t, J=7.5, 1H), 7.02 (d, J=7.6, 1H), 6.95-6.90 (m, 1H), 6.83 (dd, J=1.1, 7.9, 1H), 6.48 (d, J=7.9, 1H), 6.45-6.40 (m, 1H), 6.01 (s, 1H), 5.75 (d, J=2.1, 1H), 5.70 (d, J=3.0, 1H), 4.93 (d, J=2.0, 1H), 3.55 (s, 3H), 3.27 (s, 3H), 2.20 (s, 3H). $^{13}$C NMR (151 MHz, CD$_2$Cl$_2$) δ 159.59, 152.98, 152.03, 151.67, 137.36, 132.01, 130.96, 130.17, 130.06, 129.08, 128.49, 128.27, 126.49, 124.82, 123.35, 121.10, 119.45, 117.42, 110.32, 109.74, 106.21, 105.24, 48.76, 32.04, 27.90, 13.70. MS (ES+) (m/z): [M+1]$^+$ calculated for C$_{26}$H$_{23}$N$_4$O$_3$, 439.18. found 439.12.

Example 4

Synthesis of PPQ-1

7,9-Dimethyl-6-(5-methylfuran-2-yl)-5-(methylsulfonyl)-11-phenyl-5,6-dihydropyrimido[4',5'-3,4]pyrrolo[1,2-a]quinoxaline-8,10-(7H,9H)-dione (PPQ-1).

Synthesis of PPQ-102 was performed as described in Example 3. In a 5 mL pear shaped flask PPQ-102 (21 mg, 48.9 µmol) was dissolved in dry chloroform (1 mL). Methanesulfonyl chloride (5.5 µL, 7.7 mg, 67.2 µmol) was added followed by triethylamine (14 µL, 10.2 mg, 100 µmol), and the reaction was stirred for 30 min. TLC showed starting material so additional methanesulfonyl chloride (5.5 µL, 7.7 mg, 67.2 µmol) and triethylamine (14 µL, 10.2 mg, 100 µmol) were added. After 1 h TLC showed minimal starting material. The reaction was quenched and then purified by TLC-prep to give PPQ-1 (17.9 mg, 72.5%) as an amorphous solid. $^1$H NMR (600 MHz, CD$_2$Cl$_2$) δ 7.84 (d, J=7.6, 1H), 7.60 (t, J=7.3, 1H), 7.52-7.46 (m, 2H), 7.28 (t, J=7.3, 1H), 7.17-7.12 (m, 1H), 6.98-6.93 (m, 1H), 6.87-6.79 (m, 2H), 6.62 (d, J=8.3, 1H), 5.74 (d, J=3.1, 1H), 5.72 (s, 1H), 3.56 (s, 3H), 3.27 (s, 3H), 2.63 (s, 3H), 2.20 (s, 3H). $^{13}$C NMR (151 MHz, CD$_2$Cl$_2$) δ 159.36, 154.22, 151.76, 147.04, 132.08, 131.48, 130.59, 129.87, 129.78, 129.70, 129.63, 128.85, 128.40, 127.85, 127.73, 126.98, 124.94, 121.86, 111.93, 108.78, 106.40, 105.74, 52.08, 37.83, 32.39, 28.00, 13.77. MS (ES+) (m/z): [M+1]$^+$ calculated for $C_{27}H_{25}N_4O_5S$, 517.15. found 517.10.

Example 5

Synthesis of PPQ-2

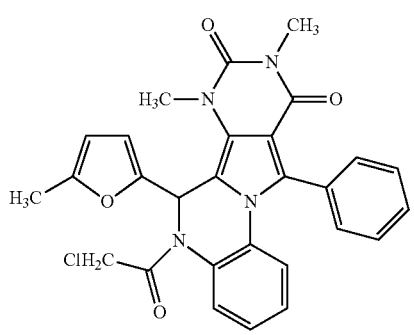

5-(2-Chloroacetyl)-7,9-dimethyl-6-(5-methylfuran-2-yl)-11-phenyl-5,6-dihydropyrimido[4',5'-3,4]pyrrolo[1,2-a]quinoxaline-8,10-(7H,9H)-dione (PPQ-2).

In a 15 mL pear shaped flask PPQ-102 (163 mg, 371 μmol) (see Example 3 for synthesis of PPQ-102) was dissolved in dry $CH_2Cl_2$ (3 mL). Triethylamine (80 μL, 58 mg, 574 μmol) was added followed by chloroacetyl chloride (30 μL, 43 mg, 377 μmol) and the reaction was stirred for 1 h. The reaction was found to be incomplete by TLC so additional chloroacetyl chloride (10 μL, 14.2 mg, 126 μmol) was added. After 1 h, TLC indicated no remaining starting material. The reaction was extracted with dilute citric acid, dried over $NaSO_4$, and diluted with ethanol (9 mL). The solution was placed on a rotary evaporator until a beige precipitate ceased to form. The mixture was then cooled in an ice bath and the precipitate was collected by filtration, washed with ethanol, and dried in vacuo to give PPQ-2 (170 mg, 89%) $^1$H NMR (600 MHz, $CD_2Cl_2$) δ 7.86 (d, J=7.1, 1H), 7.58 (t, J=7.1, 1H), 7.55 (s, 1H), 7.47 (t, J=7.5, 1H), 7.33-7.25 (m, J=1.2, 7.9, 2H), 7.14 (td, J=1.2, 7.8, 1H), 7.02 (d, J=7.1, 1H), 6.97-6.92 (m, 1H), 6.64 (dd, J=1.0, 8.3, 1H), 5.71-5.66 (m, 2H), 4.41 (dd, J=13.3, 62.4, 2H), 3.58 (s, 3H), 3.27 (s, 3H), 2.16 (s, 3H). $^{13}$C NMR (151 MHz, $CD_2Cl_2$) δ 165.09, 159.44, 153.82, 151.78, 147.81, 132.01, 131.13, 130.15, 129.80, 129.45, 129.01, 128.62, 128.39, 127.39, 126.73, 126.01, 124.66, 122.57, 111.58, 110.34, 106.22, 105.44, 47.66, 42.19, 32.24, 27.97, 13.7.1. MS (ES+) (m/z): [M+1]$^+$ calculated for $C_{28}H_{24}ClN_4O_4$, 515.15. found 515.07.

Example 6

Synthesis of PPQ-3

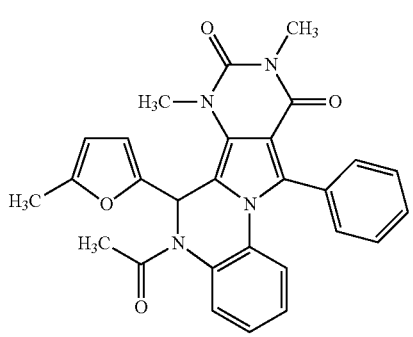 [SMILES: CC(=O)N1c2ccccc2-n2c(-c3ccccc3)c3c(=O)n(C)c(=O)n(C)c3c2C1c1ccc(C)o1]

5-Acetyl-7,9-dimethyl-6-(5-methylfuran-2-yl)-11-phenyl-5,6.-dihydropyrimido[4',5'-3,4]pyrrolo[1,2-a]quinoxaline-8,10-(7H,9H)-dione (PPQ-3).

In a 5 mL round bottom flask PPQ-102 (50 mg, 114 μmol) (see Example 3 for synthesis of PPQ-102) and DMAP (1.2 mg, 9.8 μmol) were stirred vigorously in acetic anhydride (2.16 g, 2.0 mL, 2.12 mmol) at 100° C. for 24 h. The reaction was then poured into water (20 mL) while stirring, alkalinized with sodium carbonate, and stirred at room temperature for 30 min. The mixture was then extracted with $CH_2Cl_2$ (3×15 mL), the organic layers combined and dried over $Na_2SO_4$. The solvent was removed on a rotary evaporator and the residue purified by TLC prep to give PPQ-3 (49.0 mg, 89.4%) as a white solid after drying under high vacuum; m.p. 245-246° C. $^1$H NMR (600 MHz, $CD_2Cl_2$) δ 7.85 (d, J=7.6, 1H), 7.62 (s, 1H), 7.57 (t, J=7.5, 1H), 7.46 (t, J=7.5, 1H), 7.29 (t, J=7.5, 1H), 7.25 (d, J=7.9, 1H), 7.12 (t, J=7.7, 1H), 7.02 (d, J=7.6, 1H), 6.88 (t, J=7.9, 1H), 6.61 (d, J=8.3, 1H), 5.68 (d, J=2.8, 1H), 5.66 (d, J=3.0, 1H), 3.59 (s, 3H), 3.26 (s, 3H), 2.32 (s, 3H), 2.16 (s, 3H). $^{13}$C NMR (151 MHz, $CD_2Cl_2$) δ 168.72, 159.44, 153.42, 151.71, 148.56, 131.96, 130.53, 130.22, 130.08, 129.88, 129.48, 129.24, 128.51, 128.22, 126.79, 126.25, 126.22, 124.17, 122.13, 110.99, 110.93, 106.01, 105.15, 46.12, 32.13, 27.89, 22.59, 13.68. MS (ES+) (m/z): [M+1]$^+$ calculated for $C_{28}H_{25}N_4O_4$, 481.19. found 481.08.

Example 7

Synthesis of PPQ-4

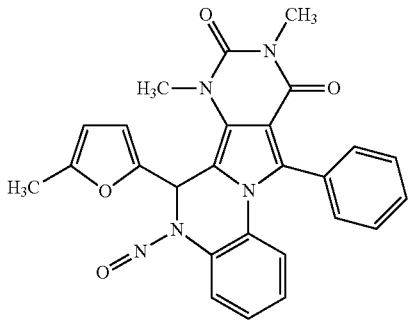 [SMILES: Cc1ccc(C2c3c4c(c(-c5ccccc5)n3-c3ccccc3N2N=O)c(=O)n(C)c(=O)n4C)o1]

7,9-Dimethyl-6-(5-methylfuran-2-yl)-5-nitroso-11-phenyl-5,6. -dihydropyrimido[4',5'-3,4]pyrrolo[1,2-a]quinoxaline-8,10-(7H,9H)-dione (PPQ-4).

In a 5 mL pear shaped flask PPQ-102 (25 mg, 57 µmol) (see Example 3 for synthesis of PPQ-102) was dissolved in dichloromethane (2 mL), and 90% t-butyl nitrite (15.6 mg, 18 µL, 136 µmol) was added. The reaction was maintained at room temperature for 30 min, and then dried in vacuo. The residue was purified by TLC prep to give PPQ-4 (21 mg, 78.8%) as a foam after drying under high vacuum. $^1$H NMR (600 MHz, CD$_2$Cl$_2$) δ 7.89 (s, 1H), 7.83 (d, J=7.7, 1H), 7.76 (d, J=8.0, 1H), 7.60 (t, J=7.6, 1H), 7.50 (t, J=7.5, 1H), 7.32 (t, J=7.5, 1H), 7.25 (t, J=7.7, 1H), 7.04-6.99 (m, 2H), 6.72 (d, J=8.4, 1H), 5.83 (d, J=3.1, 1H), 5.74 (d, J=2.6, 1H), 3.61 (s, 3H), 3.24 (s, 3H), 2.12 (s, 3H). 13C NMR (151 MHz, CD$_2$Cl$_2$) δ 159.25, 154.07, 151.80, 147.00, 131.92, 131.57, 130.23, 129.99, 129.64, 129.02, 128.75, 128.59, 127.65, 127.09, 126.22, 125.56, 121.70, 120.79, 111.19, 106.94, 106.39, 106.02, 43.31, 32.13, 27.97, 13.68. MS (ES+) (m/z): [M+1]$^+$ calculated for $C_{26}H_{22}N_5O_4$, 468.17. found 468.08.

Example 8

Synthesis of PPQ-5

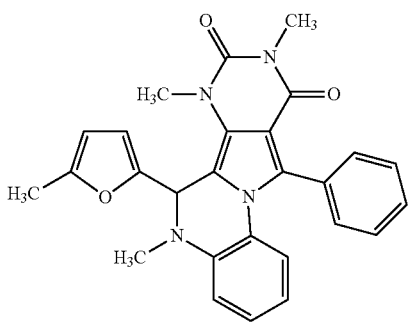 [SMILES: Cc1ccc(C2c3c4c(c(-c5ccccc5)n3-c3ccccc3N2C)c(=O)n(C)c(=O)n4C)o1]

6-(N-methyl-2-aminophenyl)-1,3-dimethyl-5-phenyl-1Hpyrrolo[3,4-d]pyrimidine-2,4(3H,6H)-dione (5c). In a 25 mL round bottom flask N-methyl-1,2-phenylenediamine (200 µl, 215 mg, 1.76 mmol) and EtOH (10 mL) were stirred. Ketone 4a (296 mg, 878 µmol) (see Example 2 for synthesis of 4a) was added and the mixture was stirred vigorously at reflux for 30 min during which a precipitate formed. The reaction was then chilled in an ice bath. The precipitate was collected by filtration and washed with cold ethanol to yield 5c (0.263 g, 83%) as an off-white powder. $^1$H NMR (600 MHz, DMSO-d6) δ 7.30-7.26 (m, 2H), 7.24-7.16 (m, 4H), 6.93 (d, J=1.0, 1H), 6.86 (d, J=7.7, 1H), 6.62 (d, J=8.3, 1H), 6.49 (t, J=7.5, 1H), 5.07 (d, J=4.8, 1H), 3.33 (s, 3H), 3.20 (s, 3H), 2.64 (d, J=4.9, 3H). $^{13}$C NMR (151 MHz, DMSO-d6) δ 159.08, 150.91, 145.66, 133.75, 130.36, 129.99, 129.34, 129.10, 128.58, 127.95, 127.15, 123.52, 114.95, 110.52, 105.63, 102.41, 31.56, 29.65, 27.41. MS (ES+) (m/z): [M+1]$^+$ calculated for $C_{21}H_{21}N_4O_2$, 361.17. found 361.10.

5,7,9-Trimethyl-6-(5-methylfuran-2-yl)-11-phenyl-5,6-dihydropyrimido[4',5'-3,4]pyrrolo[1,2-a]quinoxaline-8,10-(7H,9H)-dione (PPQ-5). In a 10 mL pear shaped flask was placed 5c (100 mg, 277 mmol), 5-methyl-2-furaldehyde (39 µL, 43.1 mg, 392 µmol), a magnetic stir bar, a small crystal of p-toluene-sulfonic acid, and 1,2-dichloroethane (3 mL). The mixture was refluxed until homogenous, with no starting material remaining as determined by TLC. The reaction was then concentrated in vacuo and diluted with ethanol (7 mL) causing a precipitate to form. The precipitate was collected by filtration and washed with cold ethanol to yield PPQ-5 (98.6 mg, 78.5%), as a white waxy solid; m.p. 174-175° C. $^1$H NMR (600 MHz, CD$_2$Cl$_2$) δ 7.83 (d, J=7.5, 1H), 7.56 (t, J=7.5, 1H), 7.44 (t, J=7.5, 1H), 7.27 (t, J=7.4, 1H), 7.07-7.01 (m, 1H), 6.96 (d, J=7.5, 1H), 6.76 (d, J=7.3, 1H), 6.60-6.53 (m, 1H), 6.51-6.44 (m, 1H), 5.82 (s, 1H), 5.72 (d, J=2.2, 1H), 5.58 (d, J=3.1, 1H), 3.55 (s, 3H), 3.25 (s, 3H), 3.10 (s, 3H), 2.16 (s, 3H). $^{13}$C NMR (151 MHz, CD$_2$Cl$_2$) δ 159.63, 152.80, 151.97, 150.12, 139.23, 132.10, 130.94, 130.05, 129.59, 128.97, 128.47, 128.20, 126.71, 125.50, 122.36, 121.08, 118.70, 115.02, 112.17, 109.76, 106.14, 105.23, 55.89, 38.32, 32.37, 27.89, 13.73. MS (ES+) (m/z): [M+1]$^+$ calculated for $C_{27}H_{25}N_4O_3$, 453.19. found 453.17.

Example 9

Synthesis of PPQ-6

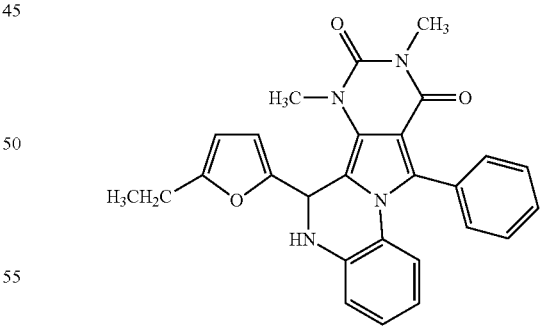

7,9-Dimethyl-6-(5-ethylfuran-2-yl)-11-phenyl-5,6-dihydropyrimido[4',5'-3,4]pyrrolo[1,2-a]quinoxaline-8,10-(7H,9H)-dione (PPQ-6). In a 5 mL pear shaped flask was placed 5a (50 mg, 144 µmol) (see Example 3 for synthesis of 5a), 5-ethyl-2-furaldehyde (17.5 µL, 18.4 mg, 149 µmol), a small crystal of p-toluene-sulfonic acid and 1,2-dichloroethane (1.5 mL). The mixture was refluxed for 34 min, concentrated in vacuo, and triturated with 2-butanone to give a white waxy precipitate. The precipitate was collected by filtration and washed with cold 2-butanone to yield PPQ-6 (37 mg, 57%); m.p. 224° C. $^1$H NMR (600 MHz, CD$_2$Cl$_2$) δ 7.80 (d, J=7.6, 1H), 7.56 (t, J=7.5, 1H), 7.45 (t, J=7.5, 1H), 7.35 (s, OH), 7.29 (t, J=7.5, 1H), 7.02 (d, J=7.7, 1H), 6.94-6.89 (m, 1H), 6.82 (dd, J=1.2, 7.9, 1H), 6.48 (d, J=7.6, 1H), 6.46-6.40 (m, 1H), 6.01 (s, 1H), 5.75 (d, J=3.1, 1H), 5.72 (d, J=2.8, 1H), 4.91 (d, J=2.1, 1H), 3.56 (s, 3H), 3.27 (s, 3H), 2.54 (q, J=7.6, 2H), 1.12 (t, J=7.6, 3H). $^{13}$C NMR (151 MHz, CD$_2$Cl$_2$) δ 159.59, 158.54, 152.03, 151.57, 137.43, 132.01, 130.96, 130.18, 130.06, 129.08, 128.55, 128.49, 128.27, 126.50, 124.87, 123.35, 121.11, 119.47, 117.38, 110.39, 109.39, 105.23, 104.50, 48.82, 32.05, 27.90, 21.51, 11.79. MS (ES+) (m/z): [M+1]$^+$ calculated for C$_{27}$H$_{25}$N$_4$O$_3$, 453.19. found 453.11.

Example 10

Synthesis of PPQ-7

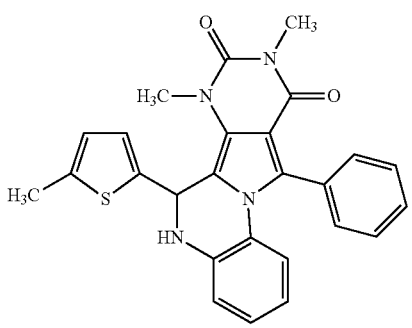 [SMILES: Cc1ccc(C2Nc3ccccc3-n3c(-c4ccccc4)c4c(=O)n(C)c(=O)n(C)c4c32)s1]

7,9-Dimethyl-6-(5-methylthiophene-2-yl)-11-phenyl-5,6-dihydropyrimido[4',5'-3,4]pyrrolo[1,2-a]quinoxaline-8,10-(7H,9H)-dione (PPQ-7).

In a 5 mL pear shaped flask was placed 5a (50 mg 144 μmol) (see Example 3 for synthesis of 5a), 5-methyl-2-thiophenecarbaldehyde (16 μL, 18.7 mg, 148 μmol), a small crystal of p-toluene-sulfonic acid and 1,2-dichloroethane (3 mL). The mixture was refluxed for 30 min, concentrated in vacuo, and diluted with ethanol (6 mL) to slowly form a waxy white solid. The precipitate was collected by filtration and washed with cold ethanol to yield PPQ-7 (48.9 mg, 74.5%). $^1$H NMR (600 MHz, CD$_2$Cl$_2$) δ 7.81 (d, J=7.6, 1H), 7.56 (t, J=7.5, 1H), 7.45 (t, J=7.5, 1H), 7.29 (t, J=7.5, 1H), 7.02 (d, J=7.7, 1H), 6.95-6.90 (m, 1H), 6.78 (dd, J=1.2, 7.9, 1H), 6.53-6.42 (m, 4H), 6.21 (d, J=2.4, 1H), 4.61 (d, J=2.4, 1H), 3.54 (s, 3H), 3.24 (s, 3H), 2.31 (s, 3H). $^{13}$C NMR (151 MHz, CD$_2$Cl$_2$) δ 159.55, 152.00, 143.36, 140.95, 136.88, 132.05, 130.94, 130.05, 130.00, 129.12, 128.51, 128.29, 126.59, 125.75, 125.04, 124.96, 122.89, 121.20, 119.68, 117.81, 112.59, 105.26, 50.49, 32.22, 27.89, 15.52. MS (ES+) (m/z): [M+1]$^+$ calculated for C$_{26}$H$_{23}$N$_4$O$_2$S, 455.15. found 455.08.

Example 11

Synthesis of PPQ-8

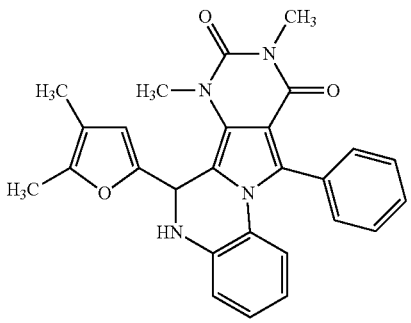 [SMILES: Cc1cc(C2Nc3ccccc3-n3c(-c4ccccc4)c4c(=O)n(C)c(=O)n(C)c4c32)oc1C]

7,9-Dimethyl-6-(4,5-dimethylfuran-2-yl)-11-phenyl-5,6-dihydropyrimido[4',5'-3,4]pyrrolo[1,2-a]quinoxaline-8,10-(7H,9H)-dione (PPQ-8).

In a 5 mL pear shaped flask was placed 5a (100 mg, 289 μmol) (see Example 3 for synthesis of 5a), 4,5-dimethyl-2-furaldehyde (37 μL, 37.6 mg, 303 μmol), a small crystal of p-toluene-sulfonic acid, and 1,2-dichloroethane (2 mL). The mixture was refluxed until homogenous, concentrated to dryness in vacuo and triturated with benzene and then ethanol to give PPQ-8 (89 mg, 68%) as a white waxy solid. $^1$H NMR (600 MHz, CD$_2$Cl$_2$) δ 7.81 (d, J=7.7, 1H), 7.56 (t, J=7.5, 1H), 7.45 (t, J=7.5, 1H), 7.29 (t, J=7.5, 1H), 7.02 (d, J=7.7, 1H), 6.92 (td, J=1.3, 7.8, 1H), 6.83 (dd, J=1.2, 7.9, 1H), 6.48 (d, J=8.0, 1H), 6.45-6.39 (m, 1H), 5.97 (s, 1H), 5.61 (s, 1H), 4.91 (d, J=2.1, 1H), 3.54 (s, 3H), 3.27 (s, 3H), 2.10 (s, 3H), 1.72 (s, 3H). $^{13}$C NMR (151 MHz, CD$_2$Cl$_2$) δ 159.58, 152.03, 150.33, 148.13, 137.37, 131.99, 131.02, 130.10, 130.05, 129.07, 128.49, 128.28, 126.46, 124.78, 123.27, 121.07, 119.37, 117.37, 114.69, 112.22, 110.37, 105.25, 48.72, 31.97, 27.90, 11.48, 9.80. MS (ES+) (m/z): [M+1]$^+$ calculated for C$_{27}$H$_{25}$N$_4$O$_3$, 453.19. found 453.24.

Example 12

Synthesis of PPQ-9

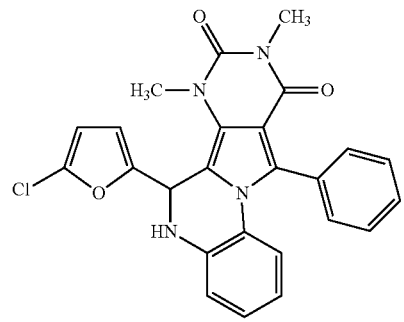 [SMILES: Cn1c(=O)c2c(-c3ccccc3)n3c(c2n(C)c1=O)C(c1ccc(Cl)o1)Nc1ccccc1-3]

6(5-Chlorofuran-2-yl)-7,9-dimethyl-11-phenyl-5,6-dihydropyrimido[4',5'-3,4]pyrrolo[1,2-a]quinoxaline-8,10-(7H,9H)-dione (PPQ-9). In a 5 mL pear shaped flask was placed 5a (100 mg, 289 μmol) (see Example 3 for synthesis of 5a), 5-chloro-2-furaldehyde (39.8 mg, 305 μmol), a small crystal of p-toluene-sulfonic acid, and 1,2-dichloroethane (1.5 mL). The mixture was refluxed for ~2 min until homogenous, concentrated in vacuo and then diluted with ethanol (5 mL). The solution was placed in a freezer overnight to give a light orange precipitate. The precipitate was collected by filtration and rinsed with cold ethanol to give PPQ-9 (107.6 mg, 81.2%). No m.p. (slow decomposition). $^1$H NMR (600 MHz, CD$_2$Cl$_2$) δ 7.80 (d, J=7.6, 1H), 7.56 (t, J=7.5, 1H), 7.45 (t, 1H), 7.29 (t, J=7.5, 1H), 7.01 (d, J=7.7, 1H), 6.95-6.91 (m, 1H), 6.84 (dd, J=1.1, 7.9, 1H), 6.50-6.42 (m, 2H), 6.03 (s, 1H), 5.98 (d, J=3.3, 1H), 5.86 (d, J=3.3, 1H), 4.89 (s, 1H), 3.53 (s, 3H), 3.26 (s, 3H). $^{13}$C NMR (151 MHz, CD$_2$Cl$_2$) δ 159.49, 153.07, 151.99, 136.79, 136.60, 131.97, 130.80, 130.57, 130.01, 129.19, 128.52, 128.32, 126.63, 124.79, 123.73, 121.12, 119.76, 117.49, 111.56, 109.12, 107.16, 105.29, 48.62, 32.06, 27.92. MS (ES+) (m/z): [M+1]$^+$ calculated for C$_{25}$H$_{20}$ClN$_4$O$_3$, 459.12. found 458.98.

Example 13

Synthesis of PPQ-10

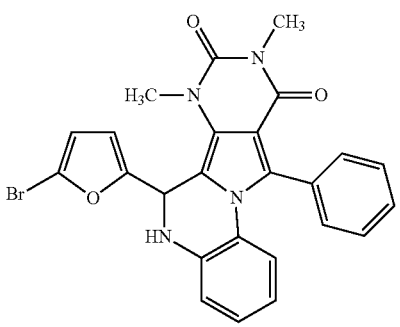

6-(5-Bromofuran-2-yl)-7,9-dimethyl-11-phenyl-5,6-dihydropyrimido[4',5'-3,4]pyrrolo[1,2-a]quinoxaline-8,10-(7H,9H)-dione (PPQ-10). In a 5 mL pear shaped flask was placed 5a (100 mg, 289 μmol) (see Example 3 for synthesis of 5a), 5-bromo-2-furaldehyde (53 mg, 303 μmol), a small crystal of p-toluene-sulfonic acid, and 1,2-dichloroethane (2 mL). The mixture was refluxed until homogenous, about 5 min, concentrated in vacuo and then diluted with ethanol (10 mL). An orange precipitate slowly formed which was aided by chilling the mixture in a freezer. The resulting solids were collected by filtration and rinsed with cold ethanol to give PPQ-10 (107.2 mg, 73.7%) as an orange powder. No m.p. (slow decomposition). $^1$H NMR (600 MHz, CD$_2$Cl$_2$) δ 7.80 (d, J=7.6, 1H), 7.56 (t, J=7.5, 1H), 7.45 (t, J=7.5, 1H), 7.29 (t, J=7.5, 1H), 7.02 (d, J=7.7, 1H), 6.96-6.90 (m, 1H), 6.84 (dd, J=1.1, 7.9, 1H), 6.48 (d, J=7.7, 1H), 6.47-6.41 (m, 1H), 6.12 (d, J=3.3, 1H), 6.04 (d, J=1.7, 1H), 5.85 (dd, J=0.8, 3.3, 1H), 4.95 (d, J=2.3, 1H), 3.53 (s, 3H), 3.27 (s, 3H). $^{13}$C NMR (151 MHz, CD$_2$Cl$_2$) δ 159.49, 155.46, 151.98, 136.82, 131.97, 130.80, 130.56, 130.01, 129.18, 128.52, 128.31, 126.63, 124.76, 123.70, 122.37, 121.12, 119.72, 117.48, 112.20, 111.90, 109.18, 105.28, 48.62, 32.08, 27.93. MS (ES+) (m/z): [M+1]$^+$ calculated for C$_{25}$H$_{20}$BrN$_4$O$_3$, 503.07. found 503.00.

Example 14

Synthesis of PPQ-11

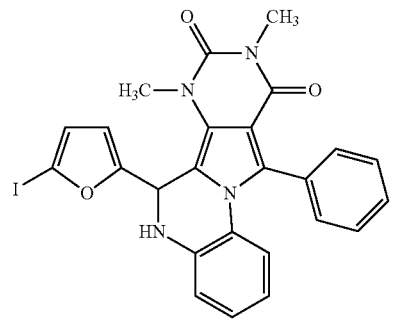 [SMILES: Cn1c(=O)c2c(-c3ccccc3)n3c(c2n(C)c1=O)C(c1ccc(I)o1)Nc1ccccc1-3]

7,9-Dimethyl-6-(5-iodofuran-2-yl)-11-phenyl-5,6-dihydropyrimido[4',5'-3,4]pyrrolo[1,2-a]quinoxaline-8,10-(7H,9H)-dione (PPQ-11) In a 5 mL pear shaped flask was placed 5a (150 mg, 433 μmol) (see Example 3 for synthesis of 5a), 5-iodo-2-furaldehyde (106 mg, 478 μmol), a small crystal of p-toluene-sulfonic acid, a magnetic stir bar, and 1,2-dichloroethane (2 mL). The mixture was refluxed until homogenous, about 5 min, concentrated in vacuo and then diluted with ethanol (10 mL). A yellow precipitate slowly formed which was collected by filtration and rinsed with cold ethanol to give PPQ-11 (223 mg, 93.6%), as a light orange powder. No m.p. (slow decomposition). $^1$H NMR (600 MHz, CD$_2$Cl$_2$) δ 7.80 (d, J=7.7, 1H), 7.56 (t, J=7.5, 1H), 7.45 (t, J=7.5, 1H), 7.29 (t, J=7.5, 1H), 7.02 (d, J=7.7, 1H), 6.93 (td, J=1.4, 7.9, 1H), 6.83 (dd, J=1.2, 7.9, 1H), 6.48 (d, J=7.3, 1H), 6.46-6.41 (m, 1H), 6.34 (d, J=3.3, 1H), 6.09 (d, J=2.0, 1H), 5.78 (d, J=3.3, 1H), 4.95 (d, J=2.4, 1H), 3.53 (s, 3H), 3.26 (s, 3H). $^{13}$C NMR (151 MHz, CD$_2$Cl$_2$) δ 159.50, 158.97, 151.98, 136.86, 131.97, 130.80, 130.52, 130.01, 129.17, 128.51, 128.30, 126.62, 124.75, 123.64, 121.12, 120.97, 119.70, 117.47, 112.15, 109.34, 105.28, 88.96, 48.57, 32.10, 27.93. MS (ES+) (m/z): [M+1]+ calculated for C$_{25}$H$_{20}$IN$_4$O$_3$, 551.06. found 551.01.

Example 15

Synthesis of PPQ-12

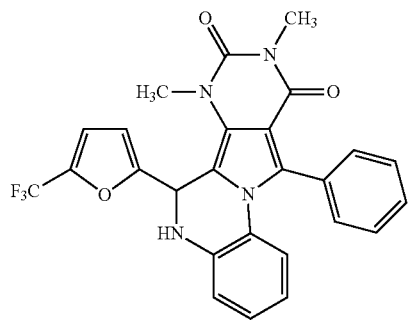 [SMILES: Cn1c(=O)c2c(-c3ccccc3)n3c(c2n(C)c1=O)C(c1ccc(C(F)(F)F)o1)Nc1ccccc1-3]

7,9-Dimethyl-11-phenyl-6-(5-trifluoromethylfuran-2-yl)-5,6-dihydropyrimido[4',5'-3,4]pyrrolo[1,2-a]quinoxaline-8,10-(7H,9H)-dione (PPQ-12). In a 5 mL pear shaped flask was placed 5a (100 mg, 289 µmol) (see Example 3 for synthesis of 5a), 5-trifluoromethyl-2-furaldehyde (50 mg, 305 µmol), a small crystal of p-toluene-sulfonic acid, and 1,2-dichloroethane (2 mL). The mixture was refluxed for ~5 min until homogenous, concentrated in vacuo and diluted with ethanol (8 mL). The solution was placed in a freezer for 4 days during which yellow crystals formed. The crystals were filtered and rinsed with ethanol to give PPQ-12 (126 mg, 88.5%); m.p. 256-257° C. 1H NMR (600 MHz, CD2Cl2) δ 7.80 (d, J=7.7, 1H), 7.56 (t, J=7.4, 1H), 7.46 (tt, J=1.2, 7.5, 1H), 7.30 (t, J=7.4, 1H), 7.02 (d, J=7.7, 1H), 6.93 (ddd, J=1.6, 7.1, 8.0, 1H), 6.85 (dd, J=1.2, 7.9, 1H), 6.61 (dd, J=1.0, 3.4, 1H), 6.51-6.42 (m, J=4.1, 7.1, 8.3, 2H), 6.10 (s, 1H), 5.95 (d, J=3.5, 1H), 4.96 (d, J=2.5, 1H), 3.55 (s, 3H), 3.26 (s, 3H). $^{13}$C NMR (151 MHz, CD$_2$Cl$_2$) δ 159.47, 156.71, 151.99, 141.85, 141.57, 141.29, 141.01, 136.75, 131.97, 130.76, 130.72, 129.99, 129.24, 128.55, 128.34, 126.74, 124.80, 123.79, 121.71, 121.18, 119.94, 119.91, 118.17, 117.43, 112.80, 112.78, 110.02, 109.09, 105.31, 48.56, 32.14, 27.94. MS (ES+) (m/z): [M+1]$^+$ calculated for C$_{26}$H$_{20}$F$_3$N$_4$O$_3$, 493.15. found 493.08.

Example 16

Synthesis of PPQ-13

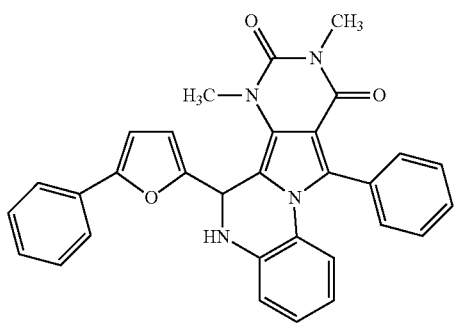 [SMILES: Cn1c(=O)c2c(-c3ccccc3)n3c(c2n(C)c1=O)C(c1ccc(-c2ccccc2)o1)Nc1ccccc1-3]

7,9-Dimethyl-11-phenyl-6-(5-phenylfuran-2-yl)-5,6-dihydropyrimido[4',5'-3,4]pyrrolo[1,2-a]quinoxaline-8,10-(7H,9H)-dione (PPQ-13). In a 5 mL pear shaped flask was placed 5a (100 mg, 289 µmol) (see Example 3 for synthesis of 5a), 5-phenyl-2-furaldehyde (52 mg, 302 µmol), a small crystal of p-toluene-sulfonic acid, and 1,2-dichloroethane (2 mL). The mixture was refluxed for ~5 min until homogenous, concentrated slightly in vacuo and diluted with ethanol (10 mL). A white waxy precipitate formed almost immediately, which was then chilled, filtered and washed with ethanol to give PPQ-13 (141.5 mg, 97.9%). $^1$H NMR (600 MHz, CD$_2$Cl$_2$) δ 7.81 (d, J=7.7, 1H), 7.57 (t, J=7.6, 1H), 7.54-7.50 (m, 2H), 7.46 (t, J=7.5, 1H), 7.35 (t, J=7.8, 2H), 7.30 (t, J=7.5, 1H), 7.24 (t, J=7.4, 1H), 7.04 (d, J=7.7, 1H), 6.92 (td, J=1.3, 7.9, 1H), 6.85 (dd, J=1.3, 7.9, 1H), 6.52 (d, J=7.5, 1H), 6.48-6.44 (m, 2H), 6.14 (d, J=1.3, 1H), 5.97 (d, J=3.3, 1H), 4.94 (s, 1H), 3.62 (s, 3H), 3.26 (s, 3H). 13C NMR (151 MHz, CD$_2$Cl$_2$) δ 159.55, 154.06, 153.27, 152.02, 137.34, 132.03, 130.90, 130.35, 130.27, 130.04, 129.13, 128.95, 128.51, 128.29, 127.88, 126.58, 124.92, 123.65, 123.48, 121.20, 119.63, 117.44, 110.72, 110.15, 105.71, 105.29, 48.85, 32.22, 27.91. MS (ES+) (m/z): [M+1]$^+$ calculated for C$_{31}$H$_{25}$N$_4$O$_3$, 501.19. found 501.13.

Example 17

Synthesis of PPQ-14

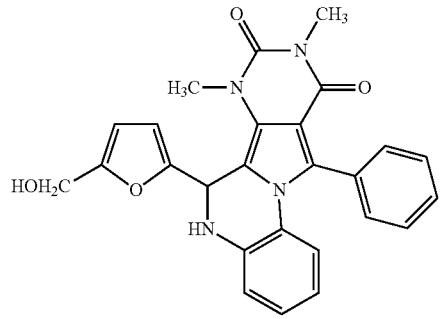 [SMILES: Cn1c(=O)c2c(-c3ccccc3)n3c(c2n(C)c1=O)C(c1ccc(CO)o1)Nc1ccccc1-3]

7,9-Dimethyl-11-phenyl-6-(5-hydroxymethylfuran-2-yl)-5,6-dihydropyrimido[4',5'-3,4]pyrrolo[1,2-a]quinoxaline-8,10-(7H,9H)-dione (PPQ-14). In a 5 mL pear shaped flask was placed 5a (50 mg, 144 µmol) (see Example 3 for synthesis of 5a), 5-hydroxymethyl-2-furaldehyde (18.8 mg, 149 µmol), TFA (5 µL, 7.4 mg, 65 µmol) and 1,2-dichloroethane (1.5 mL). The mixture was refluxed for 10 min forming a precipitate. The reaction was continued for 5 min before chilling in an ice bath. The precipitate was filtered and washed with cold 1,2-dichloroethane to give PPQ-14 (44.9 mg, 68.4%), as a white waxy solid. 1H NMR (600 MHz, CD$_2$Cl$_2$) δ 7.79 (d, J=7.5, 1H), 7.56 (t, J=7.5, 1H), 7.45 (t, J=7.5, 1H), 7.29 (t, J=7.4, 1H), 7.01 (d, J=7.6, 1H), 6.93-6.90 (m, 1H), 6.83 (dd, J=1.3, 7.9, 1H), 6.47 (dd, J=1.2, 8.3, 1H), 6.45-6.40 (m, 1H), 6.07-6.03 (m, 2H), 5.79 (d, J=3.1, 1H), 4.90 (s, 1H), 4.47 (s, 2H), 3.54 (s, 3H), 3.25 (s, 3H), 1.83 (s, 1H). $^{13}$C NMR (151 MHz, CD$_2$Cl$_2$) δ 159.54, 154.73, 153.68, 152.02, 137.18, 131.99, 130.88, 130.36, 130.03, 129.14, 128.51, 128.30, 126.56, 124.86, 123.51, 121.13, 119.62, 117.40, 109.93, 109.77, 108.60, 105.27, 57.39, 48.78, 32.09, 27.90. MS (ES+) (m/z): [M+1]$^+$ calculated for C$_{26}$H$_{23}$N$_4$O$_4$, 455.171931. found 455.15.

Example 18

Synthesis of PPQ-15

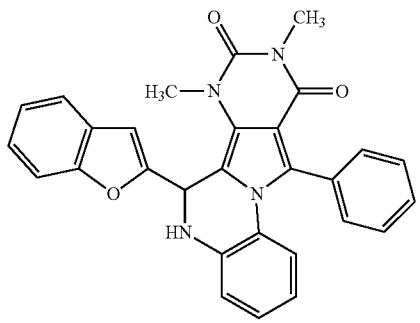 [SMILES: Cn1c(=O)c2c(-c3ccccc3)n3c(c2n(C)c1=O)C(c1cc2ccccc2o1)Nc1ccccc1-3]

6-(Benzofuran-2-yl)-7,9-dimethyl-11-phenyl-5,6-dihydropyrimido[4',5'-3,4]pyrrolo[1,2-a]quinoxaline-8,10-(7H, 9H)-dione (PPQ-15). In a 5 mL pear shaped flask was placed 5a (100 mg, 289 μmol) (see Example 3 for synthesis of 5a), 2-benzofurancarboxaldehyde (52 mg, 302 μmol), a small crystal of p-toluene-sulfonic acid, and 1,2-dichloroethane (2 mL). The mixture was refluxed for several min to give a white precipitate. The reaction was chilled in an ice bath, filtered, and the precipitate washed with cold 1,2-dichloroethane to give PPQ-15 (125 mg, 91.2%) as a white very waxy solid; m.p. 294-295° C. 1H NMR (600 MHz, $CD_2Cl_2$) δ 7.82 (d, J=7.6, 1H), 7.57 (t, J=7.6, 1H), 7.46 (t, J=7.5, 1H), 7.41 (d, J=8.3, 1H), 7.38 (d, J=7.6, 1H), 7.30 (t, J=7.5, 1H), 7.23 (t, J=7.4, 1H), 7.13 (t, J=7.4, 1H), 7.04 (d, J=7.7, 1H), 6.89 (t, J=7.5, 1H), 6.85 (d, J=6.7, 1H), 6.49 (d, J=8.2, 1H), 6.42 (t, J=7.1, 1H), 6.27 (s, 1H), 6.20 (s, 1H), 5.03 (s, 1H), 3.58 (s, 3H), 3.27 (s, 3H). $^{13}$C NMR (151 MHz, $CD_2Cl_2$) δ 159.53, 156.19, 155.16, 152.02, 136.95, 131.99, 130.88, 130.59, 130.00, 129.19, 128.55, 128.34, 127.75, 126.62, 124.85, 124.82, 123.83, 123.25, 121.35, 121.13, 119.76, 117.42, 111.32, 109.46, 106.07, 105.35, 49.10, 32.09, 27.93. MS (ES+) (m/z): $[M+1]^+$ calculated for $C_{29}H_{23}N_4O_3$, 475.18. found 475.01.

Example 19

Synthesis of BPO-16

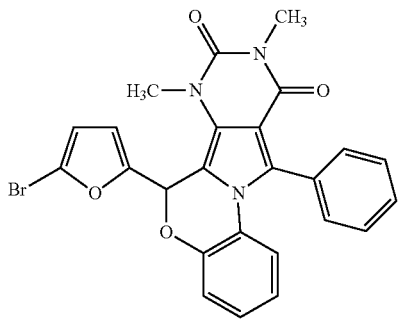

1,3-Dimethyl-6-(2-hydroxyphenyl)-5-phenyl-1H-pyrrolo[3,4-d]pyrimidine-2,4(3H,6H)-dione (5e). In a 25 mL round bottom was placed o-aminophenol (163 mg, 1.5 mmol) and EtOH (10 mL). The mixture was warmed until homogenous and then compound 4a (250 mg, 741 μmol) was added (see Example 2 for synthesis of 4a). The mixture was stirred vigorously at reflux during which a precipitate formed. After 1 h the mixture was cooled in an ice bath, filtered, and the precipitate washed with cold EtOH to yield 5e (248 mg, 96.4%) as a white powder. $^1$H NMR (600 MHz,) δ 10.02 (s, 1H), 7.29-7.26 (m, 2H), 7.24-7.17 (m, 4H), 7.10 (dd, J=1.6, 7.8, 1H), 6.96 (s, 1H), 6.90 (dd, J=1.1, 8.2, 1H), 6.77 (td, J=1.2, 7.6, 1H), 3.34 (s, 3H), 3.21 (s, 3H). $^{13}$C NMR (151 MHz, DMSO d6) δ 159.11, 152.86, 150.91, 133.81, 130.35, 129.98, 129.67, 129.13, 128.58, 127.83, 127.18, 125.95, 118.99, 116.39, 106.16, 101.88, 31.50, 27.46. MS (ES+) (m/z): $[M+1]^+$ calculated for $C_{20}H_{18}N_3O_3$, 348.13. found 348.11.

6-(5-Bromofuran-2-yl)-7,9-dimethyl-11-phenyl-6H-benzo[b]pyrimido[4',5'-3,4]pyrrolo[1,2-d]oxazine-8,10-(7H,9H)-dione (BPO-16). 5-bromo-2-furaldehyde (186 mg, 1.06 mmol), 5e (300 mg, 864 μmol), chloroform (6 mL) and TFA (10 μL, 14.9 mg, 130 μmol) were sealed in a Emrys 2-5 mL process vial 5 and submerged to the level of solvent in an oil bath at 150° C. for 19 min. The reaction was allowed to cool, filtered through a celite plug to remove impurities, and concentrated to dryness in vacuo. The residue was dissolved in a minimum volume of $CH_2Cl_2$ and then diluted with ethanol (15 mL). The solution was then placed on a rotary evaporator to remove $CH_2Cl_2$. Once the solution began to crystallize the mixture was allowed to stand. The mixture was then cooled, filtered, and the crystals rinsed with cold ethanol to give BPO-16 (365 mg, 83.8%). No m.p. (slow decomposition). $^1$H NMR (600 MHz, $CD_2Cl_2$) δ 7.79 (d, J=7.6, 1H), 7.58 (t, J=7.5, 1H), 7.49 (t, J=7.5, 1H), 7.33 (t, J=7.5, 1H), 7.07 (d, J=7.6, 1H), 7.05-6.98 (m, 2H), 6.79 (s, 1H), 6.64 (ddd, J=2.2, 6.7, 8.6, 1H), 6.53 (d, J=8.6, 1H), 6.14 (d, J=3.4, 1H), 5.98 (dd, J=0.8, 3.4, 1H), 3.47 (s, 3H), 3.26 (s, 3H). $^{13}$C NMR (151 MHz, $CD_2Cl_2$) δ 159.35, 152.32, 151.83, 145.46, 131.86, 130.86, 130.19, 129.94, 129.53, 128.66, 128.49, 127.11, 125.85, 124.38, 124.11, 122.54, 120.39, 119.72, 114.75, 112.35, 106.50, 105.58, 68.13, 32.42, 27.94. MS (ES+) (m/z): $[M+1]^+$ calculated for $C_{25}H_{19}BrN_3O_4$, 504.06. found 504.03.

Example 20

Synthesis of BPO-17

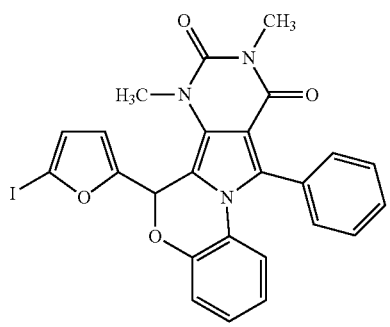 [SMILES: Cn1c(=O)c2c(-c3ccccc3)n3c(c2n(C)c1=O)C(c1ccc(I)o1)Oc1ccccc1-3]

7,9-Dimethyl-6-(5-iodofuran-2-yl)-11-phenyl-6Hbenzo[b]pyrimido[4',5'-3,4]pyrrolo[1,2-d]oxazine-8,10-(7H,9H)-dione (BPO-17). 5-iodo-2-furaldehyde (84 mg, 378 μmol), 5e (100 mg, 288 μmol) (see Example 19 for synthesis of 5e), chloroform (1 mL), and TFA (10 μL, 14.9 mg, 130 μmol) were sealed in a Emrys 2-5 mL process vial and submerged to the level of solvent in an oil bath at 150° C. for 19 min. The reaction was cooled in an ice bath, filtered through a celite plug and dried in vacuo. The residue was then purified via flash chromatography to give BPO-17 (68.4 mg, 43%). $^1$H NMR (600 MHz, $CD_2Cl_2$) δ 7.79 (d, J=7.6, 1H), 7.58 (t, J=7.6, 1H), 7.49 (t, J=7.5, 1H), 7.33 (t, J=7.5, 1H), 7.07 (d, J=7.6, 1H), 7.05-6.98 (m, 2H), 6.84 (s, 0.7H), 6.80 (s, 0.3H), 6.67-6.61 (m, J=2.3, 5.5, 6.7, 1H), 6.53 (d, J=8.0, 1H), 6.36 (d, J=3.3, 0.7H), 6.15 (d, J=3.4, 0.3H), 5.99 (d, J=3.3, 0.3H), 5.92 (d, J=3.3, 0.7H), 3.47 (s, 0.74H), 3.47 (s, 2.27H), 3.26 (s, 3H). $^{13}$C NMR (151 MHz, $CD_2Cl_2$) δ 159.34, 155.77, 152.32, 151.81, 145.49, 145.45, 131.85, 130.84, 130.80, 130.19, 129.94, 129.51, 128.65, 128.48, 127.09, 125.84, 124.37, 124.32, 124.10, 122.53, 122.50, 121.06, 120.37, 119.70, 114.89, 114.74, 112.34, 106.66, 106.49, 105.56, 91.02, 68.03, 32.42, 27.93. MS (ES+) (m/z): [M+1]⁺ calculated for C₂₅H₁₉IN₃O₄, 552.04. found 552.07.

Example 21

Synthesis of BPO-18

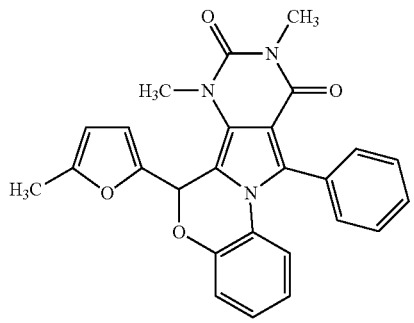 [SMILES: Cc1ccc(C2Oc3ccccc3-n3c(-c4ccccc4)c4c(=O)n(C)c(=O)n(C)c4c32)o1]

7,9-Dimethyl-6-(5-methylfuran-2-yl)-11-phenyl-6H-benzo[b]pyrimido[4',5'-3,4]pyrrolo[1,2-d]oxazine-8,10-(7H,9H)-dione (BPO-18). 5-methylfurfural (8 µL, 8.9 mg, 80 µmol), 5e (25 mg, 72 µmol) (see Example 19 for synthesis of 5e), chloroform (3 mL) and a small crystal of TsOH were sealed in a Emrys 2-5 mL process vial and submerged to the level of solvent in an oil bath at 150° C. for 35 min. Once the tube cooled, the contents were purified by TLC-prep to give BPO-18 (15.6 mg, 49.4%) as a waxy white powder. ¹HNMR (600 MHz, CD₂Cl₂) δ 7.80 (d, J=7.6, 1H), 7.58 (t, J=7.5, 1H), 7.48 (t, J=7.5, 1H), 7.32 (t, J=7.4, 1H), 7.07 (d, J=7.6, 1H), 7.03-6.97 (m, 2H), 6.77 (s, 1H), 6.63 (ddd, J=3.1, 5.7, 8.6, 1H), 6.53 (d, J=8.0, 1H), 5.85 (d, J=3.1, 1H), 5.77 (d, J=2.2, 1H), 3.47 (s, 3H), 3.26 (s, 3H), 2.22 (s, 3H). ¹³C NMR (151 MHz, CD₂Cl₂) δ 159.44, 154.52, 151.86, 148.60, 145.78, 131.90, 130.43, 130.36, 129.99, 129.42, 128.62, 128.44, 126.93, 126.01, 123.90, 122.25, 120.35, 119.67, 113.05, 107.72, 106.40, 105.51, 68.58, 32.37, 27.91, 13.81. MS (ES+) (m/z): [M+1]⁺ calculated for C₂₆H₂₂N₃O₄, 440.16. found 440.11.

Example 22

Synthesis of BPO-19

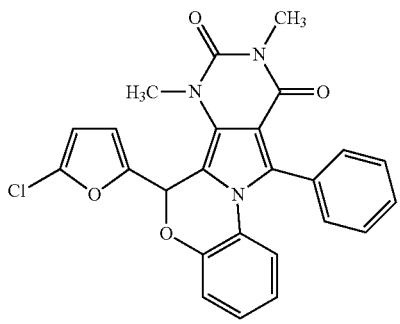 [SMILES: Cn1c(=O)c2c(-c3ccccc3)n3c(c2n(C)c1=O)C(c1ccc(Cl)o1)Oc1ccccc1-3]

5-m-Tolyl-1,3,6-trimethylpyrimidine-2,4(1H,3H)-dione (3d). In a 100 mL round bottom flask equipped with a condenser and an air lock was placed compound 2 (see FIG. 3) (5.00 g, 32.4 mmol), anhydrous zinc chloride 3 (4.45 g, 32.6 mmol), dry chlorobenzene (20 mL) and m-tolyl chloride (4.6 mL, 5.38 g, 34.8 mmol). The reaction was brought to reflux in an oil bath and vigorously stirred for 3 h. After cooling, water (40 mL) was added through the condenser, dropwise at first and then with increasing speed. The condenser was then rearranged for distillation and the chlorobenzene was removed by azeotropic distillation. The solution was then cooled in an ice bath, and diethyl ether (30 mL) was added while stirring to give a precipitate. The precipitate was filtered and recrystallized from 2-propanol to yield 3d (1.11 g, 26.3%); m.p. 136.8-139° C. ¹H NMR (600 MHz, CD₂Cl₂) δ 7.68-7.66 (m, 1H), 7.65-7.62 (m, 1H), 7.44-7.40 (m, 1H), 7.35 (t, J=7.6, 1H), 3.46 (s, 3H), 3.30 (s, 3H), 2.40 (s, 3H), 2.18 (s, 3H). ¹³C NMR (151 MHz, CD₂Cl₂) δ 194.00, 161.07, 152.22, 151.98, 139.22, 138.16, 134.94, 130.03, 129.01, 126.93, 113.36, 32.36, 28.32, 21.54, 17.99. MS (ES+) (m/z): [M+1]⁺ calculated for C₁₅H₁₇N₂O₃, 273.12. found 237.10.

6-(Bromomethyl)-5-m-tolyl-1,3-dimethylpyrimidine-2,4(1H,3H)-dione (4d).

In a 25 mL 2-neck round bottom flask equipped with a condenser, addition funnel and air lock, compound 3d (1.00 g, 3.67 mmol) was dissolved in CH₂Cl₂ (6 mL) and held at reflux. Bromine (200 µL, 0.624 g, 3.9 mmol) was mixed with CH₂Cl₂ (9 mL) in the addition funnel and added dropwise to the solution of 3d at such a rate that the color was discharged between drops. The last few drops caused the reaction to stay brown. The reaction continued for 10 min before the color was discharged by the addition of a few drops of acetone. TLC showed the reaction was quantitative. The reaction was dried in vacuo and the remaining solid crystallized from 2-propanol to yield 4d (1.20 g, 93%); m.p. 136.1-137° C. ¹H NMR (600 MHz, CD₂Cl₂) δ 7.67 (s, 1H), 7.63 (d, J=7.8, 1H), 7.45 (d, J=7.5, 1H), 7.37 (t, J=7.6, 1H), 4.22 (s, 2H), 3.60 (d, J=6.6, 3H), 3.30 (d, J=7.7, 3H), 2.41 (s, 3H). ¹³C NMR (151 MHz, CD₂Cl₂) δ 193.00, 160.95, 152.09, 149.09, 139.30, 137.77, 135.37, 130.22, 129.04, 127.11, 115.04, 31.98, 28.62, 23.75, 21.55. MS (ES+) (m/z): [M+1]⁺ calculated for C₁₅H₁₆BrN₂O₃, 351.03. found 350.99.

1,3-Dimethyl-6-(2-hydroxyphenyl)-5-m-tolyl-1H-pyrrolo[3,4-d]pyrimidine-2,4(3H,6H)-dione (5d). In a 25 mL round bottom flask 2-aminophenol (683 mg, 6.26 mmol) was dissolved in warm EtOH (10 mL) and compound 4d (296 mg, 878 µmol) was added while stirring. The reaction was refluxed 20 min to give a white precipitate. The reaction was then cooled in an ice bath, filtered, and the precipitate washed with cold ethanol to yield 5d (1.08 g, 96.3%) as a off white powder. ¹H NMR (600 MHz, DMSO-d6) δ 10.02 (s, 1H), 7.20 (td, J=1.6, 8.2, 1H), 7.16 (s, 1H), 7.10-7.06 (m, 2H), 7.04 (d, J=7.6, 1H), 7.01 (d, J=7.5, 1H), 6.93 (s, 1H), 6.90 (dd, J=0.8, 8.2, 1H), 6.77 (t, J=7.6, 1H), 3.33 (s, 3H), 3.20 (s, 3H), 2.19 (s, 3H). ¹³C NMR (151 MHz, DMSO-d6) δ 159.10, 152.91, 150.91, 136.04, 133.96, 131.15, 129.93, 129.59, 129.13, 128.54, 128.51, 127.28, 127.03, 126.03, 118.94, 116.34, 106.07, 101.81, 31.48, 27.47, 20.97. MS (ES+) (m/z): [M+1]⁺ calculated for C₂₁H₁₉N₃O₃, 362.15. found 362.09.

6-(5-Chlorofuran-2-yl)-7,9-dimethyl-11-(m-tolyl)-6Hbenzo[b]pyrimido[4',5'-3,4]pyrrolo[1,2-d]oxazine-8,10-(7H,9H)-dione (BPO-19). 5-chlorofurfural (43 mg, 329 µmol), 5d (100 mg, 277 µmol), a small crystal of TsOH, and 1,2-dichloroethane (2.5 mL) were placed in an Emrys 2-5 mL process vial and submerged to the level of solvent in an oil bath at 150° C. for 20 min. Once the reaction had cooled the contents were purified by TLC prep to give BPO-19 (88 mg, 67%) as an off white solid. ¹H NMR (600 MHz, CD₂Cl₂) δ 7.59 (s, 0.5H), 7.56 (d, J=7.6, 0.5H), 7.46 (t, J=7.6, 0.5H), 7.30 (d, J=7.7, 1H), 7.21 (t, J=7.6, 0.5H), 7.06-6.98 (m, 2H), 6.89 (s, 0.5H), 6.85 (d, J=7.6, 0.5H), 6.77 (s, 1H), 6.65 (qd, J=2.3, 6.3, 1H), 6.54 (dd, J=8.2, 12.6, 1H), 6.00 (s, 2H), 3.47 (s, 3H), 3.25 (d, J=6.6, 3H), 2.47 (s, 1.5H), 2.23 (s, 1.5H). $^{13}$C NMR (151 MHz, CD$_2$Cl$_2$) δ 159.33, 151.85, 150.01, 145.39, 145.34, 138.58, 138.43, 138.10, 132.23, 131.16, 131.13, 130.32, 130.29, 130.17, 130.14, 128.80, 128.52, 128.38, 127.07, 127.05, 126.92, 125.93, 124.30, 122.55, 122.50, 120.37, 120.33, 119.64, 114.40, 107.31, 106.26, 106.21, 105.55, 105.49, 68.10, 32.40, 32.37, 27.94, 27.92, 21.64, 21.35. MS (ES+) (m/z): [M+1]$^+$ calculated for C$_{26}$H$_{21}$ClN$_3$O$_4$, 474.12. found 474.02.

Example 23

Synthesis of BPO-20

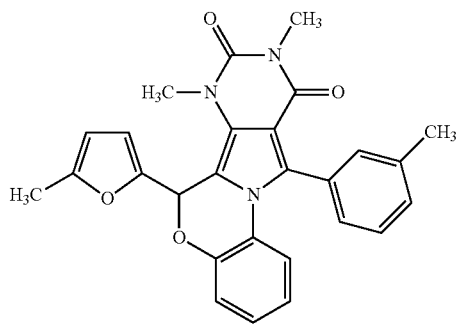

7,9-Dimethyl-6-(5-methylfuran-2-yl)-11-(m-tolyl)-6H-benzo[b]pyrimido[4',5'-3,4]pyrrolo[1,2-d]oxazine-8,10-(7H,9H)-dione (BPO-20).

5-Methylfurfural (33 μL, 37 mg, 332 mol), 5d (100 mg, 277 mol) (see Example 22 for synthesis of 5d), TFA (5 μL, 7.4 mg, 65 μmol), and chloroform (3 mL) were sealed in a Emrys 2-5 mL process vial and submerged to the level of solvent in an oil bath at 150° C. for 24 min. Once the reaction had cooled, the contents were purified by flash chromatography to give BPO-20 (92 mg, 74%) with a trace amount of impurity. The product was dissolved in a minimum volume of CH$_2$Cl$_2$ and then diluted with methanol (6 mL). The solution was placed on a rotary evaporator until a precipitate began to form. The mixture was then cooled, the precipitate filtered and washed with cold methanol to give BPO-20 (64 mg, 51%) as a pure ivory colored powder. $^1$H NMR (600 MHz, CD$_2$Cl$_2$) δ 7.60 (s, 0.5H), 7.57 (d, J=7.6, 0.5H), 7.47 (t, J=7.6, 0.5H), 7.30 (d, J=7.7, 1H), 7.21 (t, J=7.6, 0.5H), 7.05-6.97 (m, 2H), 6.91 (s, 0.5H), 6.86 (d, J=7.6, 0.5H), 6.77 (s, 1H), 6.67-6.60 (m, 1H), 6.55 (dd, J=8.3, 11.3, 1H), 5.85 (d, J=2.8, 1H), 5.77 (d, J=2.5, 1H), 3.47 (s, 3H), 3.26 (d, J=6.2, 3H), 2.48 (s, 1.5H), 2.23 (s, 1.5H), 2.23 (s, 3H). $^{13}$C NMR (151 MHz, CD$_2$Cl$_2$) δ 159.44, 159.43, 154.49, 151.89, 148.66, 145.72, 145.67, 138.52, 138.37, 132.28, 130.75, 130.72, 130.38, 130.33, 130.31, 130.19, 128.84, 128.48, 128.34, 126.98, 126.89, 126.87, 126.08, 123.82, 122.27, 122.22, 120.34, 120.30, 119.59, 113.01, 107.52, 107.47, 106.40, 105.49, 105.42, 68.53, 32.37, 32.34, 27.91, 27.89, 21.64, 21.35, 13.81. MS (ES+) (m/z): [M+1]$^+$ calculated for C$_{27}$H$_{24}$N$_3$O$_4$, 454.18. found 454.10.

Example 24

Synthesis of BPO-21

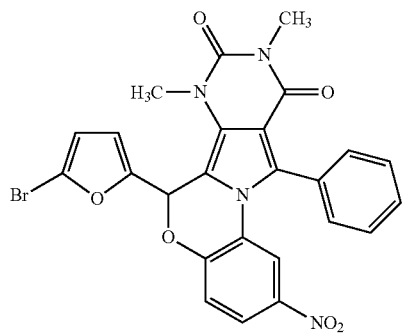 [SMILES: Cn1c(=O)c2c(-c3ccccc3)n3c(c2n(C)c1=O)C(c1ccc(Br)o1)Oc1ccc([N+](=O)[O-])cc1-3]

6-(2-hydroxy-5-nitrophenyl)-1,3-dimethyl-5-phenyl-1Hpyrrolo[3,4-d]pyrimidine-2,4(3H,6H)-dione (5g). In a 25 mL round bottom flask was placed 4a (1.00 g, 2.97 mmol) (see Example 2 for synthesis of 4a), 2-amino-4-nitrophenol (921 mg, 5.98 mmol), and methanol (12 mL). The reaction was stirred at reflux for 5 h, then cooled in an ice bath. The precipitate was filtered and rinsed with cold methanol to give 5g (1.32 g, 94%). $^1$H NMR (600 MHz, DMSO-d6) δ 11.72 (s, 1H), 8.19 (d, J=2.8, 1H), 8.15 (dd, J=2.9, 9.1, 1H), 7.31-7.21 (m, 5H), 7.08 (s, 1H), 7.01 (d, J=9.1, 1H), 3.34 (s, 3H), 3.21 (s, 3H). $^{13}$C NMR (151 MHz, DMSO-d6) δ 159.26, 159.03, 150.85, 138.89, 134.18, 130.34, 129.34, 128.85, 128.14, 127.36, 126.15, 126.09, 125.45, 116.60, 105.95, 102.41, 31.52, 27.48. MS (ES+) (m/z): [M+1]$^+$ calculated for C$_{20}$H$_{17}$N$_4$O$_5$, 393.12. found 393.02.

6-(5-bromofuran-2-yl)-7,9-Dimethyl-2-nitro-11-phenyl-6H-benzo[b]pyrimido[4',5'-3,4]pyrrolo[1,2-d]oxazine-8,10-(7H,9H)-dione (BP0-21).

Pyrrole 5g (225 mg, 573 μmol), 5-bromofurfural (130 mg, 743 μmol), 1,2-dicholoroethane (4 mL), TFA (10 μL, 14.9 mg, 130 mol) and 3 Å molecular sieve (500 mg, 8-12 mesh) were sealed in a Emrys 2-5 mL process vial and submerged to the level of solvent in an oil bath at 150° C. for 100 min. Upon cooling the reaction turned dark green and some impurities precipitated. The reaction was filtered through a celite plug and dried in vacuo. The residue was dissolved in CH$_2$Cl$_2$ (3 mL) and then diluted with ethanol (15 mL). The solution was then placed on a rotary evaporator until small crystals began to form. The mixture was cooled and the crystals were collected by filtration and rinsed with cold ethanol to give BPO-21 (204 mg, 65%). $^1$H NMR (600 MHz, CD$_2$Cl$_2$) δ 7.91 (dd, J=2.6, 8.9, 1H), 7.84 (d, J=7.7, 1H), 7.69 (t, J=7.6, 1H), 7.58 (t, J=7.5, 1H), 7.39 (d, J=2.6, 1H), 7.37 (t, J=7.6, 1H), 7.18 (d, J=8.9, 1H), 7.07 (d, J=7.7, 1H), 6.92 (s, 1H), 6.17 (d, J=3.4, 1H), 6.03 (d, J=3.4, 1H), 3.48 (s, 4H), 3.27 (s, 3H). $^{13}$C NMR (151 MHz, CD$_2$Cl$_2$) δ 159.10, 151.70, 151.31, 150.71, 142.06, 131.75, 131.63, 130.16, 129.53, 129.32, 129.18, 129.07, 125.55, 124.83, 124.74, 122.43, 120.23, 115.93, 115.22, 112.56, 106.48, 105.26, 68.75, 32.40, 28.01. MS (ES+) (m/z): [M+1]$^+$ calculated for C$_{25}$H$_{18}$BrN$_4$O$_6$, 549.04. found 549.05.

Example 25

Synthesis of BPO-22

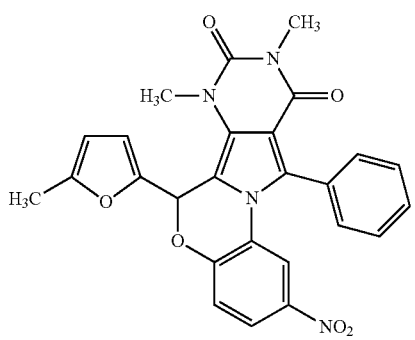 [SMILES: Cc1ccc(C2Oc3ccc([N+](=O)[O-])cc3-n3c(-c4ccccc4)c4c(=O)n(C)c(=O)n(C)c4c32)o1]

7,9-Dimethyl-6-(5-methylfuran-2-yl)-2-nitro-11-phenyl-6H-benzo[b]pyrimido[4',5'-3,4]pyrrolo[1,2-d]oxazine-8,10-(7H,9H)-dione (BPO-22).

Pyrrole 5g (250 mg, 637 μmol) (see Example 24 for synthesis of 5g), 5-methylfurfural (76 μl, 84 mg, 764 μmol), chloroform (8 mL), and TFA (10 pt, 14.9 mg, 130 μmol) were sealed in a Emrys 2-5 mL process vial and submerged to the level of solvent in an oil bath at 150° C. for 2.7 h. The reaction was then cooled and dried in vacuo. The residue was purified by flash chromatography to give BPO-22 (245 mg, 79%) as a yellow foam after drying under high vacuum. To convert the foam to a powder, the foam was dissolved in CH$_2$Cl$_2$ (3 mL) and then diluted with methanol (15 mL). The volume of solvent was then reduced on a rotary evaporator. Once the solution began to precipitate the mixture was allowed to stand until precipitation ceased. The mixture was then cooled, filtered, and the precipitate rinsed with cold methanol to give BPO-22 (179 mg). The mother liquor was reduced to yield additional BPO-22 (38 mg). $^1$H NMR (600 MHz, CD$_2$Cl$_2$) δ 7.89 (dd, J=2.6, 8.9, 1H), 7.84 (d, J=7.7, 1H), 7.68 (t, J=7.6, 1H), 7.57 (t, J=7.5, 1H), 7.39 (d, J=2.4, 1H), 7.36 (t, J=7.6, 1H), 7.14 (d, J=8.9, 1H), 7.07 (d, J=7.7, 1H), 6.90 (s, 1H), 5.91 (d, J=3.1, 1H), 5.79 (d, J=2.9, 1H), 3.48 (s, 3H), 3.26 (s, 3H), 2.20 (s, 3H). $^{13}$C NMR (151 MHz, CD$_2$Cl$_2$) δ 159.20, 155.08, 151.75, 151.18, 147.73, 141.85, 131.80, 131.20, 130.05, 129.59, 129.51, 129.14, 129.02, 125.71, 124.23, 122.28, 120.11, 115.90, 113.51, 106.62, 106.51, 106.41, 69.32, 32.37, 27.98, 13.81. MS (ES+) (m/z): [M+1]$^+$ calculated for C$_{26}$H$_{21}$N$_4$O$_6$, 485.15. found 485.03

Example 26

Synthesis of PPQ-23

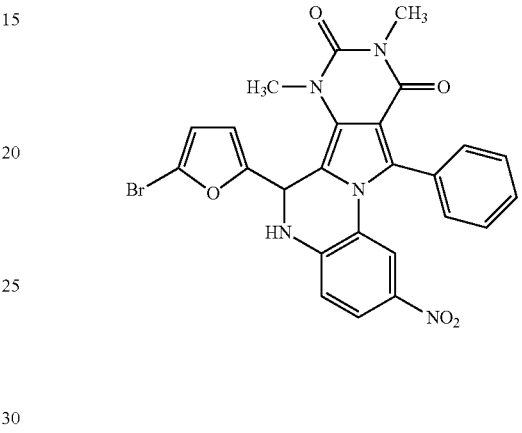

6-(2-Amino-5-nitrophenyl)-1,3-dimethyl-5-phenyl-1H-pyrrolo[3,4-d]pyrimidine-2,4(3H,6H)-dione (5b). In a 25 mL round bottom flask 4-nitro 1,2-phenylenediamine (300 mg, 1.96 mmol), and 4a (330 mg, 979 mmol) (see Example 2 for synthesis of 4a) were combined in ethanol (10 mL). The stirred mixture was brought to reflux for 3 h during which a yellow precipitate formed. The mixture was then chilled in an ice bath, filtered, and the precipitate washed with cold ethanol to give 5b (340 mg, 88.7%) as a waxy shiny yellow solid; mp>300° C. $^1$H NMR (600 MHz, DMSO-d6) δ 7.97 (dd, J=2.7, 9.2, 1H), 7.86 (d, J=2.6, 1H), 7.37-7.32 (m, 2H), 7.28-7.24 (m, 4H), 7.05 (s, 1H), 6.75 (d, J=9.2, 1H), 6.65 (s, 2H), 3.35 (s, 3H), 3.21 (s, 3H). $^{13}$C NMR (151 MHz, DMSO-d6) δ 159.06, 151.66, 150.89, 135.01, 133.84, 130.38, 129.34, 129.02; 128.32, 127.38, 126.19, 126.05, 121.34, 114.31, 105.49, 102.98, 31.59, 27.46. MS (ES+) (m/z): [M+1]$^+$ calculated for C$_{20}$H$_{18}$N$_5$O$_4$, 392.135880. found 392.03.

6-(5-Bromofuran-2-yl)-7,9-dimethyl-2-nitro-11-phenyl-5,6-dihydropyrimido[4',5'-3,4]pyrrolo[1,2-a]quinoxaline-8,10-(7H,9H)-dione (PPQ-23). In a 5 mL pear shaped flask was placed 5b (100 mg, 256 umol), 5-bromo-2-furaldehyde (50 mg, 286 μmol), TFA (10 μL, 14.9 mg, 130 μmol), and chloroform (2.5 mL). The mixture was refluxed for 1 h, dried in vacuo, and purified by flash chromatography. The desired fractions were combined and dried in vacuo. The remaining solid was triturated in hot benzene and filtered to give PPQ-23 (103 mg, 73.6%) as a bright yellow solid. $^1$H NMR (600 MHz, CD$_2$Cl$_2$) δ 7.84 (d, J=7.7, 1H), 7.82 (dd, J=2.4, 8.9, 1H), 7.66 (t, J=7.3, 1H), 7.53 (t, J=7.5, 1H), 7.37 (d, J=2.3, 1H), 7.33 (t, J=7.6, 1H), 7.02 (d, J=7.7, 1H), 6.89 (d, J=8.9, 1H), 6.16 (d, J=2.3, 1H), 6.15 (d, J=3.4, 1H), 5.90 (dd, J=0.8, 3.4, 1H), 5.71 (d, J=2.5, 1H), 3.54 (s, 3H), 3.28 (s, 3H). $^{13}$C NMR (151 MHz, CD$_2$Cl$_2$) δ 159.31, 154.54, 151.89, 142.72, 139.43, 131.86, 131.25, 130.03, 129.79, 129.55, 129.05, 128.93, 123.95, 123.30, 122.99, 122.41, 116.84, 116.62, 112.38, 111.97, 107.73, 106.20, 48.22, 32.03, 28.02. MS (ES+) (m/z): [M+1]+ calculated for $C_{25}H_{20}BrN_4O_3$, 548.06. found 547.96.

Example 27

Synthesis of BPO-24

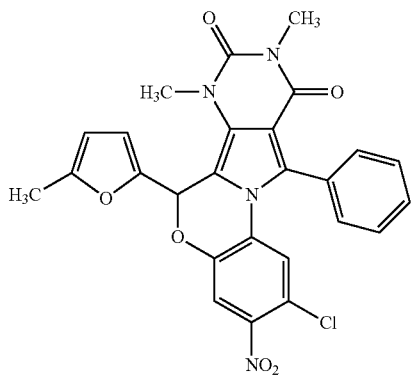 [SMILES: Cc1ccc(C2Oc3cc([N+](=O)[O-])c(Cl)cc3-n3c(-c4ccccc4)c4c(=O)n(C)c(=O)n(C)c4c32)o1]

6-(5-Chloro-2-hydroxy-4-nitrophenyl)-1,3-dimethyl-5-phenyl-1H-pyrrolo[3,4-d]pyrimidine-2,4(3H,6H)-dione (5f). In a 10 mL round bottom flask was placed 4a (200 mg, 595 mmol) (see Example 2 for synthesis of 4a), 2-amino-4-chloro-5-nitrophenol (236 mg, 1.25 mmol), and ethanol (5 mL). The reaction was stirred at reflux for 5 h, then cooled and placed in a freezer. After several hours yellow crystals formed, which were filtered and rinsed with cold ethanol to give 5f (225 mg, 89%). $^1$H NMR (600 MHz, DMSO-d6) δ 11.33 (s, 1H), 7.79 (s, 1H), 7.44 (s, 1H), 7.30 (s, 5H), 7.10 (s, 1H), 3.33 (s, 3H), 3.20 (s, 3H). $^{13}$C NMR (151 MHz, DMSO-d6) δ 158.98, 152.39, 150.82, 147.31, 134.14, 131.79, 130.50, 130.32, 129.23, 128.96, 128.33, 127.48, 113.90, 112.93, 105.91, 102.66, 31.55, 27.51. MS (ES+) (m/z): [M+1]+ calculated for $C_{20}H_{16}ClN_4O_5$, 427.08. found 427.12.

2-Chloro-7,9-Dimethyl-6-(5-methylfuran-2-yl)-3-nitro-11-phenyl-6H-benzo[b]pyrimido[4',5'-3,4]pyrrolo[1,2-d]oxazine-8,10-(7H,9H)-dione (BPO-24).

Pyrrole 5f (97 mg, 227 µmol), 5-methylfurfural (25 µL, 27.7 mg, 252 µmol), TFA (5 µL, 7.4 mg, 65 mmol), 1,2-dichloroethane (2 mL) and a stir bar were sealed in a Emrys 2-5 mL process vial and submerged to the level of solvent in an oil bath at 150° C. for 2 h. The reaction was then cooled, diluted with ethanol (8 mL), and placed in a freezer. After several hours a precipitate formed, which was filtered and rinsed with cold ethanol to give BPO-24 (80 mg, 68%). $^1$H NMR (600 MHz, CD$_2$Cl$_2$) δ 7.80 (d, J=7.7, 1H), 7.64 (dd, J=6.1, 7.0, 2H), 7.58 (t, J=7.5, 1H), 7.42 (t, J=7.2, 1H), 7.08 (d, J=7.7, 1H), 6.87 (s, 1H), 6.58 (s, 1H), 5.92 (d, J=3.2, 1H), 5.82 (d, J=2.3, 1H), 3.47 (s, 3H), 3.26 (s, 3H), 2.23 (s, 3H). $^{13}$C NMR (151 MHz, CD$_2$Cl$_2$) δ 159.06, 155.28, 151.65, 147.36, 144.47, 144.05, 131.75, 131.54, 130.24, 130.02, 129.76, 129.15, 129.12, 128.96, 124.45, 122.71, 120.59, 117.46, 113.80, 107.06, 106.79, 106.71, 69.18, 32.36, 28.02, 13.84. MS (ES+) (m/z): [M+1]+ calculated for $C_{26}H_{20}ClN_4O_6$, 519.11. found 519.14.

Example 28

Synthesis of BPO-25

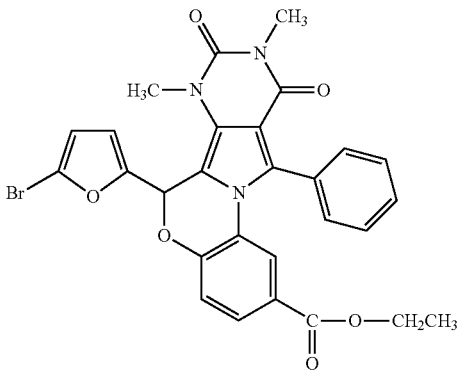 [SMILES: CCOC(=O)c1ccc2c(c1)-n1c(-c3ccccc3)c3c(=O)n(C)c(=O)n(C)c3c1C(c1ccc(Br)o1)O2]

Ethyl 6-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylate (BPO-25). (See also Example 2). Pyrrole 5h (500 mg, 1.19 mmol), 5-bromofurfural (240 mg, 1.37 mmol), chloroform (7 mL), TFA (10 µL, 14.8 mg, 130 mol), and 3 Å molecular sieves (2.0 g, 8-12 mesh beads) were sealed in an Emrys 10-20 mL process vial and submerged to the level of solvent in an oil bath at 150° C. (An Emrys process vial is a commercially available thick walled vessel much like a test tube typically used for microwave reactions that may be sealed using a disposable plastic-lined metal cap. Precautions should be taken because the reaction vessel is under pressure when heated.) The reaction was stirred for 24 min then removed from the oil bath. Once the internal pressure had dropped the reaction vial was rapidly cooled in water. After cooling, the reaction was filtered through celite into a 50 mL recovery flask and the dried in vacuo. The residue was dissolved in a minimum amount of CH$_2$Cl$_2$ and quickly diluted with warm ethanol (25 mL). Fine crystals began to form immediately. The mixture was then placed on a rotary evaporator and the CH$_2$Cl$_2$ was removed to increase the quantity of crystals. The mixture was then chilled, filtered, and the crystals rinsed with cold ethanol to give BPO-25 (0.500 g, 76.4%) as fine white needle like crystals. No m.p. (slow decomposition). $^1$H NMR (600 MHz, CD$_2$Cl$_2$) δ 7.81 (d, J=7.7, 1H), 7.68 (dd, J=1.9, 8.4, 1H), 7.63 (t, J=7.5, 1H), 7.52 (t, J=7.5, 1H), 7.34 (t, J=7.5, 1H), 7.23 (d, J=1.8, 1H), 7.09 (d, J=8.4, 1H), 7.06 (d, J=7.7, 1H), 6.86 (s, 1H), 6.14 (d, J=3.4, 1H), 5.98 (d, J=2.9, 1H), 4.11 (dq, J=7.2, 10.7, 1H), 4.00 (dq, J=7.1, 10.7, 1H), 3.48 (s, 3H), 3.26 (s, 3H), 1.14 (t, J=7.1, 3H). $^{13}$C NMR (151 MHz, CD$_2$Cl$_2$) δ 165.03, 159.26, 151.87, 151.79, 149.08, 131.78, 131.27, 130.00, 129.80, 129.68, 128.84, 128.81, 128.29, 125.40, 124.69, 124.47, 124.42, 121.57, 119.64, 114.91, 112.43, 105.93, 105.67, 68.40, 61.28, 32.38, 27.95, 14.20. MS (ES+) (m/z): [M+1]$^+$ calculated for $C_{28}H_{23}BrN_3O_6$, 576.08. found 576.04.

Example 29

Synthesis of BPO-26

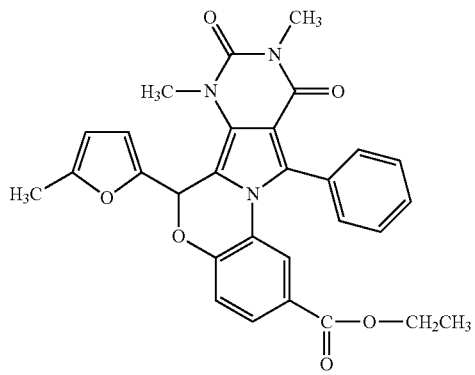 [SMILES: CCOC(=O)c1ccc2c(c1)-n1c(-c3ccccc3)c3c(=O)n(C)c(=O)n(C)c3c1C(c1ccc(C)o1)O2]

Ethyl 7,9-Dimethyl-8,10-dioxo-6-(5-methylfuran-2-yl)-11-phenyl-7,8,9,10-tetrahydro-6H-benzo[b]pyrimido[4',5':3,4]pyrrolo[1,2-d][1,4]oxazine-2-carboxylate (BPO-26). Pyrrole 5h (138 mg, 329 µmol) (see Example 2 for synthesis of 5h), 5-methylfurfural (36 µL, 39.9 mg, 362 µmol), chloroform (3 mL), and TFA (5 µL, 7.4 mg, 65 µmol) sealed in a Emrys 2-5 mL process vial and submerged in an oil bath at 150° C. for 2 h. After cooling the reaction was dried in vacuo. The residue was dissolved in a minimum volume of $CH_2Cl_2$ and then diluted with ethanol (10 mL). The solution was then placed on a rotary evaporator and solvent removed until the mixture ceased to precipitate. The mixture was then chilled, filtered, and the precipitate rinsed with cold ethanol to give BPO-26 (168 mg, 82%). $^1$H NMR (600 MHz, $CD_2Cl_2$) δ 7.81 (d, J=7.7, 1H), 7.67 (dd, J=1.9, 8.4, 1H), 7.63 (t, J=7.5, 1H), 7.52 (t, J=7.5, 1H), 7.34 (t, J=7.5, 1H), 7.23 (d, J=1.8, 1H), 7.09-7.02 (m, J=4.5, 8.0, 2H), 6.83 (s, 1H), 5.85 (d, J=3.2, 1H), 5.76 (d, J=2.5, 1H), 4.10 (dq, J=7.1, 10.7, 1H), 3.99 (dq, J=7.1, 10.7, 1H), 3.48 (s, 3H), 3.26 (s, 3H), 2.21 (s, 3H), 1.14 (t, J=7.1, 3H). $^{13}$C NMR (151 MHz, $CD_2Cl_2$) δ 165.10, 159.37, 154.76, 151.83, 149.47, 148.20, 131.81, 130.84, 130.16, 129.72, 129.70, 128.80, 128.76, 128.13, 125.54, 124.38, 123.96, 121.54, 119.56, 113.22, 106.89, 106.49, 105.84, 68.89, 61.22, 32.34, 27.92, 14.20, 13.80. MS (ES+) (m/z): [M+1]$^+$ calculated for $C_{29}H_{26}N_3O_6$, 512.18. found 512.22.

Example 30

Biological Techniques and Methods

Cell Culture and Plate Reader Assay of CFTR Inhibition—Fischer rat thyroid (FRT) cells co-expressing human wild type CFTR and the halide indicator YFP-H148Q were cultured in 96-well black-walled microplates (Corning Costar) at a density of 20,000 cells per well in Coon's modified F12 medium containing 10% fetal bovine serum, 2 mM L-glutamine, 100 U/mL penicillin and 100 µg/mL streptomycin. CFTR chloride conductance was assayed at 48 h after plating on a FluoStar fluorescence plate reader (BMG Lab Technologies) as described (see, e.g., Ma et al., *J Clin Invest.* 2002, supra). Each well was washed 3 times with PBS, leaving 60 µL PBS. Test compounds were added and incubated with the cells for 45 min. Then, 5 µL of a CFTR-activating cocktail (10 µM forskolin, 100 µM IBMX, 20 µM apigenin in PBS) was added. After 15 min, each well was assayed for iodide influx by recording fluorescence continuously (200 ms per point) for 2 s (baseline) and then for 10 s after rapid addition of 160 µL of isosmolar PBS in which 137 mM chloride was replaced by iodide. The initial rate of iodide influx was computed from fluorescence data by non-linear regression.

Short-Circuit Current—Snapwell inserts containing CFTR-expressing FRT cells were mounted in an Ussing chamber. The hemichambers contained 5 mL of buffer containing 75 mM NaCl and 75 mM Na gluconate (apical) and 150 mM NaCl (basolateral) (pH 7.3), and the basolateral membrane was permeabilized with 250 µg/mL amphotericin B, as described (see, e.g., Sonawane et al., *FASEB J* 2006, supra). Short-circuit current was recorded continuously using a DVC-1000 voltage clamp (World Precision Instruments) using Ag/AgCl electrodes and 3 M KCl agar bridges.

In Vitro Metabolism in Hepatic Microsomes—A compound of structure (I) was incubated for specified times at 37° C. with rat liver microsomes (e.g., 1 mg protein/ml; Sigma-Aldrich, St. Louis, Mo.) in potassium phosphate buffer (100 mM) containing NADPH (0 or 1 mM). The mixture was then chilled on ice, and 0.5 ml of ice-cold ethyl acetate was added. Samples were centrifuged for 15 min at 3,000 rpm, and the supernatant was evaporated to dryness under nitrogen. The residue was dissolved in 150 µl mobile phase (acetonitrile:water 3:1, containing 0.1% formic acid) for LC/MS analysis. Reverse-phase HPLC separations were carried out using a Waters C18 column (2.1×100 mm, 3.5 mm particle size) equipped with a solvent delivery system (Waters model 2690, Milford, Mass.). The solvent system consisted of a linear gradient from 5 to 95% acetonitrile run over 16 min (0.2 mL/min flow rate). Mass spectra were acquired on an Alliance HT 2790+ZQ mass spectrometer using negative ion detection.

Mouse Pharmacokinetics and Renal Accumulation—A compound of structure (I) was formulated at 1 mg/mL in 5% DMSO, 2.5% Tween-80 and 2.5% PEG400 in $H_2O$, based on formulations used for compounds of similar polarity and chemical properties. Male mice in a CD1 genetic background (age 8-10 weeks, 25-35 g) were administered 300 µL of the BPO-27 formulation by intraperitoneal injection. At specified times kidneys were removed following renal arterial perfusion with PBS. Kidneys were weighed, mixed with acetic acid (100 µl per 1 g tissue) and ethyl acetate (10 mL per 1 g tissue), and homogenized. The homogenate was centrifuged at 3,000 rpm for 15 min. Calibration standards were prepared in kidney homogenates from control mice to which was added known amounts of BPO-27. The ethyl acetate-containing supernatant was dried under nitrogen and the residue was reconstituted in acetonitrile:$H_2O$ (3:1) containing 0.1% formic acid. For analysis of blood and urine, fluids were diluted with equal volume of water and extracted with ethyl acetate. LC/MS analysis was carried out as described herein.

Liquid Chromatography/Mass Spectrometry—Compounds (each at 5 µM) were incubated for specified times at 37° C. with rat liver microsomes (1 mg protein/ml; Sigma-Aldrich, St. Louis, Mo.) in potassium phosphate buffer (100 mM) containing NADPH (0 or 1 mM). The mixture was then chilled on ice, and 0.5 ml of ice-cold ethyl acetate was added. Samples were centrifuged for 15 min at 3,000 rpm, and the supernatant was evaporated to dryness under nitrogen. The residue was dissolved in 150 mobile phase (acetonitrile:water 3:1, containing 0.1% formic acid) for LC/MS analysis.

Reverse-phase HPLC separations were carried out using a Waters C18 column (2.1×100 mm, 3.5 mm particle size) equipped with a solvent delivery system (Waters model 2690, Milford, Mass.). The solvent system consisted of a linear gradient from 5 to 95% acetonitrile run over 16 min (0.2 mL/min flow rate). Mass spectra were acquired on an Alliance HT 2790+ZQ mass spectrometer using negative ion detection, scanning from 150 to 1500 Da. The electrospray ion source parameters were as follows: capillary voltage 3.5 kV (positive ion mode), cone voltage 37 V, source temperature 120° C., desolvation temperature 250° C., cone gas flow 25 L/h, and dessolvation gas flow 350 L/h.

Embryonic Organ Culture Model of PKD—Mouse embryos were obtained at embryonic day 13.5 (E13.5). Metanephroi were dissected and placed on transparent Falcon 0.4-mm diameter porous cell culture inserts as described (see, e.g., Tradtrantip et al., *J. Med. Chem.* 2009, supra). To the culture inserts was added DMEM/Ham's F-12 nutrient medium supplemented with 2 mM L-glutamine, 10 mM HEPES, 5 μg/mL insulin, 5 μg/mL transferrin, 2.8 nM selenium, 25 ng/ml prostaglandin E, 32 pg/ml T3, 250 U/ml penicillin, and 250 μg/ml streptomycin. Kidneys were maintained in a 37° C. humidified $CO_2$ incubator for up to 8 days. Culture medium containing 100 μM 8-Br-cAMP, with or without test compound, was replaced (in the lower chamber) every 12 h. Kidneys were photographed using a Nikon inverted microscope (Nikon TE 2000-S) equipped with 2× objective lens, 520 nm bandpass filter, and high-resolution CCD camera. Percentage cyst area was calculated as total cyst area divided by total kidney area.

Example 31

Identification and Characterization of PPQ Analogs

Figure 6:
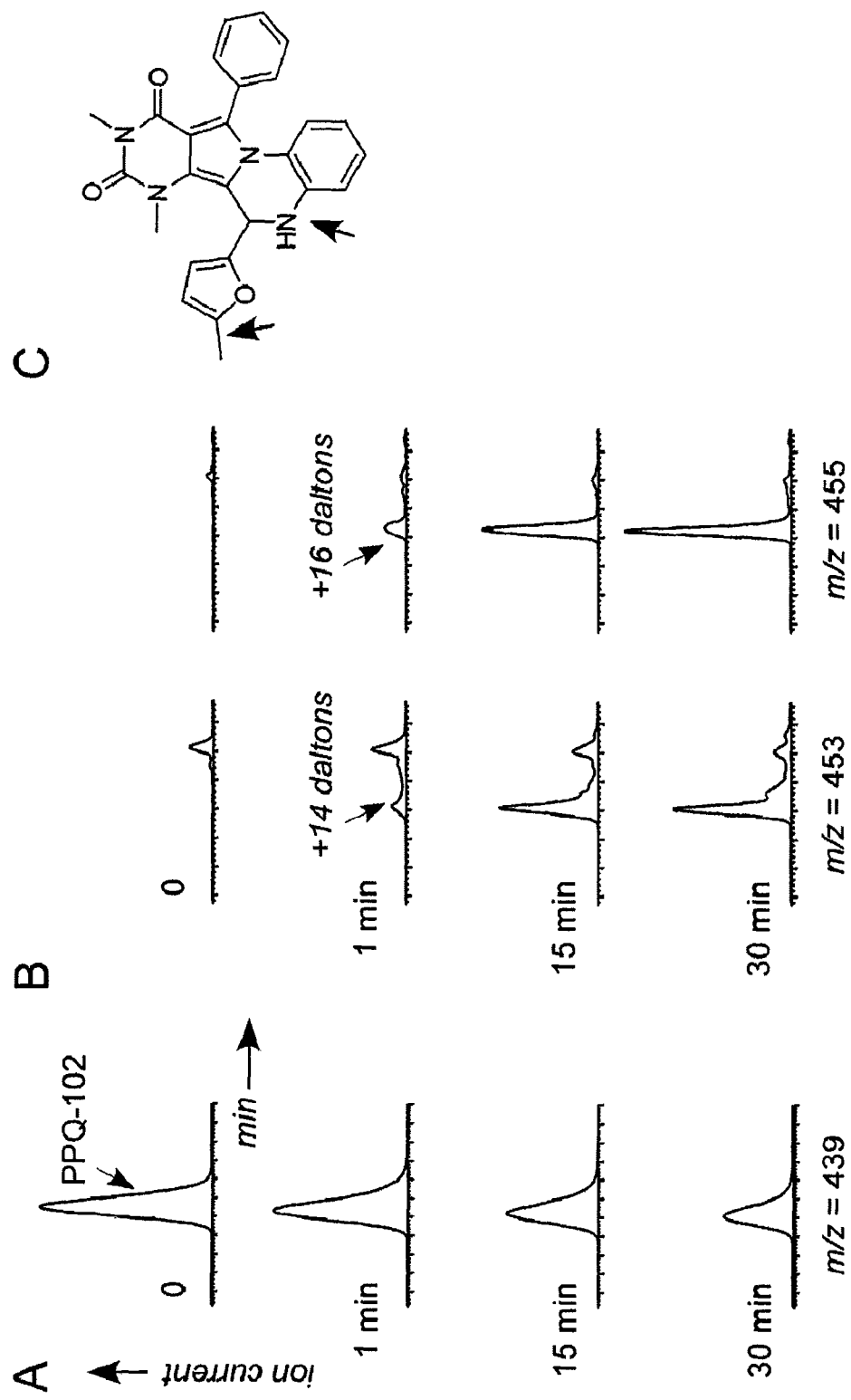
FIGS. 6A-6C illustrate metabolism of the compound, PPQ-102, in hepatic microsomes.

PPQ-102 is a small-molecule inhibitor of CFTR chloride conductance with efficacy in preventing and reversing cyst formation in an organ culture model of PKD (see, e.g., Tradtrantip et al., *J. Med. Chem.* 2009, supra; Int'l Patent Appl. Publication No. WO 2011/019737). Preliminary analysis of the metabolic stability and aqueous solubility of PPQ-102, indicated poorer metabolic stability and lower water solubility (~2 μM in albumin-free saline) than desired for optimal drugability. In vitro metabolic stability was determined by compound incubation with hepatic microsomes at 37° C. for specified times in the absence vs. presence of NADPH, following by LC/MS analysis. Shown in FIG. 6A is PPQ-102 disappearance in hepatic microsomes in the presence of NADPH, with ~60% disappearance in 30 min.

No loss of PPQ-102 was seen in the absence of NADPH. PPQ-102 was undetectable in serum, kidney, and urine at 30-60 min after intravenous bolus administration of 300 μg PPQ-102 in mice using an LC/MS assay with sensitivity better than 100 nM. Though the precise metabolic fate of PPQ-102 is not known, structural considerations and the presence of prominent metabolites at +14 and +16 daltons (see FIG. 6B) suggested possible oxidation, aromatization, and hydroxylation (see FIG. 6C). To improve on the drug-like properties of PPQ-102, a series of compound analogs were synthesized and tested.

Figure 7:
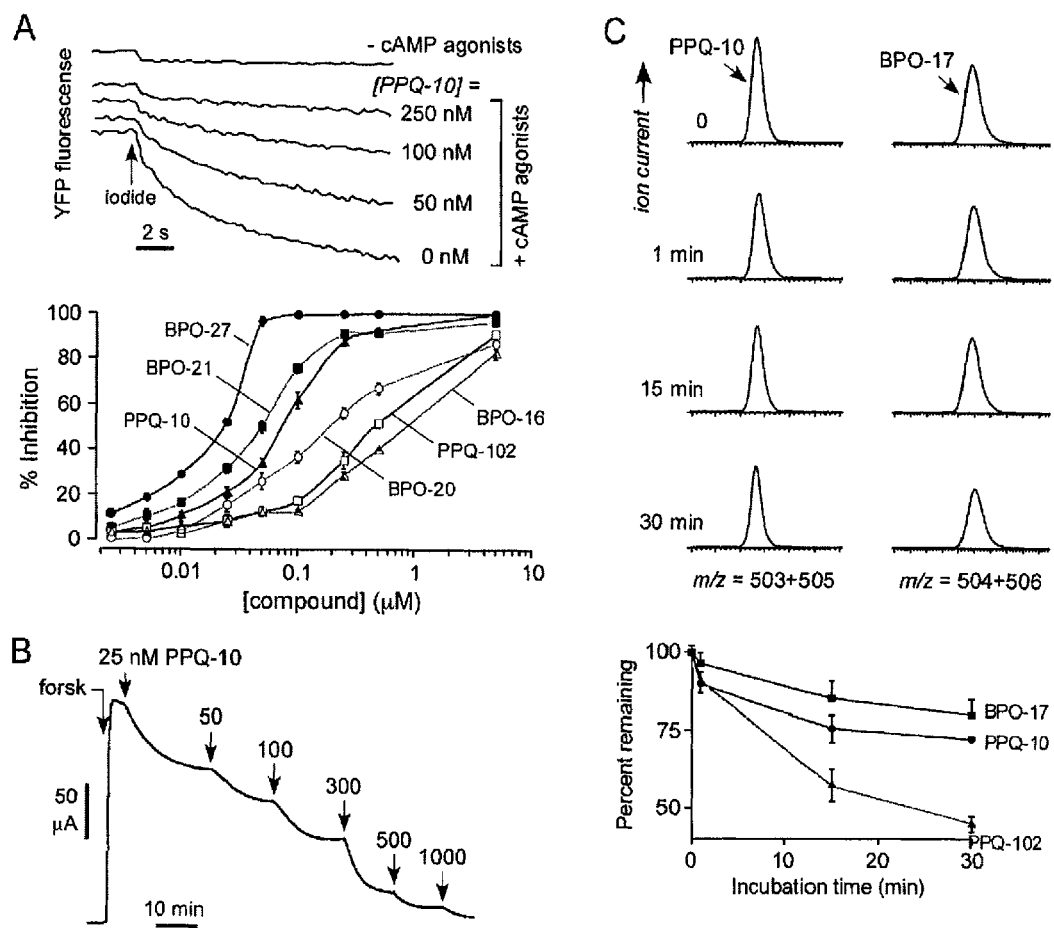
FIGS. 7A-7C present results from experiments performed to characterize PPQ analogs.

Initial testing of the compounds for the capability to inhibit CFTR was performed using a plate-reader assay in which iodide influx was measured in FRT cells co-expressing human wild type CFTR and the iodide-sensing yellow fluorescent protein YFP-H148Q/I152L. FIG. 7A (top) shows representative fluorescence data for inhibition of CFTR-mediated iodide influx by one of the synthesized PPQ analogs, which had a reduced negative slope after iodide addition with increasing inhibition concentration. FIG. 7A (bottom) shows concentration-inhibition data for selected compounds. Table B below provides $IC_{50}$ values for PPQ and BPO compounds.

TABLE B

CFTR inhibition of BPO and PPQ analogs.

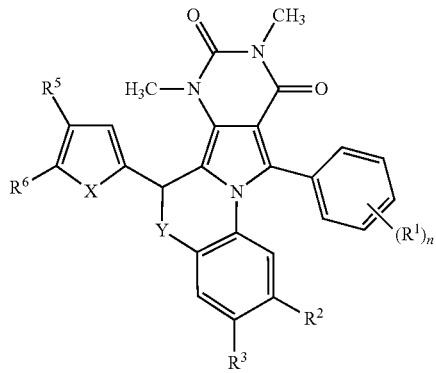

| Compound | X | Y | $R^1$ | $R^2$ | $R^3$ | $R^4$ | $R^5$ | $R^6$ | $IC_{50}$ (μm)$^A$ | $IC_{50}$ (μM)$^B$ |
|---|---|---|---|---|---|---|---|---|---|---|
| PPQ-102 | O | N($R^4$) | H | H | H | H | H | Me | 0.25 | 0.1 |
| PPQ-1 | O | N($R^4$) | H | H | H | $CH_3SO_2$ | H | Me | inactive | |
| PPQ-2 | O | N($R^4$) | H | H | H | $ClCH_2CO_2$ | H | Me | inactive | |
| PPQ-3 | O | N($R^4$) | H | H | H | $CH_3CO_2$ | H | Me | inactive | |
| PPQ-4 | O | N($R^4$) | H | H | H | NO | H | Me | 2 | |
| PPQ-5 | O | N($R^4$) | H | H | H | Me | H | Me | 1 | |
| PPQ-6 | O | N($R^4$) | H | H | H | H | H | Et | 0.3 | |
| PPQ-7 | S | N($R^4$) | H | H | H | H | H | Me | 1.7 | |
| PPQ-8 | O | N($R^4$) | H | H | H | H | Me | Me | 1.7 | |
| PPQ-9 | O | N($R^4$) | H | H | H | H | H | Cl | 0.15 | |
| PPQ-10 | O | N($R^4$) | H | H | H | H | H | Br | 0.09 | 0.05 |
| PPQ-11 | O | N($R^4$) | H | H | H | H | H | I | 0.17 | 0.1 |

TABLE B-continued

CFTR inhibition of BPO and PPQ analogs.

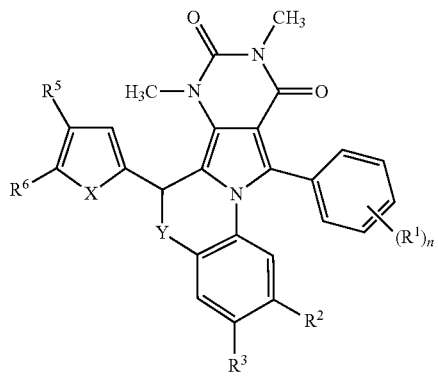

| Compound | X | Y | R¹ | R² | R³ | R⁴ | R⁵ | R⁶ | IC$_{50}$ (μm)$^A$ | IC$_{50}$ (μM)$^B$ |
|---|---|---|---|---|---|---|---|---|---|---|
| PPQ-12 | O | N(R⁴) | H | H | H | H | H | CF₃ | 0.35 | |
| PPQ-13 | O | N(R⁴) | H | H | H | H | H | Ph | inactive | |
| PPQ-14 | O | N(R⁴) | H | H | H | H | H | CH₂OH | inactive | |
| PPQ-15 | O | N(R⁴) | H | H | H | H | —(CH₂)₄— | | inactive | |
| BPO-16 | O | O | H | H | H | | H | Br | 0.2 | 0.09 |
| BPO-17 | O | O | H | H | H | | H | I | 0.5 | |
| BPO-18 | O | O | H | H | H | | H | Me | 0.15 | |
| BPO-19 | O | O | (m-)Me | H | H | | H | Cl | 0.37 | |
| BPO-20 | O | O | (m-)Me | H | H | | H | Me | 0.6 | |
| BPO-21 | O | O | H | NO₂ | H | | H | Br | 0.12 | 0.025 |
| BPO-22 | O | O | H | NO₂ | H | | H | Me | 0.1 | 0.025 |
| PPQ-23 | O | N(R⁴) | H | NO₂ | H | H | H | Br | 0.17 | |
| BPO-24 | O | O | H | Cl | NO₂ | | H | Me | 0.17 | |
| BPO-25 | O | O | H | COOEt | H | | H | Br | 0.05 | 0.025 |
| BPO-26 | O | O | H | COOEt | H | | H | Me | 0.08 | |
| BPO-27 | O | O | H | COOH | H | | H | Br | 0.04 | 0.008 |
| (R)-BPO-27 | O | O | H | COOH | H | | H | Br | — | 0.004 |

$^A$Determined by micro-plate reader assay
$^B$Determined by short-circuit current assay The relative IC$_{50}$ values obtained from the plate reader assay are useful for comparisons. Absolute IC$_{50}$ values obtained from the plate-reader assay are approximate, generally underestimating compound potency because of assay non-linearities, pH-dependent YFP fluorescence, the use of iodide instead of chloride, and compound dilution at the start of the assay (see, e.g., Galietta et al., Am. J. Physiol. Cell Physiol. 281:C1734-42 (2001)).

Quantitative concentration-inhibition data for the most potent compounds were obtained by analysis of short-circuit current, which represents a definitive electrophysiological measure of compound potency. Current was measured in CFTR-expressing FRT cells in which the basolateral membrane was permeabilized and in the presence of a transepithelial chloride concentration gradient, so that current is a quantitative linear measure of CFTR function. CFTR was activated by forskolin, followed by serial additions of increasing concentrations of test compounds. FIG. 7B illustrates a representative short-circuit current measurement. Increased CFTR chloride conductance was observed following addition the cAMP agonist forskolin. Conductance was reduced in a concentration-dependent manner by a PPQ inhibitor, with complete inhibition observed at high inhibitor concentration.

Initial synthesis efforts focused on preventing aromatization, which was initially achieved by derivatizing the secondary amine of PPQ-102 to give analogs PPQ-(1-5). The PPQ-102-derived amides PPQ-(1-3) were found to be substantially less active than PPQ-102. Because the loss of the basic amine coincided with a loss in activity, nitrosamine PPQ-4 was synthesized, but attempts to reduce the nitrosamine to a strongly basic hydrazine only yielded PPQ-102. To maintain basicity and to prevent aromatization, synthesis of the N-methyl analog PPQ-5 was attempted via reductive alkylation using formaldehyde, but these efforts were unsuccessful. However, the N-methyl precursor 5c was obtained in good yield from N-methyl-1,2-phenylenediamine and 4a. Pyrrole 5c was then used to synthesize PPQ-5, which was weakly active.

Re-examination of SAR data obtained from ~350 commercially available analogs (see, e.g., Tradtrantip et al., J. Med. Chem. 2009, supra; Int'l Patent Appl. Publication No. WO 2011/019737) suggested that the 5-position of the furan ring in PPQ-102 was privileged. Therefore, compounds PPQ-(6-15) were synthesized to probe the steric and electronic requirements for activity of the furyl moiety. Substituting bromine at the 5-position of the furyl ring yielded PPQ-10, which was substantially more stable than PPQ-102 and had similar CFTR inhibition potency (see FIGS. 5B, 5C). To further probe oxidative aromatization as a metabolic pathway, the secondary amine of PPQ-10 was replaced by oxygen forming an ether bridge, which is unable to undergo oxidation. The resulting benzoxazine BPO-16 had similar CFTR inhibition potency (see FIG. 7A) and better stability than PPQ-102. Synthesis of BPO-(17-18) confirmed CFTR inhibition activity (see Table B) and improved stability (see FIG. 7C) imparted by bromine and illustrated the synergy between the 5-bromofuran moiety and the ether bridge.

Figure 8:
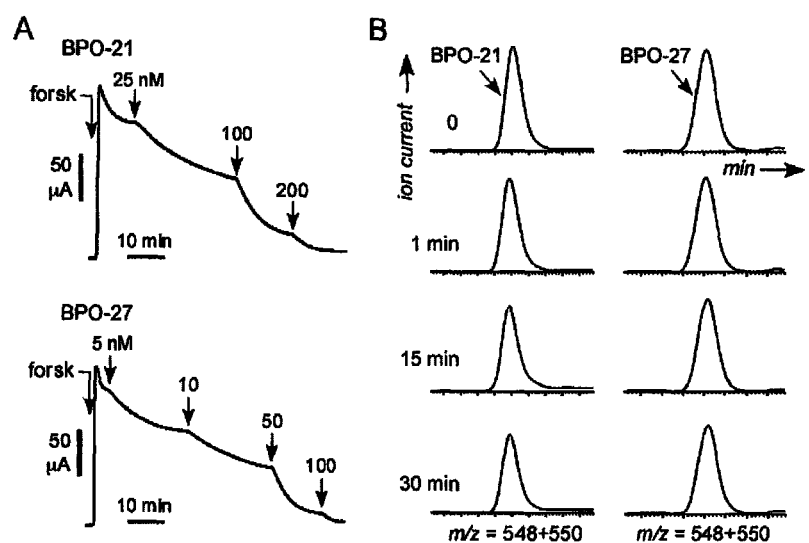
FIGS. 8A-8B illustrate data for PPQ CFTR inhibitors with high potency, metabolic stability and water solubility.

Previous SAR data (see, e.g., Tradtrantip et al., J. Med. Chem. 2009, supra) showed that an m-tolyl moiety (R¹=Me)

increased CFTR inhibition potency. However, synthesis of BPO-(19-20) revealed that the m-tolyl moiety reduced CFTR inhibition in the BPO series. To increase the polarity and hence the aqueous solubility of BPO-16, a nitro group was introduced at $R^2$. The resulting compound, BPO-21, had substantially greater CFTR inhibition potency (see FIG. 8A) with excellent metabolic stability in hepatic microsomes (see FIG. 8B). BPO-22 and PPQ-23 showed that the increased CFTR inhibition activity conferred by the nitro substituent at $R^2$ was independent of both the 5-bromo substituent and the ether bridge.

To increase compound polarity further, the nitro functionality at $R_2$ in BPO-21 was replaced with a carboxyl moiety to provide BPO-27. BPO-27 was the most potent CFTR inhibitor with $IC_{50}$~8 nM (see FIG. 8A), and had excellent stability in hepatic microsomes with <5% compound loss in 30 min (see FIG. 8B). At physiological pH BPO-27 is deprotonated and thus substantially more polar then PPQ-102 (clogP 1.76 for BPO-27 vs. clogP4.92 for PPQ-102) and with solubility of 17 μM in a pH 7.4 aqueous phosphate buffer. BPO-27 was synthesized by hydrolysis of the ethyl ester BPO-25, which, interestingly, also had excellent CFTR inhibition activity, and could potentially serve as a pro-drug of BPO-27, to facilitate efficient intestinal absorption and cell accumulation following de-esterification by ubiquitous intracellular esterases.

SAR analysis suggests that the relative stability of BPO-27 compared with PPQ-102 is the consequence of the 5-Br substituted furan and the ether bridge, which largely prevent hydroxylation and aromatization modifications. The greatly improved water solubility of BPO-27 compared with PPQ-102 is a consequence of the carboxylic acid substituent, which is charged at physiological pH. The carboxylic acid addition also, unexpectedly, improved CFTR inhibition potency.

Example 32

Reduction of Cyst Growth in a PKD Kidney Organ Culture Model

Figure 9:
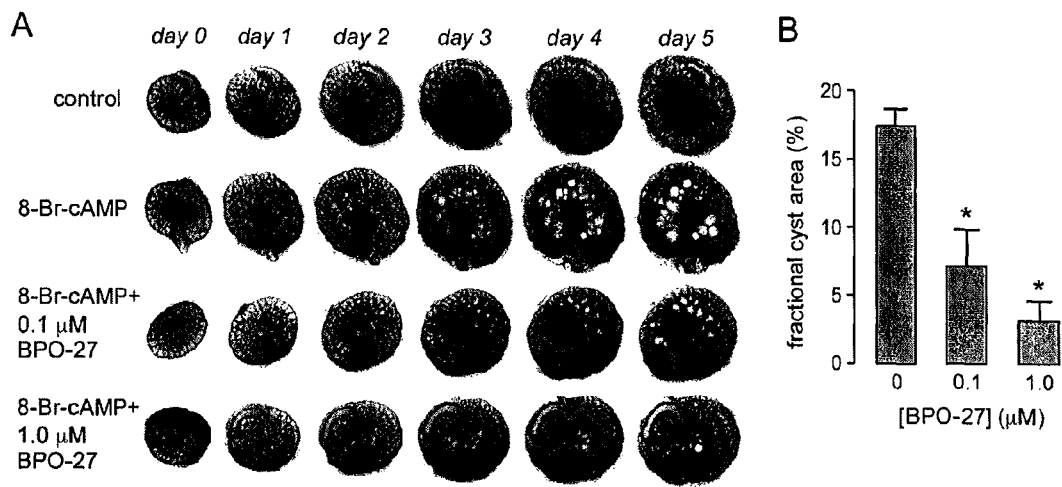
FIGS. 9A and 9B demonstrate that compound BPO-27 reduced renal cytogenesis.

An established embryonic ex vivo kidney organ culture model of PKD was used to test BPO-27 (racemic mixture of R and S forms) efficacy in reducing cAMP agonist-induced renal cystogenesis (see Example 30). Progressive renal cyst formation and growth in 8-Br-cAMP agonist-treated cultures, as seen by transmitted light microscopy, is shown in FIG. 9A. Kidney growth without cyst formation was observed in the absence of 8-Br-cAMP. Cyst growth in the 8-Br-cAMP-treated kidney was remarkably reduced by inclusion of BPO-27 in the culture medium. As quantified by percentage area occupied by cysts, BPO-27 inhibited cyst growth with $IC_{50}$ of approximately 100 nM (see FIG. 9B), much better than that of >500 nM measured for PPQ-102 (see, e.g., Tradtrantip et al., *J. Med. Chem.* 2009, supra). Thus, racemic BPO-27 was shown to have prevented and reversed renal cyst formation in an embryonic kidney culture model of PKD.

Example 33

CFTR Inhibition of Isolated Enantiomers of BPO-27

The racemic mixture of BPO-27 was further separated into its respective isolated enantiomers, namely, (R)-BPO-27 and (S)-BPO-27. See, Example 2A. As shown herein, while the (R)-BPO-27 enantiomer strongly inhibited CFTR chloride conductance with $IC_{50}$-4 nM, the other enantiomer, (S)-BPO-27, was inactive.

Figure 10:
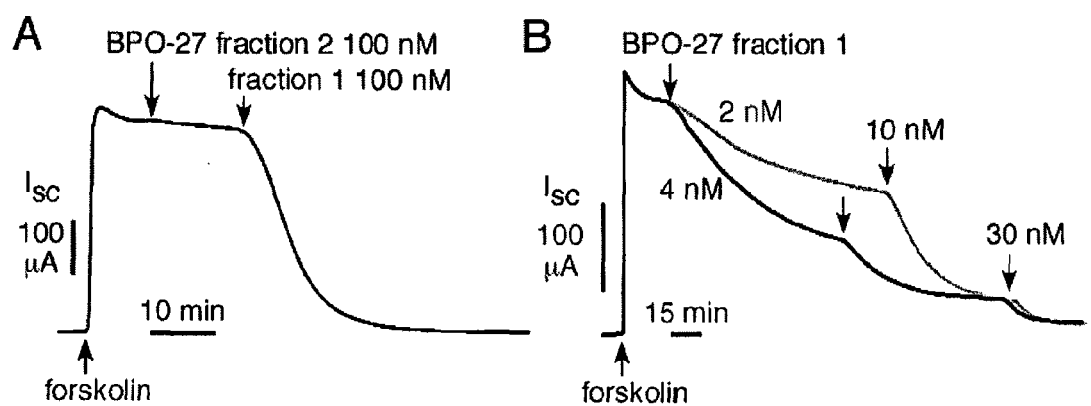
FIG. 10A-10B show CFTR inhibition activity of enantiomerically pure BPO-27 fractions. Short-circuit current was measured in FRT epithelial cells expressing human wildtype CFTR in presence of a transepithelial chloride gradient and following permeabilization of the basolateral membrane. CFTR chloride conductance was stimulated by 10 µM forskolin.

CFTR inhibition potency was measured by short-circuit current analysis in FRT epithelial cells expressing human CFTR in presence of a transepithelial chloride gradient and in which the basolateral membrane was permeabilized with amphotericin B. Under these conditions short-circuit current is proportional to CFTR chloride conductance. FIG. 10A shows no significant inhibition by BPO-27 fraction 1 at 100 nM, whereas BPO-27 fraction 2 at 100 nM completed inhibited current. FIG. 10B shows the fraction 2 concentration-dependence, giving an $IC_{50}$ of approximately 4 nM, as compared to approximately 8 nM for racemic BPO-27 (Example 31).

Example 34

In Vitro Metabolic Stability and Pharmacokinetics of Isolated Enantiomers

Figure 11:
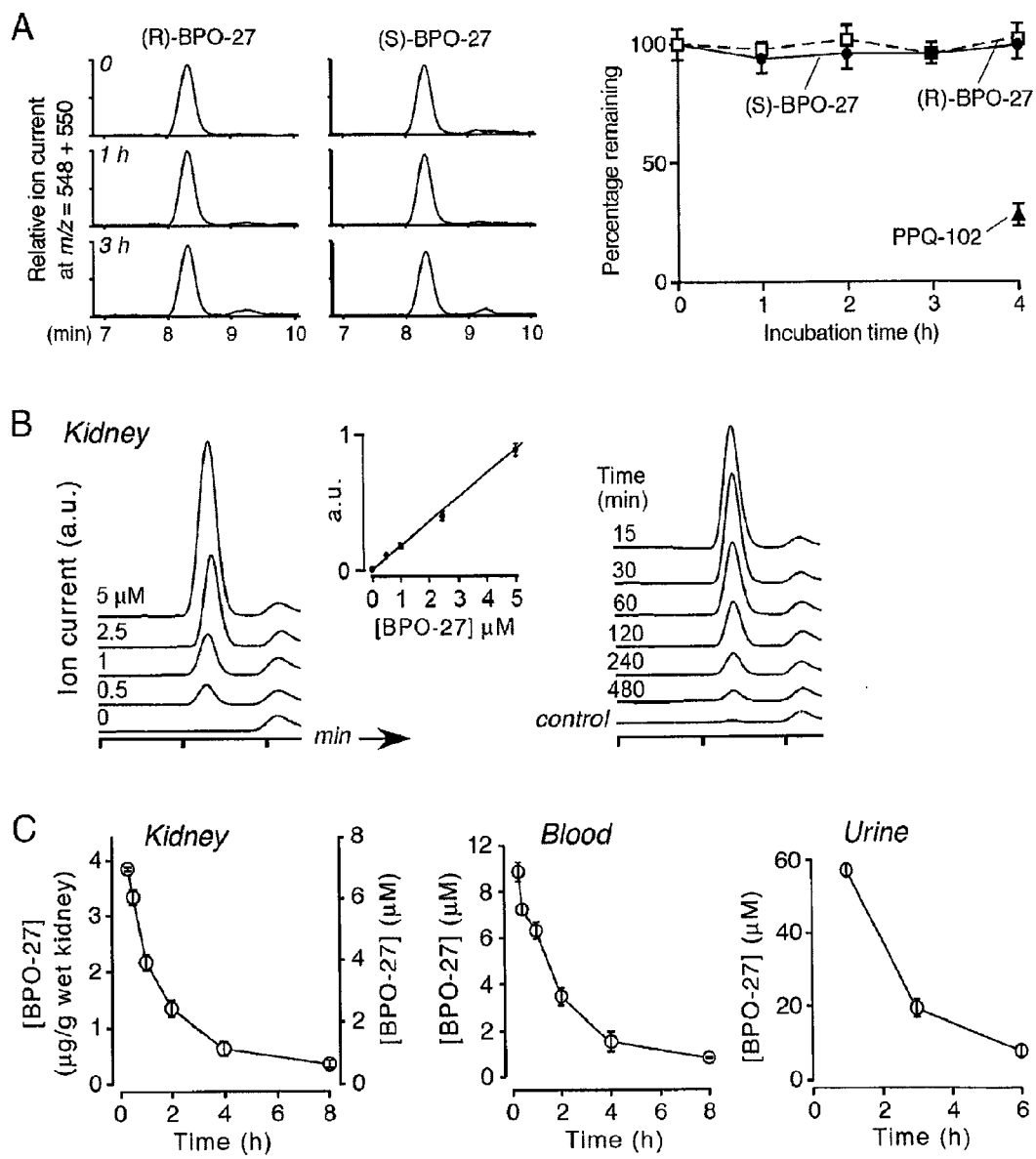
FIG. 11A-11C show in vitro metabolic stability and of BPO-27.

The in vitro metabolic stability of (R)-BPO-27 and (S)-BPO-27 was studied using hepatic microsomes. Following compound incubation with hepatic microsomes in the presence of NADPH, remaining non-metabolized compound was assayed by LC/MS. FIG. 11A shows little metabolism of either BPO-27 isoform. As a control, PPQ-102 was >75% metabolized at 4 h when tested in parallel.

BPO-27 pharmacokinetics in mice was measured following bolus intraperitoneal administration in an aqueous formulation in 5% DMSO, 2.5% Tween-80 and 2.5% PEG400 in water. BPO-27 was measured by LC/MS in kidney, blood and urine. FIG. 11B (left) shows ion current in calibration studies in which specified amounts of BPO-27 were added to kidney homogenates. The assay was linear with a detection sensitivity of better than 100 nM BPO-27. FIG. 11B (right) shows the disappearance kinetics of BPO-27 from kidney following bolus intraperitoneal administration. FIG. 11C summarizes the deduced BPO-27 concentrations in kidney, blood and urine over time. The $t_{1/2}$ for disappearance of the original compound was approximately 2 h. Compound concentration remained at predicted therapeutic levels (i.e., at levels much greater than 4 nM, which is the $IC_{50}$) for many hours following single dose administration.

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheetare incorporated herein by reference, in their entirety. Aspects of the embodiments can be modified, if necessary, to employ concepts of the various patents, applications, and These and other changes can be made to the embodiments in light of the above-detailed publications to provide yet further embodiments. description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A compound having the following structure (I):

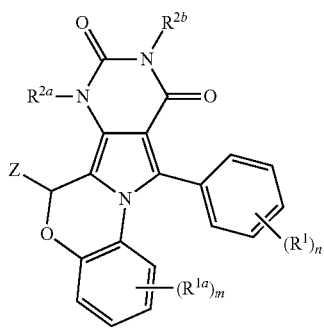

as an isolated enantiomer or a racemic mixture of enantiomers, or as a pharmaceutically acceptable salt, hydrate, solvate, or N-oxide, thereof, wherein:

m is 1, 2, 3, or 4;

n is 1, 2, 3, 4 or 5;

p is an integer from 0 to 4;

q is an integer from 1 to 4;

$R^1$ at each occurrence is the same or different and independently H, halo, haloalkyl, $C_1$-$C_6$ alkyl, —$(CH_2)_p$—C(O)—$R^{4a}$, —S(O)$_2R^{4a}$, —NO$_2$, or tetrazolyl;

$R^{1a}$ at each occurrence is the same or different and independently H, halo, haloalkyl, $C_1$-$C_6$ alkyl, —$(CH_2)_p$—C(O)—$R^{4a}$, —S(O)$_2R^{4a}$, —NO$_2$, or tetrazolyl;

$R^{2a}$ and $R^{2b}$ are each the same or different and independently H, or $C_1$-$C_6$ alkyl;

$R^{4a}$ is —$OR^7$, —$NR^7R^8$, —$O(CH_2)_q$—$OC(O)R^7$, or an amino acid residue;

$R^7$ and $R^8$ are each the same or different and independently H, $C_1$-$C_{20}$ alkyl, a saccharide, or an amino acid residue; and Z is aryl or heteroaryl, wherein the amino acid residue is selected from residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine, 3,5-diiodotyrosine, glycosylated threonine, glyclosylated serine, and glycosylated asparagine.

2. The compound of claim 1, wherein $R^{2a}$ and $R^{2b}$ are each methyl, and Z is optionally substituted furanyl or optionally substituted thienyl, and the compound has the following structure (IA) or (IB), respectively:

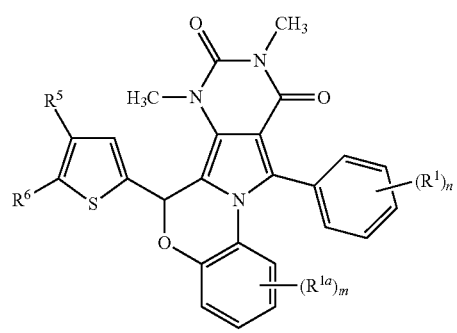

as an isolated enantiomer or a racemic mixture of enantiomers, or as a pharmaceutically acceptable salt, hydrate, solvate, or N-oxide thereof, wherein:

m is 1, 2, 3, or 4;

n is 1, 2, 3, 4 or 5;

p is an integer from 0 to 4;

q is an integer from 1 to 4;

$R^1$ at each occurrence is the same or different and independently H, halo, haloalkyl, $C_{1-6}$ alkyl, —$(CH_2)_p$—C(O)—$R^{4a}$, —S(O)$_2R^{4a}$, —NO$_2$, or tetrazolyl;

$R^{1a}$ at each occurrence is the same or different and independently H, halo, haloalkyl, $C_{1-6}$ alkyl, —$(CH_2)_p$—C(O)—$R^{4a}$, —S(O)$_2R^{4a}$, —NO$_2$, or tetrazolyl;

$R^{4a}$ is —$OR^7$, —$NR^7R^8$, —$O(CH_2)_q$—$OC(O)R^7$, or an amino acid residue;

$R^5$ is H, halo, or $C_{1-6}$ alkyl;

$R^6$ is H, halo, $C_{1-6}$ alkyl, or $C_{1-6}$ haloalkyl; and $R^7$ and $R^8$ are each the same or different and independently H, $C_{1-20}$ alkyl, a saccharide, or an amino acid residue, wherein the amino acid residue is selected from residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine, 3,5-diiodotyrosine, glycosylated threonine, glycosylated serine, and glycosylated asparagine.

3. The compound of claim 1, wherein $R^{2a}$ and $R^{2b}$ are each methyl, p is 0, $R^{4a}$ is —$OR^7$ is Z is optionally substituted furanyl, n is 1 and R¹ is meta to the linking carbon and the compound has the following structure (IA1):

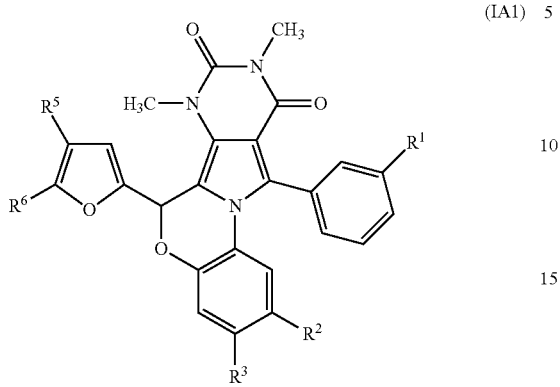

(IA1)

wherein:
R¹ is H, halo, or $C_{1-6}$ alkyl;
R² and R³ are each the same or different and independently H, halo, —NO$_2$, $C_{1-6}$ alkyl, tetrazolyl, —S(O)$_2$OR⁷, or —C(=O)OR⁷;
R⁵ is H, halo, or $C_{1-6}$ alkyl;
R⁶ is halo, $C_1$-$C_6$ alkyl, or $C_{1-6}$ haloalkyl; and
R⁷ is H, $C_{1-6}$ alkyl, a saccharide, or an amino acid residue, selected residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine, 3,5-diiodotyrosine, glycosylated threonine, glycosylated serine, and glycosylated asparagine.

4. The compound of claim 1, wherein R²ᵃ and R²ᵇ are each methyl, p is 0, R⁴ᵃ is —OR⁷, Z is optionally substituted thienyl, n is 1 and R¹ is meta to the linking carbon, and the compound has the following structure (IB1):

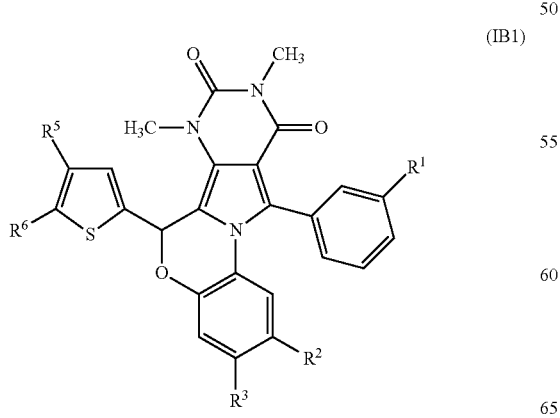

(IB1)

wherein:
R¹ is H, halo, or $C_{1-6}$ alkyl;
R² and R³ are each the same or different and independently H, halo, —NO$_2$, $C_{1-6}$ alkyl, tetrazolyl, —S(O)$_2$OR⁷, or —C(=O)OR⁷;
R⁵ is H, halo, or $C_{1-6}$ alkyl;
R⁶ is halo, $C_{1-6}$ alkyl, or $C_{1-6}$ haloalkyl; and
R⁷ is H, $C_{1-6}$ alkyl, a saccharide, or an amino acid residue selected from residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine, 3,5-diiodotyrosine, glycosylated threonine, glyclosylated serine, and glycosylated asparagine.

5. The compound of claim 1, wherein R²ᵃ and R²ᵇ are each methyl, and Z is optionally substituted phenyl, and the compound has the following structure (IC):

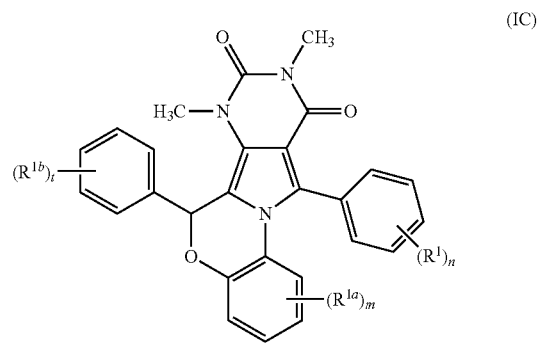

(IC)

as an isolated enantiomer or a racemic mixture of enantiomers, or as a pharmaceutically acceptable salt, hydrate, solvate, or N-oxide thereof, wherein:
m is 1, 2, 3, or 4;
n is 1, 2, 3, 4 or 5;
p is an integer from 0 to 4;
q is an integer from 1 to 4;
t is 1, 2, 3, 4 or 5;
R¹ at each occurrence is the same or different and independently H, halo, haloalkyl, $C_{1-6}$ alkyl, —(CH$_2$)$_p$—C(O)—R⁴ᵃ, —S(O)$_2$R⁴ᵃ, —NO$_2$, or tetrazolyl;
R¹ᵃ at each occurrence is the same or different and independently H, halo, haloalkyl, $C_{1-6}$ alkyl, —(CH$_2$)$_p$—C(O)—R⁴ᵃ, —S(O)$_2$R⁴ᵃ, —NO$_2$, or tetrazolyl;
R¹ᵇ at each occurrence is the same or different and independently H, halo, —OH, —NO$_2$, $C_{1-6}$ alkyl, $C_{2-6}$ alkenyl, or $C_{1-6}$ alkoxy;
R⁴ᵃ is —OR⁷, —NR⁷R⁸, —O(CH$_2$)$_q$—OC(O)R⁷, or an amino acid residue;
R⁷ and R⁸ are each the same or different and independently H, $C_{1-20}$ alkyl, a saccharide, or an amino acid residue, wherein the amino acid residue is selected from residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine, 3,5-diiodotyrosine, glycosylated threonine, glycosylated serine, and glycosylated asparagine.

6. The compound of claim 1, wherein $R^{2a}$ and $R^{2b}$ are each methyl, p is 0, $R^{4a}$ is —$OR^7$, n is 1, and $R^1$ is meta to the linking carbon and the compound has the following structure:

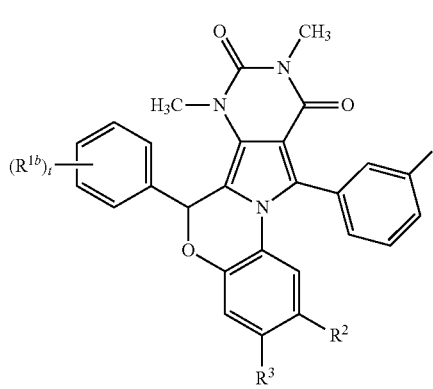

(IC1)

wherein:

$R^1$ is H, halo, or $C_1$-$C_6$ alkyl;

$R^2$ and $R^3$ are each the same or different and independently H, halo, —$NO_2$, $C_{1-6}$ alkyl, tetrazolyl, —$S(O)_2OR^7$, or —$C(=O)OR^7$;

t is 1, 2, 3, 4 or 5;

$R^{1b}$ at each occurrence is the same or different and independently H, halo, —OH, —$NO_2$, $C_{1-6}$ alkoxy, or $C_{1-6}$ alkyl; and $R^7$ is H, $C_{1-6}$ alkyl, a saccharide, or an amino acid residue selected from residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine, 3,5-diiodotyrosine, glycosylated threonine, glycosylated serine, and glycosylated asparagine.

7. A compound having the following structure (II):

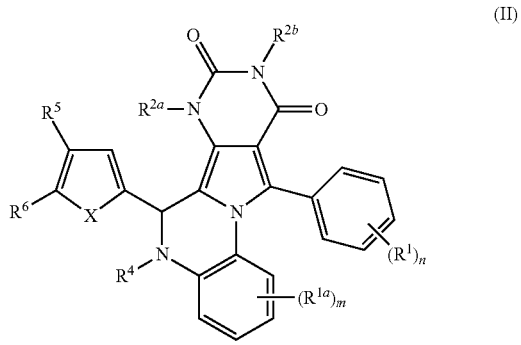

(II)

as an isolated enantiomer or a racemic mixture of enantiomers, or as a pharmaceutically acceptable salt, hydrate, solvate, or N-oxide thereof, wherein:

m is 1, 2, 3, or 4;

n is 1, 2, 3, 4 or 5;

p is an integer from 0 to 4;

q is an integer from 1 to 4;

X is O or S;

$R^1$ at each occurrence is the same or different and independently H, halo, haloalkyl, $C_{1-6}$ alkyl, —$(CH_2)_p$—C(O)—$R^{4a}$, —$S(O)_2R^{4a}$, —$NO_2$, or tetrazolyl;

$R^{1a}$ at each occurrence is the same or different and independently H, halo, haloalkyl, $C_{1-6}$ alkyl, —$(CH_2)_p$—C(O)—$R^{4a}$, —$S(O)_2R^{4a}$, —$NO_2$, or tetrazolyl;

$R^{2a}$ and $R^{2b}$ are each the same or different and independently H or $C_{1-6}$ alkyl;

$R^{4a}$ is —$OR^7$, —$NR^7R^8$, —$O(CH_2)_q$—$OC(O)R^7$, an amino acid residue;

$R^4$ is H, —N(=O), $C_{1-6}$ alkyl, or haloalkyl;

$R^5$ is H, halo, or $C_{1-6}$ alkyl;

$R^6$ is halo; and $R^7$ and $R^8$ are each the same or different and independently H, $C_1$-$C_{20}$ alkyl, a saccharide, or an amino acid residue wherein the amino acid residue is selected from residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine, 3,5-diiodotyrosine, glycosylated threonine, glycosylated serine, and glycosylated asparagine.

8. The compound of claim 7, wherein $R^{2a}$ and $R^{2b}$ are each methyl, p is 0, $R^{4a}$ is —$OR^7$, n is 1 and $R^1$ is meta to the linking carbon, and the compound has the following structure (IIA):

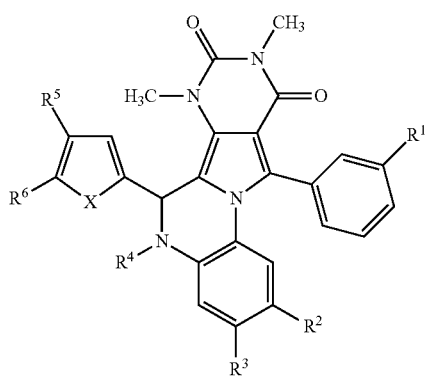

(IIA)

wherein:
X is O or S;
R¹ is H, halo, or $C_{1-3}$ alkyl;
R² is H, halo, —NO₂, or —C(=O)OR⁷;
R³ is H or —NO₂;
R⁴ is —N(=O), $C_{1-3}$ alkyl, or H;
R⁵ is H or $C_{1-3}$ alkyl;
R⁶ halo; and
R⁷ is H, $C_{1-6}$ alkyl, a saccharide, an amino acid residue of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, proparagylglycine, sarcosine, methionine sulfone tert-butylglycine 3,5-dibromotyrosine, 3,5-diiodotyrosine, glycosylated threonine, glyclosylated serine, and glycosylated asparagine.

9. The compound of claim 1, wherein (a) each R¹ is H; (b) at least one R¹ is methyl or ethyl; (c) at least one R¹ is methyl and each remaining R¹ is H; or (d) at least one R¹ is ethyl and each remaining R¹ is H.

10. The compound of either claim 1, wherein m=2 and p=0 and (a) at least one of $R^{1a}$ is halo, —NO₂, $C_{1-3}$ alkyl, —C(O)—$R^{4a}$; or (b) each of $R^{1a}$ is H.

11. The compound of claim 5, wherein (a) each R¹ is H; (b) at least one R¹ is methyl or ethyl; (c) at least one R¹ is methyl and each remaining R¹ is H; or (d) at least one R¹ is ethyl and each remaining R¹ is H.

12. The compound of claim 5, wherein m=2 and p=0 and (a) at least one of $R^{1a}$ is halo, —NO₂, $C_{1-3}$ alkyl, —C(O)—$R^{4a}$; or (b) each of $R^{1a}$ is H.

13. The compound of claim 6, wherein (a) R² is H, halo, —NO₂, or —C(=O)OR⁷, wherein R⁷ is H or $C_1$-$C_6$ alkyl; (b) R² is H, halo, —NO₂, or —C(=O)OR⁷, wherein R⁷ is H, —CH₃, —CH₂CH₃, or —CH₂CH₂CH₃; (c) R² is H, chloro, or —NO₂; (d) R² is —C(=O)OR⁷, wherein R⁷ is H, —CH₃, or —CH₂CH₃; or (e) R² is chloro.

14. The compound of claim 5, wherein (a) t=2 and each $R^{1b}$ is the same or different and independently H, —OH, halo, —NO₂, $C_{1-3}$ alkyl, or $C_{1-3}$ alkoxy; or (b) t=1 and $R^{1b}$ is —OH, halo, —NO₂, $C_{1-3}$ alkyl, or (c) t=2 and each $R^{1b}$ is the same or different and indepentdly H, —OH, chloro, fluoro, —NO₂, methyl or methoxy; or (d) t=1 and $R^{1b}$ is —OH, chloro, flouro, —NO₂, methyl, or methooxy; (e) each $R^{1b}$ is H.

15. The compound of claim 3 wherein (a) R² is H, halo, —NO₂, or —C(=O)OR⁷, wherein R⁷ is H or $C_{1-6}$ alkyl; (b) R² is H, halo, —NO₂, or —C(=O)OR⁷, wherein R⁷ is H, —CH₃, —CH₂CH₃, or —CH₂CH₂CH₃; (c) R² is H, chloro, or —NO₂; (d) R² is —C(=O)OR⁷, wherein R⁷ is H, —CH₃, or —CH₂CH₃; or (e) R² is chloro.

16. The compound of claim 4 wherein (a) R² is H, halo, —NO₂, or —C(=O)OR⁷, wherein R⁷ is H or $C_{1-6}$ alkyl; (b) R² is H, halo, —NO₂, or —C(=O)OR⁷, wherein R⁷ is H, —CH₃, —CH₂CH₃, or —CH₂CH₂CH₃; (c) R² is H, chloro, or —NO₂; (d) R² is —C(=O)OR⁷, wherein R⁷ is H, —CH₃, or —CH₂CH₃; or (e) R² is chloro.

17. The compound of claim 2, wherein (a) each R¹ is H; (b) at least one R¹ is methyl or ethyl; (c) at least one R¹ is methyl and each remaining R¹ is H; or (d) at least one R¹ is ethyl and each remaining R¹ is H.

18. The compound of claim 7, wherein (a) each R¹ is H; (b) at least one R¹ is methyl or ethyl; (c) at least one R¹ is methyl and each remaining R¹ is H; or (d) at least one R¹ is ethyl and each remaining R¹ is H.

19. The compound of claim 2, wherein m+2 and p=0 and (a) at least one of $R^{1a}$ is halo, —NO₂, $C_1$-$C_3$ alkyl, —C(O)—$R^{4a}$; or (b) each of $R^{1a}$ is H.

20. The compound of claim 7, wherein m=2 and p=0 and (a) at least one of $R^{1a}$ is halo, —NO₂, $C_{1-3}$ alkyl, —C(O)—$R^{4a}$; or (b) each of $R^{1a}$ is H.

21. The compound of claim 2, wherein R⁶ is chloro, bromo, or iodo.

22. The compound of claim 1, wherein the compound has any one of the following structures:

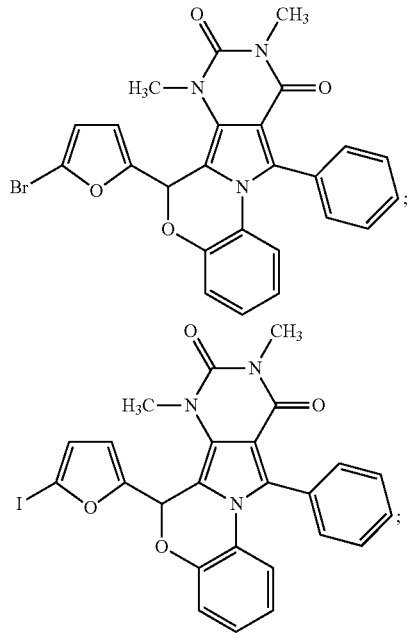

129
-continued
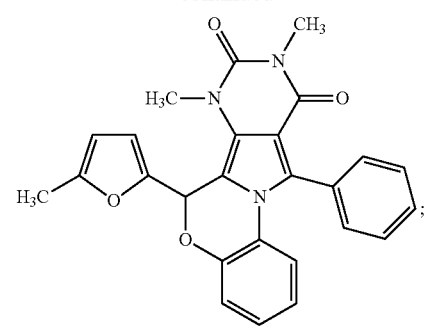
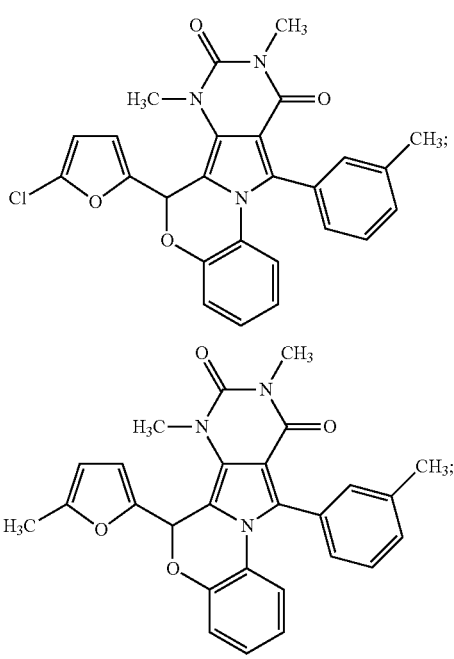
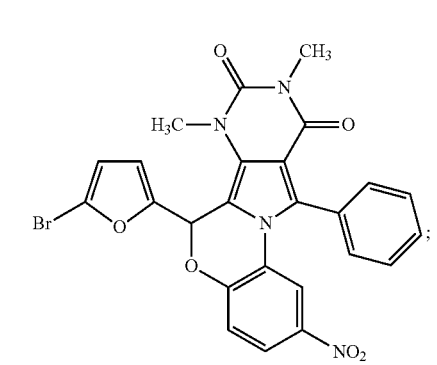
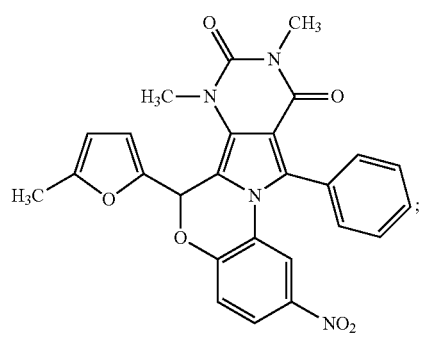
130
-continued
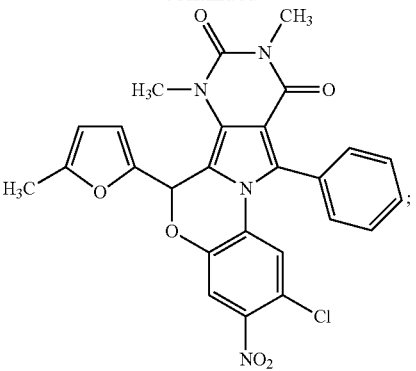
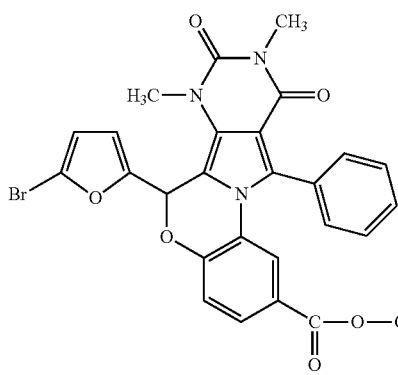
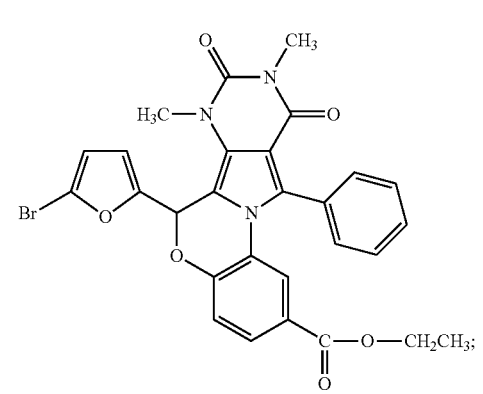
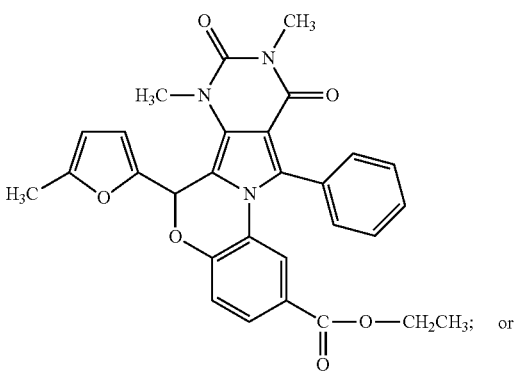 or
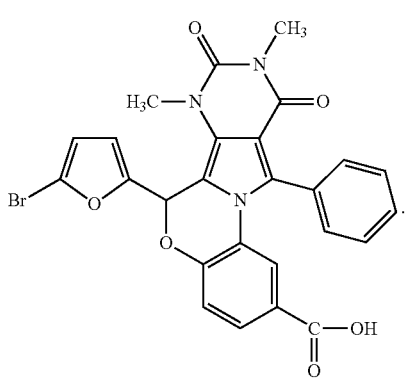 [SMILES: Cn1c(=O)c2c(-c3ccccc3)n3c(c2n(C)c1=O)C(c1ccc(Br)o1)Oc1ccc(C(=O)O)cc1-3]

23. The compound of claim 7, wherein the compound has any one of the following structures:

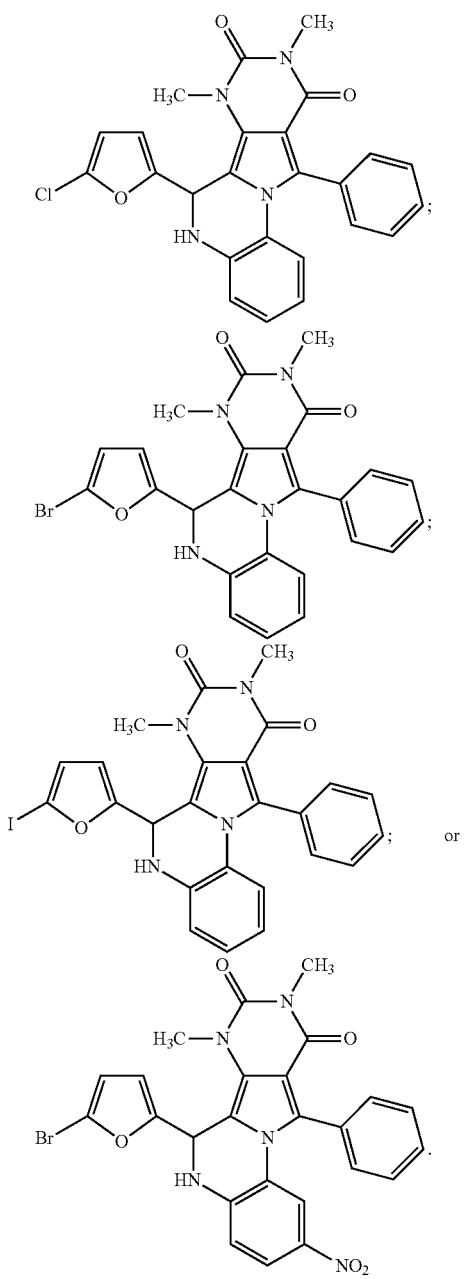

24. The compound of claim 1, wherein the compound is an isolated enantiomer in R form.

25. The compound of claim 24 wherein the compound is 6R-(5-Bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylic acid.

26. The compound of claim 1, wherein the compound is an isolated enantiomer in S form.

27. A pharmaceutical composition comprising the compound of claim 1 and a pharmaceutically suitable excipient.

28. A method for inhibiting cyst formation or inhibiting cyst enlargement, said method comprising contacting (a) a cell that comprises CFTR and (b) the pharmaceutical composition of claim 27, under conditions and for a time sufficient that permit CFTR and the compound to interact, wherein the compound inhibits CFTR-mediated ion transport.

29. A method for treating a disease, condition, or disorder that is treatable by inhibiting cystic fibrosis transmembrane conductance regulator (CFTR)-mediated ion transport, said method comprising administering to a subject the pharmaceutical composition of claim 27, thereby inhibiting CFTR-mediated ion transport.

30. The method of claim 29, wherein the disease, condition, or disorder is selected from polycystic kidney disease, aberrantly increased intestinal fluid secretion, and secretory diarrhea.

31. A pharmaceutical composition comprising the compound of claim 7 and a pharmaceutically suitable excipient.

32. A method for inhibiting cyst formation or inhibiting cyst enlargement, said method comprising contacting (a) a cell that comprises CFTR and (b) the pharmaceutical composition of claim 31, under conditions and for a time sufficient that permit CFTR and the compound to interact, wherein the compound inhibits CFTR-mediated ion transport.

33. A method for treating a disease, condition, or disorder that is treatable by inhibiting cystic fibrosis transmembrane conductance regulator (CFTR)-mediated ion transport, said method comprising administering to a subject the pharmaceutical composition of claim 31, thereby inhibiting CFTR-mediated ion transport.

34. The method of claim 33, wherein the disease, condition, or disorder is selected from polycystic kidney disease, aberrantly increased intestinal fluid secretion, and secretory diarrhea.

* * * * *

UNITED STATES PATENT AND TRADEMARK OFFICE
CERTIFICATE OF CORRECTION

PATENT NO. : 9,062,073 B2  Page 1 of 1
APPLICATION NO. : 14/119405
DATED : June 23, 2015
INVENTOR(S) : Alan S. Verkman et al.

It is certified that error appears in the above-identified patent and that said Letters Patent is hereby corrected as shown below:

Claims

Column 122, Line 67, Claim 3:
"methyl, p is 0, $R^{4a}$ is – $OR^7$ is Z is optionally substituted" is incorrect. The line should read,
--methyl, p is 0, $R^{4a}$ is –$OR^7$, Z is optionally substituted--.

Column 127, Line 49, Claim 10:
"10. The compound of either claim 1, wherein m=2 and p=0" is incorrect. The line should read,
--10. The compound of claim 1, wherein m=2 and p=0--.

Column 128, Line 1, Claim 14:
"(b) t=1 and $R^{1b}$ is –OH, halo, -$NO_2$, $C_{1-3}$ alkyl, or" is incorrect. The line should read,
--(b) t=1 and $R^{1b}$ is –OH, halo, -$NO_2$, $C_{1-3}$ alkyl, or, $C_{1-3}$ alkoxy; or--.

Column 128, Line 7, Claim 14:
"methooxy; (c) each $R^{1b}$ is H." is incorrect. The line should read, --methoxy; or (c) each $R^{1b}$ is H--.

Column 128, Line 30, Claim 19:
"19. The compound of claim 2, wherein m+2 and p=0 and" is incorrect. The line should read,
--19. The compound of claim 2, wherein m=2 and p=0 and--.

Signed and Sealed this
Twelfth Day of January, 2016

Michelle K. Lee
*Director of the United States Patent and Trademark Office*